US011548880B2

(12) United States Patent
Li

(10) Patent No.: US 11,548,880 B2
(45) Date of Patent: *Jan. 10, 2023

(54) MODULATORS OF HEMOGLOBIN

(71) Applicant: Global Blood Therapeutics, Inc., South San Francisco, CA (US)

(72) Inventor: Zhe Li, San Diego, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,625

(22) Filed: May 4, 2020

(65) Prior Publication Data
US 2021/0047309 A1    Feb. 18, 2021

Related U.S. Application Data

(63) Continuation of application No. 16/687,474, filed on Nov. 18, 2019, now Pat. No. 10,683,285.

(60) Provisional application No. 62/883,313, filed on Aug. 6, 2019, provisional application No. 62/848,773, filed on May 16, 2019, provisional application No. 62/821,314, filed on Mar. 20, 2019, provisional application No. 62/769,196, filed on Nov. 19, 2018.

(51) Int. Cl.
| C07D 413/06 | (2006.01) |
| A61K 31/5377 | (2006.01) |
| A61K 31/541 | (2006.01) |
| C07D 417/06 | (2006.01) |
| C07D 401/06 | (2006.01) |
| C07D 211/22 | (2006.01) |
| C07D 403/06 | (2006.01) |
| C07D 265/30 | (2006.01) |
| A61P 7/06 | (2006.01) |

(52) U.S. Cl.
CPC ........ *C07D 413/06* (2013.01); *A61K 31/5377* (2013.01); *A61K 31/541* (2013.01); *A61P 7/06* (2018.01); *C07D 211/22* (2013.01); *C07D 265/30* (2013.01); *C07D 401/06* (2013.01); *C07D 403/06* (2013.01); *C07D 417/06* (2013.01)

(58) Field of Classification Search
CPC .. C07D 413/06; C07D 211/22; C07D 265/30; C07D 401/06; C07D 403/06; C07D 417/06
See application file for complete search history.

(56) References Cited

U.S. PATENT DOCUMENTS

| 4,410,537 A | 10/1983 | Kneen |
| 4,535,183 A | 8/1985 | Kneen |
| 5,679,678 A | 10/1997 | Binder et al. |
| 6,242,644 B1 | 6/2001 | Ackermann et al. |
| 6,472,349 B1 | 10/2002 | Hamprecht et al. |
| 7,160,910 B2 | 1/2007 | Safo et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,137,118 B2 | 11/2018 | Li et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,493,035 B2 | 12/2019 | Dalziel et al. |
| 10,683,285 B2 * | 6/2020 | Li ..................... A61K 31/5377 |
| 2007/0293698 A1 | 12/2007 | Quick et al. |
| 2010/0210651 A1 | 8/2010 | Hernandez et al. |
| 2014/0271591 A1 | 9/2014 | Sinha et al. |
| 2014/0274961 A1 | 9/2014 | Metcalf et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0344472 A1 | 12/2015 | Metcalf et al. |

(Continued)

FOREIGN PATENT DOCUMENTS

| EP | 0054924 | 6/1982 |
| JP | 57-145844 | 9/1982 |

(Continued)

OTHER PUBLICATIONS

Zawilska. Pharmacological Reports, 2013, 65, 1-14 (Year: 2013).*
U.S. Appl. No. 16/588,753, filed Sep. 30, 2019, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.

(Continued)

*Primary Examiner* — Noble E Jarrell
(74) *Attorney, Agent, or Firm* — Sheppard Mullin Richter & Hampton LLP

(57) ABSTRACT

The present disclosure relates generally to compounds and pharmaceutical compositions suitable as modulators of hemoglobin, and methods for their use in treating disorders mediated by hemoglobin.

20 Claims, No Drawings

(56) References Cited

U.S. PATENT DOCUMENTS

| | | | |
|---|---|---|---|
| 2015/0344483 | A1 | 12/2015 | Metcalf et al. |
| 2016/0024127 | A1 | 1/2016 | Harris et al. |
| 2016/0038474 | A1 | 2/2016 | Sinha et al. |
| 2016/0083343 | A1 | 3/2016 | Xu et al. |
| 2016/0083348 | A1 | 3/2016 | Xu et al. |
| 2016/0206604 | A1 | 7/2016 | Metcalf et al. |
| 2016/0206614 | A1 | 7/2016 | Metcalf et al. |
| 2016/0207904 | A1 | 7/2016 | Li et al. |
| 2016/0346263 | A1 | 12/2016 | Li et al. |
| 2017/0107199 | A1 | 4/2017 | Metcalf et al. |
| 2017/0157101 | A1 | 6/2017 | Ramos et al. |
| 2017/0355713 | A1 | 12/2017 | Harris et al. |
| 2018/0186807 | A1 | 7/2018 | Yee et al. |
| 2019/0010121 | A1 | 1/2019 | Xu et al. |
| 2019/0010176 | A1 | 1/2019 | Harris |
| 2019/0106404 | A1 | 4/2019 | Li et al. |
| 2019/0111037 | A1 | 4/2019 | Li et al. |
| 2019/0112287 | A1 | 4/2019 | Metcalf et al. |
| 2019/0160060 | A1 | 5/2019 | Metcalf et al. |
| 2019/0202782 | A1 | 7/2019 | Xu et al. |
| 2019/0255031 | A1 | 8/2019 | Li et al. |

FOREIGN PATENT DOCUMENTS

| | | |
|---|---|---|
| JP | S-63258463 | 10/1988 |
| WO | WO-2004/014899 | 2/2004 |
| WO | WO-2004/111031 | 12/2004 |
| WO | WO-2007/003962 | 1/2007 |
| WO | WO-2007/009389 | 1/2007 |
| WO | WO-2008/066145 | 6/2008 |
| WO | WO-2009/011850 | 1/2009 |
| WO | WO-2009/136889 | 11/2009 |
| WO | WO 2009/153191 | 12/2009 |
| WO | WO-2013/102142 | 7/2013 |
| WO | WO-2013/102145 | 7/2013 |
| WO | WO-2014/150268 | 9/2014 |

OTHER PUBLICATIONS

Abdulmalik et al., Sickle cell disease: current therapeutic approaches, Expert Opinion Ther. Patents, 2005, vol. 15(11), pp. 1497-1506.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
CAS Reg. No. 921186-17-6, entered into STN on Feb. 15, 2007.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
International Preliminary Report on Patentability for PCT/US2014/022769 dated Sep. 15, 2015. 8 pages.
International Search Report and Written Opinion dated Jul. 4, 2014 for PCT Application No. PCT/US2014/022769. 11 pages.
Nnamani, et al., "Pyridyl derivatives of benzaldehyde as potential antisickling agents," Chem. Biodivers., (2008), 5(9):1762-1769.
Patani, et al. Bioisosterism: A Rational Approach in Drug Design. J. Chem Rev. 1996, 96(8), pp. 3147-3176.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Schudel, et al. Uber die Chemie des Vitamins E. Helvetica Chimica Acta. 1963; 66:636-649.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
Tsuge, et al. Suppressive Effect of Vitamin B6-Sugar Derivatives on The Proliferation of Feline Mammary Tumor Cell, FRM. Vitamins (Japan), 2006; 80(11):537-542. (In Japanese with English Abstract).
Yoon et al., The Chirality Conversion Reagent for Amino Acids Based on Salicyl Aldehyde. Bull. Korean Chem. Soc., (2012), 33:1715-1718.

\* cited by examiner

MODULATORS OF HEMOGLOBIN

CROSS-REFERENCE TO RELATED APPLICATIONS

This application is a continuation of U.S. application Ser. No. 16/687,474, filed Nov. 18, 2019, now U.S. Pat. No. 10,683,285, which claims the benefit under 35 U.S.C. § 119(e) of U.S. Provisional Application No. 62/769,196, filed Nov. 19, 2018, U.S. Provisional Application No. 62/821,314, filed Mar. 20, 2019, U.S. Provisional Application No. 62/848,773, filed May 16, 2019, and U.S. Provisional Application No. 62/883,313, filed Aug. 6, 2019, each of which is hereby incorporated by reference in its entirety.

FIELD

Provided herein are compounds and pharmaceutical compositions suitable as modulators of hemoglobin, and methods for their use in treating disorders mediated by hemoglobin.

BACKGROUND

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin A (HbA).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels.

2-hydroxy-6-((2-(1-isopropyl-1H-pyrazol-5-yl)pyridin-3-yl)methoxy)benzaldehyde (also known as voxelotor or GBT440), a modulator of hemoglobin that increases the affinity of hemoglobin for oxygen and consequently inhibits polymerization of HbS when subjected to hypoxic conditions, is currently in Phase 3 clinical trials for the treatment of sickle cell disease (NCT03036813).

WO 2014/150268 describes modulators of hemoglobin that are structurally related to the compounds disclosed herein.

A need exists for compounds that can treat disorders that are mediated by abnormal Hb such as HbS and methods of treating such disorders. Compounds that have an improved pharmacokinetic profile relative to known modulators of hemoglobin while maintaining or improving efficacy are of particular interest, as such compounds would allow for favorable dosing regimens (e.g., lower and/or less frequent doses).

SUMMARY

Provided herein is a compound of formula I:

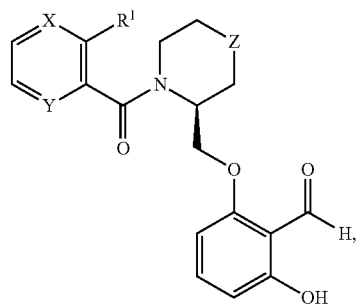

I or an isotopically enriched analog, stereoisomer, mixture of stereoisomers, or prodrug thereof, or a pharmaceutically acceptable salt of each thereof, wherein:
X is CH or N;
Y is CH or N;
Z is absent, $CH_2$, O, or S; and
$R^1$ is mono-hydroxy-($C_{1-4}$alkyl), di-hydroxy-($C_{1-4}$ alkyl), —$CH_2CH_2OCH_3$, —$CH_2CH_2CN$, or

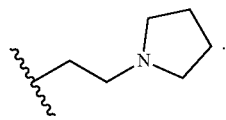 [SMILES: *CCN1CCCC1]

Some embodiments provide for pharmaceutical compositions comprising a compound as described herein, or an isotopically enriched analog, stereoisomer, mixture of stereoisomers, or prodrug thereof, or a pharmaceutically acceptable salt of each thereof, and a pharmaceutically acceptable excipient. Some embodiments provide for pharmaceutical compositions comprising a compound as described herein or a pharmaceutically acceptable salt thereof, and a pharmaceutically acceptable excipient. Some embodiments provide for pharmaceutical compositions comprising a compound as described herein and a pharmaceutically acceptable excipient.

Also provided herein are methods for increasing oxygen affinity of hemoglobin (e.g., hemoglobin S) in a subject in need thereof, comprising administering to the subject a compound as described herein or a pharmaceutical composition as described herein.

Also provided herein are methods for treating a disorder mediated by hemoglobin in a subject in need thereof, comprising administering to the subject a compound as described herein or a pharmaceutical composition as described herein.

Also provided herein are methods for treating sickle cell disease in a subject in need thereof, comprising administering to the subject a compound as described herein or a pharmaceutical composition as described herein.

DETAILED DESCRIPTION

Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms. In another example, "$C_{1-4}$ alkyl" indicates that the alkyl group has from 1 to 4 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last-mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—".

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR$^y$)(NR$^z_2$), wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp³ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to —$NR^yC(=NR^z)(NR^yR^z)$, wherein each $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Imino" refers to a group —$C(NR^y)R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —$C(O)NR^yC(O)R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6, or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, or 1 to 3) hydrogen atoms are replaced by a halogen.

"Hydroxyalkyl" refers to an alkyl group as defined above, wherein one or more (e.g., 1 to 6, or 1 to 3) hydrogen atoms are replaced by a hydroxy group. A "mono-hydroxy-($C_{1-4}$ alkyl)" refers to a $C_{1-4}$ alkyl group as defined above, wherein one hydrogen atom is replaced by a hydroxy group. A "di-hydroxy-($C_{1-4}$ alkyl)" refers to a $C_{1-4}$ alkyl group as defined above, wherein two hydrogen atoms are replaced by hydroxy groups.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —$NR^y$—, —O—, —S—, —S(O)—, —$S(O)_2$—, and the like, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur.

The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl.

Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group —CR(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R$^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R$^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclyl-alkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, NR$^g$C(=O)OR$^h$ NR$^g$S(=O)$_{1-2}$R$^h$, C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. In certain embodiments, "substituted" also means any of the above groups in which one or more (e.g., 1 to 5, or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, I$^{123}$I, and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like. In some embodiments, a pharmaceutically acceptable salt does not include a salt of a primary amine.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the invention may be reduced in vivo to a —CH$_2$OH moiety.

The term "hydroxy protecting group" refers to a chemical moiety which is added to, and later removed from, a hydroxy functionality to obtain chemoselectivity in a subsequent chemical reaction. Exemplary protecting groups, as well as the methods for deprotection, include, but are not limited to, acetyl (Ac) (removed by acid or base), benzoyl (Bz) (removed by acid or base), benzyl (Bn) (removed by hydrogenolysis), β-methoxyethoxymethyl ether (MEM) (removed by acid), dimethoxytrityl or [bis-(4-methoxyphenyl)phenylmethyl] (DMT) (removed by weak acid), methoxymethyl ether (MOM) (removed by acid), methoxytrityl or [(4-methoxyphenyl)diphenylmethyl] (MMT) (removed by acid and hydrogenolysis), p-methoxybenzyl ether (PMB) (removed by acid, hydrogenolysis, or oxidation), methylthiomethyl ether (removed by acid), pivaloyl (Piv) (removed by acid, base or reductant agents), tetrahydropyranyl (THP) (removed by acid), tetrahydrofuran (THF) (removed by acid), trityl (triphenylmethyl, Tr) (removed by acid and hydrogenolysis), silyl ether (e.g., trimethylsilyl (TMS), tert-butyldimethylsilyl (TBDMS), tri-iso-propylsilyloxymethyl (TOM), and triisopropylsilyl (TIPS) ethers) (removed by acid or fluoride ion, such as NaF, TBAF (tetra-n-butylammonium fluoride, HF-Py, or HF-NEt3)), methyl ethers (removed by cleavage is by TMSI in dichloromethane or acetonitrile or chloroform, or BBr3 in DCM), ethoxyethyl ethers (EE) (removed by 1N hydrochloric acid).

Compounds

Provided herein are compounds that are useful as modulators of hemoglobin. It is contemplated that compounds disclosed herein have an improved pharmacokinetic profile relative to known modulators of hemoglobin while maintaining or improving efficacy. It is further contemplated that compounds disclosed herein have an improved safety pharmacological profile relative to known modulators of hemoglobin.

Provided herein is a compound of formula I:

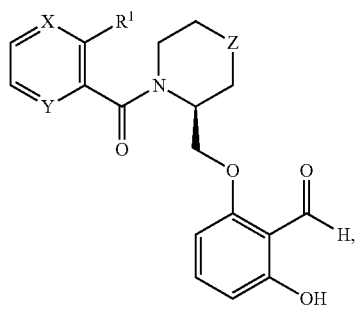

or an isotopically enriched analog, stereoisomer, mixture of stereoisomers, or prodrug thereof, or a pharmaceutically acceptable salt of each thereof, wherein X, Y, Z, and $R^1$ are as defined herein.

In some embodiments, X is CH or N. In some embodiments, X is CH. In some embodiments, X is N.

In some embodiments, Y is CH or N. In some embodiments, Y is CH. In some embodiments, Y is N.

In some embodiments, X is CH or N; and Y is CH. In some embodiments, X is CH; and Y is CH. In some embodiments, X is N; and Y is CH. In some embodiments, X is CH; and Y is N. In some embodiments, X is N; and Y is N.

In some embodiments, Z is absent, $CH_2$, O, or S. In some embodiments, Z is $CH_2$, O, or S. In some embodiments, Z is O or S. In some embodiments, Z is absent, $CH_2$, or O. In some embodiments, Z is absent. In some embodiments, Z is $CH_2$. In some embodiments, Z is O. In some embodiments, Z is S.

In some embodiments, $R^1$ is mono-hydroxy-($C_{1-4}$ alkyl), di-hydroxy-($C_{1-4}$ alkyl), —$CH_2CH_2OCH_3$, —$CH_2CH_2CN$, or

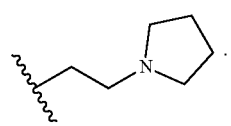 [SMILES: *CCN1CCCC1]

In some embodiments, $R^1$ is mono-hydroxy-($C_{1-4}$ alkyl), di-hydroxy-($C_{1-4}$ alkyl), —$CH_2CH_2CN$, or

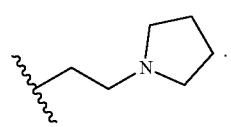

In some embodiments, $R^1$ is mono-hydroxy-($C_{1-4}$ alkyl), di-hydroxy-($C_{1-4}$ alkyl), —$CH_2CH_2OCH_3$, or —$CH_2CH_2CN$. In some embodiments, $R^1$ is mono-hydroxy-($C_{1-4}$ alkyl), di-hydroxy-($C_{1-4}$ alkyl), or —$CH_2CH_2CN$.

In some embodiments, $R^1$ is —$CH_2OH$, —$CH_2CH_2OH$, —$CH_2CH_2OCH_3$, —$CH_2CH_2CN$, or

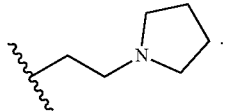

In some embodiments, $R^1$ is —$CH_2OH$, —$CH_2CH_2OH$, —$CH_2CH_2CN$, or

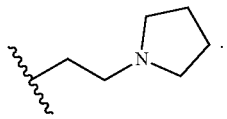

In some embodiments, $R^1$ is —$CH_2OH$, —$CH_2CH_2OH$, —$CH_2CH_2OCH_3$, or —$CH_2CH_2CN$. In some embodiments, $R^1$ is —$CH_2OH$, —$CH_2CH_2OH$, or —$CH_2CH_2CN$. In some embodiments, $R^1$ is —$CH_2OH$ or —$CH_2CH_2OH$. In some embodiments, $R^1$ is —$CH_2OH$. In some embodiments, $R^1$ is —$CH_2CH_2OH$. In some embodiments, $R^1$ is —$CH_2CH_2OCH_3$. In some embodiments, $R^1$ is —$CH_2CH_2CN$. In some embodiments, $R^1$ is

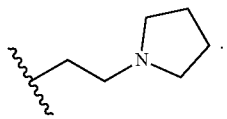 [SMILES: *CCN1CCCC1]

In some embodiments, $R^1$ is mono-hydroxy-($C_{1-4}$ alkyl) or di-hydroxy-($C_{1-4}$ alkyl). In some embodiments, $R^1$ is mono-hydroxy-($C_{1-4}$ alkyl). In some embodiments, $R^1$ is di-hydroxy-($C_{2-4}$ alkyl). In some embodiments, $R^1$ is mono-hydroxy-($C_{1-3}$ alkyl) or di-hydroxy-($C_{1-3}$ alkyl). In some embodiments, $R^1$ is mono-hydroxy-($C_{1-3}$ alkyl). In some embodiments, $R^1$ is di-hydroxy-($C_{2-3}$ alkyl). In some embodiments, $R^1$ is mono-hydroxy-($C_{1-3}$ alkyl) or di-hydroxy-($C_{1-2}$ alkyl).

In some embodiments, $R^1$ is hydroxymethyl, 1-hydroxyethyl, 2-hydroxyethyl, 1,2-dihydroxyethyl, 2-hydroxypropyl, 3-hydroxypropyl, or 2-hydroxy-2-methylpropyl. In some embodiments, $R^1$ is hydroxymethyl, 1-hydroxyethyl, 2-hydroxyethyl, 1,2-dihydroxyethyl, or 2-hydroxypropyl. In some embodiments, $R^1$ is hydroxymethyl, 1-hydroxyethyl, 2-hydroxyethyl, or 2-hydroxypropyl.

In some embodiments, $R^1$ is hydroxymethyl (i.e., —$CH_2OH$) or 2-hydroxyethyl (i.e., —$CH_2CH_2OH$). In some embodiments, $R^1$ is hydroxymethyl.

In some embodiments, $R^1$ is 1-hydroxyethyl or 2-hydroxyethyl. In some embodiments, $R^1$ is 1-hydroxyethyl. In some embodiments, $R^1$ is

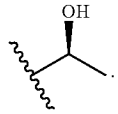

In some embodiments, $R^1$ is

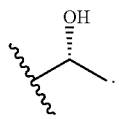

In some embodiments, $R^1$ is 2-hydroxyethyl. In some embodiments, $R^1$ is 1,2-dihydroxyethyl. In some embodiments, $R^1$ is

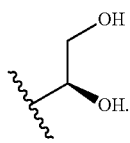

In some embodiments, $R^1$ is

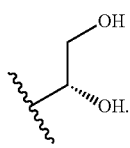

In some embodiments, $R^1$ is 2-hydroxypropyl. In some embodiments, $R^1$ is

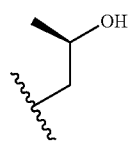 [SMILES: *C[C@@H](C)O]

In some embodiments, $R^1$ is

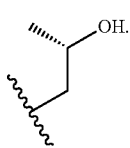 [SMILES: *C[C@H](C)O]

In some embodiments, $R^1$ is 3-hydroxypropyl.
In some embodiments, $R^1$ is 2-hydroxy-2-methylpropyl.
In some embodiments, $R^1$ is

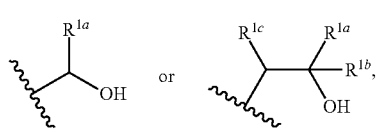

wherein $R^{1a}$ is hydrogen or methyl; $R^{1b}$ is hydrogen or methyl; and $R^{1c}$ is hydrogen or hydroxy.

Any of the combinations of X, Y, Z, and R are encompassed and provided by this disclosure.

Some embodiments provide for a compound of formula I:

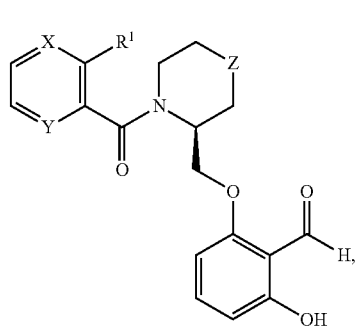

or an isotopically enriched analog, stereoisomer, mixture of stereoisomers, or prodrug thereof, or a pharmaceutically acceptable salt of each thereof, wherein:
X is CH or N;
Y is CH or N;
Z is absent, $CH_2$, O, or S; and
$R^1$ is $-CH_2OH$, $-CH_2CH_2OH$, $-CH_2CH_2OCH_3$, $-CH_2CH_2CN$, or

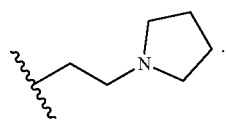 [SMILES: *CCN1CCCC1]

Some embodiments provide for a compound of formula I:

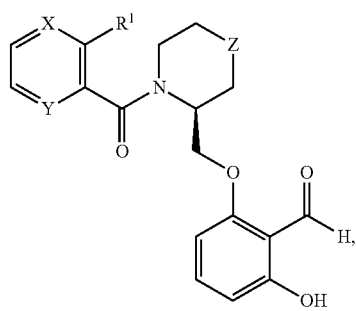

or an isotopically enriched analog, stereoisomer, mixture of stereoisomers, or prodrug thereof, or a pharmaceutically acceptable salt of each thereof, wherein:
X is CH or N;
Y is CH or N;
Z is absent, $CH_2$, or O; and
$R^1$ is $-CH_2OH$, $-CH_2CH_2OH$, $-CH_2CH_2OCH_3$, $-CH_2CH_2CN$, or

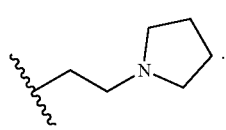 [SMILES: *CCN1CCCC1]

In some embodiments, Y is CH; and Z is $CH_2$.

Some embodiments provide for a compound of formula Ia:

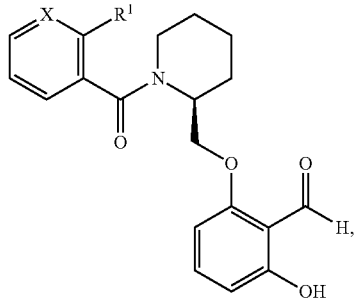

Ia or an isotopically enriched analog, stereoisomer, mixture of stereoisomers, or prodrug thereof, or a pharmaceutically acceptable salt of each thereof, wherein:
X is CH or N; and
$R^1$ is —CH$_2$OH, —CH$_2$CH$_2$OH, —CH$_2$CH$_2$OCH$_3$, —CH$_2$CH$_2$CN, or

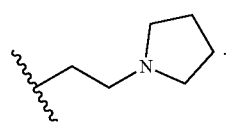 [SMILES: *CCN1CCCC1]

.

In some embodiments, X is CH or N; Y is CH; Z is CH$_2$, O, or S; and $R^1$ is a mono-hydroxy-(C$_{1-4}$ alkyl) or di-hydroxy-(C$_{1-4}$ alkyl) moiety as described herein.

In some embodiments, X is CH or N; Y is CH; Z is CH$_2$, O, or S; and $R^1$ is a mono-hydroxy-(C$_{1-4}$ alkyl) moiety as described herein.

In some embodiments, X is N; Y is CH; Z is CH$_2$, O, or S; and $R^1$ is a mono-hydroxy-(C$_{1-4}$ alkyl) moiety as described herein.

In some embodiments, X is N; Y is CH; Z is O or S; and $R^1$ is mono-hydroxy-(C$_{1-4}$ alkyl) moiety as described herein.

In some embodiments, X is N; Y is CH; Z is CH$_2$, O, or S; and $R^1$ is —CH$_2$OH or —CH$_2$CH$_2$H. In some embodiments, X is N; Y is CH; Z is O or S; and $R^1$ is —CH$_2$OH or —CH$_2$CH$_2$OH. In some embodiments, X is N; Y is CH; Z is CH$_2$; and $R^1$ is —CH$_2$OH or —CH$_2$CH$_2$OH. In some embodiments, X is N; Y is CH; Z is O; and $R^1$ is —CH$_2$OH or —CH$_2$CH$_2$OH. In some embodiments, X is N; Y is CH; Z is S; and $R^1$ is —CH$_2$OH or —CH$_2$CH$_2$OH.

Some embodiments provide for a compound of formula Ib:

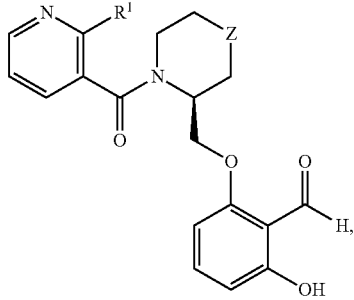

Ib or an isotopically enriched analog, stereoisomer, mixture of stereoisomers, or prodrug thereof, or a pharmaceutically acceptable salt of each thereof, wherein:
Z is CH$_2$, O, or S; and
$R^1$ is a mono-hydroxy-(C$_{1-4}$ alkyl) moiety as described herein.

In some embodiments, X is CH or N; Y is CH; Z is CH$_2$, O, or S; and $R^1$ is a di-hydroxy-(C$_{2-4}$ alkyl) moiety as described herein. In some embodiments, X is CH; Y is CH; Z is CH$_2$, O, or S; and $R^1$ is a di-hydroxy-(C$_{2-4}$ alkyl) moiety as described herein. In some embodiments, X is CH; Y is CH; Z is O or S; and $R^1$ is a di-hydroxy-(C$_{2-4}$ alkyl) moiety as described herein. In some embodiments, X is CH; Y is CH; Z is CH$_2$; and $R^1$ is a di-hydroxy-(C$_{2-4}$ alkyl) moiety as described herein. In some embodiments, X is CH; Y is CH; Z is O; and $R^1$ is a di-hydroxy-(C$_{2-4}$ alkyl) moiety as described herein. In some embodiments, X is CH; Y is CH; Z is S; and $R^1$ is di-hydroxy-(C$_{2-4}$ alkyl) moiety as described herein.

Some embodiments provide for a compound of formula Ic:

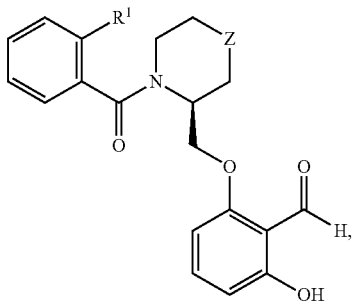

Ic or an isotopically enriched analog, stereoisomer, mixture of stereoisomers, or prodrug thereof, or a pharmaceutically acceptable salt of each thereof, wherein:
Z is CH$_2$, O, or S; and
$R^1$ is a di-hydroxy-(C$_{1-4}$ alkyl) moiety as described herein.

Provided herein is a compound of formula:

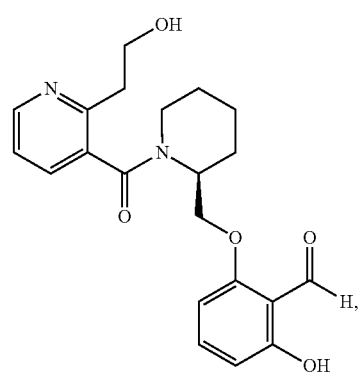

-continued
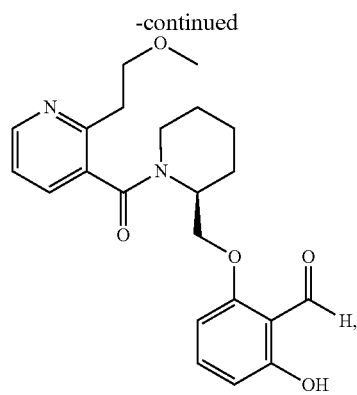
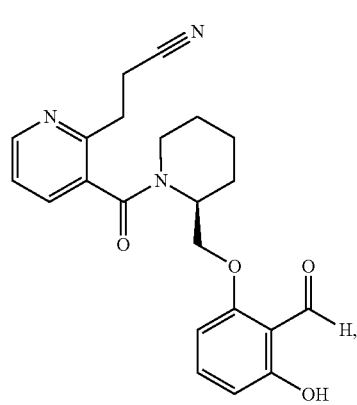
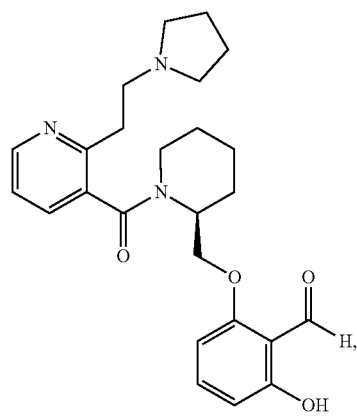
-continued
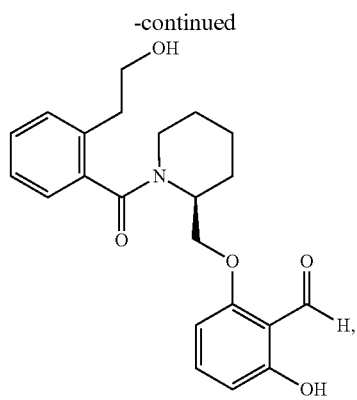
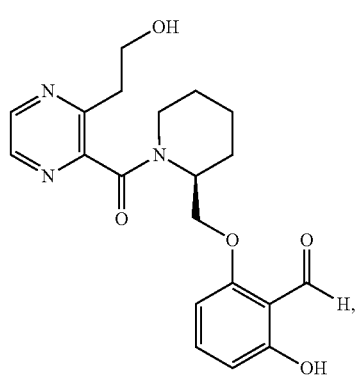
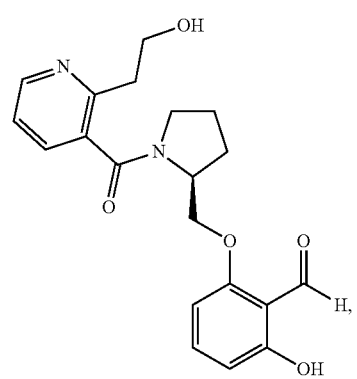

-continued
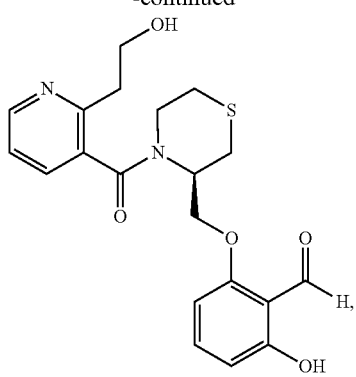
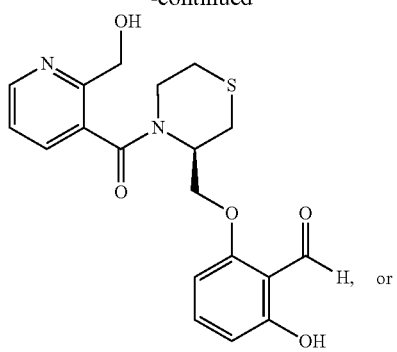
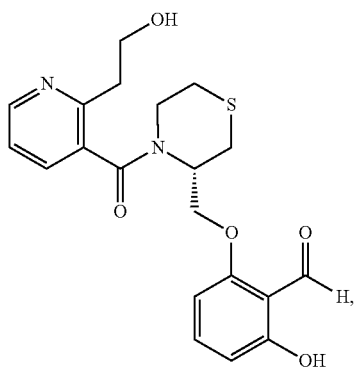
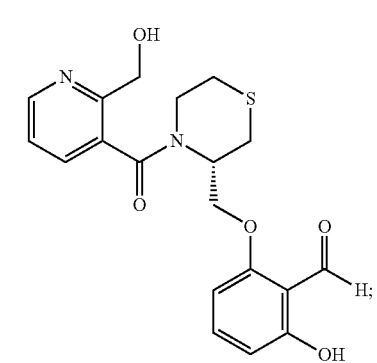
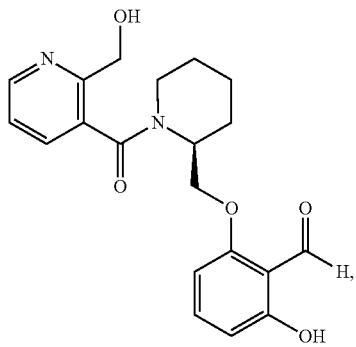
or an isotopically enriched analog, stereoisomer, mixture of stereoisomers, or prodrug thereof, or a pharmaceutically acceptable salt of each thereof.
Provided herein is a compound of formula:
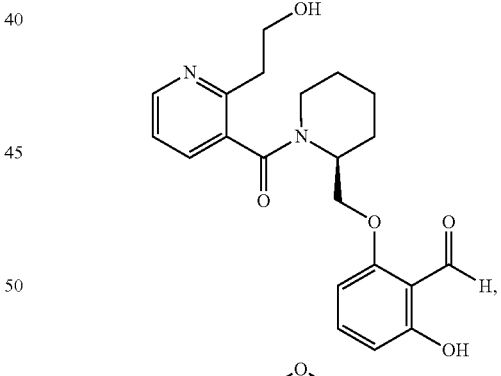
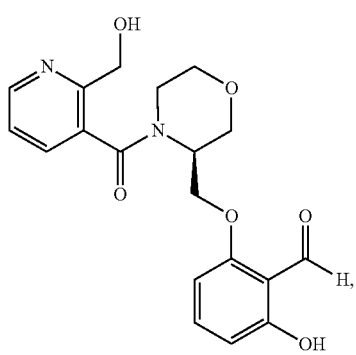
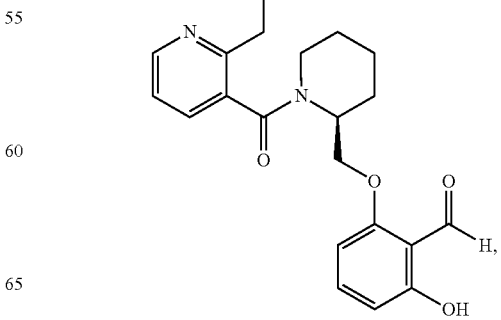

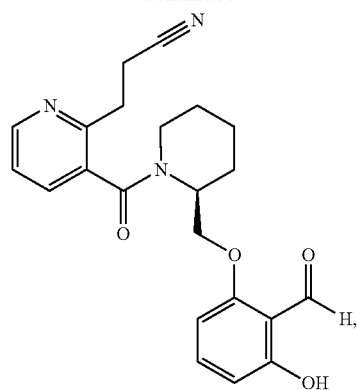
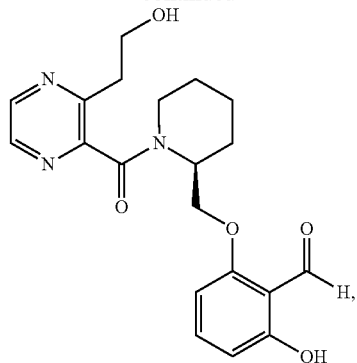
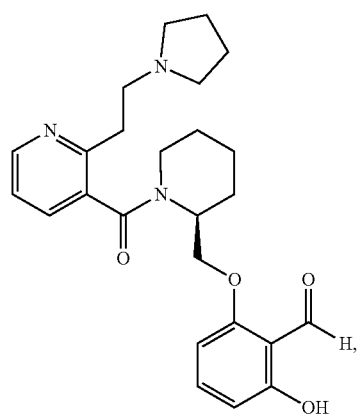
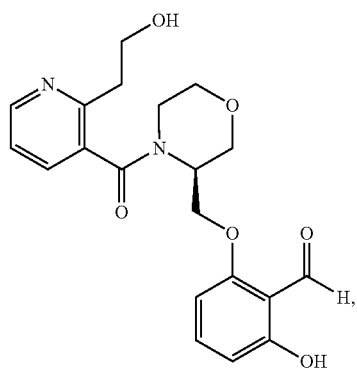
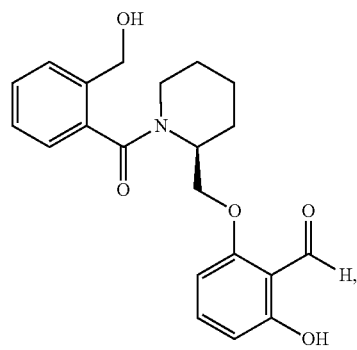
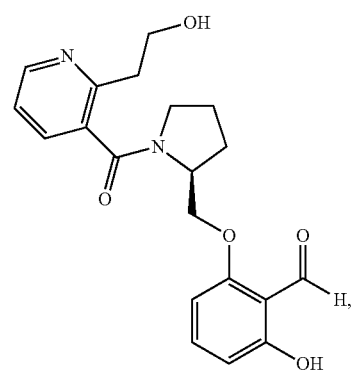
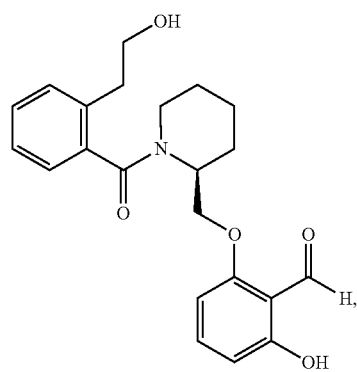
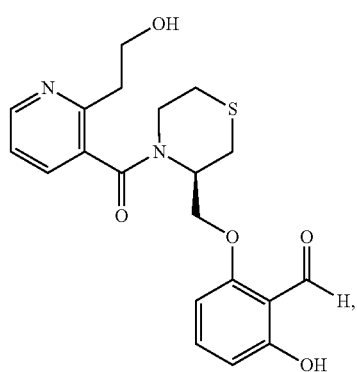

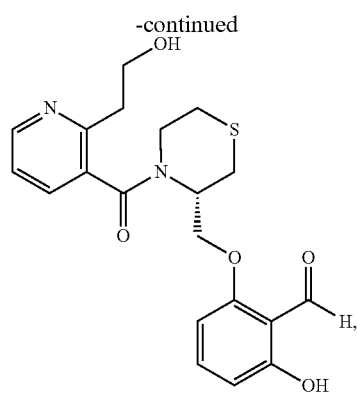
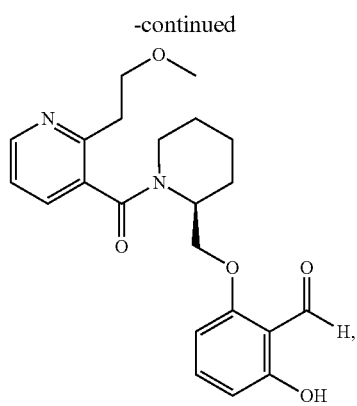
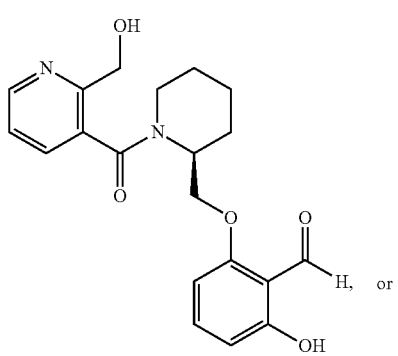
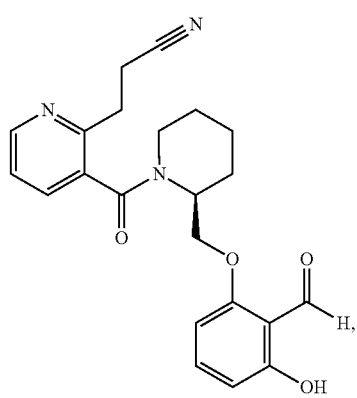
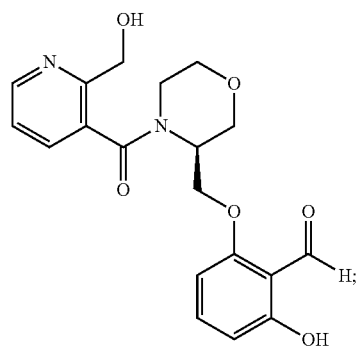
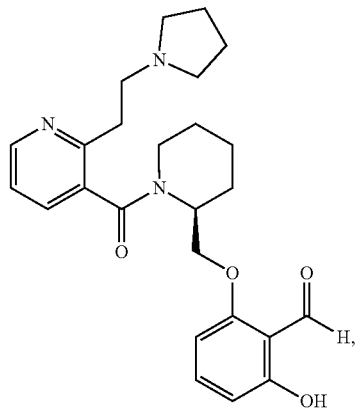
or an isotopically enriched analog, stereoisomer, mixture of stereoisomers, or prodrug thereof, or a pharmaceutically acceptable salt of each thereof.
Provided herein is a compound of formula:
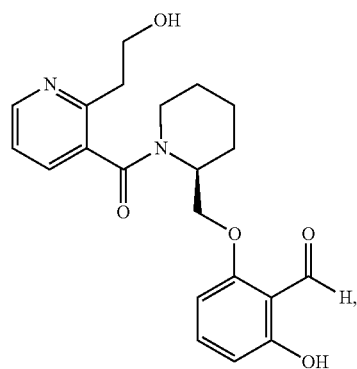
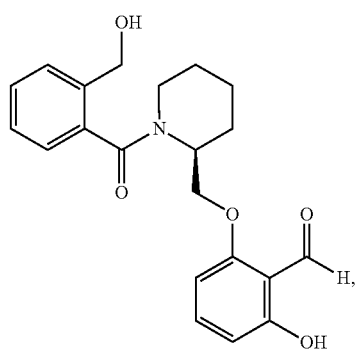

-continued
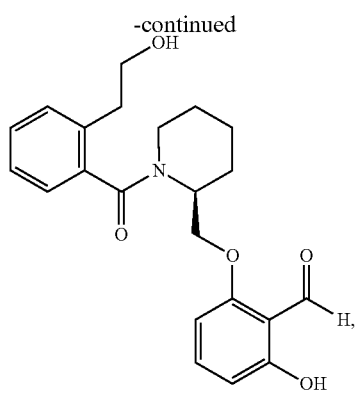
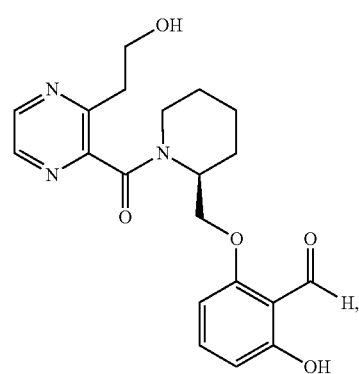
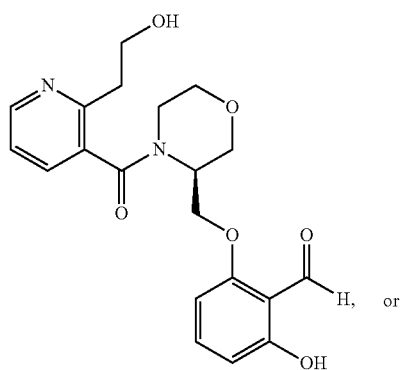
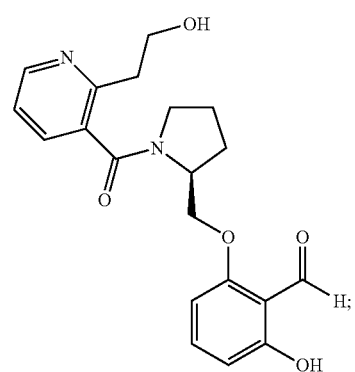
or an isotopically enriched analog, stereoisomer, mixture of stereoisomers, or prodrug thereof, or a pharmaceutically acceptable salt of each thereof.
Provided herein is a compound of formula:
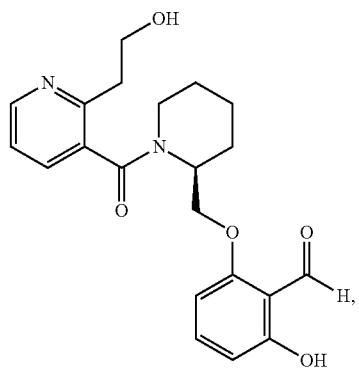
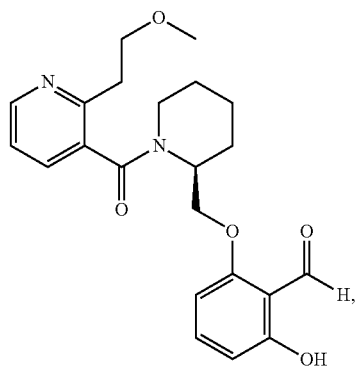
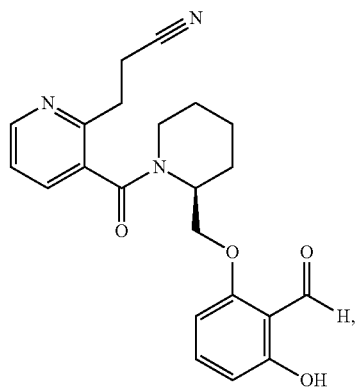
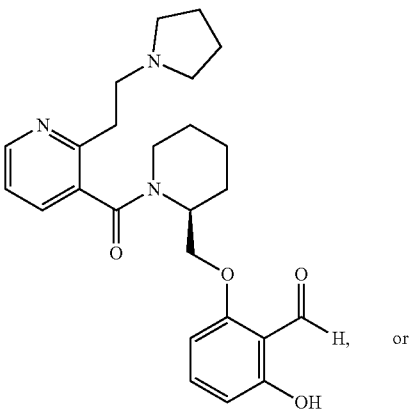

-continued
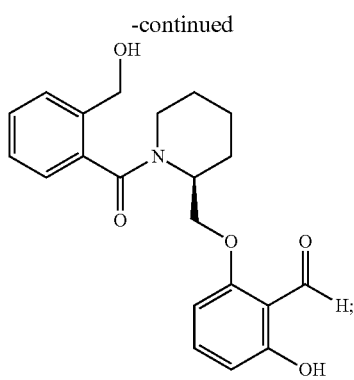
or an isotopically enriched analog, stereoisomer, mixture of stereoisomers, or prodrug thereof, or a pharmaceutically acceptable salt of each thereof.
Provided herein is a compound of formula:
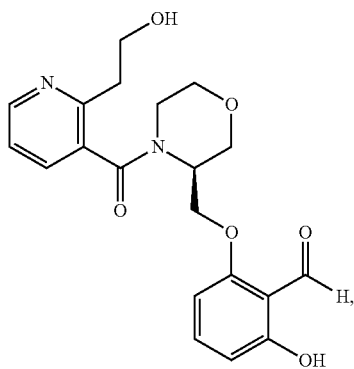
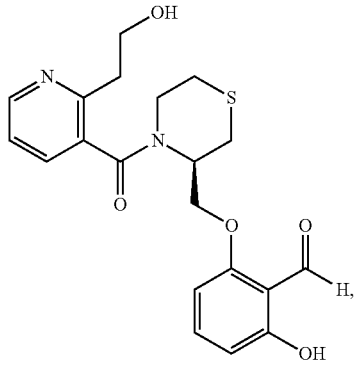
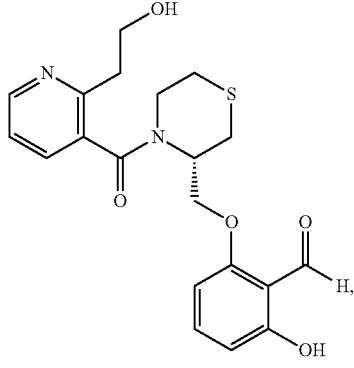
-continued
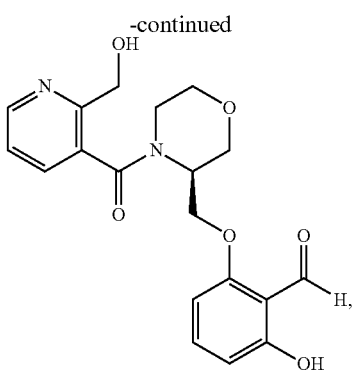
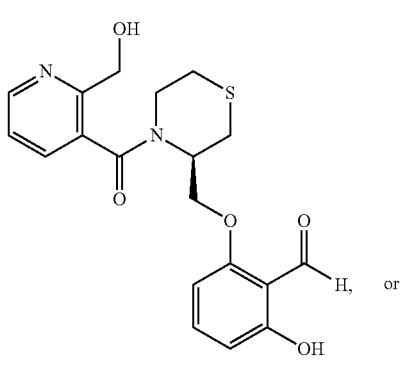
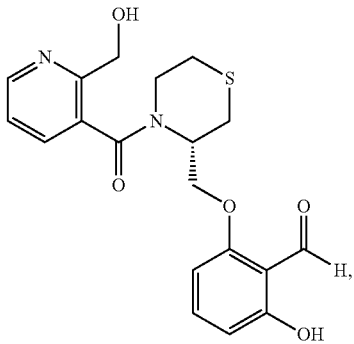
or a pharmaceutically acceptable salt of each thereof.
In some embodiments, the compound is:
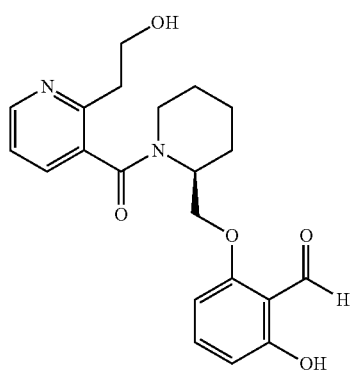
or a pharmaceutically acceptable salt thereof.

In some embodiments, the compound is:

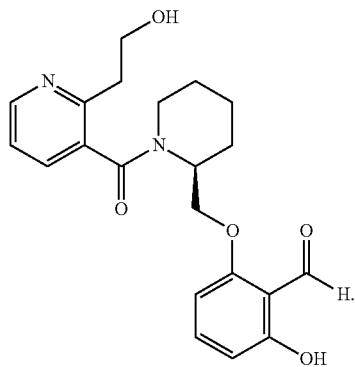

In some embodiments, the compound is:

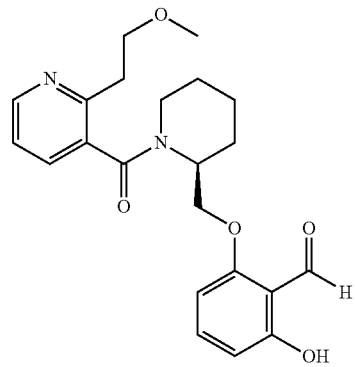 [SMILES: COCCc1ncccc1C(=O)N1CCCC[C@H]1COc1cccc(O)c1C=O]

or a pharmaceutically acceptable salt thereof.
In some embodiments, the compound is:

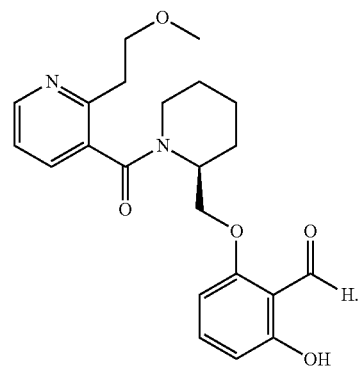

In some embodiments, the compound is:

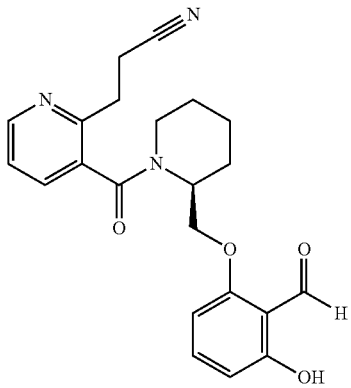

or a pharmaceutically acceptable salt thereof.
In some embodiments, the compound is:

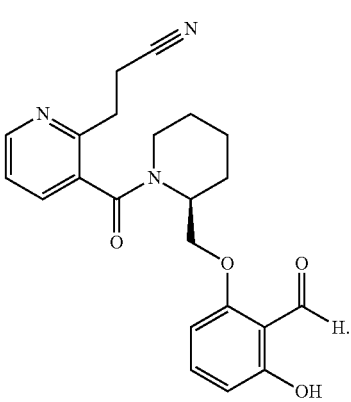

In some embodiments, the compound is:

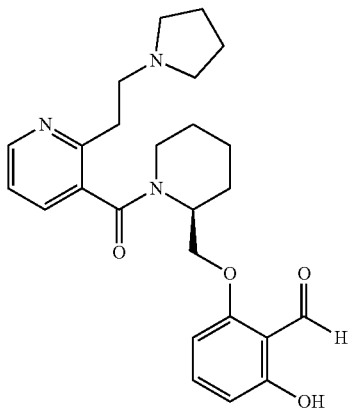

or a pharmaceutically acceptable salt thereof.

In some embodiments, the compound is:

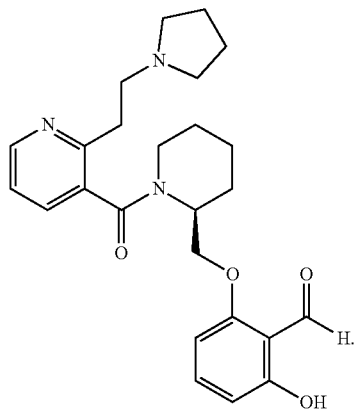

In some embodiments, the compound is:

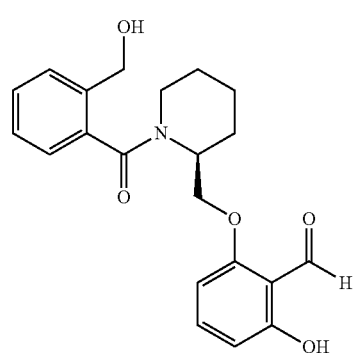

or a pharmaceutically acceptable salt thereof.
In some embodiments, the compound is:

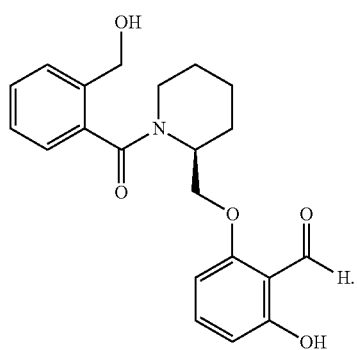

In some embodiments, the compound is:

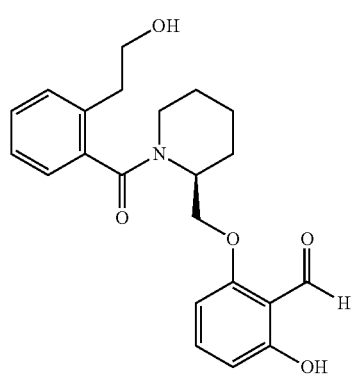

or a pharmaceutically acceptable salt thereof.
In some embodiments, the compound is:

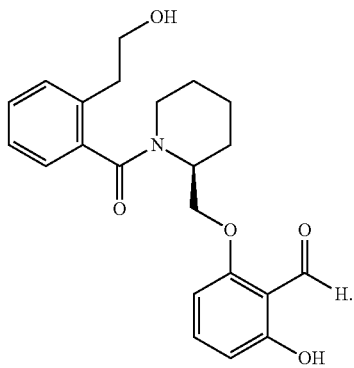

In some embodiments, the compound is:

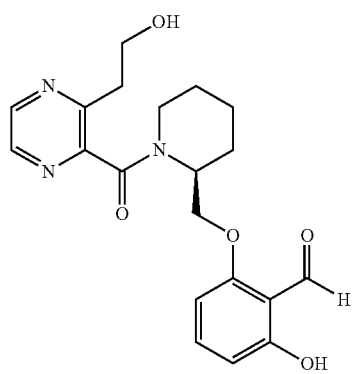

or a pharmaceutically acceptable salt thereof.

In some embodiments, the compound is:

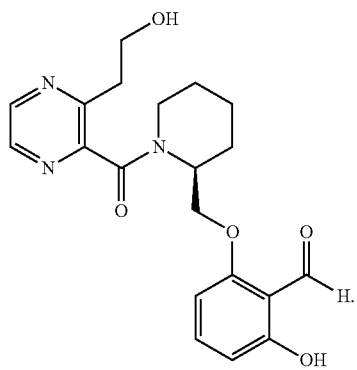

In some embodiments, the compound is:

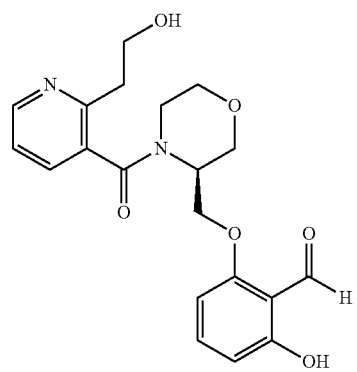

or a pharmaceutically acceptable salt thereof.
In some embodiments, the compound is:

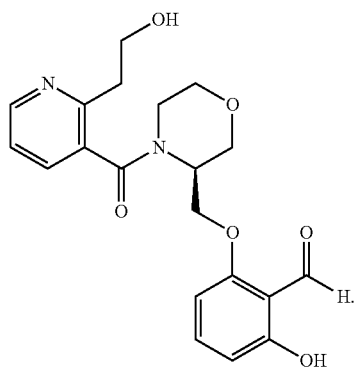

In some embodiments, the compound is:

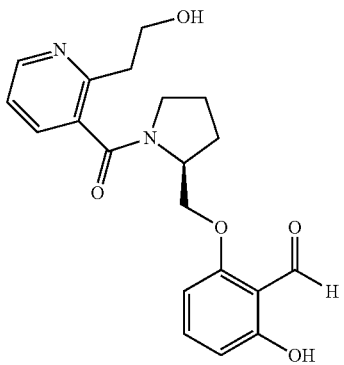 [SMILES: O=Cc1c(O)cccc1OC[C@@H]1CCCN1C(=O)c1cccnc1CCO]

or a pharmaceutically acceptable salt thereof.
In some embodiments, the compound is:

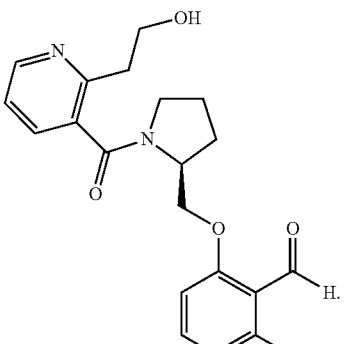

In some embodiments, the compound is:

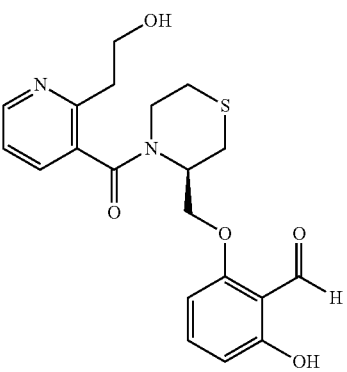

or a pharmaceutically acceptable salt thereof.

In some embodiments, the compound is:

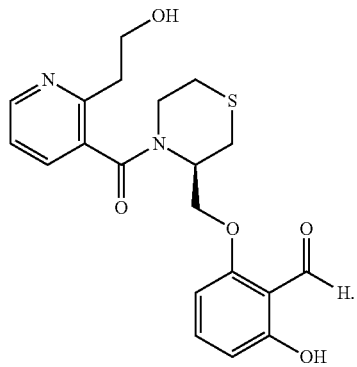

In some embodiments, the compound is:

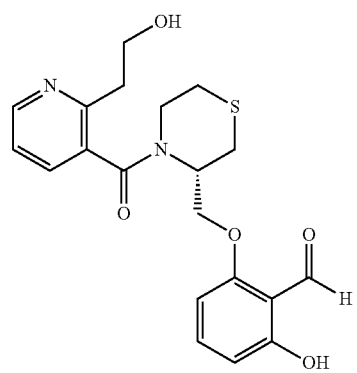

or a pharmaceutically acceptable salt thereof.
In some embodiments, the compound is:

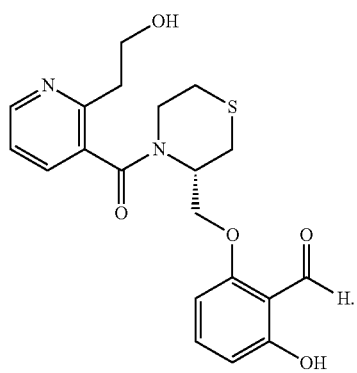

In some embodiments, the compound is:

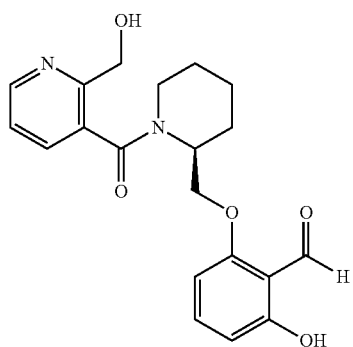

or a pharmaceutically acceptable salt thereof.
In some embodiments, the compound is:

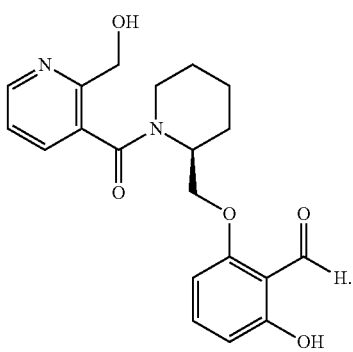

In some embodiments, the compound is:

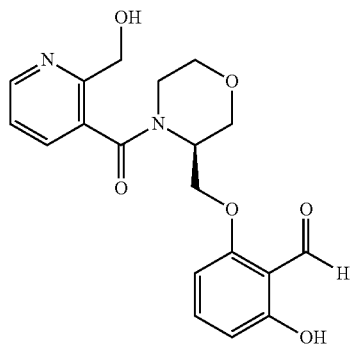

or a pharmaceutically acceptable salt thereof.

In some embodiments, the compound is:

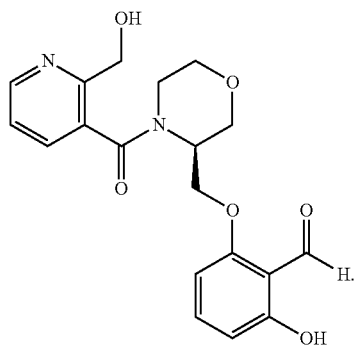

In some embodiments, the compound is:

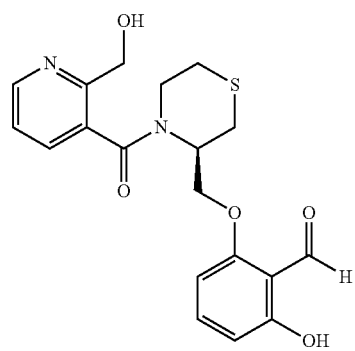

or a pharmaceutically acceptable salt thereof.
In some embodiments, the compound is:

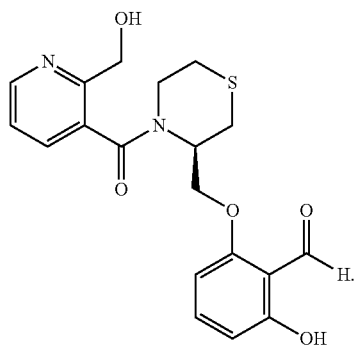

In some embodiments, the compound is:

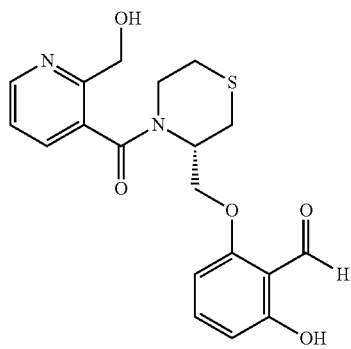

or a pharmaceutically acceptable salt thereof.
In some embodiments, the compound is:

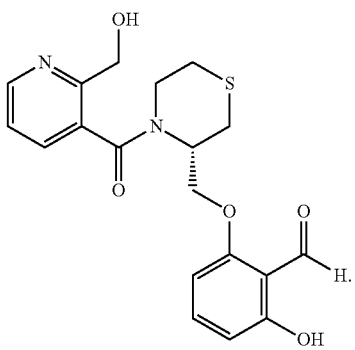

Provided herein is a compound selected from Table 1, or an isotopically enriched analog, stereoisomer, mixture of stereoisomers, or prodrug thereof, or a pharmaceutically acceptable salt of each thereof. Provided herein is a compound selected from Table 1, or a pharmaceutically acceptable salt thereof. Provided herein is a compound selected from Table 1.

Provided herein is a compound selected from Table 2, or an isotopically enriched analog, stereoisomer, mixture of stereoisomers, or prodrug thereof, or a pharmaceutically acceptable salt of each thereof. Provided herein is a compound selected from Table 2, or a pharmaceutically acceptable salt thereof. Provided herein is a compound selected from Table 2.

Compound numbers and IUPAC names of compounds described herein are summarized in Table 1 and Table 2.

TABLE 1

| Compound Number | Structure | IUPAC name |
| --- | --- | --- |
| 1 | 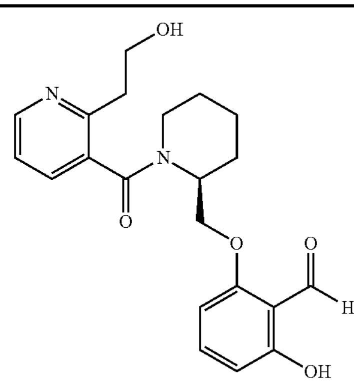 | (S)-2-hydroxy-6-((1-(2-(2-hydroxyethyl)nicotinoyl)-piperidin-2-yl)methoxy)-benzaldehyde |

TABLE 1-continued

| Compound Number | Structure | IUPAC name |
| --- | --- | --- |
| 2 | 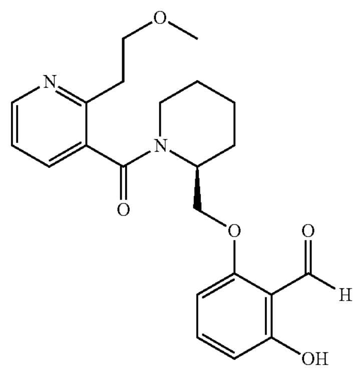 [SMILES: COCCc1ncccc1C(=O)N1CCCC[C@H]1COc1cccc(O)c1C=O] | (S)-2-hydroxy-6-((1-(2-(2-methoxyethyl)nicotinoyl)-piperidin-2-yl)methoxy)-benzaldehyde |
| 3 | 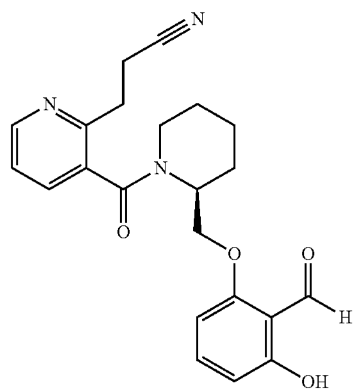 [SMILES: N#CCCc1ncccc1C(=O)N1CCCC[C@H]1COc1cccc(O)c1C=O] | (S)-3-(3-(2-((2-formyl-3-hydroxyphenoxy)methyl)-piperidine-1-carbonyl)-pyridin-2-yl)propanenitrile |
| 4 | 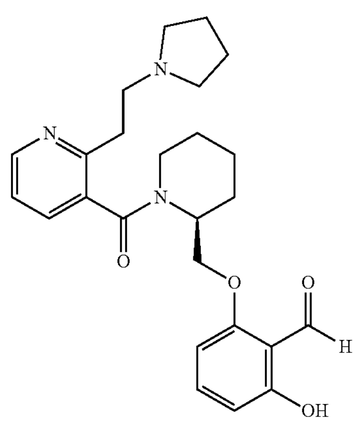 [SMILES: O=Cc1c(O)cccc1OC[C@@H]1CCCCN1C(=O)c1cccnc1CCN1CCCC1] | (S)-2-hydroxy-6-((1-(2-(2-(pyrrolidin-1-yl)ethyl)-nicotinoyl)piperidin-2-yl)methoxy)benzaldehyde |
| 5 | 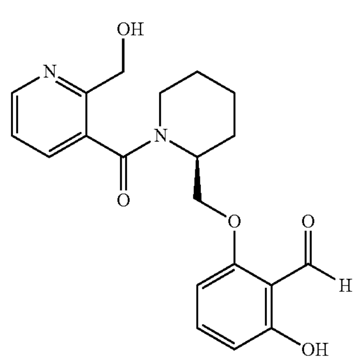 [SMILES: O=Cc1c(O)cccc1OC[C@@H]1CCCCN1C(=O)c1cccnc1CO] | (S)-2-hydroxy-6-((1-(2-(hydroxymethyl)benzoyl)-piperidin-2-yl)methoxy)-benzaldehyde |

TABLE 1-continued

| Compound Number | Structure | IUPAC name |
|---|---|---|
| 6 | 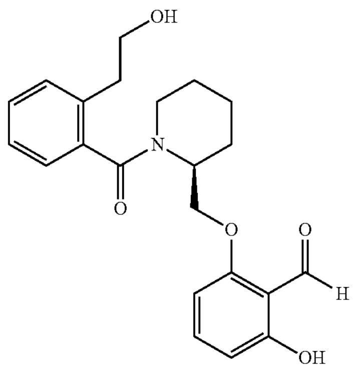 [SMILES: O=Cc1c(O)cccc1OC[C@@H]1CCCCN1C(=O)c1ccccc1CCO] | (S)-2-hydroxy-6-((1-(2-(2-hydroxyethyl)benzoyl)-piperidin-2-yl)methoxy)-benzaldehyde |
| 7 | 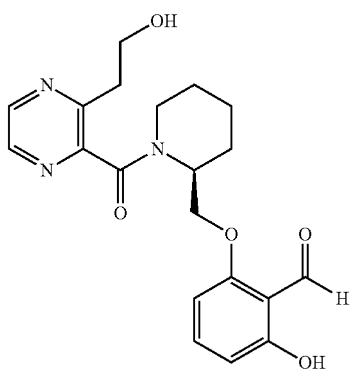 [SMILES: O=Cc1c(O)cccc1OC[C@@H]1CCCCN1C(=O)c1nccnc1CCO] | (S)-2-hydroxy-6-((1-(3-(2-hydroxyethyl)pyrazine-2-carbonyl)piperidin-2-yl)methoxy)benzaldehyde |
| 8 | 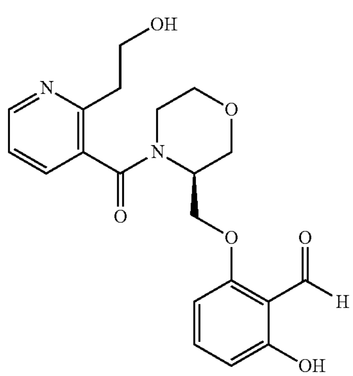 [SMILES: O=Cc1c(O)cccc1OC[C@@H]1COCCN1C(=O)c1cccnc1CCO] | (S)-2-hydroxy-6-((4-(2-(2-hydroxyethyl)-nicotinoyl)morpholin-3-yl)methoxy)benzaldehyde |
| 9 | 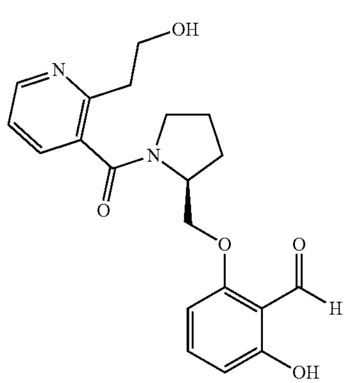 [SMILES: O=Cc1c(O)cccc1OC[C@@H]1CCCN1C(=O)c1cccnc1CCO] | (S)-2-hydroxy-6-((1-(2-(2-hydroxyethyl)-nicotinoyl)pyrrolidin-2-yl)methoxy)benzaldehyde |

TABLE 1-continued

| Compound Number | Structure | IUPAC name |
|---|---|---|
| 10 (Enantiomer 2) | 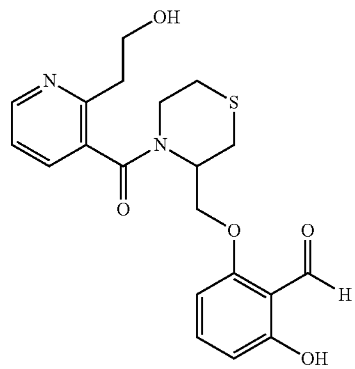 [SMILES: O=Cc1c(O)cccc1OCC1CSCCN1C(=O)c1cccnc1CCO] | 2-hydroxy-6-((4-(2-(2-hydroxyethyl)nicotinoyl)-thiomorpholin-3-yl)-methoxy)benzaldehyde |
| 10 (Enantiomer 1) | 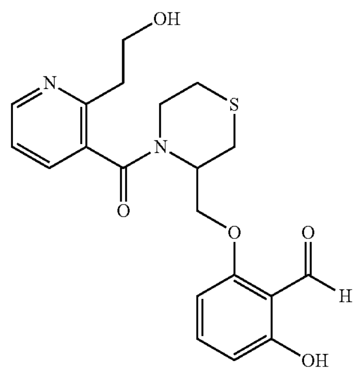 [SMILES: O=Cc1c(O)cccc1OCC1CSCCN1C(=O)c1cccnc1CCO] | 2-hydroxy-6-((4-(2-(2-hydroxyethyl)nicotinoyl)-thiomorpholin-3-yl)-methoxy)benzaldehyde |
| 11 | 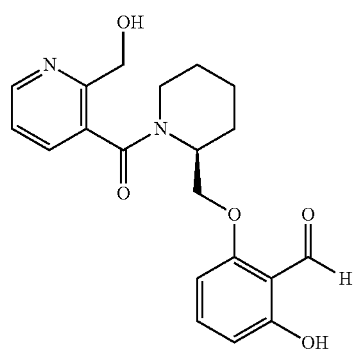 [SMILES: O=Cc1c(O)cccc1OC[C@@H]1CCCCN1C(=O)c1cccnc1CO] | (S)-2-hydroxy-6-((1-(2-(hydroxymethyl)nicotinoyl)-piperidin-2-yl)methoxy)-benzaldehyde |
| 12 | 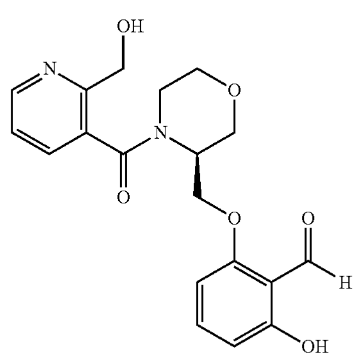 [SMILES: O=Cc1c(O)cccc1OC[C@@H]1COCCN1C(=O)c1cccnc1CO] | (S)-2-hydroxy-6-((4-(2-(hydroxymethyl)nicotinoyl)-morpholin-3-yl)methoxy)-benzaldehyde |

TABLE 1-continued

| Compound Number | Structure | IUPAC name |
| --- | --- | --- |
| 13 (Enantiomer 1) | 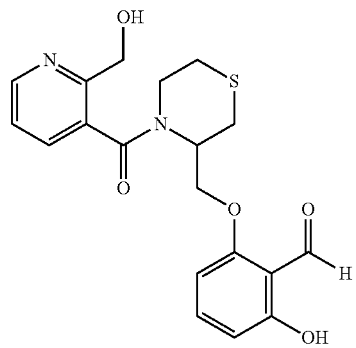 [SMILES: O=Cc1c(O)cccc1OCC1CSCCN1C(=O)c1cccnc1CO] | 2-hydroxy-6-((4-(2-(hydroxymethyl)nicotinoyl)-thiomorpholin-3-yl)-methoxy)benzaldehyde |
| 13 (Enantiomer 2) | 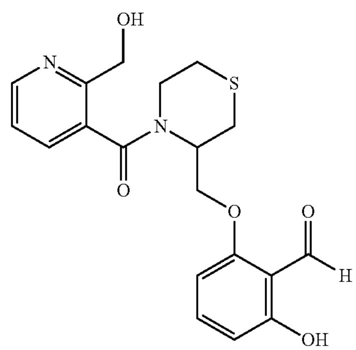 [SMILES: O=Cc1c(O)cccc1OCC1CSCCN1C(=O)c1cccnc1CO] | 2-hydroxy-6-((4-(2-(hydroxymethyl)nicotinoyl)-thiomorpholin-3-yl)-methoxy)benzaldehyde |
| 14 | 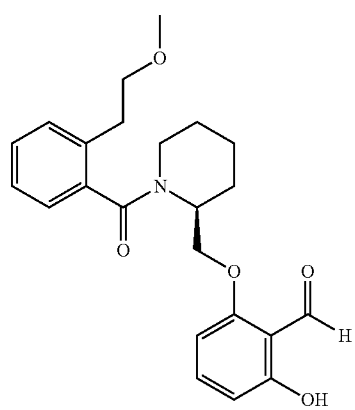 [SMILES: COCCc1ccccc1C(=O)N1CCCC[C@H]1COc1cccc(O)c1C=O] | (S)-2-hydroxy-6-((1-(2-(2-methoxyethyl)benzoyl)-piperidin-2-yl)methoxy)-benzaldehyde |
| 15 | 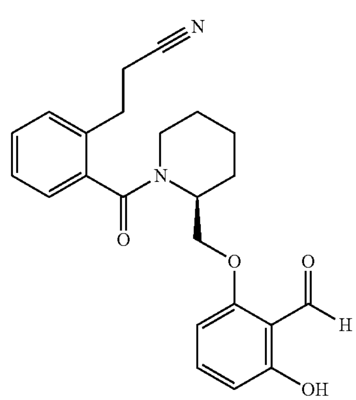 [SMILES: N#CCCc1ccccc1C(=O)N1CCCC[C@H]1COc1cccc(O)c1C=O] | (S)-3-(2-(2-((2-formyl-3-hydroxyphenoxy)methyl)-piperidine-1-carbonyl)-phenyl)propanenitrile |

TABLE 1-continued

| Compound Number | Structure | IUPAC name |
|---|---|---|
| 16 | 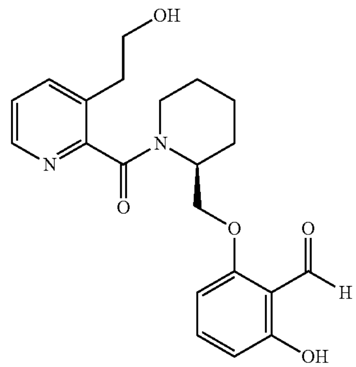 [SMILES: O=Cc1c(O)cccc1OC[C@@H]1CCCCN1C(=O)c1ncccc1CCO] | (S)-2-hydroxy-6-((1-(3-(2-hydroxyethyl)picolinoyl)-piperidin-2-yl)methoxy)-benzaldehyde |
| 17 | 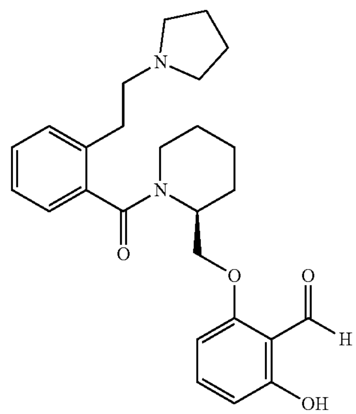 [SMILES: O=Cc1c(O)cccc1OC[C@@H]1CCCCN1C(=O)c1ccccc1CCN1CCCC1] | (S)-2-hydroxy-6-((1-(2-(2-(pyrrolidin-1-yl)ethyl)-benzoyl)piperidin-2-yl)-methoxy)benzaldehyde |
| 18 | 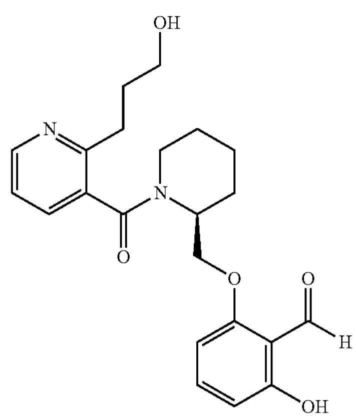 [SMILES: O=Cc1c(O)cccc1OC[C@@H]1CCCCN1C(=O)c1cccnc1CCCO] | (S)-2-hydroxy-6-((1-(2-(3-hydroxypropyl)nicotinoyl)-piperidin-2-yl)methoxy)-benzaldehyde |
| 19 | 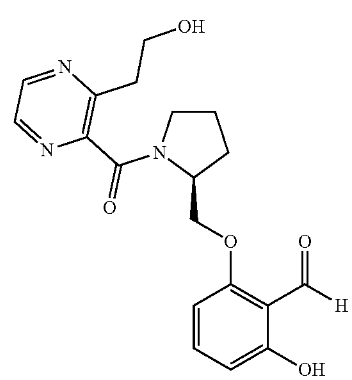 [SMILES: O=Cc1c(O)cccc1OC[C@@H]1CCCN1C(=O)c1nccnc1CCO] | (S)-2-hydroxy-6-((1-(3-(2-hydroxyethyl)pyrazine-2-carbonyl)pyrrolidin-2-yl)-methoxy)benzaldehyde |

TABLE 1-continued
| Compound Number | Structure | IUPAC name |
|---|---|---|
| 20 | 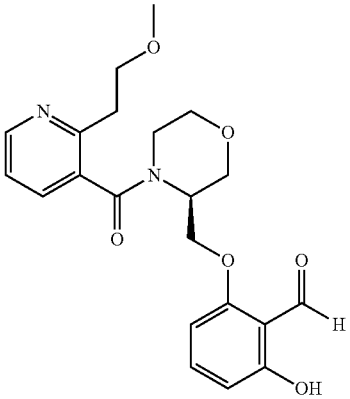 [SMILES: COCCc1ncccc1C(=O)N1CCOC[C@H]1COc1cccc(O)c1C=O] | (S)-2-hydroxy-6-((4-(2-(2-methoxyethyl)nicotinoyl)-morpholin-3-yl)methoxy)-benzaldehyde |
| 21 | 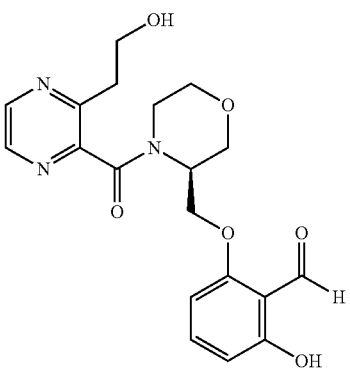 [SMILES: O=Cc1c(O)cccc1OC[C@@H]1COCCN1C(=O)c1nccnc1CCO] | (S)-2-hydroxy-6-((4-(3-(2-hydroxyethyl)pyrazine-2-carbonyl)morpholin-3-yl)methoxy)benzaldehyde |
| 22 | 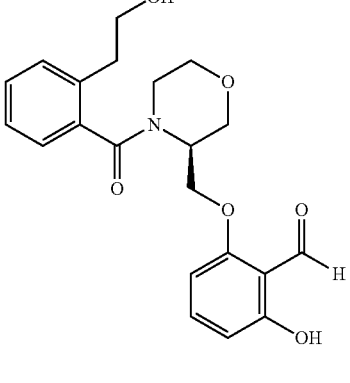 | (S)-2-hydroxy-6-((4-(2-(2-hydroxyethyl)benzoyl)-morpholin-3-yl)methoxy)-benzaldehyde |
| 23 | 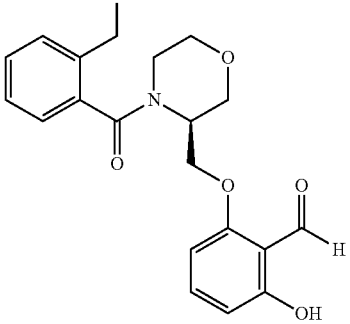 | (S)-2-hydroxy-6-((4-(2-(hydroxymethyl)benzoyl)-morpholin-3-yl)methoxy)-benzaldehyde |

TABLE 1-continued

| Compound Number | Structure | IUPAC name |
|---|---|---|
| 24 | 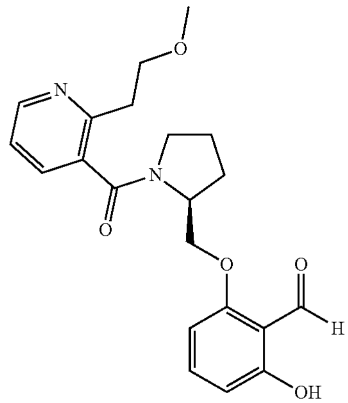 [SMILES: COCCc1ncccc1C(=O)N1CCC[C@H]1COc1cccc(O)c1C=O] | (S)-2-hydroxy-6-((1-(2-(2-methoxyethyl)nicotinoyl)-pyrrolidin-2-yl)methoxy)-benzaldehyde |
| 25 | 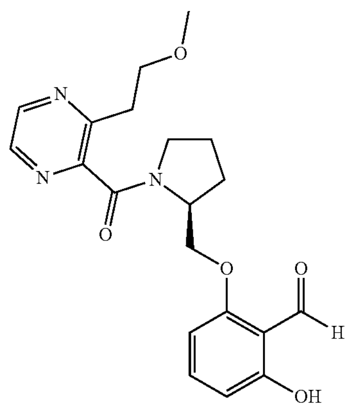 [SMILES: COCCc1nccnc1C(=O)N1CCC[C@H]1COc1cccc(O)c1C=O] | (S)-2-hydroxy-6-((1-(3-(2-methoxyethyl)pyrazine-2-carbonyl)pyrrolidin-2-yl)-methoxy)benzaldehyde |
| 26 | 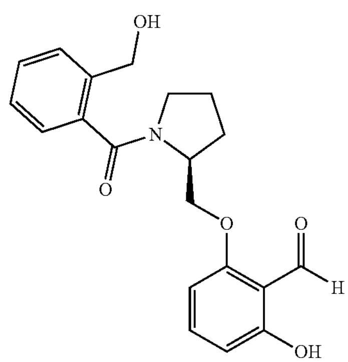 [SMILES: O=Cc1c(O)cccc1OC[C@@H]1CCCN1C(=O)c1ccccc1CO] | (S)-2-hydroxy-6-((1-(2-(hydroxymethyl)benzoyl)-pyrrolidin-2-yl)methoxy)-benzaldehyde |
| 27 | 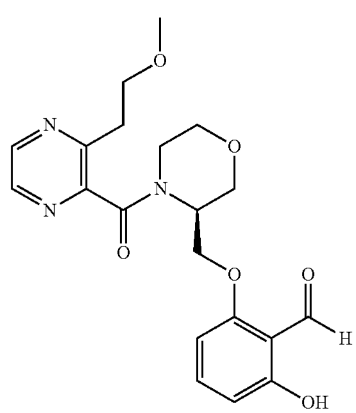 [SMILES: COCCc1nccnc1C(=O)N1CCOC[C@H]1COc1cccc(O)c1C=O] | (S)-2-hydroxy-6-((4-(3-(2-methoxyethyl)pyrazine-2-carbonyl)morpholin-3-yl)-methoxy)benzaldehyde |

TABLE 1-continued

| Compound Number | Structure | IUPAC name |
|---|---|---|
| 28 | 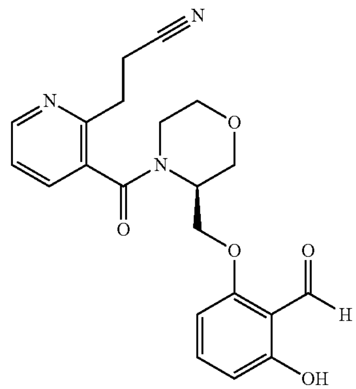 [SMILES: N#CCCc1ncccc1C(=O)N1CCOC[C@H]1COc1cccc(O)c1C=O] | (S)-3-(3-(3-((2-formyl-3-hydroxyphenoxy)methyl)-morpholine-4-carbonyl)-pyridin-2-yl)propanenitrile |
| 29 | 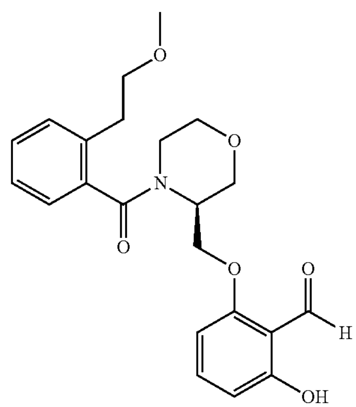 [SMILES: COCCc1ccccc1C(=O)N1CCOC[C@H]1COc1cccc(O)c1C=O] | (S)-2-hydroxy-6-((4-(2-(2-methoxyethyl)benzoyl)-morpholin-3-yl)methoxy)-benzaldehyde |
| 30 | 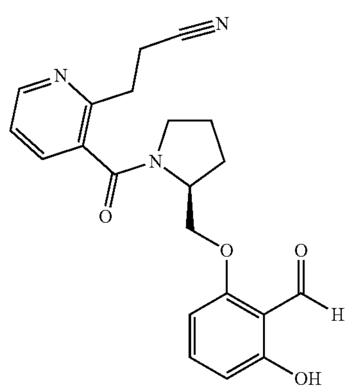 [SMILES: N#CCCc1ncccc1C(=O)N1CCC[C@H]1COc1cccc(O)c1C=O] | (S)-3-(3-(2-((2-formyl-3-hydroxyphenoxy)methyl)-pyrrolidine-1-carbonyl)-pyridin-2-yl)propanenitrile |
| 31 | 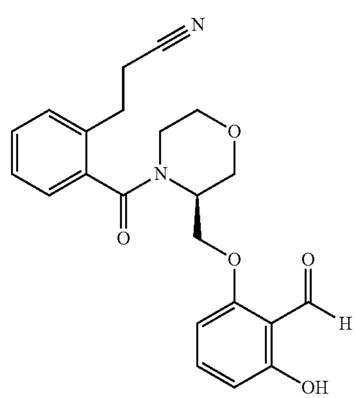 [SMILES: N#CCCc1ccccc1C(=O)N1CCOC[C@H]1COc1cccc(O)c1C=O] | (S)-3-(2-(3-((2-formyl-3-hydroxyphenoxy)methyl)-morpholine-4-carbonyl)-(phenyl)propanenitrile |

TABLE 1-continued

| Compound Number | Structure | IUPAC name |
|---|---|---|
| 32 | 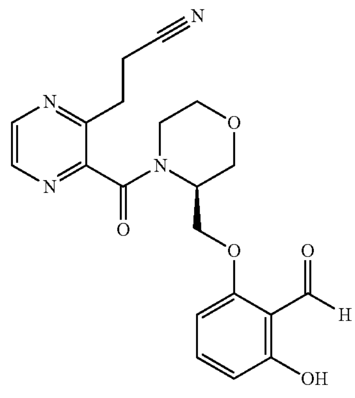 [SMILES: N#CCCc1nccnc1C(=O)N1CCOC[C@H]1COc1cccc(O)c1C=O] | (S)-3-(3-(3-((2-formyl-3-hydroxyphenoxy)methyl)-morpholine-4-carbonyl)-pyrazin-2-yl)propanenitrile |
| 33 | 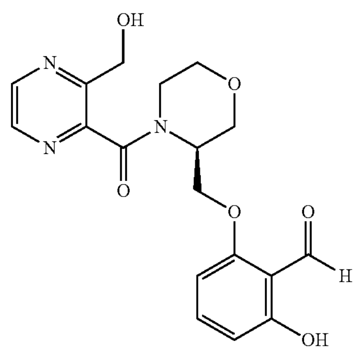 [SMILES: O=Cc1c(O)cccc1OC[C@@H]1COCCN1C(=O)c1nccnc1CO] | (S)-2-hydroxy-6-((4-(3-(hydroxymethyl)pyrazine-2-carbonyl)morpholin-3-yl)methoxy)benzaldehyde |
| 34 | 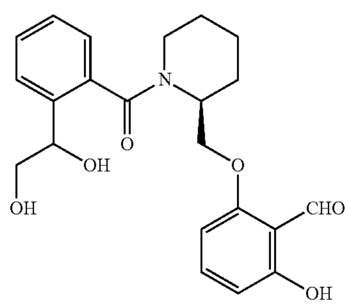 [SMILES: O=Cc1c(O)cccc1OC[C@@H]1CCCCN1C(=O)c1ccccc1C(O)CO] | 2-(((2S)-1-(2-(1,2-dihydroxyethyl)benzoyl)-piperidin-2-yl)methoxy)-6-hydroxybenzaldehyde |
| 34 (Diastereomer 1) | 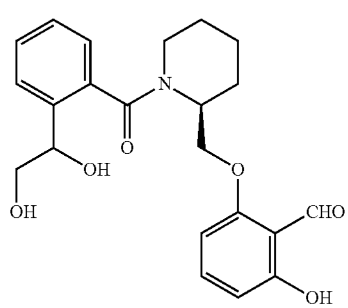 [SMILES: O=Cc1c(O)cccc1OC[C@@H]1CCCCN1C(=O)c1ccccc1C(O)CO] | 2-(((2S)-1-(2-(1,2-dihydroxyethyl)benzoyl)-piperidin-2-yl)methoxy)-6-hydroxybenzaldehyde |

TABLE 1-continued

| Compound Number | Structure | IUPAC name |
|---|---|---|
| 34 (Diastereomer 2) | 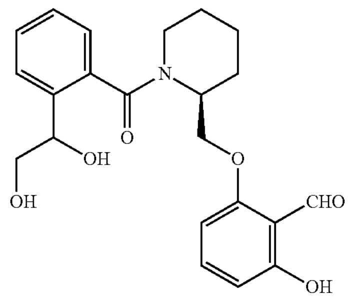 [SMILES: O=Cc1c(O)cccc1OC[C@@H]1CCCCN1C(=O)c1ccccc1C(O)CO] | 2-(((2S)-1-(2-(1,2-dihydroxyethyl)benzoyl)-piperidin-2-yl)methoxy)-6-hydroxybenzaldehyde |
| 35 (Diastereomer 1) | 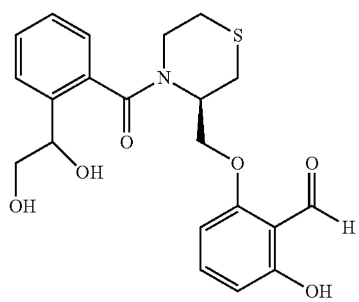 [SMILES: O=Cc1c(O)cccc1OC[C@@H]1CSCCN1C(=O)c1ccccc1C(O)CO] | 2-(((3R)-4-(2-(1,2-dihydroxyethyl)benzoyl)-thiomorpholin-3-yl)-methoxy)-6-hydroxy-benzaldehyde |
| 35 (Diastereomer 2) | 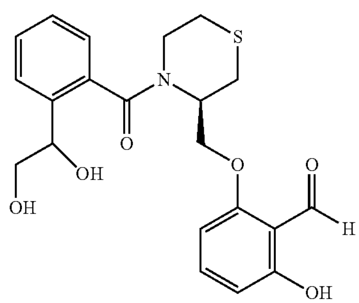 [SMILES: O=Cc1c(O)cccc1OC[C@@H]1CSCCN1C(=O)c1ccccc1C(O)CO] | 2-(((3R)-4-(2-(1,2-dihydroxyethyl)benzoyl)-thiomorpholin-3-yl)-methoxy)-6-hydroxy-benzaldehyde |
| 36 | 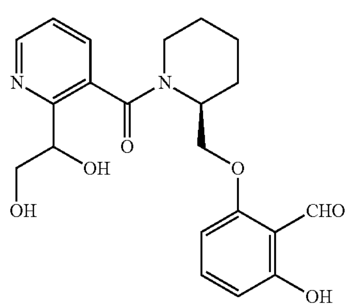 [SMILES: O=Cc1c(O)cccc1OC[C@@H]1CCCCN1C(=O)c1cccnc1C(O)CO] | 2-{[(2S)-1-[2-(1,2-dihydroxyethyl)pyridine-3-carbonyl]piperidin-2-yl]methoxy}-6-hydroxy-benzaldehyde |
| 37 | 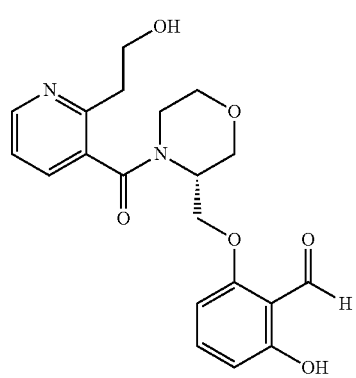 [SMILES: O=Cc1c(O)cccc1OC[C@H]1COCCN1C(=O)c1cccnc1CCO] | (R)-2-hydroxy-6-((4-(2-(2-hydroxyethyl)-nicotinoyl)morpholin-3-yl)methoxy)benzaldehyde |

TABLE 1-continued

| Compound Number | Structure | IUPAC name |
| --- | --- | --- |
| 38 | 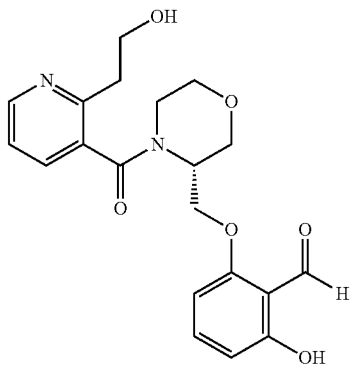 [SMILES: O=Cc1c(O)cccc1OC[C@H]1COCCN1C(=O)c1cccnc1CCO] | (R)-2-hydroxy-6-((1-(2-(2-hydroxyethyl)-nicotinoyl)piperidin-2-yl)methoxy)benzaldehyde |
| 39 | 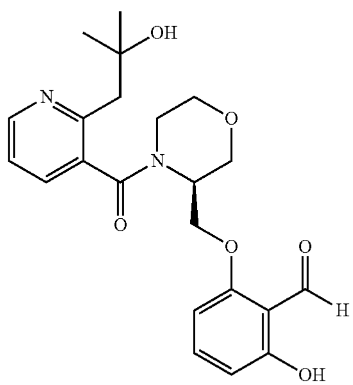 [SMILES: CC(C)(O)Cc1ncccc1C(=O)N1CCOC[C@H]1COc1cccc(O)c1C=O] | (S)-2-hydroxy-6-((4-(2-(2-hydroxy-2-methylpropyl)-nicotinoyl)morpholin-3-yl)methoxy)benzaldehyde |
| 40 | 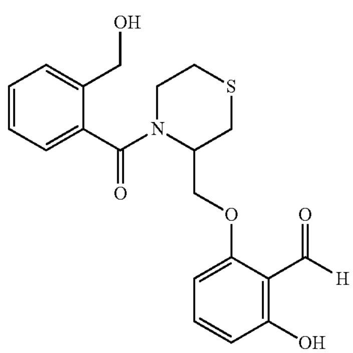 [SMILES: O=Cc1c(O)cccc1OCC1CSCCN1C(=O)c1ccccc1CO] | 2-hydroxy-6-((4-(2-(hydroxymethyl)benzoyl)-thiomorpholin-3-yl)-methoxy)benzaldehyde |
| 40 (Enantiomer 1) | 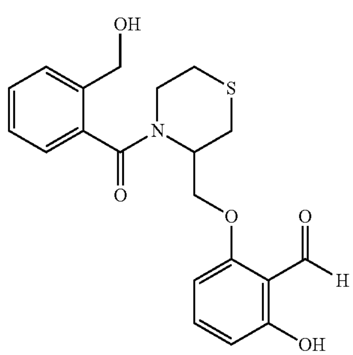 [SMILES: O=Cc1c(O)cccc1OCC1CSCCN1C(=O)c1ccccc1CO] | 2-hydroxy-6-((4-(2-(hydroxymethyl)benzoyl)-thiomorpholin-3-yl)-methoxy)benzaldehyde |

TABLE 1-continued

| Compound Number | Structure | IUPAC name |
|---|---|---|
| 40 (Enantiomer 2) | 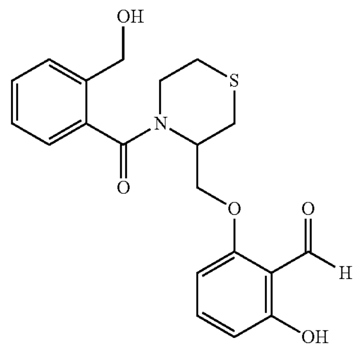 [SMILES: O=Cc1c(O)cccc1OCC1CSCCN1C(=O)c1ccccc1CO] | 2-hydroxy-6-((4-(2-(hydroxymethyl)benzoyl)-thiomorpholin-3-yl)-methoxy)benzaldehyde |
| 41 (Diastereomer 1) | 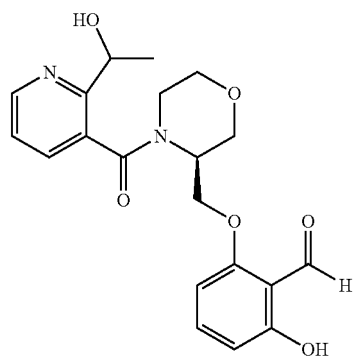 [SMILES: CC(O)c1ncccc1C(=O)N1CCOC[C@H]1COc1cccc(O)c1C=O] | 2-hydroxy-6-(((3S)-4-(2-(1-hydroxyethyl)-nicotinoyl)morpholin-3-yl)methoxy)benzaldehyde |
| 41 (Diastereomer 2) | 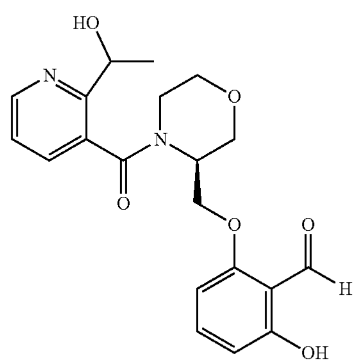 [SMILES: CC(O)c1ncccc1C(=O)N1CCOC[C@H]1COc1cccc(O)c1C=O] | 2-hydroxy-6-(((3S)-4-(2-(1-hydroxyethyl)-nicotinoyl)morpholin-3-yl)methoxy)benzaldehyde |
| 42 (Diastereomer 1) | 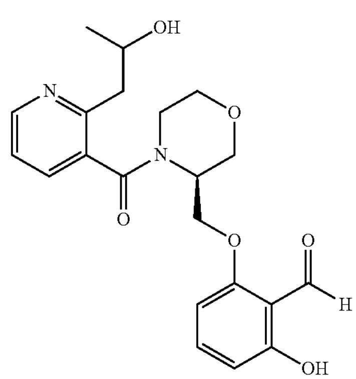 [SMILES: CC(O)Cc1ncccc1C(=O)N1CCOC[C@H]1COc1cccc(O)c1C=O] | 2-hydroxy-6-(((3S)-4-(2-(2-hydroxypropyl)-nicotinoyl)morpholin-3-yl)methoxy)benzaldehyde |

TABLE 1-continued

| Compound Number | Structure | IUPAC name |
|---|---|---|
| 42 (Diastereomer 2) | 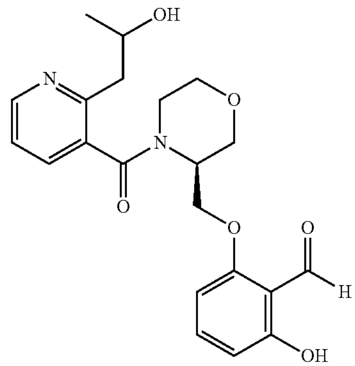 [SMILES: CC(O)Cc1ncccc1C(=O)N1CCOC[C@H]1COc1cccc(O)c1C=O] | 2-hydroxy-6-(((3S)-4-(2-(2-hydroxypropyl)-nicotinoyl)morpholin-3-yl)methoxy)benzaldehyde |
| 43 (Diastereomer 1) | 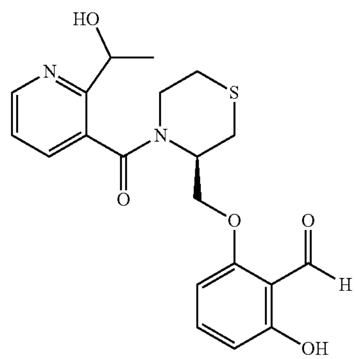 | 2-hydroxy-6-(((3R)-4-(2-(1-hydroxyethyl)nicotinoyl)-thiomorpholin-3-yl)-methoxy)benzaldehyde |
| 43 (Diastereomer 2) | 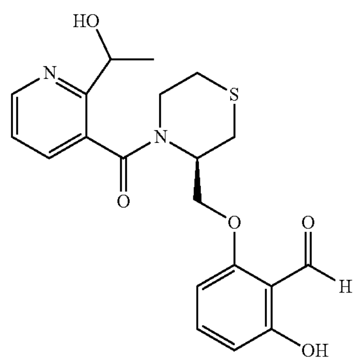 | 2-hydroxy-6-(((3R)-4-(2-(1-hydroxyethyl)nicotinoyl)thiomorpholin-3-yl)-methoxy)benzaldehyde |
| 44 (Diastereomer 1) | 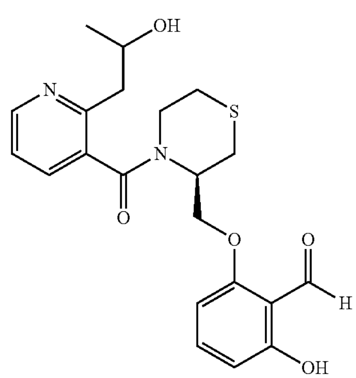 [SMILES: CC(O)Cc1ncccc1C(=O)N1CCSC[C@H]1COc1cccc(O)c1C=O] | 2-hydroxy-6-(((3R)-4-(2-(2-hydroxypropyl)nicotinoyl)thiomorpholin-3-yl)-methoxy)benzaldehyde |

TABLE 1-continued
| Compound Number | Structure | IUPAC name |
|---|---|---|
| 44 (Diastereomer 2) | 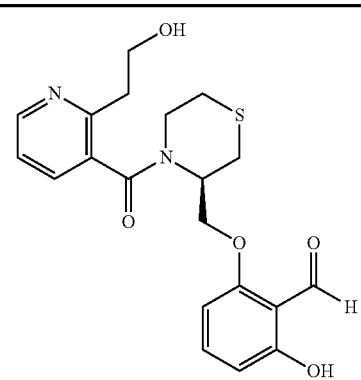 | 2-hydroxy-6-(((3R)-4-(2-(2-hydroxypropyl)nicotin-oyl)thiomorpholin-3-yl)-methoxy)benzaldehyde |
TABLE 2
| Structure |
|---|
| 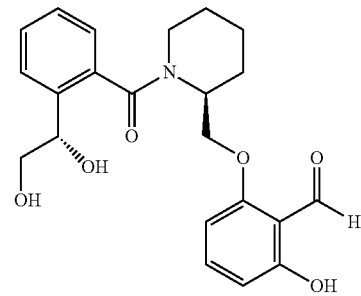 [SMILES: O=Cc1c(O)cccc1OC[C@@H]1CCCCN1C(=O)c1ccccc1[C@H](O)CO] |
| 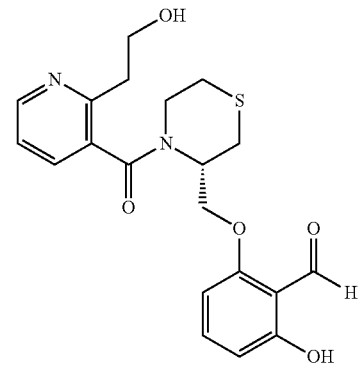 |
| 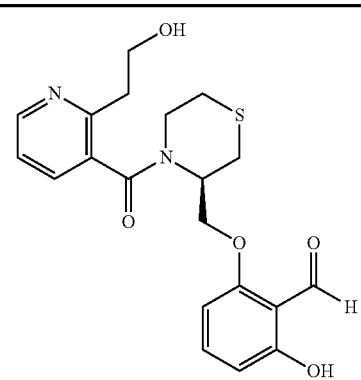 |
TABLE 2-continued
| Structure |
|---|
| 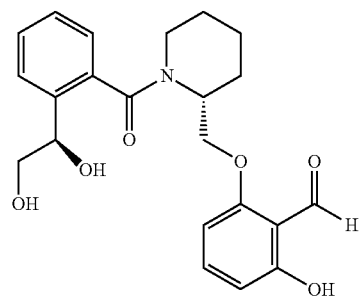 [SMILES: O=Cc1c(O)cccc1OC[C@H]1CCCCN1C(=O)c1ccccc1[C@@H](O)CO] |
| 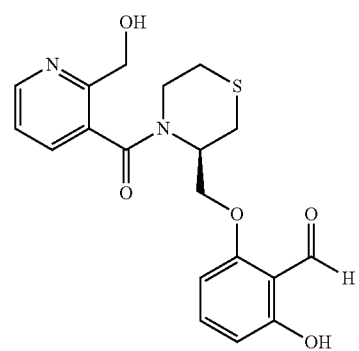 [SMILES: O=Cc1c(O)cccc1OC[C@@H]1CSCCN1C(=O)c1cccnc1CO] |
| 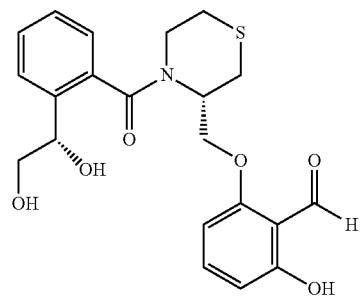 [SMILES: O=Cc1c(O)cccc1OC[C@H]1CSCCN1C(=O)c1ccccc1[C@H](O)CO] |

TABLE 2-continued
Structure
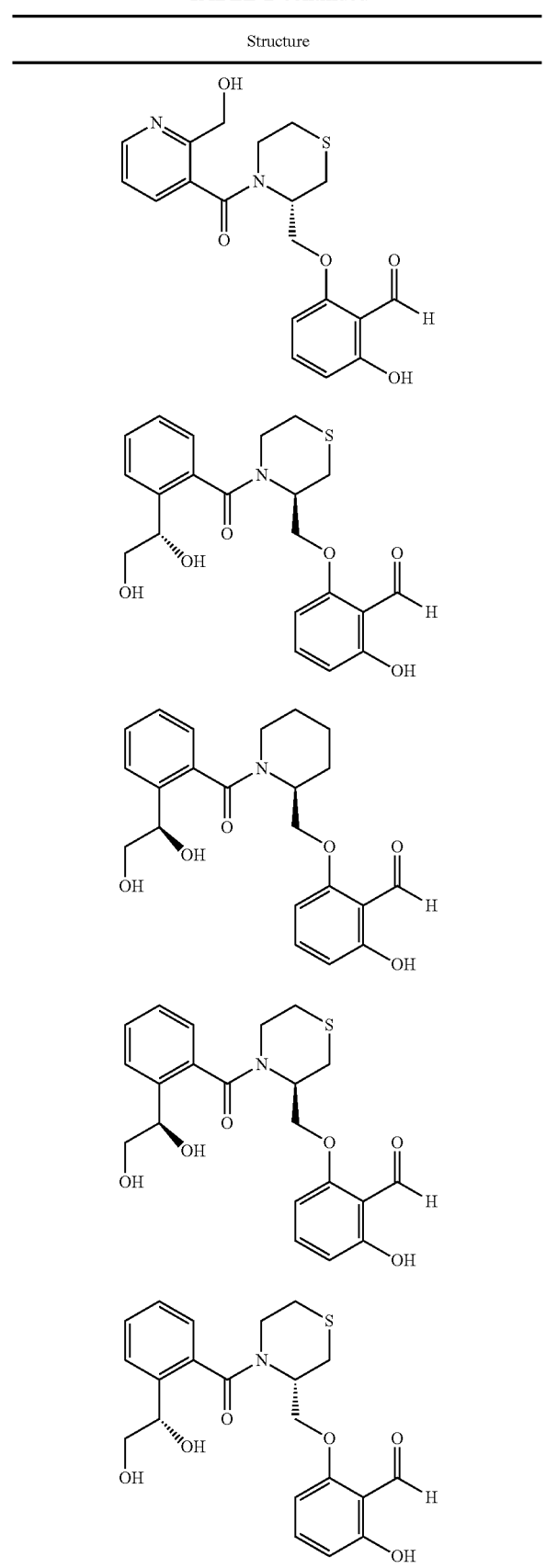
TABLE 2-continued
Structure
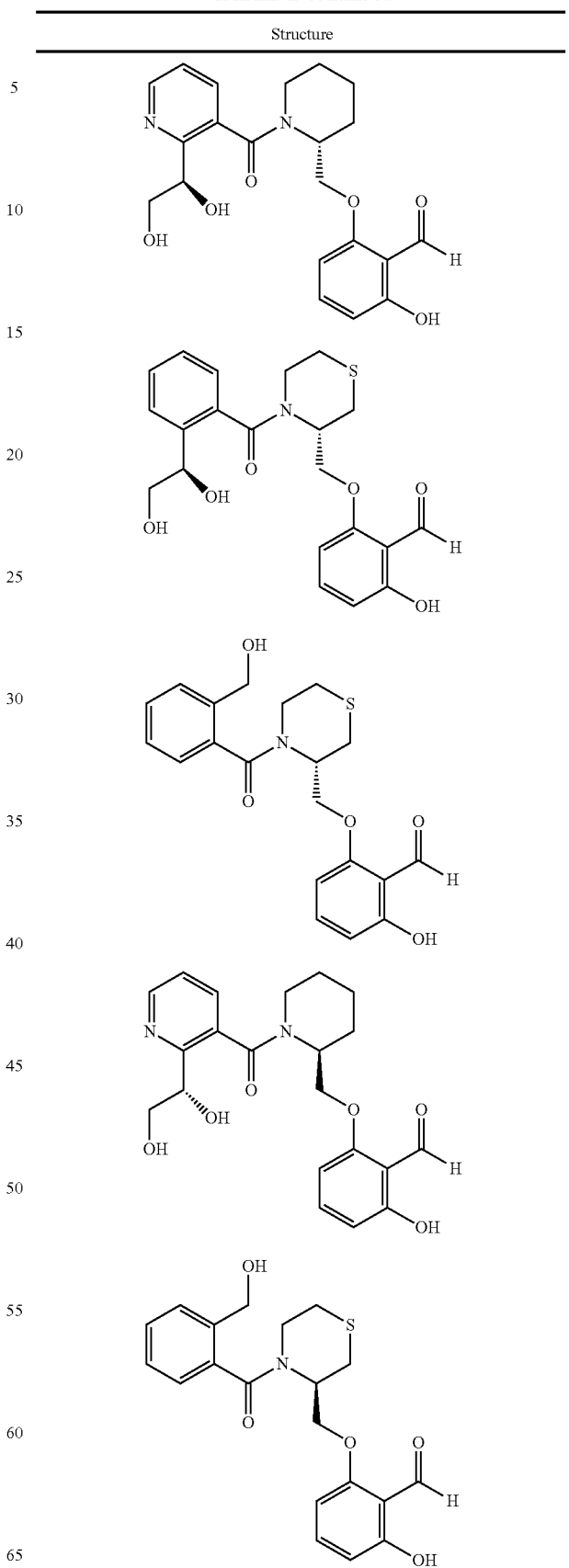

TABLE 2-continued
| Structure |
|---|
| 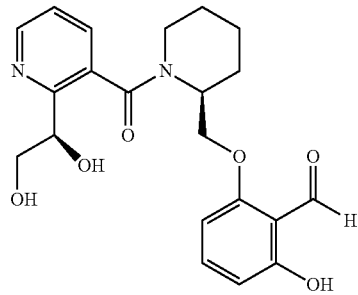 [SMILES: O=Cc1c(O)cccc1OC[C@@H]1CCCCN1C(=O)c1cccnc1[C@@H](O)CO] |
| 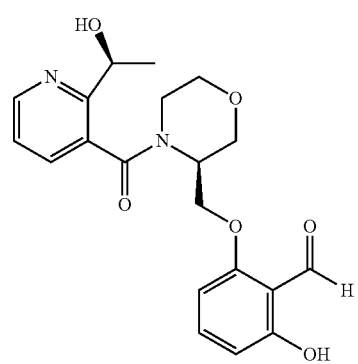 [SMILES: C[C@H](O)c1ncccc1C(=O)N1CCOC[C@H]1COc1cccc(O)c1C=O] |
| 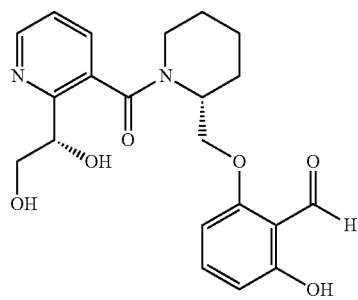 [SMILES: O=Cc1c(O)cccc1OC[C@H]1CCCCN1C(=O)c1cccnc1[C@H](O)CO] |
| 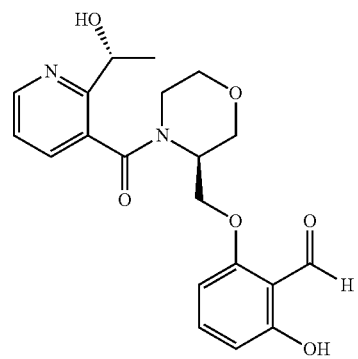 |
TABLE 2-continued
| Structure |
|---|
| 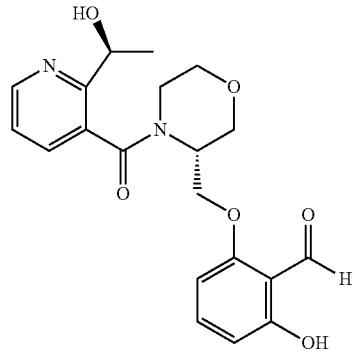 [SMILES: C[C@H](O)c1ncccc1C(=O)N1CCOC[C@@H]1COc1cccc(O)c1C=O] |
| 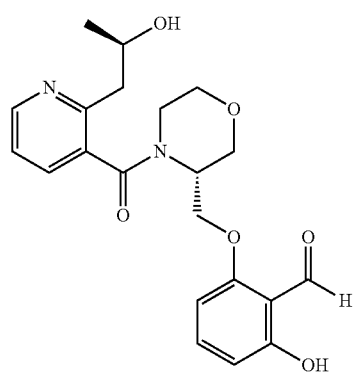 [SMILES: C[C@@H](O)Cc1ncccc1C(=O)N1CCOC[C@@H]1COc1cccc(O)c1C=O] |
| 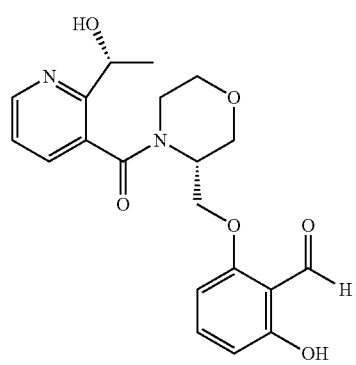 |
| 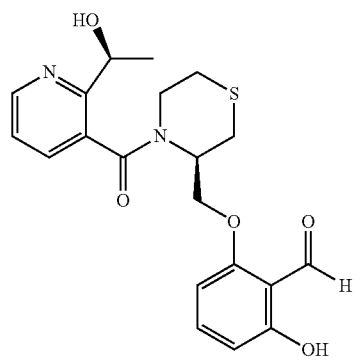 [SMILES: C[C@H](O)c1ncccc1C(=O)N1CCSC[C@H]1COc1cccc(O)c1C=O] |

TABLE 2-continued
| Structure |
|---|
| 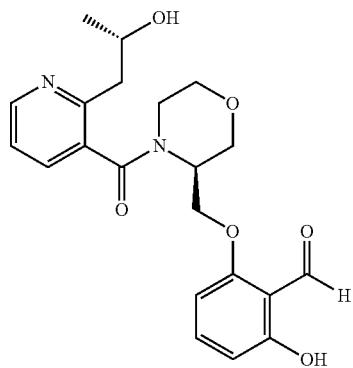 [SMILES: C[C@H](O)Cc1ncccc1C(=O)N1CCOC[C@H]1COc1cccc(O)c1C=O] |
| 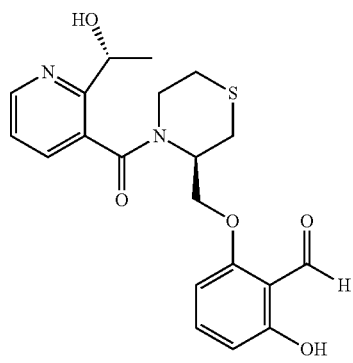 |
| 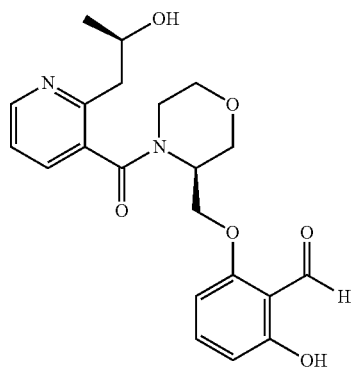 [SMILES: C[C@@H](O)Cc1ncccc1C(=O)N1CCOC[C@H]1COc1cccc(O)c1C=O] |
| 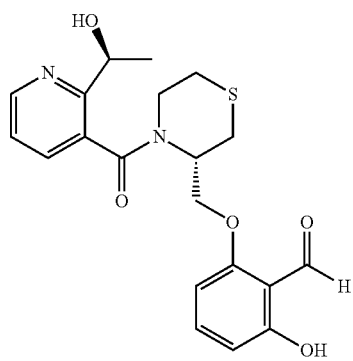 [SMILES: C[C@H](O)c1ncccc1C(=O)N1CCSC[C@@H]1COc1cccc(O)c1C=O] |
TABLE 2-continued
| Structure |
|---|
| 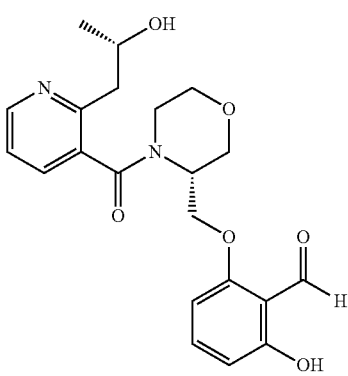 [SMILES: C[C@H](O)Cc1ncccc1C(=O)N1CCOC[C@@H]1COc1cccc(O)c1C=O] |
| 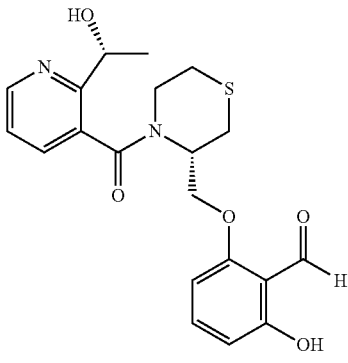 |
| 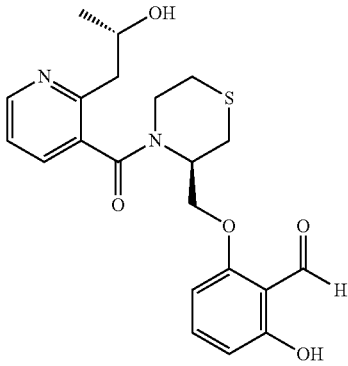 [SMILES: C[C@H](O)Cc1ncccc1C(=O)N1CCSC[C@H]1COc1cccc(O)c1C=O] |
| 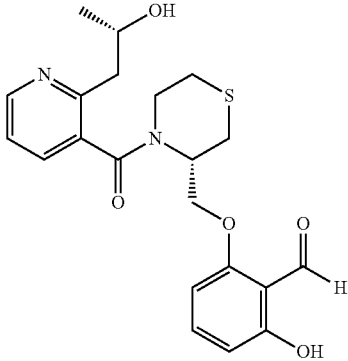 [SMILES: C[C@H](O)Cc1ncccc1C(=O)N1CCSC[C@@H]1COc1cccc(O)c1C=O] |

TABLE 2-continued

Structure

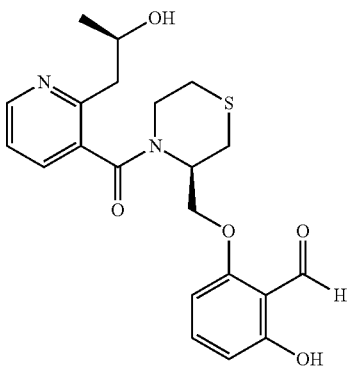

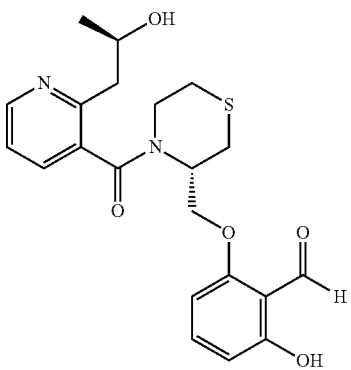

Provided herein is a compound selected from Table 6, or an isotopically enriched analog, stereoisomer, mixture of stereoisomers, or prodrug thereof, or a pharmaceutically acceptable salt of each thereof, and excluding Reference Compound A, B, and C. Provided herein is a compound selected from Table 6, or a pharmaceutically acceptable salt thereof, and excluding Reference Compound A, B, and C. Provided herein is a compound selected from Table 6 and excluding Reference Compound A, B, and C.

Provided herein is a compound selected from Table 7, or an isotopically enriched analog, stereoisomer, mixture of stereoisomers, or prodrug thereof, or a pharmaceutically acceptable salt of each thereof, and excluding Reference Compound A and B. Provided herein is a compound selected from Table 7, or a pharmaceutically acceptable salt thereof, and excluding Reference Compound A and B. Provided herein is a compound selected from Table 7 and excluding Reference Compound A and B.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease.

The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals.

Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The term "hemoglobin" as used herein refers to any hemoglobin protein, including normal hemoglobin (HbA) and abnormal hemoglobin, such as sickle hemoglobin (HbS).

The term "sickle cell disease" refers to diseases mediated by sickle hemoglobin (HbS) that results from a single point mutation in the hemoglobin (Hb). Sickle cell diseases include sickle cell anemia (HbSS), hemoglobin SC disease (HbSC), hemoglobin S beta-plus-thalassemia (HbS/β+) and hemoglobin S beta-zero-thalassemia (HbS/β0).

Provided herein are methods for treating sickle cell disease (SCD). Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels. It is contemplated that an approach to therapy would be to maintain the HbS in the oxygenated state, as polymerization occurs only in the deoxygenated state under hypoxic conditions.

In some embodiments, provided herein is a method for increasing oxygen affinity of hemoglobin S in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for increasing oxygen affinity of hemoglobin S in a subject in need thereof, comprising administering to the subject a compound as described herein or a pharmaceutical composition as described herein.

In some embodiments, provided herein is a method for treating a disorder mediated by hemoglobin in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for treating a disorder mediated by hemoglobin in a subject in need thereof, comprising administering to the subject a compound as described herein or a pharmaceutical composition as described herein. In some embodiments, the disorder is a hemoglobinopathy.

In some embodiments, the hemoglobin is sickle hemoglobin.

In some embodiments, provided herein is a method for treating sickle cell disease in a subject in need thereof, comprising administering to the subject a compound as described herein or an isotopically enriched analog, stereoisomer, mixture of stereoisomers, or prodrug thereof, or a pharmaceutically acceptable salt of each thereof, or a pharmaceutical composition as described herein. In some embodiments, provided herein is a method for treating sickle cell disease in a subject in need thereof, comprising administering to the subject a compound as described herein or a pharmaceutical composition as described herein.

Pharmaceutical Compositions and Modes of Administration

Compounds provided herein are usually administered in the form of pharmaceutical compositions. Thus, provided herein are also pharmaceutical compositions that comprise one or more of the compounds described herein or an isotopically enriched analog, stereoisomer, mixture of stereoisomers, or prodrug thereof, or a pharmaceutically acceptable salt of each thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or an isotopically enriched analog, stereoisomer, mixture of stereoisomers, or prodrug thereof, or a pharmaceutically acceptable salt of each thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or an isotopically enriched analog, stereoisomer, mixture of stereoisomers, or prodrug thereof, or a pharmaceutically acceptable salt of each thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or an isotopically enriched analog, stereoisomer, mixture of stereoisomers, or prodrug thereof, or a pharmaceutically acceptable salt of each thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

In some embodiments, a compound of formula I can be synthesized by exemplary synthetic pathways as shown in Schemes A and B.

In some embodiments of Scheme A, $R^2$ can be hydroxyl or chloro; $R^1$ can be mono-hydroxy-$(C_{1-4}$ alkyl), $CH_2CH_2OCH_3$, —$CH_2CH_2CN$, or

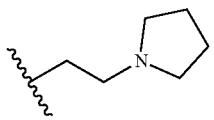 [SMILES: *CCN1CCCC1]

and X, Y, and Z are as described herein. As shown in Scheme A, compound A1 and compound A2 are coupled first utilizing standard coupling conditions to give compound A3, which can be then assembled onto 2,6-dihydroxybenzaldehyde A4 to produce compound of formula I. In some embodiments, when $R^1$ is mono-hydroxy-$(C_{1-4}$ alkyl) of a compound of formula I, the hydroxy group of the $R^1$ moiety of A1 includes a hydroxy protecting group known in the art; the protecting group may be subsequently removed after coupling A3 to A4 utilizing standard procedures, thereby producing a compound of formula I.

Scheme A

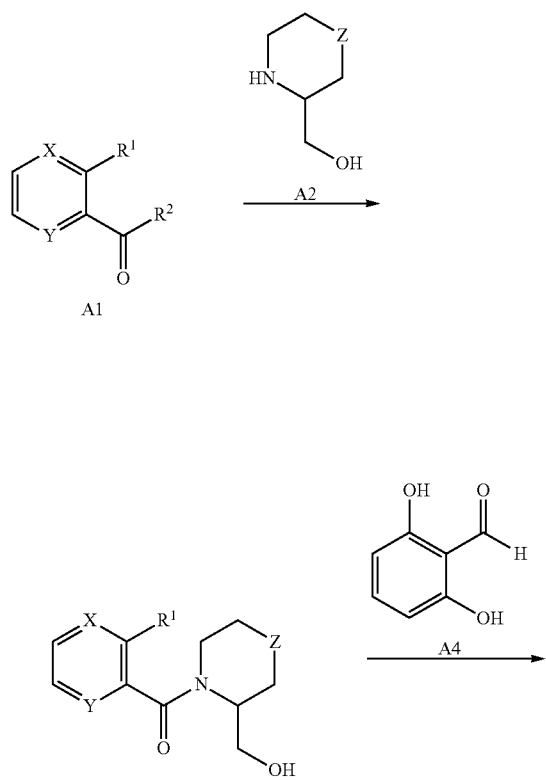

Scheme B

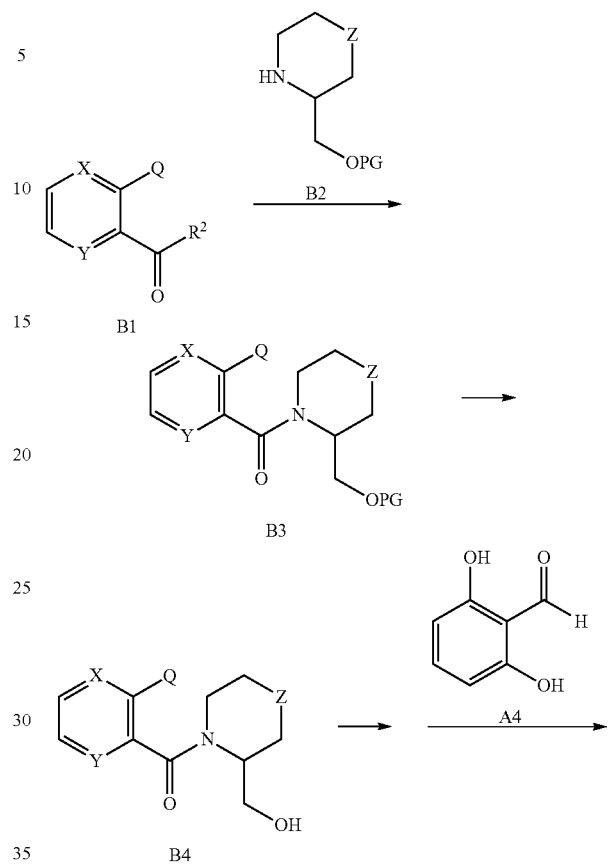

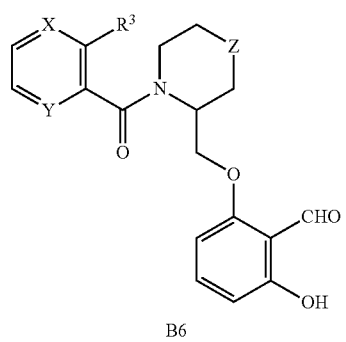

In some embodiments of Scheme B, $R^3$ can be a $C_{2-4}$alkene; $R^2$ can be hydroxyl or chloro; $R^1$ can be di-hydroxy-($C_{2-4}$ alkyl); Q is a halo; PG is a hydroxy protecting group; and X, Y, and Z are as described herein. As shown in Scheme B, compound B1 and compound B2 are coupled first utilizing standard coupling conditions to give compound B3. Standard deprotection procedures provides compound B4, which can be then assembled onto 2,6-dihydroxybenzaldehyde A4 to produce compound B5. Introduction of the alkene (e.g. via Stille coupling) provides compound B6, which can then be converted to a compound of formula I via dihydroxylation procedures known in the art.

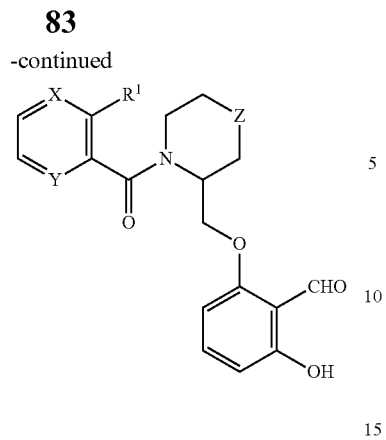

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

SYNTHETIC EXAMPLES

Example 1. Synthesis of (S)-2-hydroxy-6-((1-(2-(2-hydroxyethyl)nicotinoyl)piperidin-2-yl)methoxy)benzaldehyde, Compound 1

Compound 1 was synthesized according to Scheme 1A.

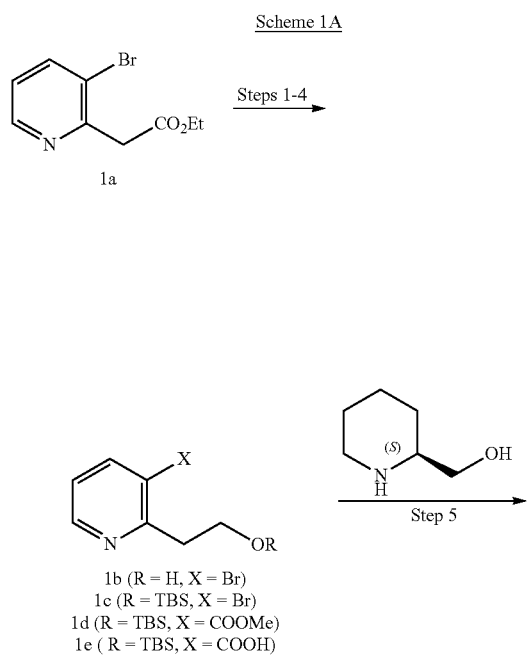

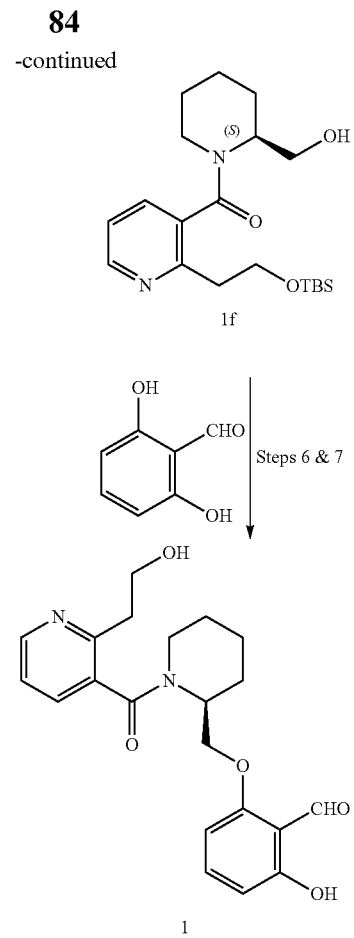

Step 1: Synthesis of 2-(3-bromopyridin-2-yl)ethan-1-ol (1b)

Into a 100-mL 3-necked round-bottom flask, was placed a solution of ethyl 2-(3-bromopyridin-2-yl)acetate (1a) (4 g, 16.39 mmol, 1 equiv) in tetrahydrofuran ("THF") (40 mL). This was followed by the addition of diisobutylaluminum hydride ("DIBAL-H") in THF (16 mL, 32.00 mmol, 1.95 equiv) dropwise with stirring at −78° C. The resulting mixture was allowed to warm to rt and was stirred for additional 3 hr at 25° C. The reaction was then quenched by the addition of 50 mL of saturated NH$_4$Cl. The resulting solution was extracted with 3×100 mL of ethyl acetate and the organic layers combined, washed with 2×100 mL of brine The separated organic layer was dried over Na$_2$SO$_4$, active carbon, filtered and then concentrated. The residue was applied onto a silica gel column and eluted with ethyl acetate/petroleum ether (1:3) to provide the title compound. LCMS (ES) [M+1]$^+$ m/z 202.0.

Step 2: Synthesis of 3-bromo-2-(2-((tert-butyldimethylsilyl)oxy)ethyl)pyridine (1c)

Into a 100-mL round-bottom flask, was placed a solution of 2-(3-bromopyridin-2-yl)ethan-1-ol (1.9 g, 9.40 mmol, 1 equiv) in dimethylformamide ("DMF") (20 mL), 1H-imidazole (1.3 g, 18.81 mmol, 2 equiv), 4-dimethylaminopyridine ("DMAP") (0.1 g, 0.94 mmol, 0.1 equiv), tert-butyl(chloro)dimethylsilane (2.8 g, 18.81 mmol, 2 equiv). The resulting solution was heated to 50° C. and stirred for 2 hr. The reaction mixture was cooled and extracted with 2×50 mL of ethyl acetate. The combined organic layers was washed with 2×50 mL of brine, dried over $Na_2SO_4$, filtered and concentrated. The residue was applied onto a silica gel column and eluted with ethyl acetate/petroleum ether (1:3) to provide the title compound. LCMS (ES) $[M+1]^+$ m/z 316.1.

Alternatively, a tert-butyldiphenylsilyl (TBDPS) protecting group can be used instead of tert-butyl(chloro)dimethylsilyl (TBS). In typical conditions, imidazole (1.5 to 4 eq) and tert-butyl(chloro)diphenylsilane (TBDPSCl (about 1 eq.) were added to a solution of alcohol 1b (1 eq) in DCM (3 to 15 V). The reaction mixture was stirred at RT for 1 to 48 hours. This gave the product (1c2) after normal workup and purification. The TBDPS group can be removed using TBAF (1-3 eq) following typical literature conditions. Compounds 8 and 12 can be synthesized using TBDPS as a protecting group.

Step 3: Synthesis of methyl 2-(2-((tert-butyldimethylsilyl)oxy)ethyl)nicotinate (1d)

Into a 250-mL sealed tube, was placed a solution of 3-bromo-2-[2-[(tert-butyldimethylsilyl)oxy] ethyl]pyridine (2.0 g, 6.32 mmol, 1 equiv) in methanol ("MeOH," 100 mL), triethylamine ("TEA," 1.3 g, 12.65 mmol, 2 equiv), and [1,1'-bis(diphenylphosphino)ferrocene]dichloropalladium (II) ("Pd(dppf)Cl$_2$," 0.5 g, 0.63 mmol, 0.1 equiv). The resulting solution was stirred for 16 hr at 100° C. under CO atmosphere (10 atm). After cooling to rt, the reaction mixture was filtered and the filtrate was concentrated. The resulting residue was applied onto a silica gel column and eluted with ethyl acetate/petroleum ether (1:3) to provide the title compound. LCMS (ES) $[M+1]^+$ m/z 296.2.
Alternative Synthesis: Scheme 1B

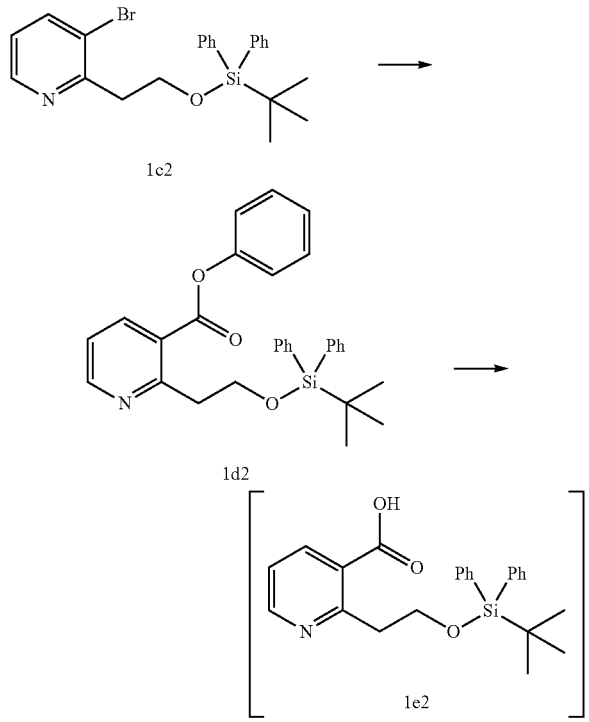

Scheme 1B

Alternatively, phenyl formate can be used to replace CO gas as a carbonyl source, in the presence of triethylamine (2 eq), catalytic amounts of palladium acetate (e.g., 0.02 eq) and tri-tert-butylphosphonium tetrafluoroborate (e.g., 0.08 eq), to convert the bromide 1c2 into carboxylate 1d2 in acetonitrile (3 to 10 V) under heating (80° C.) for 2 to 48 hours, and then directly to carboxylic acid 1e2 by hydrolysis of the ester under basic aqueous conditions ($K_2CO_3$ 2-8 eq in 3 to 10 V water; 50 to 80° C. for up to 48 hours).

Step 4: Synthesis of 2-(2-((tert-butyldimethylsilyl)oxy)ethyl)nicotinic acid (1e)

Into a 100-mL round-bottom flask, was placed a solution of methyl 2-[2-[(tert-butyldimethylsilyl) oxy]ethyl]pyridine-3-carboxylate (1.7 g, 5.75 mmol, 1 equiv) in MeOH (20 mL), and a solution of LiOH (275.6 mg, 11.51 mmol, 2 equiv) in $H_2O$ (5 mL). The resulting solution was stirred for 4 hr at 25° C. Water (10 ml) was added to the reaction mixture, crude product as precipitate was collected by filtration. The crude product was then purified by Flash-Prep-HPLC using the following conditions (IntelFlash-1): Column, C18 silica gel; mobile phase, $H_2O$:acetonitrile ("ACN")=10:1 increasing to $H_2O$:ACN=3:1 within 10 min to provide the title compound. LCMS (ES) $[M+1]^+$ m/z 282.1.

Step 5. Synthesis of (S)-(2-(2-((tert-butyldimethylsilyl)oxy)ethyl)pyridin-3-yl)(2-(hydroxymethyl)piperidin-1-yl)methanone (1f)

Into a 100-mL round-bottom flask, was placed 2-[2-[(tert-butyldimethylsilyl)oxy]ethyl]pyridine-3-carboxylic acid (1.4 g, 4.97 mmol, 1 equiv), [(2S)-piperidin-2-yl]methanol (0.9 g, 7.46 mmol, 1.5 equiv), N,N-diisopropylethylamine ("DIEA," 1.3 g, 9.95 mmol, 2 equiv), 1-[Bis(dimethylamino)methylene]-1H-1,2,3-triazolo[4,5-b]pyridinium 3-oxid hexafluorophosphate ("HATU," 2.8 g, 7.46 mmol, 1.5 equiv) and 30 mL of dichloromethane ("DCM"). The resulting reaction mixture was stirred for 2 hr at 25° C. and then diluted with 60 mL of $H_2O$. The organic phase was extracted with 3×50 mL of ethyl acetate. The combined organic layers was dried over $Na_2SO_4$, filtered and concentrated. The residue was applied onto a silica gel column and eluted with ethyl acetate/petroleum ether (1:3) to provide the title compound. LCMS (ES) $[M+1]^+$ m/z 379.2.
Steps 6 & 7: Synthesis of (S)-2-hydroxy-6-((1-(2-(2-hydroxyethyl)nicotinoyl)piperidin-2-yl)methoxy)benzaldehyde (Compound 1).

Into a 100-mL round-bottom flask, was placed a solution of [(2S)-1-(2-[2-[(tert-butyldimethylsilyl)oxy]ethyl]pyridine-3-carbonyl)piperidin-2-yl]methanol (900 mg, 2.38 mmol, 1 equiv) in DCM (8 mL), 2,6-dihydroxybenzaldehyde (656.7 mg, 4.75 mmol, 2 equiv), and triphenylphosphine ("PPh$_3$," 1247.0 mg, 4.75 mmol, 2 equiv). This was followed by the addition of a solution of di-tert-butyl azodicarboxylate ("DBAD," 1094.8 mg, 4.75 mmol, 2 equiv) in DCM (2 mL) dropwise with stirring at 0° C. The resulting solution was stirred for 2 hr at 25° C. The reaction mixture was concentrated and dissolved in 20 mL THF. To this was added tetrabutylammonium fluoride ("TBAF," 1243.1 mg, 4.75 mmol, 2 equiv). The resulting mixture was allowed to stir for 2 hr at 25° C. The reaction mixture was concentrated to give a crude product, which was purified by Prep-HPLC with the following conditions (Prep-HPLC-006): Column, XBridge Prep C18 OBD Column, 19 mm×150 mm 5um; mobile phase, Water (10 mmoL/L NH$_4$HCO$_3$+0.1% NH$_3$.H$_2$O) and ACN (14% Phase B up to 35% in 8 min, hold 95% in 1 min, down to 14% in 1 min, hold 14% in 1 min); Detector, UV 254 nm. This provided the title compound. $^1$HTEM NMR (300 MHz, 353K, dimethyl-sulfoxide ("DMSO")-d$_6$): δ 11.36 (s, 1H), 10.25 (s, 1H), 8.51 (dd, J=4.8, 1.8 Hz, 1H), 7.51-723 (m, 3H), 6.7-6.5 (m, 2H), 5.15 (s, 1H), 4.59-3.98 (m, 3H), 3.78 (br, 2H), 3.17-2.86 (m, 4H), 1.83-1.37 (m, 6H). LCMS (ES) [M+1]$^+$ m/z 385.2.

Example 2: (S)-2-hydroxy-6-((1-(2-(2-methoxy-ethyl)nicotinoyl)piperidin-2-yl)methoxy)benzaldehyde, Compound 2

Compound 2 was synthesized according to Scheme 2.

methyl 2-ethenylpyridine-3-carboxylate. LCMS (ES) [M+1]$^+$ m/z: 164.1.

Step 2: Synthesis of methyl 2-(2-methoxyethyl)pyridine-3-carboxylate (2c)

Into a 100-mL round-bottom flask, was placed a solution of methyl 2-ethenylpyridine-3-carboxylate (1.5 g, 9.19 mmol, 1.00 equiv), methanol (20 mL) and aqueous hydrogen chloride (36%, 2 mL). The resulting solution was stirred for 48 h at 60° C. The mixture was cooled and then concentrated under vacuum to give methyl 2-(2-methoxyethyl)pyridine-3-carboxylate). LCMS (ES) [M+1]$^+$ m/z: 196.1.

Scheme 2

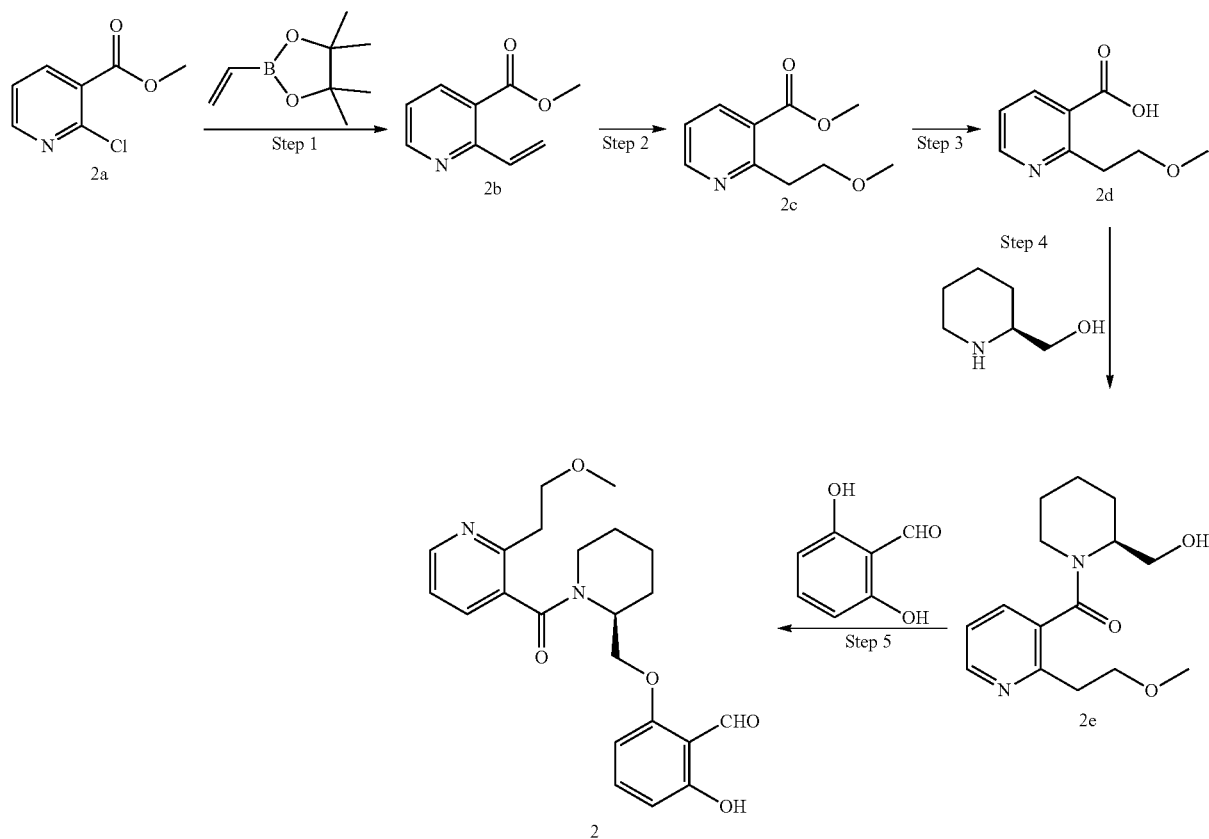

Step 1: Synthesis of methyl 2-ethenylpyridine-3-carboxylate (2b)

Into a 100-mL round-bottom flask, was placed a mixture of methyl 2-chloropyridine-3-carboxylate (3 g, 17.48 mmol, 1.00 equiv), dioxane (40 mL), water (4 mL), 2-ethenyl-4,4,5,5-tetramethyl-1,3,2-dioxaborolane (5.39 g, 34.99 mmol, 2.00 equiv), Cs$_2$CO$_3$ (11.40 g, 34.99 mmol, 2.00 equiv) and tetrakis(triphenylphosphine)palladium(0) ("Pd(PPh$_3$)$_4$," 2.02 g, 1.75 mmol, 0.10 equiv). The resulting solution was stirred for 2 h at 100° C. under N$_2$. The reaction mixture was cooled, filtered, and concentrated under vacuum.

The resulting residue was purified by a silica gel column by eluting with ethyl acetate/petroleum ether (1/2) to give 2

Step 3: Synthesis of 2-(2-methoxyethyl)pyridine-3-carboxylic acid (2d)

Into a 100-mL round-bottom flask, was placed a solution of methyl 2-(2-methoxyethyl)pyridine-3-carboxylate (2.50 g, 12.81 mmol, 1.00 equiv), methanol (30 mL), H$_2$O (6 mL) and NaOH (2.56 g, 64.00 mmol, 5.00 equiv). The resulting solution was stirred for 2 h at 50° C. The reaction was cooled, pH adjusted to 6 with addition of aqueous hydrogen chloride (2 M). The mixture was extracted with 3×50 mL of DCM/MeOH (10/1). The combined organic layers was washed with 1×100 mL of brine, dried over anhydrous sodium sulfate and concentrated under vacuum to produce (crude) 2-(2-methoxyethyl)pyridine-3-carboxylic acid. LCMS (ES) [M+1]$^+$ m/z: 182.1.

Step 4: Synthesis of [(2S)-1-[[2-(2-methoxyethyl)pyridin-3-yl]carbonyl]piperidin-2-yl]methanol (2e)

Into a 100-mL round-bottom flask, was placed a solution of 2-(2-methoxyethyl)pyridine-3-carboxylic acid (600 mg, 3.31 mmol, 1.00 equiv), dichloromethane (30 mL), (2S)-piperidin-2-ylmethanol (762 mg, 6.62 mmol, 2.00 equiv), DIEA (855 mg, 6.62 mmol, 2.00 equiv) and HATU (1.89 g, 4.97 mmol, 1.50 equiv). The resulting solution was stirred for 1 h at rt. The crude reaction mixture was filtered and concentrated. The resulting residue was purified by reverse preparative HPLC (Prep-C18, 20-45 µM, 120 g, Tianjin Bonna-Agela Technologies; gradient elution of 15% $CH_3CN$ in water to 40% $CH_3CN$ in water over a 12 min period, where both solvents contain 0.1% ammonia) to provide [(2S)-1-[[2-(2-methoxyethyl)pyridin-3-yl]carbonyl]piperidin-2-yl]methanol. LCMS (ES) [M+1]+m/z: 279.1.

Step 5: (S)-2-hydroxy-6-((1-(2-(2-methoxyethyl)nicotinoyl)piperidin-2-yl)methoxy)benzaldehyde (Compound 2)

Into a 50-mL 3-necked round-bottom flask, was placed a solution of [(2S)-1-[[2-(2-methoxyethyl)pyridin-3-yl]carbonyl]piperidin-2-yl]methanol (265 mg, 0.95 mmol, 1.00 equiv), dichloromethane (10 mL), 2,6-dihydroxybenzaldehyde (263 mg, 1.90 mmol, 2.00 equiv) and $PPh_3$ (499 mg, 1.90 mmol, 2.00 equiv). It was added the solution of dibenzyl azodicarboxylate ("DBAD") (438 mg, 1.90 mmol, 2.00 equiv) in DCM (5 mL) under $N_2$ at 0° C. The resulting solution was stirred for 2 h at room temperature. The resulting mixture was concentrated under vacuum. The residue was purified by a silica gel column eluted with ethyl acetate/petroleum ether (1/1). The crude reaction mixture was filtered and subjected to reverse preparative HPLC (Prep-C18, 5 mM XBridge column, 19×150 mm, waters; gradient elution of 22% $CH_3CN$ in water to 42% $CH_3CN$ in water over a 6 min period, where both solvents contain 0.1% trifluoroacetic acid ("TFA")) to provide 2-hydroxy-6-[(1-[hydroxy[2-(2-methoxyethyl)piperidin-3-yl]methyl]piperidin-2-yl)methoxy]cyclohexane-1-carbaldehyde. ¹HTEM NMR (300 MHz, 353 K, DMSO-$d_6$) δ 11.64 (s, 1H), 10.28 (s, 1H), 8.56 (dd, J=5.1 Hz, 1.8 Hz, 1H), 7.78-7.59 (m, 1H), 7.52 (t, J=8.1 Hz, 1H), 7.39-7.21 (m, 1H), 6.72 (s, 1H), 6.55 (d, J=8.4 Hz, 1H), 5.19 (s, 1H), 4.33-4.21 (m, 3H), 3.83-3.57 (m, 2H), 3.30-3.08 (m, 4H), 3.04-2.84 (m, 2H), 2.01-1.82 (m, 1H), 1.82-1.55 (m, 4H), 1.55-1.28 (m, 1H). LCMS (ES) [M+1]+m/z: 399.1.

Example 3: (S)-3-(3-(2-((2-formyl-3-hydroxyphenoxy)methyl)piperidine-1-carbonyl)pyridin-2-yl)propanenitrile, Compound 3

Compound 3 was synthesized according to Scheme 3.

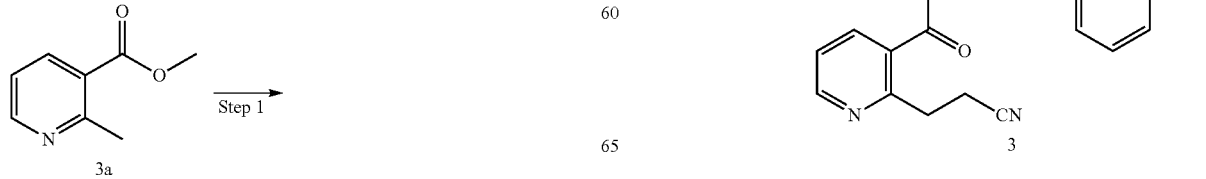

Step 1: Synthesis of methyl 2-formylnicotinate (3b)

Into a 100-mL round-bottom flask, was placed a solution of methyl 2-methylpyridine-3-carboxylate (5 g, 33.08 mmol, 1 equiv) in dioxane (50 mL), (oxo-lambda4-selanylidene)oxidane (selenium dioxide) (5.5 g, 49.61 mmol, 1.5 equiv). After stirring for 16 hr at 110° C. the reaction mixture was cooled to rt, concentrated, and diluted with 100 mL of $H_2O$. It was then extracted with 4×100 ml of ethyl acetate and the organic layers combined. The organic layers was washed with 200 ml of brine, dried over $Na_2SO_4$ and concentrated. The resulting residue was applied onto a silica gel column and eluted with ethyl acetate/petroleum ether (1:5) to provide the title compound. LCMS (ES) $[M+1]^+$ m/z 166.0.

Step 2: Synthesis of methyl (E)-2-(2-cyanovinyl)nicotinate (3c)

Into a 100-mL round-bottom flask, was placed a solution of methyl 2-formylpyridine-3-carboxylate (2.5 g, 15.14 mmol, 1 equiv) in THF (30 mL). This was followed by the addition of diethyl (cyanomethyl)phosphonate (3.2 g, 18.17 mmol, 1.2 equiv) at 0° C. and (tert-butoxy)potassium (2.5 g, 22.71 mmol, 1.5 equiv), in portions at 0° C. The resulting mixture was stirred for 16 hr at room temperature. The solids were filtered out. The filtrate was diluted with 100 mL of $H_2O$ and extracted with 2×80 mL of ethyl acetate. The combined organic layers was washed with 2×100 mL of brine, dried over $Na_2SO_4$, filtered and concentrated. The resulting residue was applied onto a silica gel column and eluted with ethyl acetate/petroleum ether (1:5) to provide the title compound. LCMS (ES) $[M+1]^+$ m/z 189.1.

Step 3: Synthesis of (E)-2-(2-cyanovinyl)nicotinic acid (3d)

Into a 100-mL round-bottom flask, was placed a solution of methyl 2-[(1E)-2-cyanoeth-1-en-1-yl]pyridine-3-carboxylate (1.4 g, 7.44 mmol, 1 equiv) in MeOH (20 mL), a solution of NaOH (0.6 g, 14.88 mmol, 2 equiv) in $H_2O$ (4 mL). After stirring for 2 hr at room temperature, the reaction was diluted with 10 mL of $H_2O$, pH adjusted to 6-7 with HCl (2 mol/L), and then concentrated. The crude product was purified by Flash-Prep-HPLC with the following conditions (IntelFlash-1): Column, C18 silica gel; mobile phase, $H_2O$:ACN=10:1 increasing to $H_2O$:ACN=1:1 with 10 min. This provided the title compound. LCMS (ES) $[M+1]^+$ m/z 175.0.

Step 4: Synthesis of 2-(2-cyanoethyl)nicotinic acid (3e)

Into a 100-mL round-bottom flask, was placed a solution of 2-[(1E)-2-cyanoeth-1-en-1-yl]pyridine-3-carboxylic acid (600 mg, 3.45 mmol, 1 equiv) in MeOH (20 mL), palladium on carbon ("Pd/C," 120 mg, 1.13 mmol, 0.33 equiv). The resulting solution was stirred for 16 hr at room temperature under $H_2$ atmosphere (20 atm). The solids were filtered out. The filtrate was concentrated to give the crude product. LCMS (ES) $[M+1]^+$ m/z 177.1.

Step 5: Synthesis of (S)-3-(3-(2-(hydroxymethyl)piperidine-1-carbonyl)pyridin-2-yl)propanenitrile (3f)

Into a 50-mL round-bottom flask, was placed a solution of 2-[(1E)-2-cyanoeth-1-en-1-yl]pyridine-3-carboxylic acid (550 mg, 3.16 mmol, 1 equiv) in DMF (6 mL), [(2S)-piperidin-2-yl]methanol (545.6 mg, 4.74 mmol, 1.5 equiv), DIEA (816.3 mg, 6.32 mmol, 2 equiv), HATU (1801.2 mg, 4.74 mmol, 1.5 equiv). The resulting solution was stirred for 4 hr at room temperature. The mixture was diluted with 40 mL of $H_2O$ and extracted with 3×30 mL of ethyl acetate. The combined organic layers was washed with 30×30 mL of brine, dried over $Na_2SO_4$, filtered and concentrated. The resulting residue was purified by Flash-Prep-HPLC with the following conditions (IntelFlash-1): Column, C18 silica gel; mobile phase, $H_2O$:ACN=10:1 increasing to $H_2O$:ACN=1:1 with 10 min. This provided the title compound. LCMS (ES) $[M+1]^+$ m/z 274.1.

Step 6: Synthesis of (S)-3-(3-(2-((2-formyl-3-hydroxyphenoxy)methyl)piperidine-1-carbonyl)pyridin-2-yl)propanenitrile (Compound 3)

Into a 50-mL round-bottom flask, was placed a solution of 3-[3-[(2S)-2-(hydroxymethyl)piperidine-1-carbonyl]pyridin-2-yl]propanenitrile (200 mg, 0.73 mmol, 1 equiv) in DCM (3 mL), 2,6-dihydroxybenzaldehyde (202.1 mg, 1.46 mmol, 2 equiv), $PPh_3$ (383.8 mg, 1.46 mmol, 2 equiv). This was followed by the addition of DBAD (337.0 mg, 1.46 mmol, 2 equiv) at 0° C. The resulting mixture was stirred for 2 hr at room temperature and then concentrated under vacuum; the residue was diluted with 5 mL of ACN and filtered. The crude product was purified by Prep-HPLC with the following conditions (Prep-HPLC-007): Column, SunFire Prep C18 OBD Column, 150 mm 5 um 10 nm; mobile phase, Water (0.1% formic acid) and MeOH (40% Phase B up to 55% in 7 min, hold 95% in 1 min, down to 40% in 1 min, hold 40% in 1 min); Detector, UV. This provided the title compound. $^1$HTEM NMR (300 MHz, 353K, DMSO-$d_6$): δ 11.60 (br, 1H), 10.27 (br, 1H), 8.60 (dd, J=4.8, 1.8 Hz, 1H), 7.61 (m, 2H), 7.52 (t, J=8.4 Hz, 1H), 7.34 (dd, J=7.6, 4.8 Hz, 1H), 6.72 (s, 1H), 6.55 (d, J=8.4 Hz, 1H), 5.16 (s, 1H), 4.49 (br, 1H), 4.32 (dd, J=10.3, 6.2 Hz, 1H), 3.21-2.89 (m, 6H), 1.91-1.46 (m, 6H). LCMS (ES) $[M+1]^+$ m/z 394.1.

Example 4: (S)-2-hydroxy-6-((1-(2-(2-(pyrrolidin-1-yl)ethyl)nicotinoyl)piperidin-2-yl)methoxy)benzaldehyde, Compound 4

Compound 4 was synthesized according to Scheme 4.

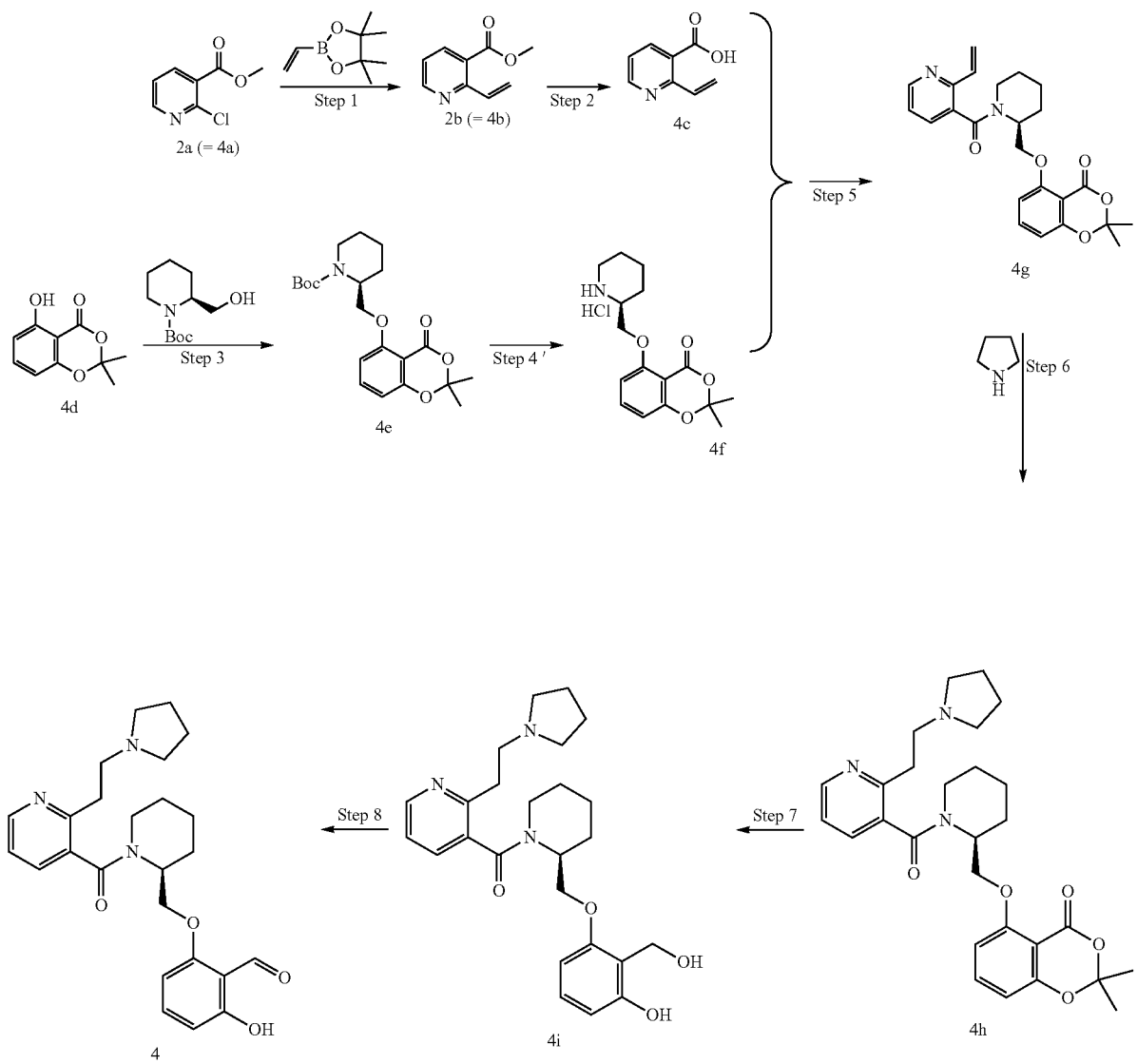

Step 1: Synthesis of methyl 2-ethenylpyridine-3-carboxylate (4b)

Into a 100-mL round-bottom flask, was placed a mixture of methyl 2-chloropyridine-3-carboxylate (3 g, 17.48 mmol, 1.00 equiv), dioxane (40 mL), water (4 mL), 2-ethenyl-4,4,5,5-tetramethyl-1,3,2-dioxaborolane (5.39 g, 34.99 mmol, 2.00 equiv), $Cs_2CO_3$ (11.40 g, 34.99 mmol, 2.00 equiv) and $Pd(PPh_3)_4$ (2.02 g, 1.75 mmol, 0.10 equiv). The resulting solution was stirred for 2 h at 100° C. under $N_2$. The reaction mixture was cooled, filtered, and concentrated under vacuum. The resulting residue was purified by a silica gel column by eluting with ethyl acetate/petroleum ether (1/2) to give 2 methyl 2-ethenylpyridine-3-carboxylate. LCMS (ES) $[M+1]^+$ m/z: 164.1.

Step 2: Synthesis of 2-ethenylpyridine-3-carboxylic acid (4c)

Into a 100-mL round-bottom flask, was placed a solution of methyl 2-ethenylpyridine-3-carboxylate (3.0 g, 18.39 mmol, 1 equiv), MeOH (50 mL), $H_2O$ (5 mL) and NaOH (3.7 g, 91.93 mmol, 5.0 equiv). After stirring for 2 h at 50° C., the reaction mixture was cooled, and pH was adjusted to 5 with addition of aqueous HCl (2 M). The resulting mixture was concentrated and diluted with 100 mL of DCM. The solids were filtered out. The mixture was concentrated. This resulted in 2-ethenylpyridine-3-carboxylic acid. LCMS (ES) $[M+1]^+$ m/z: 150.1.

Step 3: Synthesis of tert-butyl (2S)-2-[[(2,2-dimethyl-4-oxo-2,4-dihydro-1,3-benzodioxin-5-yl)oxy]methyl]piperidine-1-carboxylate (4e)

Compound 4d may be synthesized according to methods known in the art.

Into a 1000-mL round-bottom flask, was placed a solution of 5-hydroxy-2,2-dimethyl-2,4-dihydro-1,3-benzodioxin-4-one (4d, 10.0 g, 51.50 mmol, 1 equiv), THF (300 mL), tert-butyl (2S)-2-(hydroxymethyl)piperidine-1-carboxylate (22.2 g, 103.12 mmol, 2.00 equiv) and $PPh_3$ (40.5 g, 154.49 mmol, 3 equiv). It was added the solution of diisopropyl azodicarboxylate ("DIAD," 31.2 g, 154.49 mmol, 3 equiv) in THF (30 ml) dropwise at 0° C. under $N_2$. The resulting solution was stirred for 4 h at room temperature. The resulting mixture was concentrated. The residue was purified by a silica gel column by eluting with ethyl acetate/petroleum ether (1/3). This resulted in tert-butyl (2S)-2-[[(2,2-dimethyl-4-oxo-2,4-dihydro-1,3-benzodioxin-5-yl)oxy]methyl]piperidine-1-carboxylate. LCMS (ES) [M+1]+m/z: 392.2.

Step 4: Synthesis of 2,2-dimethyl-5-[[(2S)-piperidin-2-yl]methoxy]-2,4-dihydro-1,3-benzodioxin-4-one (4f)

Into a 50-mL round-bottom flask, was placed a solution of tert-butyl (2S)-2-[[(2,2-dimethyl-4-oxo-2,4-dihydro-1,3-benzodioxin-5-yl)oxy]methyl]piperidine-1-carboxylate (2.0 g, 5.10 mmol, 1 equiv), DCM (15 mL) and HCl/dioxane (4 M, 5 mL). The resulting solution was stirred for 1 h at room temperature. The resulting mixture was concentrated. This resulted in 2,2-dimethyl-5-[[(2S)-piperidin-2-yl]methoxy]-2,4-dihydro-1,3-benzodioxin-4-one. LCMS (ES) $[M+1]^+$ m/z: 292.2.

Step 5: Synthesis of 5-[[(2S)-1-(2-ethenylpyridine-3-carbonyl)piperidin-2-yl]methoxy]-2,2-dimethyl-2,4-dihydro-1,3-benzodioxin-4-one (4g)

Into a 100-mL round-bottom flask, was placed a solution of 2,2-dimethyl-5-[[(2S)-piperidin-2-yl]methoxy]-2,4-dihydro-1,3-benzodioxin-4-one hydrochloride (1.0 g, 3.05 mmol, 1 equiv), DCM (50 mL, 786.50 mmol, 257.82 equiv), 2-ethenylpyridine-3-carboxylic acid (910.0 mg, 6.10 mmol, 2.00 equiv), DIEA (2.0 g, 15.25 mmol, 5 equiv) and HATU (2.3 g, 6.10 mmol, 2 equiv) at 0° C. After stirring 2 h at room temperature, the reaction mixture was diluted with 50 mL of DCM and washed with 3×50 ml of brine. The organic layer was dried over anhydrous sodium sulfate and concentrated. The residue was purified by a silica gel column by eluting with ethyl acetate/petroleum ether (1/1). This resulted in 5-[[(2S)-1-(2-ethenylpyridine-3-carbonyl)piperidin-2-yl]methoxy]-2,2-dimethyl-2,4-dihydro-1,3-benzodioxin-4-one. LCMS (ES) $[M+1]^+$ m/z: 423.2.

Step 6: Synthesis of 2,2-dimethyl-5-[[(2S)-1-[2-[2-(pyrrolidin-1-yl)ethyl]pyridine-3-carbonyl]piperidin-2-yl]methoxy]-2,4-dihydro-1,3-benzodioxin-4-one (4 h)

Into a 50-mL round-bottom flask, was placed a solution of 5-[[(2S)-1-(2-ethenylpyridine-3-carbonyl)piperidin-2-yl] methoxy]-2,2-dimethyl-2,4-dihydro-1,3-benzodioxin-4-one (650 mg, 1.54 mmol, 1 equiv), ethanol (20 mL), pyrrolidine (218.8 mg, 3.08 mmol, 2.00 equiv) and TEA (311.4 mg, 3.08 mmol, 2 equiv). The reaction mixture was stirred for 16 h at 85° C., cooled and concentrated in vacuum. The resulting residue was purified by a silica gel column by eluting with dichloromethane/methanol (10/1). This resulted in 2,2-dimethyl-5-[[(2S)-1-[2-[2-(pyrrolidin-1-yl)ethyl]pyridine-3-carbonyl]piperidin-2-yl]methoxy]-2,4-dihydro-1,3-benzodioxin-4-one. LCMS (ES) [M+1]+m/z: 494.3.

Step 7: Synthesis of 2-(hydroxymethyl)-3-[[(2S)-1-[2-[2-(pyrrolidin-1-yl)ethyl]pyridine-3-carbonyl]piperidin-2-yl]methoxy]phenol (4i)

Into a 50-mL 3-necked round-bottom flask, was placed a solution of 2,2-dimethyl-5-[[(2S)-1-[2-[2-(pyrrolidin-1-yl)ethyl]pyridine-3-carbonyl]piperidin-2-yl]methoxy]-2,4-dihydro-1,3-benzodioxin-4-one (500 mg, 1.01 mmol, 1 equiv) and THF (10 mL). To this was added lithium aluminum hydride in THF solution ("$LiAlH_4$ THF solution," 2.03 mL, 1 M, 2.03 mmol, 2 equiv) dropwise at −78° C. under $N_2$. The resulting mixture was stirred at −78° C. for 1 h. The reaction mixture was warmed to 0° C., and then to this was added, dropwise, 0.07 mL of $H_2O$, 0.07 mL of 15% aqueous NaOH and 0.21 mL of $H_2O$. The mixture was warmed to room temperature and stirred for 30 minutes. The solids were filtered out. The filtrate was concentrated. This resulted in 2-(hydroxymethyl)-3-[[(2S)-1-[2-[2-(pyrrolidin-1-yl)ethyl]pyridine-3-carbonyl]piperidin-2-yl]methoxy]phenol. LCMS (ES) $[M+1]^+$ m/z: 440.3.

Step 8: Synthesis of (S)-2-hydroxy-6-((1-(2-(2-(pyrrolidin-1-yl)ethyl)nicotinoyl)piperidin-2-yl)methoxy)benzaldehyde (4)

Into a 50-mL round-bottom flask, was placed a mixture of 2-(hydroxymethyl)-3-[1[(2S)-1-[2-[2-(pyrrolidin-1-yl)ethyl]pyridine-3-carbonyl]piperidin-2-yl]methoxy]phenol (200 mg, 0.46 mmol, 1 equiv), DCM (10 mL) and $MnO_2$ (791.1 mg, 9.10 mmol, 20.00 equiv). The resulting mixture was stirred for 1 h at room temperature. The reaction mixture was filtered and concentrated. The resulting residue was purified by reverse phase preparative HPLC (Prep-C18, 5 mM XBridge column, 19×150 mm, waters; gradient elution of 15% MeCN in water to 35% MeCN in water over a 6 min period, where both solvents contain 0.1% TFA) to provide 2-hydroxy-6-[[(2S)-1-[2-[2-(pyrrolidin-1-yl)ethyl]pyridine-3-carbonyl]piperidin-2-yl]methoxy]benzaldehyde. $^1$H NMR (300 MHz, DMSO-$d_6$) δ 11.57 (s, 1H), 10.26 (s, 1H), 9.48 (s, 1H), 8.60 (dd, J=4.8, 1.8 Hz, 1H), 7.65 (s, 1H), 7.53 (t, J=8.3 Hz, 1H), 7.38 (dd, J=7.7, 4.8 Hz, 1H), 6.73 (s, 1H), 6.61-6.52 (m, 1H), 4.61-4.41 (m, 1H), 4.41-4.25 (m, 1H), 3.60 (t, J=7.2 Hz, 2H), 3.51-2.96 (m, 8H), 2.07-1.84 (m, 5H), 1.81-1.36 (m, 5H). LCMS (ES) $[M+1]^+$ m/z: 438.2.

Example 5: (S)-2-hydroxy-6-((1-(2-(hydroxymethyl)benzoyl)piperidin-2-yl)methoxy)benzaldehyde, Compound 5

Compound 5 was synthesized according to Scheme 5.

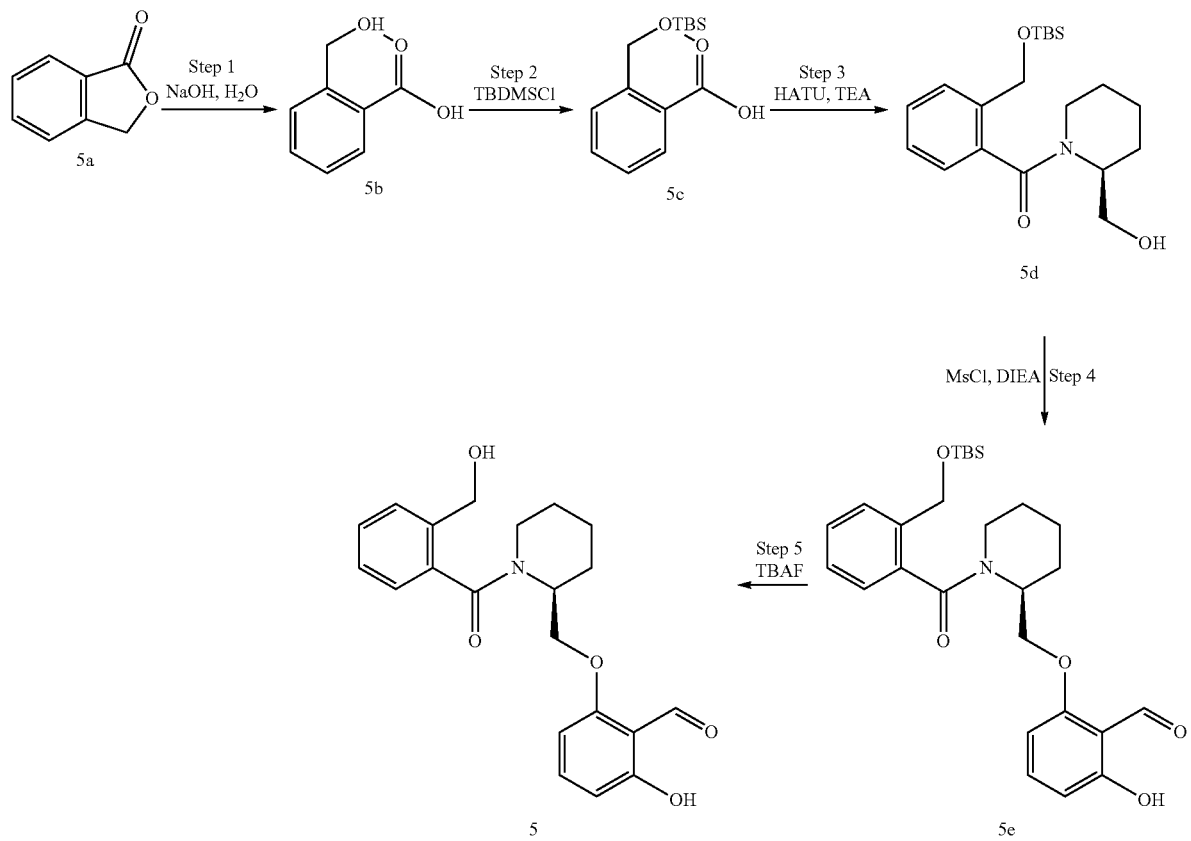

In Scheme 5, TBDMSCl refers to tert-butyldimethylsilyl chloride, and MsCl refers to mesyl chloride. Compound 5: MS m/z 370.2 [M+H]+, 392.2 [M+Na]+.

Example 6: (R)-2-hydroxy-6-((4-(2-(2-hydroxyethyl)nicotinoyl)thiomorpholin-3-yl)methoxy)benzaldehyde and (S)-2-hydroxy-6-((4-(2-(2-hydroxyethyl)nicotinoyl)thiomorpholin-3-yl)methoxy)benzaldehyde

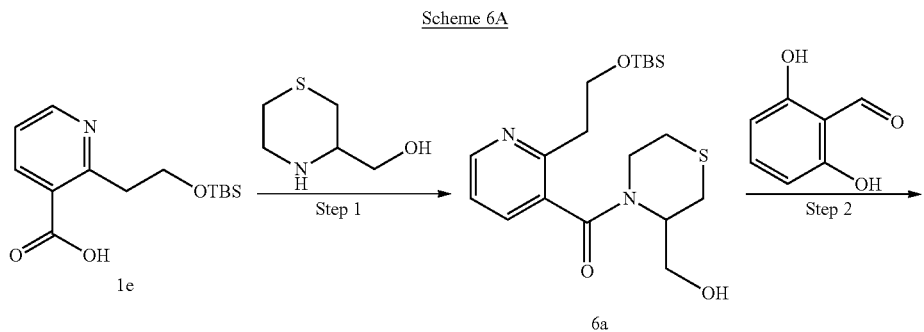

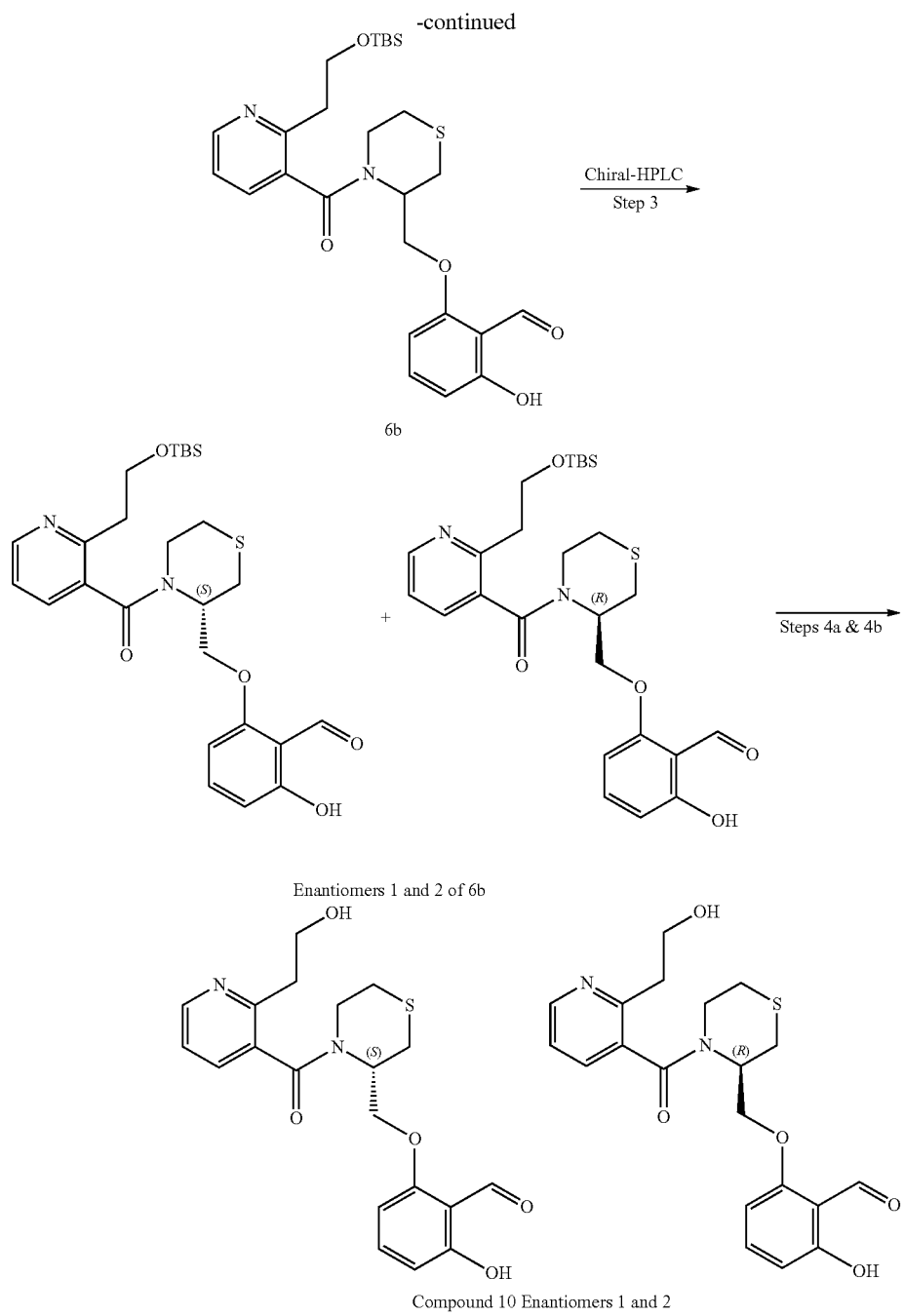

Compound 10 Enantiomers 1 and 2

Step 1: Synthesis of [4-(2-[2-[(tert-butyldimethylsilyl)oxy]ethyl]pyridine-3-carbonyl)thiomorpholin-3-yl]methanol (6a)

Into a 100-mL 3-necked round-bottom flask, was added 2-[2-[(tert-butyldimethylsilyl)oxy]ethyl]pyridine-3-carboxylic acid (2.00 g, 7.11 mmol, 1.00 equiv), thiomorpholin-3-ylmethanol (0.95 g, 7.13 mmol, 1.00 equiv), DIEA (2.76 g, 21.32 mmol, 3.00 equiv) and DCM (30.00 mL). To this mixture was added HATU (3.24 g, 8.53 mmol, 1.20 equiv), in portions at 0° C. The resulting reaction mixture was allowed to warm to room temperature and stirred for overnight. The reaction was then quenched by the addition of 30 mL of water. The resulting solution was extracted with 3×30 mL of dichloromethane and the organic layers were separated, combined and dried over anhydrous sodium sulfate and concentrated. The residue was applied onto a silica gel column with THF/petroleum ether ("PE") (30%) as eluent. The combined fractions were concentrated to produce [4-(2-[2-[(tert-butyldimethylsilyl)oxy]ethyl]pyridine-3-carbonyl)thiomorpholin-3-yl]methanol. LCMS (ES) [M+H]+ m/z: 397.

Step 2. Synthesis of 2-[[4-(2-[2-[(tert-butyldimethylsilyl)oxy]ethyl]pyridine-3-carbonyl)thiomorpholin-3-yl]methoxy]-6-hydroxybenzaldehyde (6b)

Into a 100-mL 3-necked round-bottom flask, was added [4-(2-[2-[(tert-butyldimethylsilyl)oxy]ethyl]pyridine-3-carbonyl)thiomorpholin-3-yl]methanol (1.50 g, 3.78 mmol, 1.00 equiv), 2,6-dihydroxybenzaldehyde (0.63 g, 4.56 mmol, 1.21 equiv), PPh$_3$ (1.19 g, 4.54 mmol, 1.20 equiv), and DCM (30.00 mL). To this solution was added DIAD (0.92 g, 4.54 mmol, 1.20 equiv) dropwise over 20 mins with stirring at 0° C. The resulting mixture was stirred overnight at room temperature, and was concentrated. The residue was directly applied onto a silica gel column with THF/PE (25%) as eluent. The combined fractions were concentrated to give 2-[[4-(2-[2-[(tert-butyldimethylsilyl)oxy]ethyl]pyridine-3-carbonyl)thiomorpholin-3-yl]methoxy]-6-hydroxybenzaldehyde. LCMS (ES) [M+H]+ m/z:517.

Step 3. Chiral-HPLC Separation of Compound 6b

The racemate was purified by Chiral-HPLC to give Enantiomer 1 and Enantiomer 2 of Compound 6b with the following conditions: Column, Lux Cellulose-4, 4.6*100 mm, 3 μm; mobile phase, A: n-Hexane B: Ethanol (35% B in 18 min); Flow rate: 30 mL/min; Detector, 254. LCMS (ES) [M+H]+ m/z:517 (for both compounds).

Step 4a. Removal of TBS Group to Give Compound 10, Enantiomer 1

HCl (~2M) in 5 ml of ethyl acetate ("EA") was added to Enantiomer 1 of Compound 6b (335.00 mg, 0.65 mmol, 1.00 equiv) in EA (3.00 mL) dropwise with stirring at 0° C. The resulting solution was stirred for 2 h at room temperature. The pH value of the solution was adjusted to 8 with saturated NaHCO$_3$. The resulting solution was extracted with 3×10 mL of ethyl acetate and the organic layers combined, dried over anhydrous sodium sulfate, filtered and concentrated. The crude product was purified by Prep-HPLC with the following conditions: Column, XBridge Prep C18 OBD Column, 19 cm, 150 mm, 5 um; mobile phase, Water (0.1% HCOOH) and CAN (30% Phase B up to 40% in 10 min); Detector, 254. This resulted in Enantiomer 1 of Compound 10 with retention time=4.06 min. LCMS (ES) [M+H]$^+$ m/z: 403.1; [M+Na]$^+$ m/z: 425.1.

Step 4b. Removal of TBS Group to Give Compound 10, Enantiomer 2

HCl (~2M) in 5 ml of EA was added to Enantiomer 2 of Compound 6b (335.00 mg, 0.65 mmol, 1.00 equiv) in EA (3.00 mL) dropwise with stirring at 0° C. The resulting solution was stirred for 2 h at room temperature. The pH value of the solution was adjusted to 8 with saturated NaHCO$_3$. The resulting solution was extracted with 3×10 mL of ethyl acetate and the organic layers combined, dried over anhydrous sodium sulfate, filtered and concentrated. The crude product (200 mg) was purified by Prep-HPLC with the following conditions: Column, XBridge Prep C18 OBD Column, 19 cm, 150 mm, 5um; mobile phase, Water (0.1% HCOOH) and CAN (30% Phase B up to 40% in 10 min); Detector, 254. This resulted in Enantiomer 2 of Compound 10 with retention time=5.40 min. LCMS (ES) [M+H]$^+$ m/z: 403.2; [M+Na]$^+$ m/z: 425.1.

Alternative Synthesis of (R)-2-hydroxy-6-((4-(2-(2-hydroxyethyl)nicotinoyl)thiomorpholin-3-yl)methoxy)benzaldehyde (R)-2-hydroxy-6-((4-(2-(2-hydroxyethyl)nicotinoyl)thiomorpholin-3-yl)methoxy)benzaldehyde can be made directly from chiral (R)-thiomorpholin-3-ylmethanol as depicted in Scheme 6B.

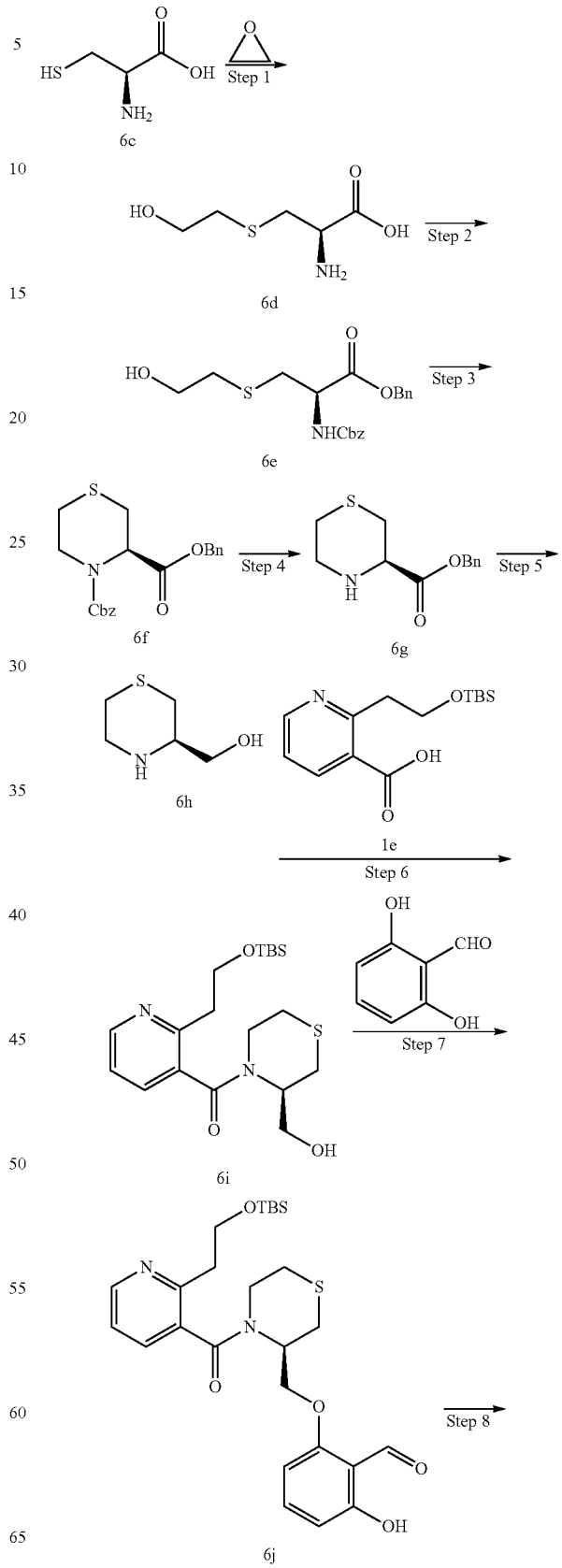

Scheme 6B

-continued

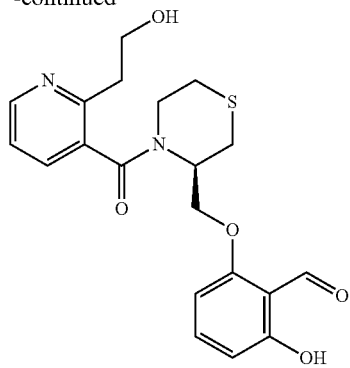

Step 1

To a solution of L-cysteine (100.0 g, 825.4 mmol, 1.0 equiv) in H₂O (1.0 L) was added NaOH (3.3 g, 82.5 mmol, 0.1 equiv). After the reaction mixture was cooled to 0° C., ethylene oxide (100.0 g, 2.26 mol, 2.75 equiv) was added dropwise. The resulting solution was stirred for 3 hr at 0-25° C. in a water/ice bath. The resulting solution was extracted with 3×500 mL of ethyl acetate to remove unchanged ethylene oxide. The aqueous layer was concentrated under reduced pressure. The crude product was triturated with EtOH (200 mL) for 1 h and filtered. This resulted in hydroxyethylcysteine. LCMS (ES) [M+1]⁺ m/z: 166.2; Retention time 0.174 min. ¹H-NMR: (300 MHz, D₂O, ppm): δ 3.83 (dd, J=3.0, 6.0 Hz, 1H), 3.67 (t, J=6.0, 2H), 3.04 (dd, J=14.8, 4.4 Hz, 1H), 2.97 (dd, J=14.8, 7.4 Hz, 1H), 2.68 (t, J=6.0, 2H).

Step 2

To a mixture of hydroxyethylcysteine (130.0 g, 786.8 mmol, 1.0 equiv) and KHCO₃ (165.4 g, 1.65 mol, 2.1 equiv) in dioxane (700 mL, 8.26 mol, 10.5 equiv) and H₂O (700 mL) was added CbzCl (147.6 g, 865 mmol, 1.1 equiv) dropwise at 0° C. over 30 min. The resulting solution was stirred for 5 h at 0-25° C. The solvents evaporated off and the residue dissolved in DMF (1000 mL). BnBr (148 g, 0.86 mol, 1.1 equiv) was added and the resulting mixture was stirred for 16 h at 0-25° C. The reaction was then quenched by the addition of 1000 mL of water. The resulting solution was extracted with 3×1000 mL of EtOAc, the combined organic layer was washed with brine, dried over anhydrous sodium sulfate and concentrated under vacuum. The residue was applied onto a silica gel column with ethyl acetate/petroleum ether (1:50 to 1:5). This resulted in benzyl (2R)-2-[[(benzyloxy)carbonyl]amino]-3-[(2-hydroxyethyl)sulfanyl]propanoate. LCMS (ES) [M+1]⁺ m/z: 390.5; Retention time 1.146 min, ¹H-NMR: (300 MHz, CDCl₃, ppm): δ 7.39-7.33 (m, 10H), 5.83 (br, 1H), 5.26 (d, J=4.7 Hz, 2H), 5.17 (s, 2H), 4.71-4.65 (m, 1H), 3.69-3.63 (m, 2H), 3.09-2.98 (m, 2H), 2.71-2.61 (m, 2H).

Step 3

Into a 2500-mL 3-necked round-bottom flask purged and maintained with an inert atmosphere of argon, was placed benzyl (2R)-2-[[(benzyloxy)carbonyl]amino]-3-[(2-hydroxyethyl)sulfanyl]propanoate (90.0 g, 231 mmol, 1.0 equiv), THF (1.0 L), DEAD (48.3 g, 277 mmol, 1.2 equiv). After the reaction was cooled to 0° C., PPh₃ (78.8 g, 300 mmol, 1.3 equiv) in THF (100 mL) was added dropwise. The resulting solution was stirred for 16 h at 0-25° C. The resulting mixture was concentrated. The residue was applied onto a silica gel column with THF/PE (1:100 to 1:5). This resulted in 3,4-dibenzyl (3R)-thiomorpholine-3,4-dicarboxylate. LCMS (ES) [M+1]⁺ m/z: 372.1; Retention time 1.312 min.

Step 4

Into a 2500-mL 3-necked round-bottom flask, was placed 3,4-dibenzyl (3R)-thiomorpholine-3,4-dicarboxylate (100.0 g, 269 mmol, 1.0 equiv), DCM (1.0 L). The reaction was cooled to 0° C., TMSI (161.6 g, 0.81 mol, 3 equiv) was added dropwise. The resulting solution was stirred for 1 h at 0-25° C. in a water/ice bath. The reaction was then quenched by the addition of 100 mL of MeOH. The resulting mixture was concentrated. The pH value of the solution was adjusted to 1 with HCl (2 mol/L). The resulting solution was extracted with 2×500 mL of MTBE, and the aqueous layers were combined. NaHCO₃ (2 mol/L) was employed to adjust the pH to 8. The resulting solution was extracted with 3×500 mL of ethyl acetate. The combined organic layer was dried over Na₂SO₄ and concentrated under reduced pressure. This resulted in benzyl (3R)-thiomorpholine-3-carboxylate. LCMS (ES) [M+1]⁺ m/z: 238.1; Retention time 1.026 min; ¹H-NMR: (300 MHz, CDCl₃, ppm): δ 7.43-7.33 (m, 5H), 5.25 (s, 2H), 3.74 (dd, J=8.6, 3.4 Hz, 1H), 3.40 (ddd, J=12.5, 4.9, 3.0 Hz, 1H), 3.04 (ddd, J=12.5, 9.8, 2.7 Hz, 1H), 2.90 (ddd, J=13.2, 3.4, 1.3 Hz, 1H), 2.82 (dd, J=13.3, 8.6 Hz, 1H), 2.70 (ddd, J=12.9, 9.8, 3.0 Hz, 1H), 2.48 (dddd, J=13.3, 4.9, 2.7, 1.3 Hz, 1H).

Step 5

To a suspension of LiAlH₄ (13.2 g, 347 mmol, 1.5 equiv) in THF (1000 mL) was added benzyl (3R)-thiomorpholine-3-carboxylate (55.0 g, 231.7 mmol, 1.0 equiv) in THF (100 mL) drop wise at 0° C. After the resulting solution was stirred for 3 hr at 0-25° C., the reaction was then quenched by the addition of 100 g of Na₂SO₄·10H₂O. The resulting solution was diluted with 500 mL of THF, and the solids were filtered out. The resulting mixture was concentrated, and the residue was applied onto a silica gel column with THF/PE (1:50 to 2:1). This resulted in (3R)-thiomorpholin-3-ylmethanol. LCMS (ES) [M+1]⁺ m/z: 134.1; Retention time 0.464 min; ¹H-NMR: (300 MHz, DMSO-d6, ppm): δ 4.64 (br, 1H), 3.26-3.17 (m, 2H), 2.81-2.68 (m, 4H), 2.43-2.26 (m, 4H).

Step 6

Into a 300-mL 3-necked round-bottom flask, was placed 2-[2-[(tert-butyldimethylsilyl)oxy]ethyl]pyridine-3-carboxylic acid (20.00 g, 71.06 mmol, 1.00 equiv), (3R)-thiomorpholin-3-ylmethanol (10.41 g, 78.14 mmol, 1.10 equiv), DCM (300.00 mL), and DIEA (18.37 g, 142.13 mmol, 2.00 equiv). This was followed by the addition of HATU (32.43 g, 85.28 mmol, 1.20 equiv), in portions at 0° C. The resulting solution was stirred for 3 h at room temperature. The reaction was then quenched by the addition of 200 mL of water. The resulting solution was extracted with 3×200 mL of dichloromethane, and the organic layers were combined and dried over anhydrous sodium sulfate and concentrated. The residue was applied onto a silica gel column with THF/PE (30%). This resulted in [(3R)-4-(2-[2-[(tert-butyldimethylsilyl)oxy]ethyl]pyridine-3-carbonyl)thiomorpholin-3-yl]methanol. LCMS (ES) [M+H]$^+$ m/z: 397.30.

Step 7

Into a 1000-mL 3-necked round-bottom flask purged and maintained with an inert atmosphere of nitrogen, was placed 2,6-dihydroxybenzaldehyde (7.52 g, 54.45 mmol, 1.20 equiv), [(3R)-4-(2-[2-[(tert-butyldimethylsilyl)oxy]ethyl] pyridine-3-carbonyl)thiomorpholin-3-yl]methanol (18.00 g, 45.38 mmol, 1.00 equiv), PPh$_3$ (14.28 g, 54.46 mmol, 1.20 equiv), and DCM (400.00 mL). This was followed by the addition of DIAD (11.01 g, 54.46 mmol, 1.20 equiv) dropwise with stirring at 0° C. The resulting solution was stirred for overnight at room temperature. The resulting mixture was concentrated. The residue was applied onto a silica gel column with THF/PE (15%). This resulted in 2-[[(3R)-4-(2-[2-[(tert-butyldimethylsilyl)oxy]ethyl]pyridine-3-carbonyl) thiomorpholin-3-yl]methoxy]-6-hydroxybenzaldehyde. LCMS (ES) [M+H]$^+$ m/z: 517.35.

Step 8

Into a 500-mL round-bottom flask, was placed 2-[[(3R)-4-(2-[2-[(tert-butyldimethylsilyl)oxy]ethyl]pyridine-3-carbonyl)thiomorpholin-3-yl]methoxy]-6-hydroxybenzaldehyde (13.50 g, 26.13 mmol, 1.00 equiv) and EA (20.00 mL). To the above HCl(g) in EA (52.25 mL, 104.50 mmol, 4.00 equiv) was introduced in dropwise with stirring at 0° C. The resulting solution was stirred for 2 h at room temperature. The reaction was then quenched by the addition of 80 mL of water. The pH value of the solution was adjusted to 7-8 with saturated Na$_2$CO$_3$. The resulting solution was extracted with 3×100 mL of dichloromethane, and the organic layers combined and dried in an oven under reduced pressure, and concentrated. The crude product was purified by Prep-HPLC with the following conditions: Column, XBridge Prep C18 OBD Column, 19 cm, 150 mm, 5um; mobile phase, Water (0.1% HCOOH) and ACN (30% Phase B up to 50% in 11 min); Detector, 254. This resulted in 2-hydroxy-6-[[(3R)-4-[2-(2-hydroxyethyl)pyridine-3-carbonyl]thiomorpholin-3-yl]methoxy]benzaldehyde.

Chiral HPLC conditions were as follows: Instrument: SHIMADZU LC-20AT; Mobile Phase A: n-Hexane (0.1% TFA); Mobile Phase B: Ethanol; Conc. of Phase B: 50.0%; Flow Rate: 1.000 mL/min; Column: Lux Cellulose-4, 4.6*100 mm, 3 μm. Chiral HPLC retention time=5.41 min.

LCMS (ES, m/z): [M+H]$^+$: 403.2; $^1$H NMR (300 MHz, DMSO-d6): δ 11.80-11.73 (m, 1H), 10.33 (br, 1H), 8.56 (dd, J=4.9, 1.8 Hz, 1H), 7.90-7.39 (m, 2H), 7.37-7.19 (m, 1H), 6.81-6.63 (m, 1H), 6.56 (d, J=8.4 Hz, 1H), 5.49-4.60 (m, 1H), 4.60-4.05 (m, 2H), 3.88-3.36 (m, 4H), 3.20-2.61 (m, 6H), 2.43 (d, J=12.6 Hz, 1H).

Based on the product of Scheme 6B, it was determined that Compound 10, Enantiomer 2 corresponds to (R)-2-hydroxy-6-((4-(2-(2-hydroxyethyl)nicotinoyl)thiomorpholin-3-yl)methoxy)benzaldehyde.

Example 7: (S)-2-hydroxy-6-((4-(2-(2-hydroxyethyl)nicotinoyl)morpholin-3-yl)methoxy)benzaldehyde, Compound 8

Compound 8 was synthesized according to Scheme 7.

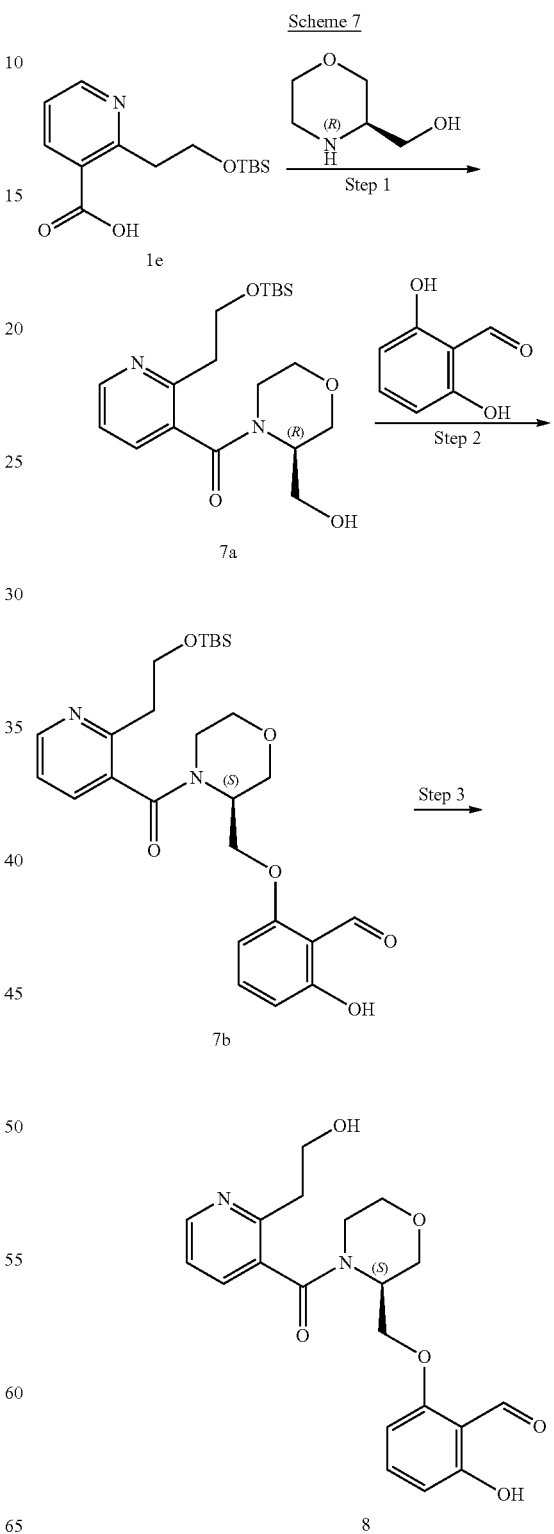

Step 1: Synthesis of (R)-(2-(2-((tert-butyldimethyl-silyl)oxy)ethyl)pyridin-3-yl)(3-(hydroxymethyl) morpholino)methanone (7a)

To a solution of 2-[2-[(tert-butyldimethylsilyl)oxy]ethyl] pyridine-3-carboxylic acid (1.50 g, 5.33 mmol, 1.00 equiv) and (3R)-morpholin-3-ylmethanol hydrochloride (0.98 g, 6.39 mmol, 1.20 equiv) in DCM (20 mL) was added DIEA (2.07 g, 15.99 mmol, 3.00 equiv), followed by the addition of HATU (2.43 g, 6.39 mmol, 1.20 equiv) in portions over 5 mins. The resulting solution was stirred for 2 hr at room temperature, diluted with 50 mL of H₂O. The resulting solution was extracted with 2×30 mL of dichloromethane and the organic layers were separated, combined, dried over anhydrous sodium sulfate, and filtered. The filtrate was concentrated to give a residue that was purified on silica gel column with ethyl acetate/petroleum ether (2/1) as eluent. This resulted in (R)-(2-(2-((tert-butyldimethylsilyl)oxy) ethyl)pyridin-3-yl)(3-(hydroxymethyl) morpholino)methanone. LCMS (ES) [M+H]⁺ m/z: 381.2.

Step 2. Synthesis of (S)-2-((4-(2-(2-((tert-butyldimethylsilyl)oxy)ethyl)nicotinoyl)morpholin-3-yl) methoxy)-6-hydroxybenzaldehyde (7b)

A solution of (R)-(2-(2-((tert-butyldimethylsilyl)oxy) ethyl)pyridin-3-yl)(3-(hydroxymethyl) morpholino)methanone (600 mg, 1.57 mmol, 1.00 equiv), 2,6-dihydroxybenzaldehyde (261 mg, 1.89 mmol, 1.20 equiv), and PPh₃ (496 mg, 1.89 mmol, 1.20 equiv) in DCM (10 mL) was purged and maintained with an inert atmosphere of nitrogen. To this mixture was added DIAD (382 mg, 1.89 mmol, 1.20 equiv) dropwise with stirring at 0° C. over 5 min. The resulting solution was stirred for 1 hr at room temperature, diluted with 20 mL of H₂O. The resulting solution was extracted with 2×20 mL of dichloromethane and the organic layers combined, dried over anhydrous sodium sulfate, and filtered. The filtrate was concentrated to give the crude product which was purified by Flash-Prep-HPLC with the following conditions (IntelFlash-1): Column, C18 silica gel; mobile phase, H₂O (0.1% HCOOH)/acetonitrile ("ACN")=2/1 increasing to H₂O (0.1% HCOOH)/ACN=1/4 within 18 min; Detector, UV 254 nm. This resulted in (S)-2-((4-(2-(2-((tert-butyldimethylsilyl)oxy)ethyl)nicotinoyl)morpholin-3-yl)methoxy)-6-hydroxybenzaldehyde. LCMS (ES) [M+H]⁺ m/z: 501.2.

Step 3. Synthesis of (S)-2-hydroxy-6-((4-(2-(2-hydroxyethyl)nicotinoyl)morpholin-3-yl)methoxy) benzaldehyde (8)

Formic acid (HCOOH, 1 ml) was added to a solution of (S)-2-((4-(2-(2-((tert-butyldimethylsilyl)oxy)ethyl)nicotinoyl)morpholin-3-yl)methoxy)-6-hydroxybenzaldehyde (450 mg, 0.89 mmol, 1.00 equiv) in ACN (5.00 mL). The resulting solution was stirred for 3 hr at 40° C., cooled room temperature and diluted with 5 mL of ACN. The mixture was concentrated to give the crude product, which was purified by Prep-HPLC with the following conditions (2 #SHI-MADZU (HPLC-01)): Column, Atlantis HILIC OBD Column, 19*150 mm*5 um; mobile phase, Water (0.1% FA) and ACN (37% PhaseB up to 45% in 10 min); Detector, UV 254 nm. This resulted in (S)-2-hydroxy-6-((4-(2-(2-hydroxyethyl)nicotinoyl)morpholin-3-yl)methoxy) benzaldehyde. LCMS (ES) [M+H]⁺ m/z: 387.1.

Example 8. (S)-2-hydroxy-6-((1-(2-(hydroxymethyl) nicotinoyl)piperidin-2-yl)methoxy)benzaldehyde, Compound 11

Compound 11 was synthesized according to Scheme 8.

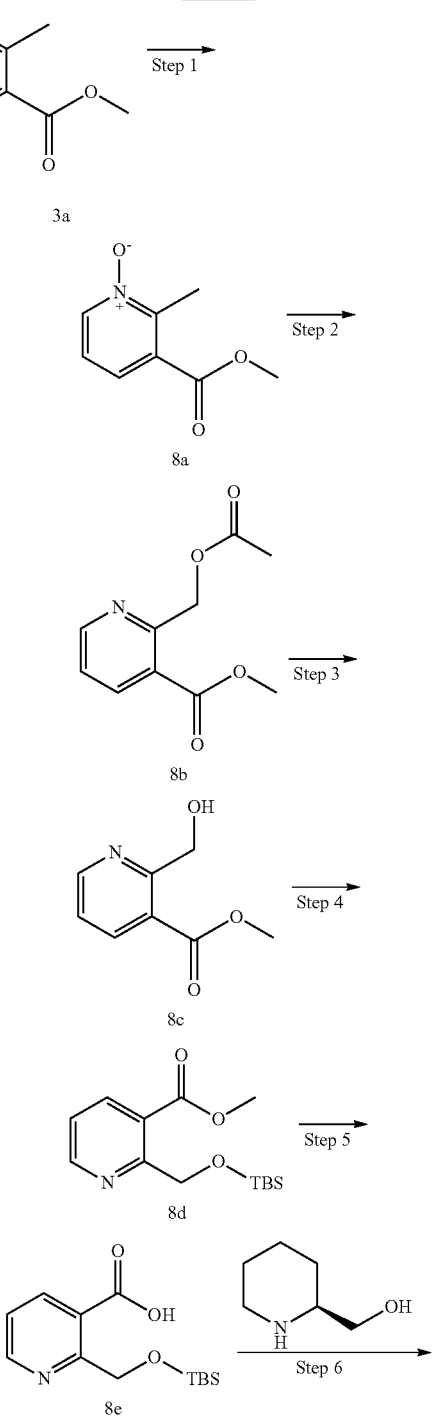

Scheme 8

-continued

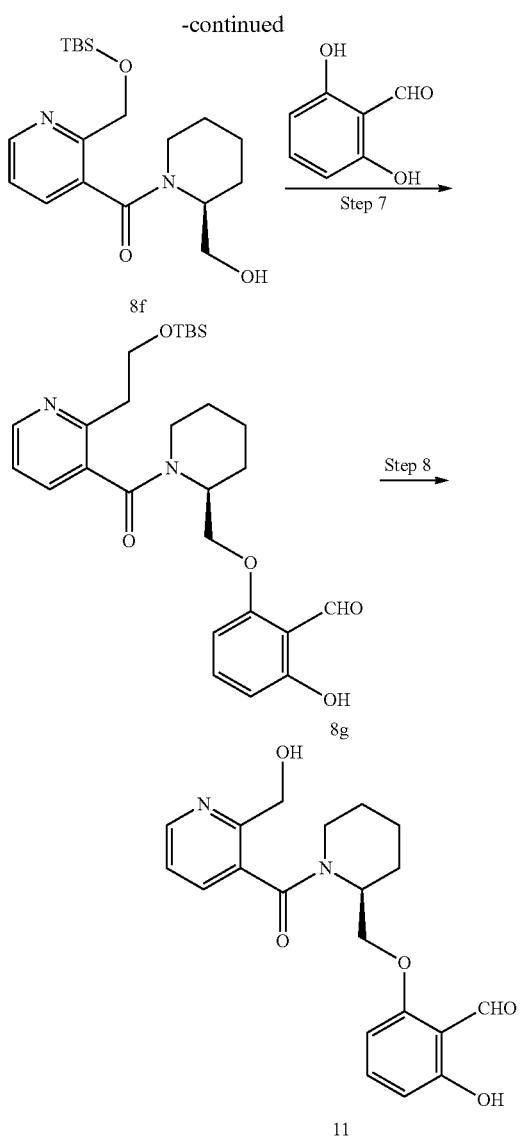

Step 1: Synthesis of 3-(methoxycarbonyl)-2-methylpyridine 1-oxide

To a solution of methyl 2-methylpyridine-3-carboxylate (15.00 g, 99.23 mmol, 1.0 equiv) in DCM (150 mL) at 0° C. was added 3-chloroperbenzoic acid ("m-CPBA," 34.4 g, 199.34 mmol, 2.0 equiv). The reaction mixture was stirred for 2 h at room temperature. The reaction was quenched with saturated aqueous $Na_2CO_3$ (100 mL), and the organic phase was separated out and dried over anhydrous sodium sulfate. The solution was filtered, and the filtrate was concentrated under reduced pressure. The residue was purified by silica gel column with dichloromethane/methanol (10/1), providing 3-(methoxycarbonyl)-2-methylpyridine 1-oxide. LCMS (ES) $[M+H]^+$ m/z: 168.

Step 2. Synthesis of methyl 2-(acetoxymethyl)nicotinate

A mixture of 3-(methoxycarbonyl)-2-methylpyridine 1-oxide (8.00 g) in acetic anhydride (80 mL) was heated for 5 h at 140° C. After being cooled to room temperature, excess liquid was removed under reduced pressure, and the residue was suspended in water (50 mL) and extracted with 3×50 mL of dichloromethane. The combined organic phase was dried over anhydrous sodium sulfate and filtered, and the filtrate was concentrated under reduced pressure. The residue was purified by silica gel column with ethyl acetate/petroleum ether (15%), providing methyl 2-(acetoxymethyl)nicotinate. LCMS (ES) $[M+H]^+$ m/z: 210.

Step 3. Synthesis of methyl 2-(hydroxymethyl)nicotinate

To a solution of methyl 2-(acetoxymethyl)nicotinate (7.90 g, 37.76 mmol, 1.0 equiv), in MeOH (80 mL) was added acetyl chloride (3.60 g, 45.86 mmol, 1.2 equiv). The reaction solution was stirred overnight at room temperature; then, the solvent was removed under reduced pressure, and the resulting residue was dissolved in water (20 mL). The pH was adjusted to 8 with $NaHCO_3$ solid and extracted with ethyl acetate (30 mL*3). The combined organic phase was dried over anhydrous sodium sulfate and filtered, and the filtrate was concentrated in vacuum. The residue was purified by silica gel column with ethyl acetate/petroleum ether (1/1), giving methyl 2-(hydroxymethyl)pyridine-3-carboxylate. LCMS (ES) $[M+1]^+$ m/z: 168.

Step 4. Synthesis of methyl 2-(((tert-butyldimethylsilyl)oxy)methyl)nicotinate Into a 100-mL 3-necked round-bottom flask, was placed methyl 2-(hydroxymethyl)pyridine-3-carboxylate (2.80 g, 16.75 mmol, 1.0 equiv), DCM (40 mL), and imidazole (2.27 g, 33.34 mmol, 2.0 equiv). This was followed by the addition of t-butyldimethylchlorosilane (4.04 g, 26.81 mmol, 1.6 equiv) at 0° C. The mixture was stirred for 2 h at room temperature. The reaction was then quenched by the addition of water (30 mL), extracted with 3×50 mL of dichloromethane. The combined organic phase was dried over anhydrous sulfate and filtered, and the filtrate was concentrated in vacuum. The residue was purified by silica gel column with ethyl acetate/petroleum ether (10%), giving methyl 2-(((tert-butyldimethylsilyl)oxy)methyl)nicotinate. LCMS (ES) $[M+1]^+$ m/z: 282.

Step 5. Synthesis of 2-(((tert-butyldimethylsilyl)oxy)methyl)nicotinic acid

Into a 100-mL 3-necked round-bottom flask, was placed methyl 2-(((tert-butyldimethylsilyl)oxy)methyl)nicotinate (4.20 g, 14.92 mmol, 1.0 equiv), MeOH (30 mL), and $H_2O$ (15 mL). This was followed by the addition of LiOH $H_2O$ (1.25 g, 29.79 mmol, 2.0 equiv) at 0° C. The mixture was stirred for 2 h at room temperature, then concentrated to remove the solvent, and the pH value of the residue was adjusted to 7 with citric acid. The solution was filtered, and the solid was dried under infrared lamp. 2-(((tert-butyldimethylsilyl)oxy)methyl)nicotinic acid was obtained. LCMS (ES) $[M+1]^+$ m/z: 268.

Step 6. Synthesis of (S)-(2-(((tert-butyldimethylsilyl)oxy)methyl)pyridin-3-yl)(2-(hydroxymethyl)piperidin-1-yl)methanone Into a 50-mL 3-necked round-bottom flask, was placed 2-(((tert-butyldimethylsilyl)oxy)methyl)nicotinic acid (615 mg, 2.30 mmol, 1.0 equiv), (2S)-piperidin-2-ylmethanol (318 mg, 2.76 mmol, 1.2 equiv), DCM (10 mL), DIEA (594 mg, 4.60 mmol, 2.0 equiv). This was followed by the addition of HATU (1.05 g, 2.76 mmol, 1.2 equiv) at 0° C. The mixture was stirred for 2 h at room temperature. The reaction mixture was concentrated to remove solvent, and the residue was purified by silica gel column with ethyl acetate/petroleum ether (80%). (S)-(2-(((tert-butyldimethylsilyl)oxy)methyl)pyridin-3-yl)(2-(hydroxymethyl)piperidin-1-yl)methanone was obtained. LCMS (ES) [M+1]$^+$ m/z: 365.

Step 7. Synthesis of (S)-2-((1-(2-(((tert-butyldimethylsilyl)oxy)methyl)nicotinoyl)piperidin-2-yl)methoxy)-6-hydroxybenzaldehyde Into a 40-mL vial purged and maintained with an inert atmosphere of nitrogen, was placed (S)-(2-(((tert-butyldimethylsilyl)oxy)methyl)pyridin-3-yl)(2-(hydroxymethyl)piperidin-1-yl)methanone (316 mg, 0.87 mmol, 1.0 equiv), 2,6-dihydroxybenzaldehyde (143 mg, 1.04 mmol, 1.2 equiv), PPh$_3$ (340 mg, 1.30 mmol, 1.5 equiv), and THF (15 mL). This was followed by the addition of DIAD (262 mg, 1.30 mmol, 1.5 equiv) at 0° C. After addition, the reaction solution was stirred overnight at room temperature and then concentrated to remove solvent. The resulting residue was purified by silica gel column with ethyl acetate/petroleum ether (1/1). (S)-2-((1-(2-(((tert-butyldimethylsilyl)oxy)methyl)nicotinoyl)piperidin-2-yl)methoxy)-6-hydroxybenzaldehyde was obtained. LCMS (ES) [M+1]$^+$ m/z: 485.

Step 8. Synthesis of (S)-2-hydroxy-6-((1-(2-(hydroxymethyl)nicotinoyl)piperidin-2-yl)methoxy)benzaldehyde Into a 50-mL round-bottom flask, was placed (S)-2-((1-(2-(((tert-butyldimethylsilyl)oxy)methyl)nicotinoyl)piperidin-2-yl)methoxy)-6-hydroxybenzaldehyde (250 mg, 0.52 mmol, 1.0 equiv) in EA (3 ml). To the above solution was added HCl(g) (2 M in EA) (5.0 mL) was added at 0° C., the mixture was allowed to stir for 1 h at room temperature. The reaction was then diluted by the addition of water (20 mL), and the pH value of the solution was adjusted to 8 with NaHCO$_3$ solid and extracted with 3×20 mL of ethyl acetate. The combined organic phase was concentrated under reduced pressure, and the residue was purified by Prep-HPLC with conditions: (2 #SHIMADZU (HPLC-01)): Column, Kinetex EVO C18 Column, 21.2*150, Sum, mobile phase, Water (0.1% Formic Acid) and CH$_3$CN (10% Phase B up to 90% within 15 min), detector, UV 254 nm. (S)-2-hydroxy-6-((1-(2-(hydroxymethyl)nicotinoyl)piperidin-2-yl)methoxy)benzaldehyde was obtained. LCMS-PH- (ES, m/z): [M+H]+: 371.1; [M+Na]+: 393.1.

Example 9. (S)-2-hydroxy-6-((4-(2-(hydroxymethyl)nicotinoyl)morpholin-3-yl)methoxy)benzaldehyde, Compound 12

Compound 12 was synthesized according to Scheme 9A.

Scheme 9A

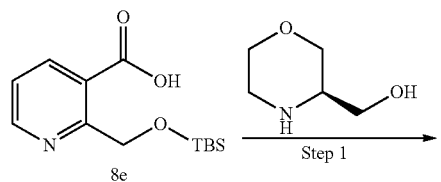

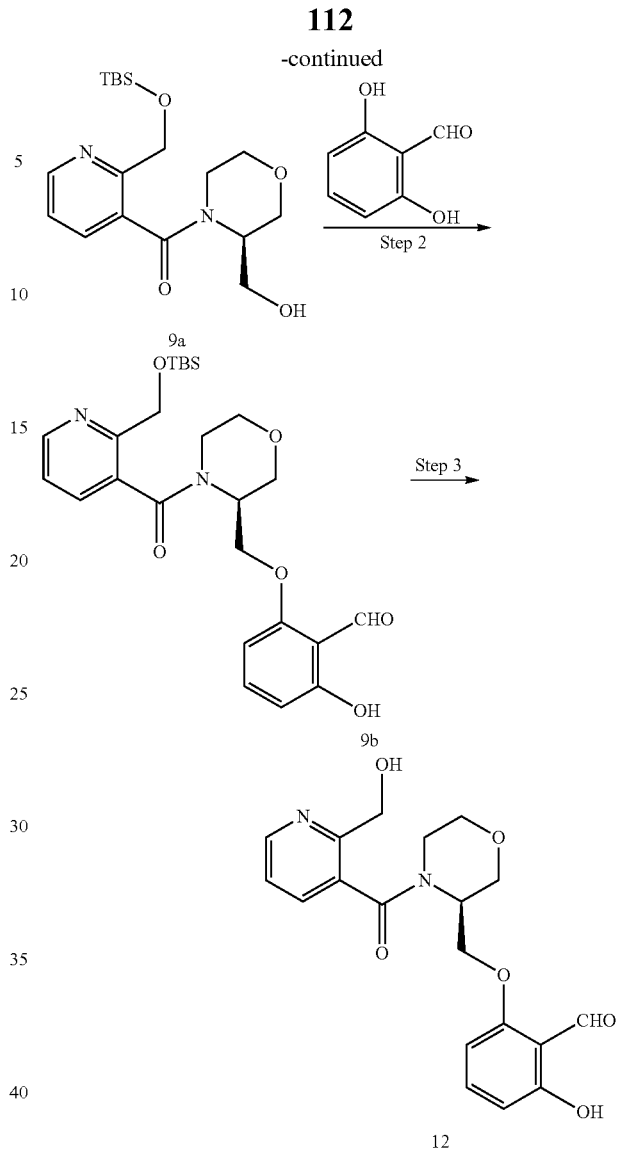

Step 1: Synthesis of (R)-(2-(((tert-butyldimethylsilyl)oxy)methyl)pyridin-3-yl)(3-(hydroxymethyl)morpholino)methanone To a solution of 2-[[(tert-butyldimethylsilyl)oxy]methyl]pyridine-3-carboxylic acid (530 mg, 1.98 mmol, 1.0 equiv), (3R)-morpholin-3-ylmethanol hydrochloride (364 mg, 2.38 mmol, 1.2 equiv), and DIEA (768 mg, 5.94 mmol, 3.0 equiv) in DCM (10 mL) was added HATU (905 mg, 2.38 mmol, 1.2 equiv) at 0° C. The reaction solution was stirred for 3 h at room temperature. The solution was then concentrated to remove the solvent, and the residue was purified by silica gel column with ethyl acetate/petroleum ether (60%). (R)-(2-(((tert-butyldimethylsilyl)oxy)methyl)pyridin-3-yl)(3-(hydroxymethyl)morpholino)methanone was obtained. LCMS (ES) [M+1]$^+$ m/z: 367.

Step 2. Synthesis of (S)-2-((4-(2-(((tert-butyldimethylsilyl)oxy)methyl)nicotinoyl)morpholin-3-yl)methoxy)-6-hydroxybenzaldehyde Into a 40-mL vial purged and maintained with an inert atmosphere of nitrogen, was placed (R)-(2-(((tert-butyldimethylsilyl)oxy)methyl)pyridin-3-yl)(3-(hydroxymethyl)morpholino)methanone (630 mg, 1.72 mmol, 1.0 equiv), 2,6-dihydroxybenzaldehyde (284 mg, 2.06 mmol, 1.2 equiv), PPh$_3$ (540 mg, 2.06 mmol, 1.2 equiv), THF (20 mL). This was followed by the addition of DBAD (474 mg, 2.06 mmol, 1.2 equiv) at 0° C. The reaction solution was stirred overnight at room temperature. The solution was concentrated in vacuum to remove the solvent, and the residue was purified by silica gel column with ethyl acetate/petroleum ether (1/1). (S)-2-((4-(2-(((tert-butyldimethylsilyl)oxy)methyl)nicotinoyl)morpholin-3-yl)methoxy)-6-hydroxybenzaldehyde was obtained. LCMS (ES) [M+1]$^+$ m/z: 487.

Step 3. Synthesis of (S)-2-hydroxy-6-((4-(2-(hydroxymethyl)nicotinoyl)morpholin-3-yl)methoxy)benzaldehyde Into a 25-mL round-bottom flask, was placed (S)-2-((4-(2-(((tert-butyldimethylsilyl)oxy)methyl)nicotinoyl)morpholin-3-yl)methoxy)-6-hydroxybenzaldehyde (380 mg, 0.78 mmol, 1.0 equiv). To the above, HCl (g) (2 M) in EA (5 mL) was added at 0° C. The reaction solution was stirred for 1 h at room temperature. The reaction was then quenched by the addition of water (10 mL), and the pH value of the solution was adjusted to 8 with NaHCO$_3$ solid and extracted with 3×10 mL of ethyl acetate. The combined organic phase was dried over anhydrous sodium sulfate and filtered, and the filtrate was concentrated under reduced pressure. The crude product was purified by Prep-HPLC with the following conditions (2 #SHIMADZU (HPLC-01)): Column, Kinetex EVO C18 Column, 21.2*150, 5 um, mobile phase, Water (0.1% Formic Acid) and CH$_3$CN (10% Phase B up to 50% within 15 min), detector, UV 254 nm. (S)-2-hydroxy-6-((4-(2-(hydroxymethyl)nicotinoyl)morpholin-3-yl)methoxy)benzaldehyde was obtained. LCMS: (ES, m/z): [M+H]$^+$: 373.1; [M+Na]$^+$: 395.1.

Alternative Synthesis: Scheme 9B

Alternatively, Compound 12 can be synthesized as shown in Scheme 9B using similar procedures described in Scheme 9A.

Scheme 9B

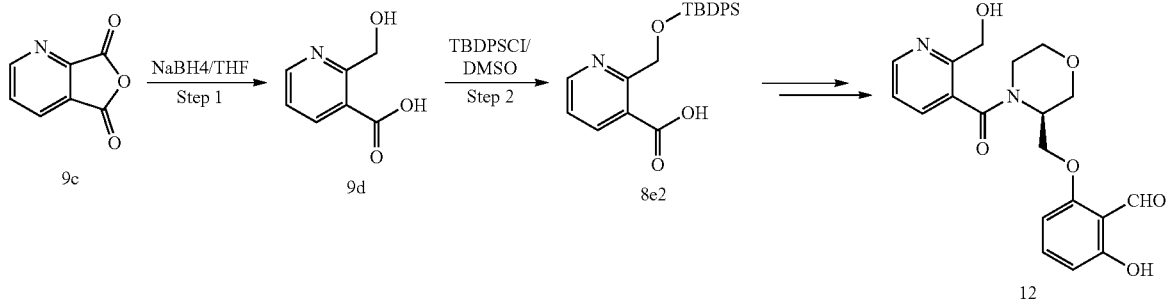

Compound 9c can be converted into 9d using methods known in the art (for example, sodium tetrahydroborate; acetic acid in tetrahydrofuran at 15° C.; for 4 h). Then, using a silyl protecting group such as TBDPS (tert-butyldiphenylsilyl), intermediate 8e2 can be converted into compound 12 using similar conditions as described in Scheme 9A.

Example 10. (S)-2-hydroxy-6-((4-(2-(hydroxymethyl)nicotinoyl)thiomorpholin-3-yl)methoxy)benzaldehyde and (R)-2-hydroxy-6-((4-(2-(hydroxymethyl)nicotinoyl)thiomorpholin-3-yl)methoxy)benzaldehyde Scheme 10A

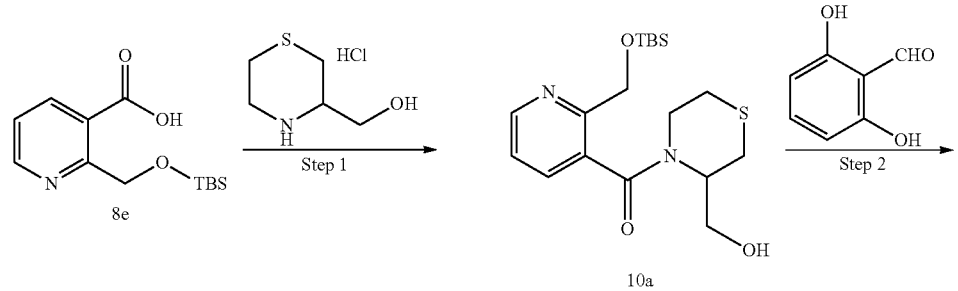

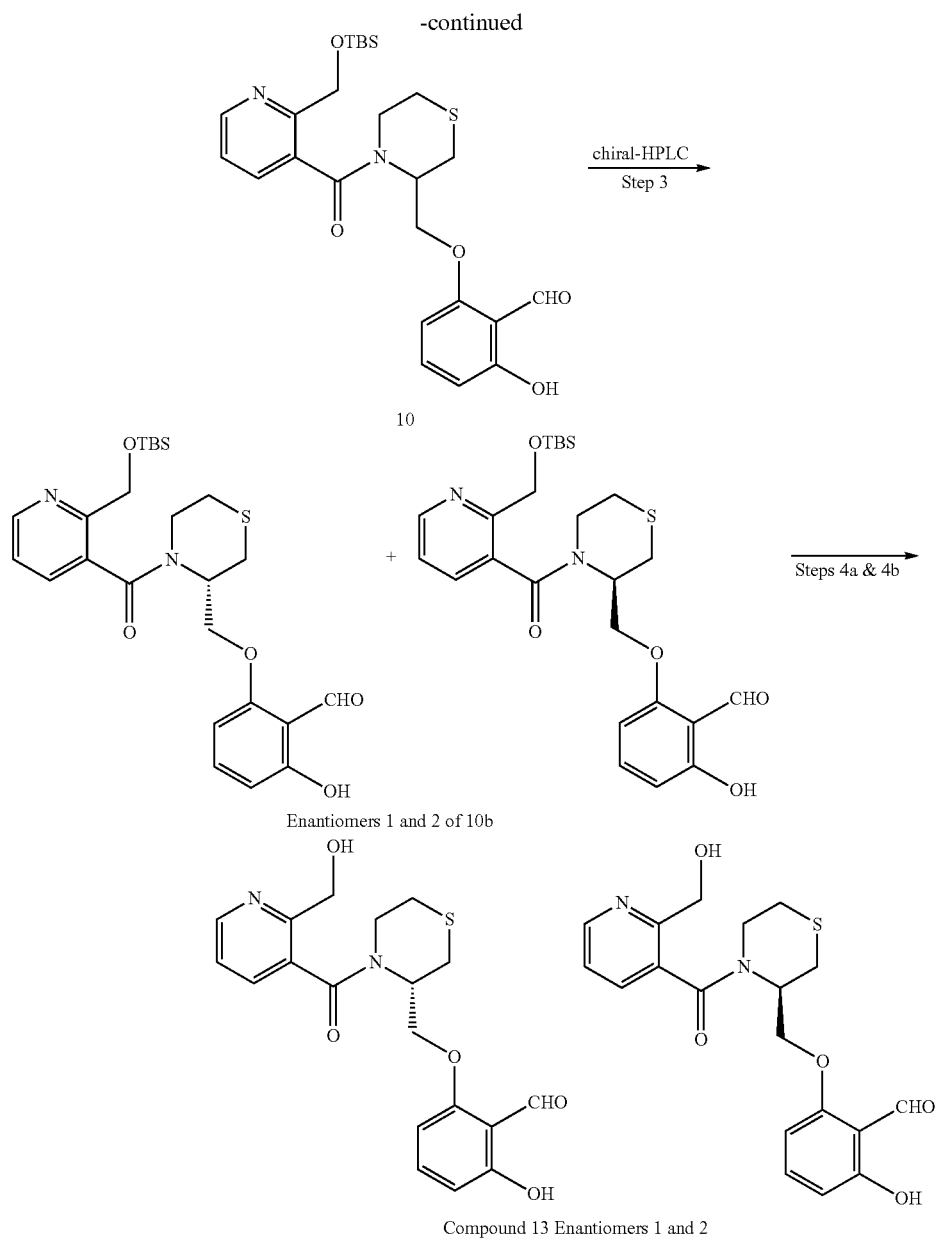

Step 1. Synthesis of (2-(((tert-butyldimethylsilyl)oxy)methyl)pyridin-3-yl)(3-(hydroxymethyl)thiomorpholino)methanone To a solution of 2-[[(tert-butyldimethylsilyl)oxy]methyl]pyridine-3-carboxylic acid (1.20 g, 4.50 mmol, 1.00 equiv) and thiomorpholin-3-ylmethanol hydrochloride (912 mg, 5.40 mmol, 1.20 equiv) in DMF under nitrogen at 0° C. was added DIEA (909 mg, 9.00 mmol, 2.00 equiv). This was followed by the addition of HATU (2.05 g, 5.40 mmol, 1.20 equiv) in several batches at 0° C. The mixture was allowed to slowly warm to room temperature and stirred for 16 h. The reaction was diluted with water (100 mL) and extracted with 3×100 mL of ethyl acetate. The combined organic layer was washed with 3×50 mL of brine, dried over anhydrous sodium sulfate, and concentrated. The residue was applied onto a silica gel column and eluted with ethyl acetate/petroleum ether (from 0% to 100% ethyl acetate). Removal of the solvents produced [4-(2-[[(tert-butyldimethylsilyl)oxy]methyl]pyridine-3-carbonyl)thiomorpholin-3-yl]methanol. LCMS (ES) [M+1]$^+$ m/z: 383.

Step 2. Synthesis of 2-((4-(2-(((tert-butyldimethylsilyl)oxy)methyl)nicotinoyl)thiomorpholin-3-yl)methoxy)-6-hydroxybenzaldehyde To a mixture of [4-(2-[[(tert-butyldimethylsilyl)oxy]methyl]pyridine-3-carbonyl)thiomorpholin-3-yl]methanol (1.20 g, 3.14 mmol, 1.00 equiv), 2,6-dihydroxybenzaldehyde (519 mg, 3.76 mmol, 1.20 equiv), and PPh$_3$ (0.99 g, 3.76 mmol, 1.20 equiv) in THF (50.0 mL) under nitrogen at 0° C. was added a solution of DBAD (0.87 g, 3.76 mmol, 1.20 equiv) in THF (1 mL) dropwise over 15 min. The resulting mixture was stirred for 16 h at room temperature. The reaction mixture was concentrated to remove solvents, and the residue was applied onto a silica gel column, eluted with ethyl acetate/petroleum ether (1:0). After removing solvents, this produced 2-[[4-(2-[[(tert-butyldimethylsilyl)oxy]methyl]pyridine-3-carbonyl)thiomorpholin-3-yl]methoxy]-6-hydroxybenzaldehyde. LCMS (ES) [M+1]+ m/z: 503.

Step 3. Chiral-HPLC Separation of Compound 10b

Racemic 2-[[4-(2-[[(tert-butyldimethylsilyl)oxy]methyl]pyridine-3-carbonyl)thiomorpholin-3-yl]methoxy]-6-hydroxybenzaldehyde was purified by Chiral-Prep-HPLC with the following conditions: Agela HP-Flash (model: HP-1000); Mobile phase: A:n-Hexane/DCM=5/1; B:Ethanol; Flow rate: 30 mL/min; Column: CHIRALPAK IG-3, 4.6*50 mm, 3 μm; and Gradient:20% B in 15 min; 220 nm.

This resulted in each of Enantiomers 1 and 2 of Compound 10b (Rt=10 min and 12 min, respectively). LCMS (ES) [M+1]+ m/z: 503.

Step 4a. Removal of TBS Group to Give Compound 13, Enantiomer 1

To a solution of Enantiomer 1 of Compound 10b (119 mg, 0.24 mmol, 1.00 equiv) in THF (10.0 mL) was added triethylamine trihydrofluoride ("TEA.3HF") (458 mg, 2.84 mmol, 12.0 equiv). The reaction was stirred for 16 h at room temperature. Solvents were removed, and the residue was applied onto a C18 silica gel column with Phase A: Water/0.05% TFA, Mobile Phase B: Acetonitrile; Flow rate: 1.5 mL/min; Gradient: 5% B to 100% B in 1.2 min, hold 0.6 min. This resulted in Compound 13, Enantiomer 1. RT=3.614 mins; LCMS (ES, m/z): [MH]+ 389.1.

Step 4b. Removal of TBS Group to Give Compound 13, Enantiomer 2

To a solution of Enantiomer 2 of Compound 10b (120 mg, 0.24 mmol, 1.00 equiv) in THF (10.0 mL) was added TEA.3HF (461 mg, 2.87 mmol, 12.0 equiv). The mixture was stirred for 16 h at room temperature. Solvents were removed, and the residue was applied onto a C18 silica gel column with Phase A: Water/0.05% TFA, Mobile Phase B: Acetonitrile; Flow rate: 1.5 mL/min; Gradient: 5% B to 100% B in 1.2 min, hold 0.6 min. This resulted in Compound 13, Enantiomer 2. RT=4.387 mins; LCMS (ES, m/z): [MH]+389.1; [MNa]+ 411.1.

Alternative synthesis of (R)-2-hydroxy-6-((4-(2-(2-hydroxyethyl)nicotinoyl)thiomorpholin-3-yl)methoxy)benzaldehyde Alternatively, (R)-2-hydroxy-6-((4-(2-(2-hydroxyethyl)nicotinoyl)thiomorpholin-3-yl)methoxy)benzaldehyde can be made directly from chiral (R)-thiomorpholin-3-ylmethanol as depicted in Scheme 10B.

Scheme 10B

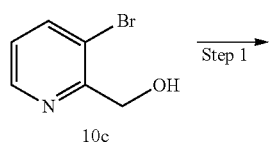
10c

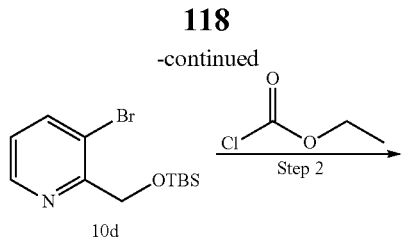
10d

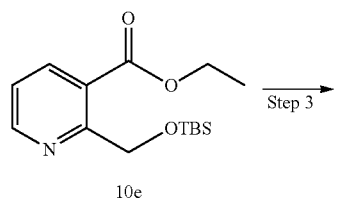
10e

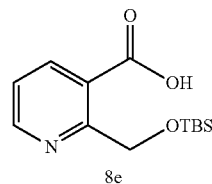
8e

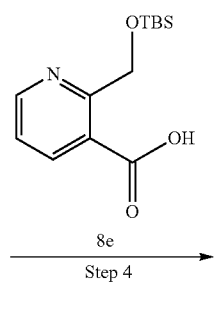
6h

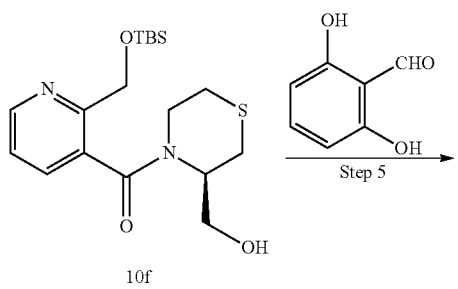
10f

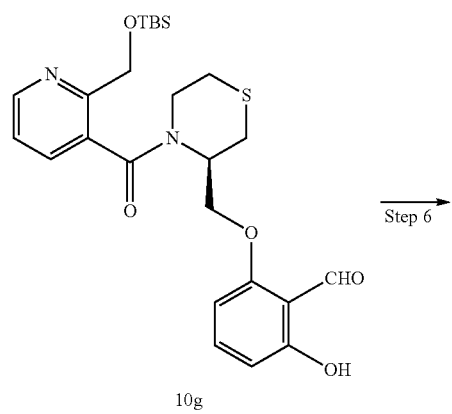
10g

119

-continued

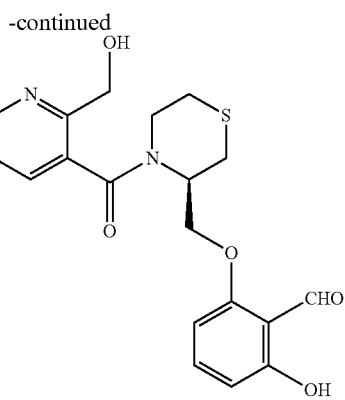

Step 1

Into a 2-L three-necked round-bottom flask, was placed a solution of (3-bromopyridin-2-yl)methanol (50 g, 0.267 mol, 1.0 equiv) in DCM (1.0 L) and 1H-imidazole (36.4 g, 0.534 mol, 2.0 equiv). After the mixture was cooled to 0° C., tert-butyl(chloro)dimethylsilane (48.1 g, 0.320 mol, 1.2 equiv) was added by three batches. The reaction solution was warmed to room temperature and stirred for 4 h. The reaction mixture was diluted with $H_2O$ (1.0 L) and extracted with 2×500 mL of DCM. The combined organic phase was dried over anhydrous sodium sulfate and filtered. The filtrate was concentrated under reduced pressure, and the residue was purified by silica gel column with ethyl acetate/petroleum ether (1:10) to provide the title compound. LCMS (ES) [M+1]$^+$ m/z 302.d

Step 2

Into a 2-L three-necked round-bottom flask purged and maintained with an inert atmosphere of nitrogen, was placed a solution of 3-bromo-2-(((tert-butyldimethylsilyl)oxy)methyl)pyridine (70.0 g, 0.233 mol, 1.0 equiv) in THF (700 mL). This was followed by the addition of n-BuLi (2.5 M in hexane) (102.5 mL, 0.256 mol, 1.1 equiv) dropwise with stirring at −78° C. After addition, the mixture was stirred for 0.5 h, and ethyl carbonochloridate (37.8 g, 0.350 mol, 1.5 equiv) was added at the same temperature and stirred for 1 h. The reaction was then quenched by the addition of 500 mL of aqueous $NH_4Cl$ and extracted with 2×600 mL of ethyl acetate. The combined organic phase was dried over anhydrous sodium sulfate and filtered, and the filtrate was concentrated under reduced pressure. The residue was purified by silica gel column with ethyl acetate/petroleum ether (1:4) to provide the title compound. LCMS (ES) [M+1]$^+$ m/z 296.

Step 3

Into a 1-L three-necked round-bottom flask, was placed ethyl 2-(((tert-butyldimethylsilyl)oxy)methyl)nicotinate (38.6 g, 0.131 mol, 1.0 equiv), MeOH (400 mL), and $H_2O$ (200 mL). This was followed by the addition of LiOH $H_2O$ (11.0 g, 0.262 mol, 2.0 equiv) at 0° C. The mixture was stirred for 2 h at room temperature. The mixture was concentrated to remove the solvent, and the pH value of the residue was adjusted to 7 with citric acid. The solution was filtered, and the solid was dried under infrared lamp. 2-(((tert-butyldimethylsilyl)oxy)methyl)nicotinic acid was obtained. LCMS (ES) [M+1]$^+$ m/z: 268.

Step 4

Compound 6h was prepared as described in Scheme 6B. To a solution of 2-[[(tert-butyldimethylsilyl)oxy]methyl] pyridine-3-carboxylic acid (10.0 g, 37.3 mmol, 1.0 equiv), DIPEA (12.1 g, 93.5 mmol, 2.5 equiv) and HATU (17.06 g, 44.877 mmol, 1.20 equiv) in DMF (100 mL) was added (3R)-thiomorpholin-3-ylmethanol (4.98 g, 37.397 mmol, 1.00 equiv) at 0° C. in portions. The resulting solution was stirred for 4 hr at 0-25° C. The reaction was then quenched by the addition of 200 mL of water. The resulting solution was extracted with 3×200 mL of ethyl acetate, dried over anhydrous sodium sulfate, and concentrated under vacuum. The residue was applied onto a silica gel column with ethyl acetate/petroleum ether (1:100 to 1:10). This resulted in [(3R)-4-(2-[[(tert-butyldimethylsilyl)oxy]methyl]pyridine-3-carbonyl)thiomorpholin-3-yl]methanol. LCMS (ES) [M+1]$^+$ m/z: 383.2; Retention time 1.138 min. $^1$H-NMR: (300 MHz, CDCl$_3$, ppm): δ 8.60 (dd, J=4.8, 1.5 Hz, 1H), 7.67-7.53 (m, 1H), 7.29-7.25 (m, 1H), 5.37-4.90 (m, 2H), 4.86-4.74 (m, 1H), 4.38-4.22 (m, 1H), 3.90-3.61 (m, 1H), 3.58-3.42 (m, 2H), 3.25-3.12 (m, 1H), 2.94-2.39 (m, 4H), 0.96-0.88 (m, 9H), 0.21-0.01 (m, 6H).

Step 5

A solution of [(3R)-4-(2-[[(tert-butyldimethylsilyl)oxy]methyl]pyridine-3-carbonyl)thiomorpholin-3-yl]methanol (11.0 g, 28.7 mmol, 1.0 equiv), 2,6-dihydroxybenzaldehyde (4.7 g, 34.5 mmol, 1.2 equiv) and PPh$_3$ (9.8 g, 37.3 mmol, 1.3 equiv) in DCM (1.1 L) was cooled to 0° C. under Ar atmosphere. A solution of DBAD (7.28 g, 230.2 mmol, 1.1 equiv) in DCM (100 mL) was added dropwise. The resulting solution was stirred for 16 hr at 0-25° C. The reaction was concentrated under vacuum. The residue was applied onto a silica gel column with ethyl acetate/petroleum ether (1:100 to 1:5). This resulted in 2-[[(3R)-4-(2-[[(tert-butyldimethylsilyl)oxy]methyl]pyridine-3-carbonyl)thiomorpholin-3-yl]methoxy]-6-hydroxybenzaldehyde. LCMS (ES) [M+1]$^+$ m/z: 503.2; Retention time 1.223 min. $^1$H-NMR: (300 MHz, DMSO-d6, ppm): δ 11.74 (br, 1H), 10.24 (br, 1H), 8.59 (dd, J=4.9, 1.7 Hz, 1H), 7.88-7.41 (m, 3H), 6.76-6.54 (m, 2H), 5.44-5.32 (m, 1H), 4.90-4.44 (m, 4H), 3.37-3.18 (m, 2H), 3.22-2.69 (m, 4H), 0.89-0.72 (m, 9H), 0.13-0.11 (m, 6H).

Step 6

Into a 500-mL 3-necked round-bottom flask, was placed 2-[[(3R)-4-(2-[[(tert-butyldimethylsilyl)oxy]methyl]pyridine-3-carbonyl)thiomorpholin-3-yl]methoxy]-6-hydroxybenzaldehyde (13.6 g, 27.0 mmol, 1.0 equiv) and THF (150 mL). After the reaction was cooled to 0° C., a solution of TEA-3HF (13.0 g, 80.9 mmol, 3.0 equiv) was added dropwise. The resulting solution was stirred for 5 h at 0-25° C. The pH value of the solution was adjusted to 8 with NaHCO$_3$ (2 mol/L). The resulting solution was extracted with ethyl acetate (200 mL×3), and the organic layers combined and concentrated. The crude product was purified by Flash-Prep-HPLC with the following conditions (Intel-Flash-1): Column, C18 silica gel; mobile phase, MeCN=10/90 increasing to MeCN=90/10; Detector, 220. This resulted in 2-hydroxy-6-[[(3R)-4-[2-(hydroxymethyl)pyridine-3-carbonyl]thiomorpholin-3-yl]methoxy]benzaldehyde. LCMS (ES, m/z): [M+H]+: 389.1; Retention time 1.060 min. Analytical SFC retention time: 3.641 min. Conditions for SFC were as follows: Instrument Name: Shimadzu LC30AD SF; Column: OD-3, 100*3.0 mm, 3 um; Column ID:

OD3SCK-TG002; Oven Temperature: 35 C; Total Flow: 2.5000 mL/min; Start Conc. of Pump B: 10.0%; BPR Pressure: 15.00 MPa.

$^1$H-NMR (300 MHz, DMSO-d6, ppm): δ 11.77 (br, 1H), 10.30 (br, 1H), 8.54 (dd, J=4.8, 1.5 Hz, 1H), 7.76-7.36 (m, 3H), 6.75-6.52 (m, 2H), 5.45-4.07 (m, 6H), 3.46-2.72 (m, 5H), 2.51-2.39 (m, 1H).

Based on the product of Scheme 10B, it was determined that Compound 13, Enantiomer 1 corresponds to (R)-2-hydroxy-6-((4-(2-(2-hydroxyethyl)nicotinoyl)thiomorpholin-3-yl)methoxy)benzaldehyde.

Example 11. (S)-2-hydroxy-6-((1-(2-(2-methoxyethyl)benzoyl)piperidin-2-yl)methoxy)benzaldehyde, Compound 14

Compound 14 was synthesized according to Scheme 11.

Scheme 11

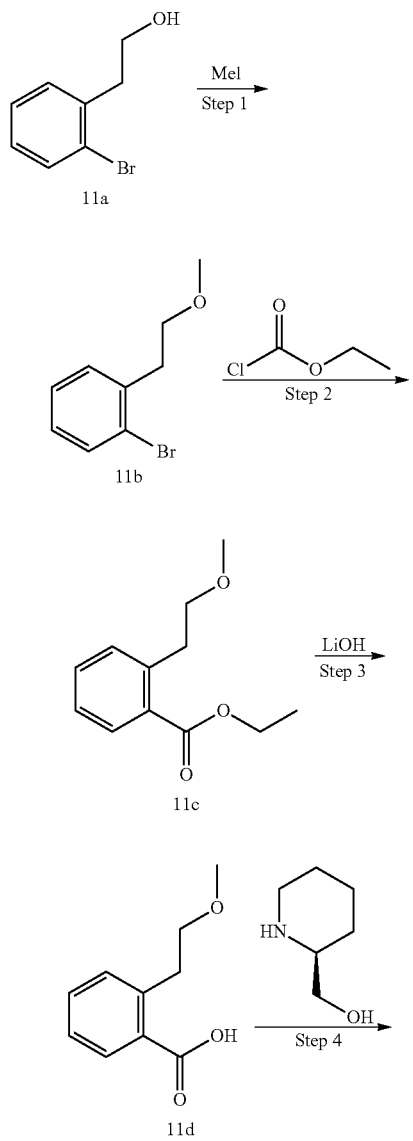

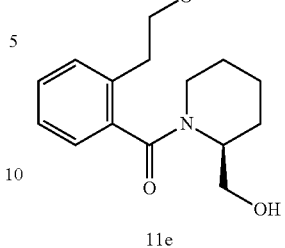

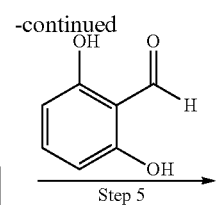

Step 1. Synthesis of 1-bromo-2-(2-methoxyethyl)benzene

Into a 500-mL 3-necked round-bottom flask purged and maintained with an inert atmosphere of nitrogen was placed 2-(2-bromophenyl)ethanol (10.0 g, 49.7 mmol, 1.00 equiv) and DMF (100 mL) cooled to 0° C. by ice water, and then NaH (2.39 g, 99.5 mmol, 2.00 equiv) was added in several portions. The resulting solution was stirred for 40 min at 0° C., and then MeI (10.59 g, 74.610 mmol, 1.50 equiv) was added dropwise with stirring at 0° C. over 15 mins. The resulting solution was allowed to warm up to room temperature with stirring for an additional 5 hr. The reaction was then quenched by the addition of water/ice. The resulting solution was extracted with 3×100 mL of ethyl acetate and the organic layers were combined and dried over anhydrous sodium sulfate and concentrated under vacuum. The residue was purified by silica gel column chromatography with ethyl acetate/hexane (1:3) as eluents. This resulted in 1-bromo-2-(2-methoxyethyl)benzene. LCMS (ES) [M+1]$^+$ m/z: 215.

Step 2. Synthesis of ethyl 2-(2-methoxyethyl)benzoate

Into a 500-mL 3-necked round-bottom flask purged and maintained with an inert atmosphere of nitrogen was placed 1-bromo-2-(2-methoxyethyl)benzene (10.0 g, 46.5 mmol, 1.00 equiv) and THF (100 mL). The mixture was cooled to −78° C., and n-butyllithium (39 mL, 97.7 mmol, 2.10 equiv) was added dropwise into the solution. The resulting solution was stirred for 40 min at −78° C., then ethyl chloroformate (7.57 g, 69.757 mmol, 1.50 equiv) was added dropwise. The resulting solution was brought to room temperature with stirring for an additional 5 min at −78° C. and then stirred for an additional 16 hr at room temperature. The reaction was then quenched by the addition of water/ice. The resulting solution was extracted with 3×100 mL of ethyl acetate, and the organic layers were combined and dried over anhydrous sodium sulfate. The residue was purified by silica gel column chromatography with ethyl acetate/petroleum ether (1:5) as eluent. This resulted in ethyl 2-(2-methoxyethyl) benzoate. LCMS (ES) [M+1]⁺ m/z: 209.

Step 3. Synthesis of 2-(2-methoxyethyl)benzoic acid

Into a 100-mL round-bottom flask was placed ethyl 2-(2-methoxyethyl)benzoate (1.20 g, 5.76 mmol, 1.00 equiv), LiOH (0.55 g, 23.0 mmol, 4.00 equiv) and THF (15.0 mL), and H₂O (3.00 mL). The resulting solution was stirred for 4 hr at 50° C. in an oil bath. The reaction mixture was cooled with a water/ice bath. The pH of the solution was adjusted to 5 with HCl (2M). The resulting solution was extracted with 3×50 mL of ethyl acetate, and the organic layers were combined and dried over anhydrous sodium sulfate and concentrated under vacuum. This resulted in 2-(2-methoxyethyl)benzoic acid. LCMS (ES) [M+1]⁺ m/z: 181.

Step 4. Synthesis of [(2S)-1-[2-(2-methoxyethyl) benzoyl]piperidin-2-yl]methanol Into a 250-mL round-bottom flask was placed 2-(2-methoxyethyl)benzoic acid (550 mg, 3.05 mmol, 1.00 equiv), (2S)-piperidin-2-ylmethanol (421 mg, 3.66 mmol, 1.20 equiv), HATU (2.32 g, 6.10 mmol, 2.00 equiv), DIEA (788 mg, 6.10 mmol, 2.00 equiv) and DCM (40.00 mL). The resulting solution was stirred for 4 hr at room temperature. The resulting solution was extracted with 3×30 mL of dichloromethane, and the organic layers were combined and dried over anhydrous sodium sulfate and concentrated under vacuum. The residue was purified by silica gel column with ethyl acetate/petroleum ether (2:5) as eluents. This resulted in [(2S)-1-[2-(2-methoxyethyl)benzoyl]piperidin-2-yl] methanol. LCMS (ES) [M+1]⁺ m/z: 278.

Step 5. Synthesis of (S)-2-hydroxy-6-((1-(2-(2-methoxyethyl)benzoyl)piperidin-2-yl)methoxy)benzaldehyde Into a 100-mL round-bottom flask purged and maintained with an inert atmosphere of nitrogen was placed [(2S)-1-[2-(2-methoxyethyl)benzoyl]piperidin-2-yl]methanol (470 mg, 1.70 mmol, 1.00 equiv), 2,6-dihydroxybenzaldehyde (468 mg, 3.39 mmol, 2.00 equiv), PPh₃ (888 mg, 3.39 mmol, 2.00 equiv) and THF (30.0 mL). The resulting solution was stirred for 15 min at 0° C., and then DIAD (685 mg, 3.39 mmol, 2.00 equiv) was added dropwise. The resulting solution was stirred for 15 min at 0° C. The resulting solution was warmed up to room temperature with stirring for an additional 16 hr. The resulting solution was extracted with 3×30 mL of ethyl acetate, and the organic layers were combined and dried over anhydrous sodium sulfate. The crude product was purified by Prep-HPLC [Column: Atlantis HILIC OBD Column, 19*150 mm*5 um; mobile phase: Water (0.1% FA) and ACN (10% PhaseB up to 50% in 10 min, up to 90% in 10 min)]. This resulted in (S)-2-hydroxy-6-((1-(2-(2-methoxyethyl)benzoyl)piperidin-2-yl)methoxy) benzaldehyde. LCMS (ES) [M+1]⁺ m/z: 398. ¹H NMR (300 MHz, DMSO-d6) 11.64 (br, 1H), 10.29 (br, 1H), 7.50-6.98 (m, 5H), 6.81-6.65 (m, 1H), 6.53 (d, J=8.4 Hz, 1H), 5.25-5.11 (m, 1H), 4.48 (d, J=11.3 Hz, 1H), 4.29 (dd, J=10.2, 6.1 Hz, 1H), 3.65-3.31 (m, 2H), 3.29-2.99 (m, 2H), 3.06 (s, 3H), 2.88-2.63 (m, 2H), 1.92-1.34 (m, 6H).

Example 12. (S)-3-(2-(2-((2-formyl-3-hydroxyphenoxy)methyl)piperidine-1-carbonyl)phenyl)propanenitrile, Compound 15

Compound 15 was synthesized according to Scheme 12.

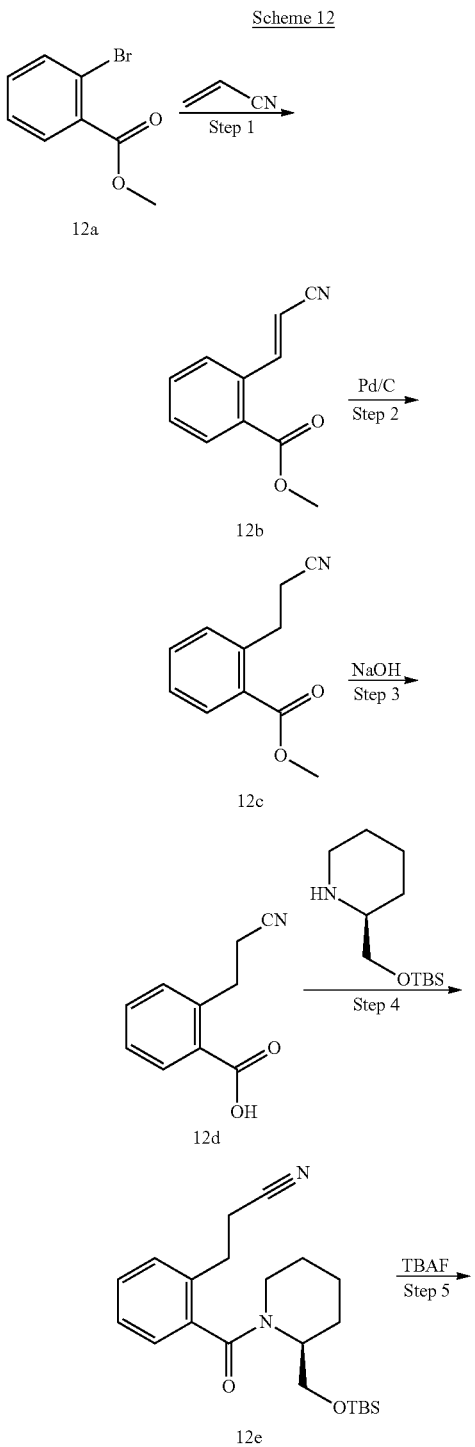

Scheme 12

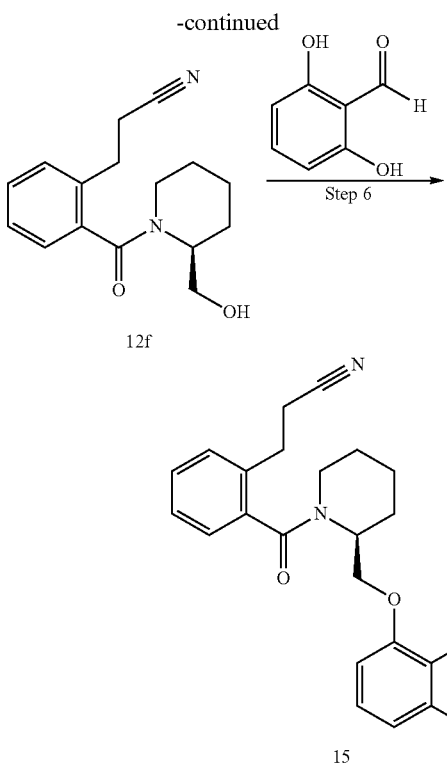

Step 1. Synthesis of methyl 2-[(E)-2-cyanoeth-1-en-1-yl]benzoate

Into a 100-mL round-bottom flask, was placed methyl 2-bromobenzoate (5.00 g, 23.251 mmol, 1.00 equiv), acrylonitrile (12.34 g, 232.508 mmol, 10.00 equiv), DIEA (6.01 g, 46.502 mmol, 2.00 equiv), and bis(tributylphosphine) palladium (1.19 g, 2.325 mmol, 0.10 equiv). The resulting solution was stirred for 16 hr at 80° C. The resulting mixture was concentrated. The residue was applied onto a silica gel column with ethyl acetate/petroleum ether (1:5) as eluents. The collected fractions were combined and concentrated. This resulted in methyl 2-[(1E)-2-cyanoeth-1-en-1-yl]benzoate. GCMS M+: 187.

Step 2. Synthesis of methyl 2-(2-cyanoethyl)benzoate

Into a 100-mL round-bottom flask, was placed methyl 2-[(1E)-2-cyanoeth-1-en-1-yl]benzoate (2.40 g, 12.8 mmol, 1.00 equiv), methanol (50 mL), and Pd/C (0.24 g). The flask was evacuated and flushed three times with nitrogen, followed by flushing with hydrogen. The mixture was stirred 16 h at room temperature under an atmosphere of hydrogen. The solids were filtered out. The resulting mixture was concentrated. This resulted in methyl 2-(2-cyanoethyl)benzoate. LCMS (ES) [M+1]+ m/z 190.1.

Step 3. Synthesis of 2-(2-cyanoethyl)benzoic acid

Into a 100-mL round-bottom flask was placed methyl 2-(2-cyanoethyl)benzoate (2.20 g, 11.627 mmol, 1.00 equiv), methanol (20 mL), water (20 mL) and sodium hydroxide (0.93 g, 23.252 mmol, 2.00 equiv). The resulting solution was stirred for 4 hr at 25° C. The reaction was then quenched by the addition of 100 mL of water. The pH value of the solution was adjusted to 5 with HCl (1 mol/L). The solids were collected by filtration. This resulted in 2-(2-cyanoethyl)benzoic acid. LCMS (ES) [M−1]− m/z 174.1.

Step 4. Synthesis of 3-[2-[(2S)-2-[[(tert-butyldimethylsilyl)oxy]methyl]piperidine-1-carbonyl]phenyl]propanenitrile Into a 100-mL round-bottom flask was placed 2-(2-cyanoethyl)benzoic acid (1.80 g, 10.275 mmol, 1.00 equiv), DCM (30.00 mL), (2S)-2-[[(tert-butyldimethylsilyl)oxy]methyl]piperidine (2.36 g, 10.275 mmol, 1.00 equiv), HATU (5.86 g, 15.412 mmol, 1.50 equiv) and DIEA (3.98 g, 30.824 mmol, 3.00 equiv). The resulting solution was stirred for 16 hr at 25° C. The resulting mixture was concentrated. The residue was purified by silica gel column chromatography with ethyl acetate/petroleum ether (1:2) as eluents. The collected fractions were combined and concentrated. This resulted in 3-[2-[(2S)-2-[[(tert-butyldimethylsilyl)oxy]methyl]piperidine-1-carbonyl]phenyl]propanenitrile. LCMS (ES) [M+1]+ m/z 387.2.

Step 5. Synthesis of 3-[2-[(2S)-2-(hydroxymethyl)piperidine-1-carbonyl]phenyl]propanenitrile Into a 100-mL round-bottom flask, was placed 3-[2-[(2S)-2-[[(tert-butyldimethylsilyl)oxy]methyl]piperidine-1-carbonyl]phenyl]propanenitrile (2.00 g, 5.173 mmol, 1.00 equiv), tetrahydrofuran (20 mL) and TBAF (0.27 g, 1.035 mmol, 0.20 equiv). The resulting solution was stirred for 2 hr at 25° C. The resulting mixture was concentrated. The residue was purified by silica gel column chromatography with ethyl acetate/petroleum ether (1:2) as eluents. The collected fractions were combined and concentrated. This resulted in 3-[2-[(2S)-2-(hydroxymethyl)piperidine-1-carbonyl]phenyl]propanenitrile. LCMS (ES) [M+1]+ m/z 273.2.

Step 6. Synthesis of (S)-3-(2-(2-((2-formyl-3-hydroxyphenoxy)methyl)piperidine-1-carbonyl)phenyl)propanenitrile Into a 50-mL round-bottom flask, was placed 3-[2-[(2S)-2-(hydroxymethyl)piperidine-1-carbonyl]phenyl]propanenitrile (100.00 mg, 0.367 mmol, 1.00 equiv), tetrahydrofuran (8.00 mL), 2,6-dihydroxybenzaldehyde (50.72 mg, 0.367 mmol, 1.00 equiv), PPh3 (115.57 mg, 0.441 mmol, 1.20 equiv), and DIAD (89.10 mg, 0.441 mmol, 1.20 equiv). The resulting solution was stirred for 16 hr at 25° C. The resulting mixture was concentrated under vacuum. The crude reaction mixture was filtered and subjected to reverse phase preparative HPLC (Prep-C18, 20-45M, 120 g, Tianjin Bonna-Agela Technologies; gradient elution of 30% MeCN in water to 40% MeCN in water over a 10 min period, where both solvents contain 0.1% FA) to provide (S)-3-(2-(2-((2-formyl-3-hydroxyphenoxy)methyl)piperidine-1-carbonyl)phenyl)propanenitrile. LCMS (ES) [M+1]+ m/z 393.2. 1H NMR (300 MHz, DMSO-d6) δ 11.72 (br, 1H), 10.21 (m, 1H), 7.67-7.22 (m, 4H), 7.06-6.33 (m, 2H), 5.31-5.15 (m, 1H), 4.70-4.12 (m, 2H), 3.39-3.12 (m, 2H), 2.86-2.67 (m, 4H), 1.93-1.25 (m, 6H).

Example 13. (S)-2-hydroxy-6-((1-(3-(2-hydroxyethyl)picolinoyl)piperidin-2-yl)methoxy)benzaldehyde, Compound 16

Compound 16 was synthesized according to Scheme 13.

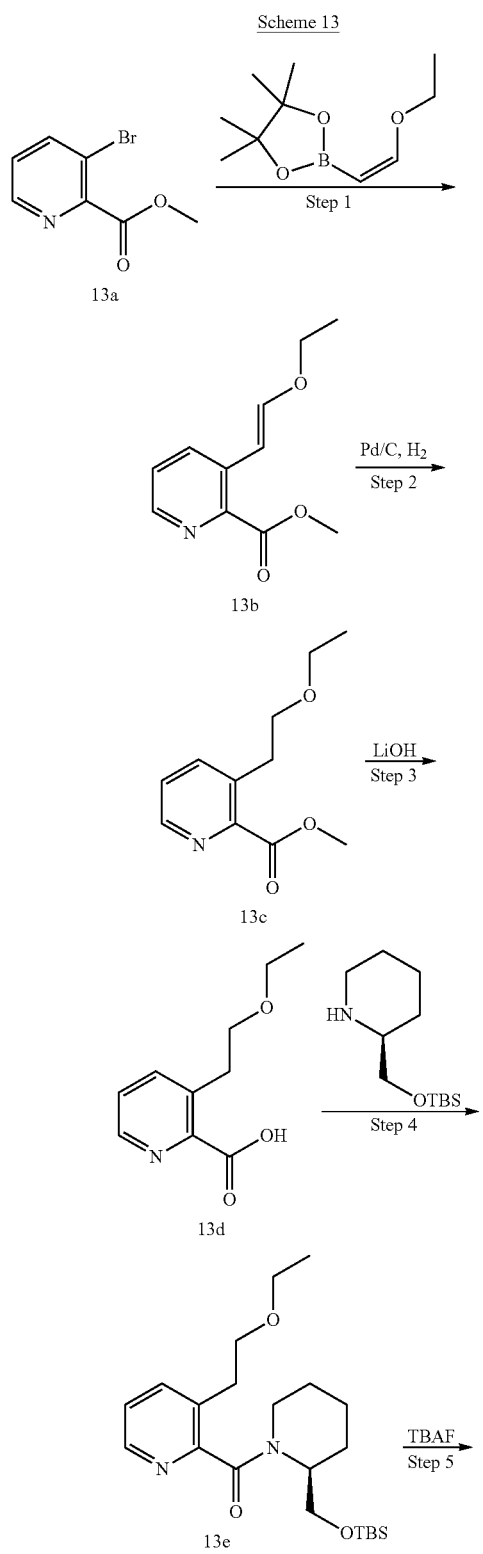
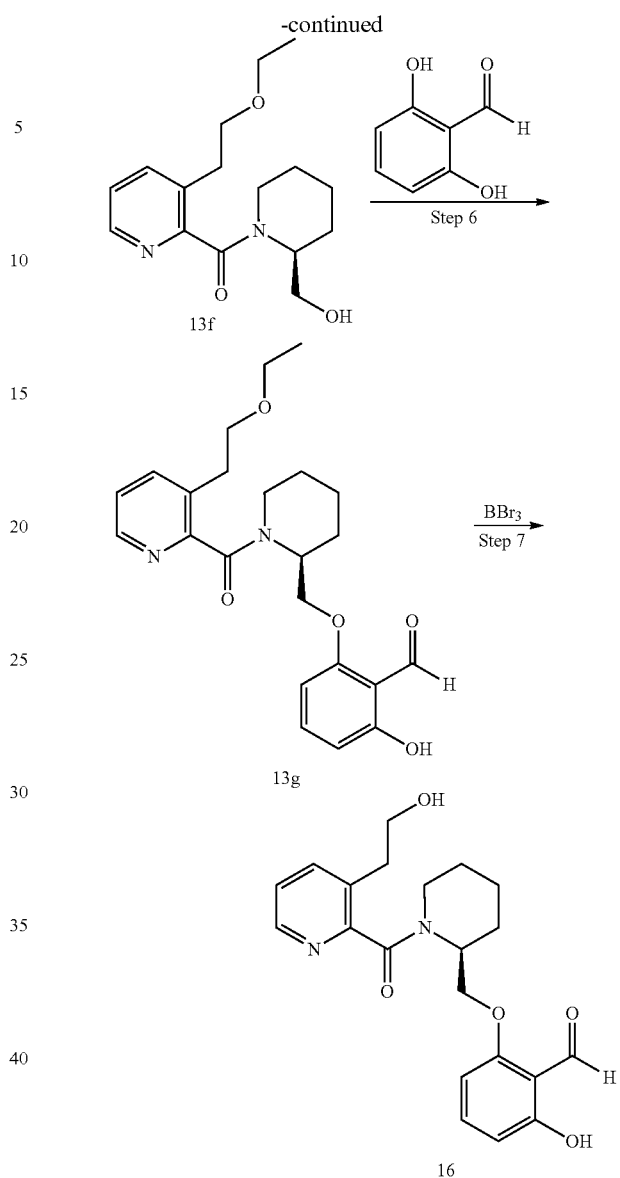

Step 1. Synthesis of methyl 3-[(E)-2-ethoxyethenyl]pyridine-2-carboxylate

Into a 100-mL round-bottom flask purged and maintained with an inert atmosphere of nitrogen, was placed 2-[(Z)-2-ethoxyethenyl]-4,4,5,5-tetramethyl-1,3,2-dioxaborolane (4.13 g, 20.85 mmol, 1.50 equiv), methyl 3-bromopyridine-2-carboxylate (3.00 g, 13.89 mmol, 1.00 equiv), dioxane (30.00 mL), H$_2$O (6.00 mL), Na$_2$CO$_3$ (4.42 g, 41.66 mmol, 3.00 equiv), and Pd(PPh$_3$)$_4$ (1.60 g, 1.39 mmol, 0.10 equiv). The resulting solution was stirred overnight at 80° C. The reaction mixture was cooled to room temperature. The solids were filtered out, and the filtrate was concentrated. The residue was purified by silica gel column chromatography with THF/PE (30%) as eluent. This resulted in methyl 3-[(E)-2-ethoxyethenyl]pyridine-2-carboxylate. LCMS (ES) [M+1]$^+$ m/z 208.

Step 2. Synthesis of methyl 3-(2-ethoxyethyl)pyridine-2-carboxylate

Into a purged 100-mL round-bottom flask was placed methyl 3-[(E)-2-ethoxyethenyl]pyridine-2-carboxylate (2.60 g, 12.55 mmol, 1.00 equiv), Pd/C (500.00 mg, 4.69 mmol, 0.37 equiv), and MeOH (30.00 mL). The flask was evacuated and flushed three times with nitrogen, followed by flushing with hydrogen. The resulting solution was stirred overnight at room temperature. The solids were filtered out, and the filtrate was concentrated. This resulted in methyl 3-(2-ethoxyethyl)pyridine-2-carboxylate. LCMS (ES) [M+1]+ m/z 210.

Step 3. Synthesis of 3-(2-ethoxyethyl)pyridine-2-carboxylic acid

Into a 100-mL round-bottom flask, was placed methyl 3-(2-ethoxyethyl)pyridine-2-carboxylate (2.50 g, 11.95 mmol, 1.00 equiv), THF (25.00 mL), H$_2$O (5.00 mL), and LiOH H$_2$O (1.00 g, 23.83 mmol, 1.99 equiv). The resulting solution was stirred for 2 h at room temperature. The resulting mixture was concentrated and was adjusted to pH 3-4 with HCl (1 mol/L). The resulting solution was extracted with 3×20 mL of ethyl acetate, and the organic layers were combined and dried over anhydrous sodium sulfate and concentrated. This resulted in 3-(2-ethoxyethyl)pyridine-2-carboxylic acid. LCMS (ES) [M+1]+ m/z 196.

Step 4. Synthesis of 2-[(2S)-2-[[(tert-butyldimethylsilyl)oxy]methyl]piperidine-1-carbonyl]-3-(2-ethoxyethyl)pyridine Into a 100-mL 3-necked round-bottom flask was placed (2S)-2-[[(tert-butyldimethylsilyl)oxy]methyl]piperidine (2.12 g, 9.22 mmol, 1.00 equiv), 3-(2-ethoxyethyl)pyridine-2-carboxylic acid (1.80 g, 9.22 mmol, 1.00 equiv), DCM (20.00 mL), Et$_3$N (1.87 g, 18.44 mmol, 2.00 equiv), EDCI (2.12 g, 11.06 mmol, 1.20 equiv), and HOBt (1.50 g, 11.06 mmol, 1.20 equiv). The resulting solution was stirred overnight at room temperature. The reaction was then quenched by the addition of 10 mL of water. The resulting solution was extracted with 3×20 mL of dichloromethane, and the organic layers were combined and dried over anhydrous sodium sulfate and concentrated. This resulted in 2-[(2S)-2-[[(tert-butyldimethylsilyl)oxy]methyl]piperidine-1-carbonyl]-3-(2-ethoxyethyl)pyridine. LCMS (ES) [M+1]+ m/z 407.

Step 5. Synthesis of [(2S)-1-[3-(2-ethoxyethyl)pyridine-2-carbonyl]piperidin-2-yl]methanol Into a 100-mL round-bottom flask, was placed 2-[(2S)-2-[[(tert-butyldimethylsilyl)oxy]methyl]piperidine-1-carbonyl]-3-(2-ethoxyethyl)pyridine (3.00 g, 7.38 mmol, 1.00 equiv), THF (20.00 mL), and TBAF/THF (14.75 mL, 14.75 mmol, 2.00 equiv). The resulting solution was stirred overnight at room temperature. The resulting mixture was concentrated. The residue was purified by silica gel column with THF/PE (45%) as eluent. This resulted in [(2S)-1-[3-(2-ethoxyethyl)pyridine-2-carbonyl]piperidin-2-yl]methanol. LCMS (ES) [M+1]+ m/z 293.

Step 6. Synthesis of 2-[[(2S)-1-[3-(2-ethoxyethyl)pyridine-2-carbonyl]piperidin-2-yl]methoxy]-6-hydroxybenzaldehyde Into a 100-mL 3-necked round-bottom flask, was placed [(2S)-1-[3-(2-ethoxyethyl)pyridine-2-carbonyl]piperidin-2-yl]methanol (1.70 g, 5.81 mmol, 1.00 equiv), 2,6-dihydroxybenzaldehyde (0.96 g, 6.95 mmol, 1.20 equiv), DCM (40.00 mL), and PPh$_3$ (1.83 g, 6.98 mmol, 1.20 equiv). This was followed by the addition of DIAD (1.41 g, 6.98 mmol, 1.20 equiv) dropwise with stirring at 0° C. The resulting solution was stirred for 4 h at room temperature. The resulting mixture was concentrated. The residue was purified by silica gel column with THF/PE (30%) as eluents. This resulted in 2-[[(2S)-1-[3-(2-ethoxyethyl)pyridine-2-carbonyl]piperidin-2-yl]methoxy]-6-hydroxybenzaldehyde. LCMS (ES) [M+1]+ m/z 413.

Step 7. Synthesis of (S)-2-hydroxy-6-((1-(3-(2-hydroxyethyl)picolinoyl)piperidin-2-yl)methoxy)benzaldehyde Into a 100-mL 3-necked round-bottom flask, was placed 2-[[(2S)-1-[3-(2-ethoxyethyl)pyridine-2-carbonyl]piperidin-2-yl]methoxy]-6-hydroxybenzaldehyde (500.00 mg, 1.21 mmol, 1.00 equiv) and DCM (20.00 mL). This was followed by the addition of BBr$_3$/DCM (12.12 mL, 12.12 mmol, 10.00 equiv) dropwise with stirring at −78° C. The resulting solution was stirred for 1 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product was purified by Prep-HPLC [Column, XBridge Prep C18 OBD Column, 19 cm, 150 mm, 5um; mobile phase, Water (0.1% HCOOH) and AcCN (30% Phase B up to 60% in 11 min); Detector, 254. This resulted in (S)-2-hydroxy-6-((1-(3-(2-hydroxyethyl)picolinoyl)piperidin-2-yl)methoxy)benzaldehyde. LCMS: (ES, m/z): [M+1]+ 385.0. $^1$H-NMR (300 MHz, DMSO-d6) δ 11.81 (s, 1H), 10.29 (d, J=6.6 Hz, 1H), 8.40-8.35 (m, 1H), 7.77 (dd, J=7.8, 1.6 Hz, 1H), 7.57-7.44 (m, 1H), 7.36 (dd, J=7.9, 4.7 Hz, 1H), 6.73 (d, J=8.3 Hz, 1H), 6.63-6.46 (m, 1H), 5.20 (s, 1H), 4.68-4.40 (m, 2H), 4.33-4.20 (m, 1H), 3.67-3.56 (m, 1H), 3.60-3.52 (m, 1H), 3.22-3.00 (m, 2H), 2.79-2.59 (m, 2H), 1.92-1.53 (m, 6H).

Example 14. (S)-2-hydroxy-6-((1-(2-(2-(pyrrolidin-1-yl)ethyl)benzoyl)piperidin-2-yl)methoxy)benzaldehyde, Compound 17

Compound 17 was synthesized according to Scheme 14.

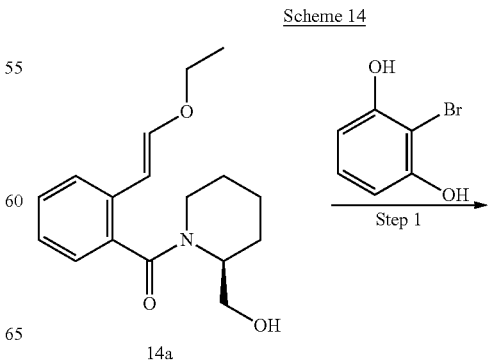

Scheme 14

14a

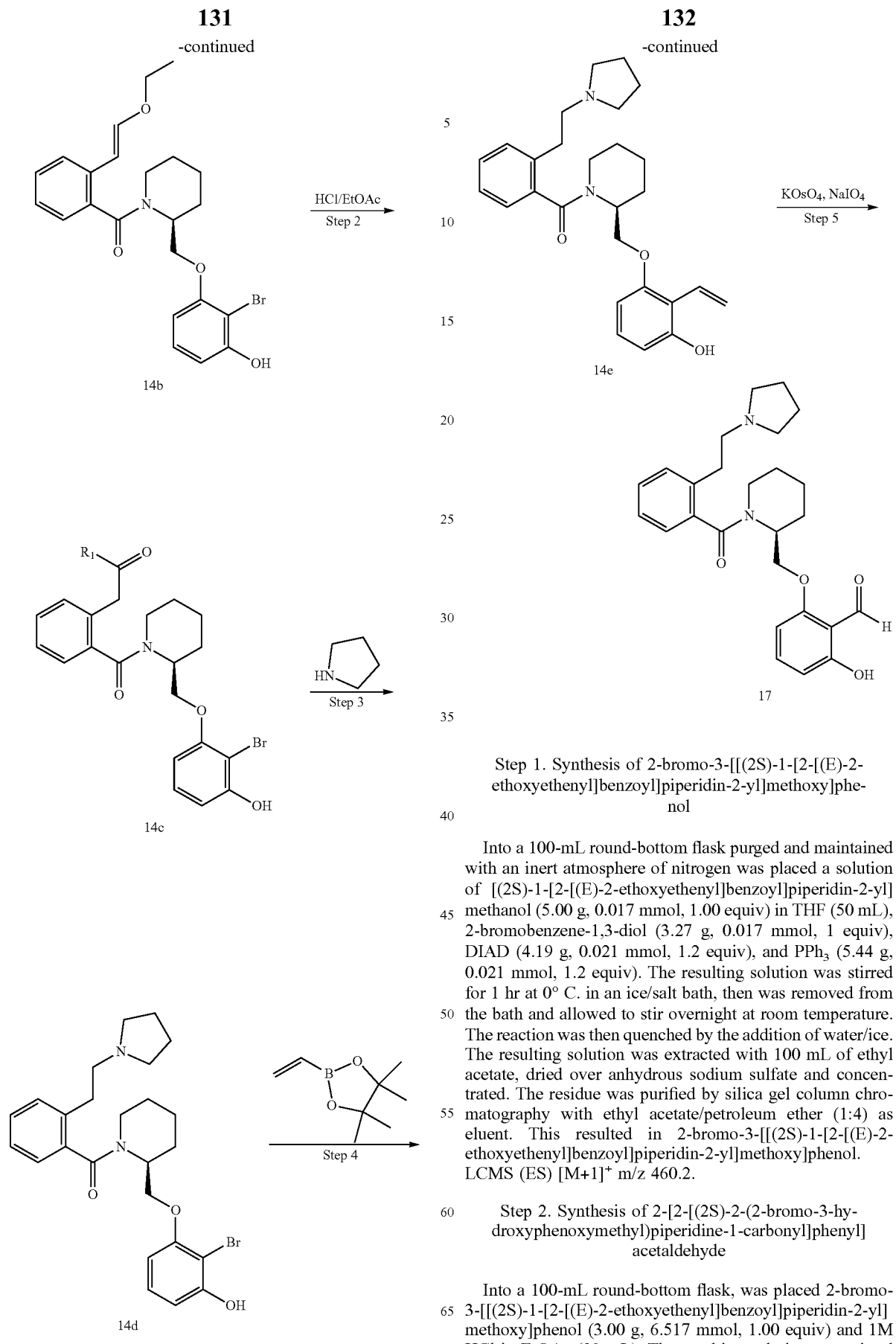

Step 1. Synthesis of 2-bromo-3-[[(2S)-1-[2-[(E)-2-ethoxyethenyl]benzoyl]piperidin-2-yl]methoxy]phenol Into a 100-mL round-bottom flask purged and maintained with an inert atmosphere of nitrogen was placed a solution of [(2S)-1-[2-[(E)-2-ethoxyethenyl]benzoyl]piperidin-2-yl]methanol (5.00 g, 0.017 mmol, 1.00 equiv) in THF (50 mL), 2-bromobenzene-1,3-diol (3.27 g, 0.017 mmol, 1 equiv), DIAD (4.19 g, 0.021 mmol, 1.2 equiv), and PPh$_3$ (5.44 g, 0.021 mmol, 1.2 equiv). The resulting solution was stirred for 1 hr at 0° C. in an ice/salt bath, then was removed from the bath and allowed to stir overnight at room temperature. The reaction was then quenched by the addition of water/ice. The resulting solution was extracted with 100 mL of ethyl acetate, dried over anhydrous sodium sulfate and concentrated. The residue was purified by silica gel column chromatography with ethyl acetate/petroleum ether (1:4) as eluent. This resulted in 2-bromo-3-[[(2S)-1-[2-[(E)-2-ethoxyethenyl]benzoyl]piperidin-2-yl]methoxy]phenol. LCMS (ES) [M+1]$^+$ m/z 460.2.

Step 2. Synthesis of 2-[2-[(2S)-2-(2-bromo-3-hydroxyphenoxymethyl)piperidine-1-carbonyl]phenyl]acetaldehyde Into a 100-mL round-bottom flask, was placed 2-bromo-3-[[(2S)-1-[2-[(E)-2-ethoxyethenyl]benzoyl]piperidin-2-yl]methoxy]phenol (3.00 g, 6.517 mmol, 1.00 equiv) and 1M HCl in EtOAc (20 mL). The resulting solution was stirred overnight at room temperature. The resulting mixture was concentrated under vacuum. This resulted in 2-[2-[(2S)-2-(2-bromo-3-hydroxyphenoxymethyl)piperidine-1-carbonyl]phenyl]acetaldehyde. LCMS (ES) [M+1]⁺ m/z 432.2.

Step 3. Synthesis of 2-bromo-3-[[(2S)-1-[2-[2-(pyrrolidin-1-yl)ethyl]benzoyl]piperidin-2-yl]methoxy]phenol Into a 100-mL round-bottom flask, was placed a solution of 2-[2-[(2S)-2-(2-bromo-3-hydroxyphenoxymethyl)piperidine-1-carbonyl]phenyl]acetaldehyde (2.20 g, 0.005 mmol, 1.00 equiv) in MeOH (10 mL), pyrrolidine (0.54 g, 0.008 mmol, 1.5 equiv), MeOH (1 equiv), and NaBH₄ (0.48 g, 0.013 mmol, 2.5 equiv). The resulting solution was stirred for 1 hr at 0° C. in an ice/salt bath. The resulting solution was stirred overnight at room temperature. The reaction was then quenched by the addition of water/ice. The resulting solution was extracted with 100 mL of dichloromethane, dried over anhydrous sodium sulfate and concentrated. The residue was purified by silica gel column chromatography with dichloromethane/methanol (1:10) as eluents. This resulted in 2-bromo-3-[[(2S)-1-[2-[2-(pyrrolidin-1-yl)ethyl]benzoyl]piperidin-2-yl]methoxy]phenol. LCMS (ES) [M+1]⁺ m/z 487.2.

Step 4. Synthesis of 2-ethenyl-3-[[(2S)-1-[2-[2-(pyrrolidin-1-yl)ethyl]benzoyl]piperidin-2-yl]methoxy]phenol Into a 25-mL round-bottom flask purged and maintained with an inert atmosphere of nitrogen, was placed 2-bromo-3-[[(2S)-1-[2-[2-(pyrrolidin-1-yl)ethyl]benzoyl]piperidin-2-yl]methoxy]phenol (600.00 mg, 1.231 mmol, 1.00 equiv) in dioxane (10 mL), 2-ethenyl-4,4,5,5-tetramethyl-1,3,2-dioxaborolane (189.59 mg, 1.231 mmol, 1 equiv), K₂CO₃ (340.24 mg, 2.462 mmol, 2 equiv), and Pd(dppf)Cl₂ (45.03 mg, 0.062 mmol, 0.05 equiv). The resulting solution was stirred overnight at 80° C. in an oil bath. The reaction was then quenched by the addition of water. The resulting solution was extracted with 100 mL of dichloromethane, dried over anhydrous sodium sulfate, and concentrated. The residue was purified by silica gel column chromatography with ethyl acetate/petroleum ether (2:1) as eluent. This resulted in 2-ethenyl-3-[[(2S)-1-[2-[2-(pyrrolidin-1-yl)ethyl]benzoyl]piperidin-2-yl]methoxy]phenol. LCMS (ES) [M+1]⁺ m/z 435.1.

Step 5. Synthesis of (S)-2-hydroxy-6-((1-(2-(2-(pyrrolidin-1-yl)ethyl)benzoyl)piperidin-2-yl)methoxy)benzaldehyde Into a 10-mL round-bottom flask, was placed a solution of 2-ethenyl-3-[[(2S)-1-[2-[2-(pyrrolidin-1-yl)ethyl]benzoyl]piperidin-2-yl]methoxy]phenol (120.00 mg, 0.276 mmol, 1.00 equiv) in acetone (5 mL), a solution of NaIO₄ (118.12 mg, 0.552 mmol, 2 equiv) in H₂O (2 mL), and K₂OsO₄·2H₂O (10.17 mg, 0.028 mmol, 0.1 equiv). The resulting solution was stirred overnight at room temperature. The solids were filtered out, and the filtrate was concentrated. The residue was purified by silica gel column chromatography with ACN: H₂O (1:4) as eluent. This resulted in (S)-2-hydroxy-6-((1-(2-(2-(pyrrolidin-1-yl)ethyl)benzoyl)piperidin-2-yl)methoxy)benzaldehyde. LCMS (ES) [M+1]⁺ m/z 437.3. 1H NMR (300 MHz, Chloroform-d) δ 12.02 (br, 1H), 10.46-10.32 (m, 1H), 7.53-7.29 (m, 3H), 7.28-7.12 (m, 2H), 6.64-6.38 (m, 2H), 5.66-5.21 (m, 1H), 4.49-3.99 (m, 2H), 3.58-2.36 (m, 10H), 2.16-1.16 (m, 10H).

Example 15. (S)-2-hydroxy-6-((1-(3-(2-hydroxyethyl)pyrazine-2-carbonyl)pyrrolidin-2-yl)methoxy)benzaldehyde, Compound 19

Compound 19 was synthesized according to Scheme 15.

Scheme 15

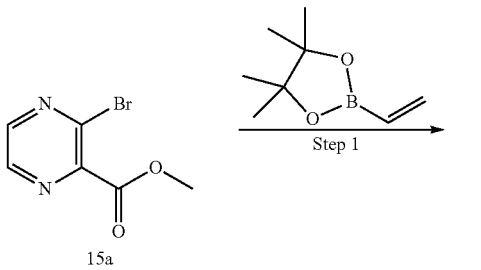

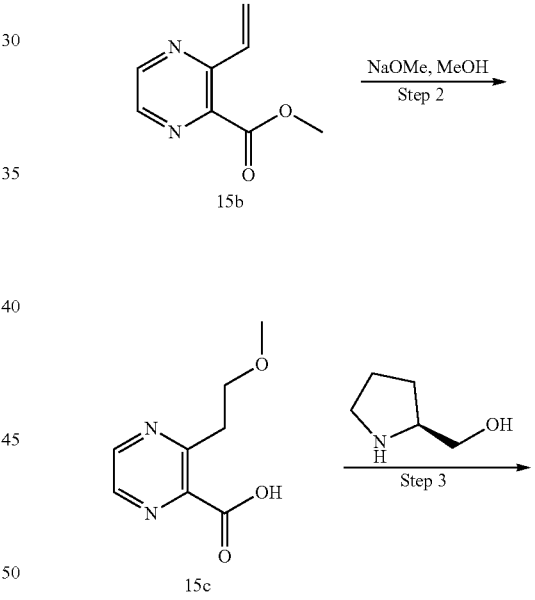

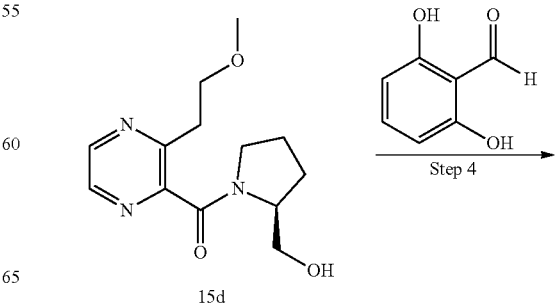

135

-continued

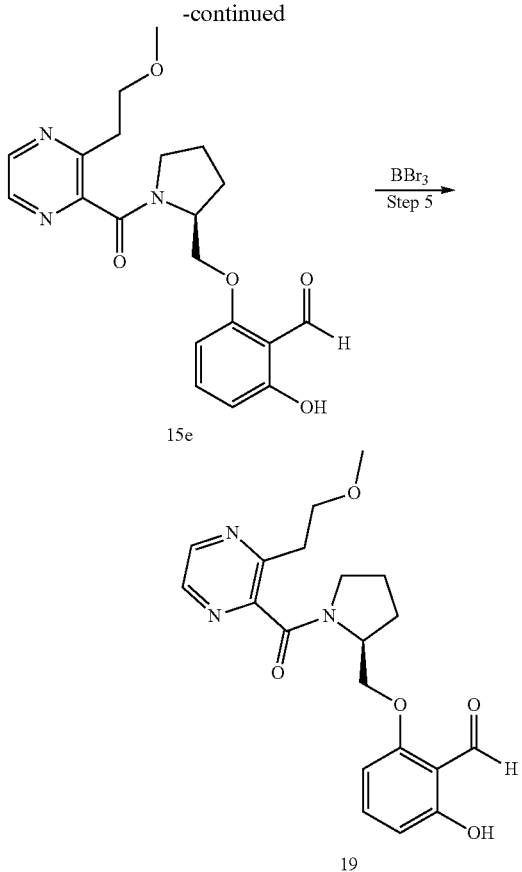

Step 1. Synthesis of methyl
3-ethenylpyrazine-2-carboxylate

Into a 250-mL round-bottom flask purged and maintained with an inert atmosphere of nitrogen, was placed methyl 3-bromopyrazine-2-carboxylate (5.00 g, 23.04 mmol, 1.00 equiv), 2-ethenyl-4,4,5,5-tetramethyl-1,3,2-dioxaborolane (4.26 g, 27.66 mmol, 1.20 equiv), dioxane (60.00 m), $H_2O$ (10.00 mL), $K_2CO_3$ (6.37 g, 46.08 mmol, 2.00 equiv), and Pd(dppf)Cl$_2$ (1.69 g, 2.30 mmol, 0.10 equiv). The resulting solution was stirred for 5 h at 80° C. The reaction mixture was cooled to room temperature. The solids were filtered out. The filtrate was concentrated, and the resulting residue was purified by silica gel column chromatography with THF/PE (15%) as eluent. This resulted in methyl 3-ethenylpyrazine-2-carboxylate. LCMS (ES) [M+1]$^+$ m/z: 165.

Step 2. Synthesis of
3-(2-methoxyethyl)pyrazine-2-carboxylic acid

Into a 250-mL round-bottom flask, was placed methyl 3-ethenylpyrazine-2-carboxylate (3.50 g, 21.32 mmol, 1.00 equiv), MeOH (40.00 mL), and NaOMe (3.46 g, 64.05 mmol, 3.00 equiv). The resulting solution was stirred overnight at 70° C. The resulting mixture was concentrated. The pH value of the solution was adjusted to 2-3 with HCl (1 mol/L). The resulting mixture was concentrated. The residue was purified by silica gel column chromatography with MeOH/DCM (10%) as eluent. This resulted in 3-(2-methoxyethyl)pyrazine-2-carboxylic acid. LCMS (ES) [M+1]$^+$ m/z: 183.

136

Step 3. Synthesis of [(2S)-1-[3-(2-methoxyethyl)
pyrazine-2-carbonyl]pyrrolidin-2-yl]methanol Into a 250-mL 3-necked round-bottom flask was placed 3-(2-methoxyethyl)pyrazine-2-carboxylic acid (1.50 g, 8.23 mmol, 1.00 equiv), prolinol (0.83 g, 8.21 mmol, 1.00 equiv), DIEA (3.19 g, 24.70 mmol, 3.00 equiv), and DMF (30.00 mL). This was followed by the addition of HATU (3.76 g, 9.88 mmol, 1.20 equiv) in portions at 0° C. The resulting solution was stirred overnight at room temperature. The crude product was purified by Prep-HPLC with the following conditions: Column, XBridge Prep C18 OBD Column, 19 cm, 150 mm, 5 um; mobile phase, Water (0.1% HCOOH) and MeCN (5% Phase B up to 20% in 10 min); Detector, 254. This resulted in [(2S)-1-[3-(2-methoxyethyl)pyrazine-2-carbonyl]pyrrolidin-2-yl]methanol. LCMS (ES) [M+1]$^+$ m/z: 266.

Step 4. Synthesis of 2-hydroxy-6-[[(2S)-1-[3-(2-
methoxyethyl)pyrazine-2-carbonyl]pyrrolidin-2-yl]
methoxy]benzaldehyde Into a 100-mL 3-necked round-bottom flask purged and maintained with an inert atmosphere of nitrogen, was placed [(2S)-1-[3-(2-methoxyethyl)pyrazine-2-carbonyl]pyrrolidin-2-yl]methanol (1.00 g, 3.77 mmol, 1.00 equiv), 2,6-dihydroxybenzaldehyde (0.62 g, 4.49 mmol, 1.19 equiv), PPh$_3$ (1.19 g, 4.52 mmol, 1.20 equiv), and DCM (30.00 mL). This was followed by the addition of DIAD (0.91 g, 4.52 mmol, 1.20 equiv) dropwise with stirring at 0° C. The resulting solution was stirred overnight at room temperature. The resulting mixture was concentrated. The residue was purified by silica gel column chromatography with EA/DCM (10%) as eluent. This resulted in 2-hydroxy-6-[[(2S)-1-[3-(2-methoxyethyl)pyrazine-2-carbonyl]pyrrolidin-2-yl]methoxy]benzaldehyde. LCMS (ES, m/z): [M+H]$^+$: 386.2

Step 5. Synthesis of (S)-2-hydroxy-6-((1-(3-(2-hy-
droxyethyl)pyrazine-2-carbonyl)pyrrolidin-2-yl)
methoxy)benzaldehyde Into a 100-mL 3-necked round-bottom flask, was placed 2-hydroxy-6-[[(2S)-1-[3-(2-methoxyethyl)pyrazine-2-carbonyl]pyrrolidin-2-yl]methoxy]benzaldehyde (360.00 mg, 0.93 mmol, 1.00 equiv) and DCM (10.00 mL). This was followed by the addition of BBr$_3$/DCM (9.34 mL, 9.34 mmol, 10.00 equiv) dropwise with stirring at −78° C. The resulting solution was stirred for 2 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product was purified by Prep-HPLC with the following conditions: Column, XBridge Prep C18 OBD Column, 19 cm, 150 mm, 5 um; mobile phase, Water (0.1% HCOOH) and ACN (20% Phase B up to 50% in 11 min); Detector, 254. This resulted in (S)-2-hydroxy-6-((1-(3-(2-hydroxyethyl)pyrazine-2-carbonyl)pyrrolidin-2-yl)methoxy)benzaldehyde. LCMS: (ES, m/z): [M+H]$^+$: 372. $^1$H-NMR: (300 MHz, DMSO-d6) δ 11.77 (s, 1H), 10.34 (s, 1H), 8.66 (t, J=2.4 Hz, 1H), 8.51-8.46 (m, 1H), 7.57-7.40 (m, 1H), 6.72 (d, J=8.3 Hz, 1H), 6.55-6.33 (m, 1H), 4.61-4.54 (m, 1H), 4.34 (d, J=4.9 Hz, 2H), 3.93-3.63 (m, 3H), 3.38-3.19 (m, 2H), 3.06-2.76 (m, 2H), 2.23-1.87 (m, 3H), 1.84-1.74 (m, 1H).

137

Example 16. 2-hydroxy-6-{[(3S)-4-[2-(2-methoxyethyl)pyridine-3-carbonyl]morpholin-3-yl]methoxy}benzaldehyde, Compound 20

Compound 20 was synthesized according to Scheme 16.

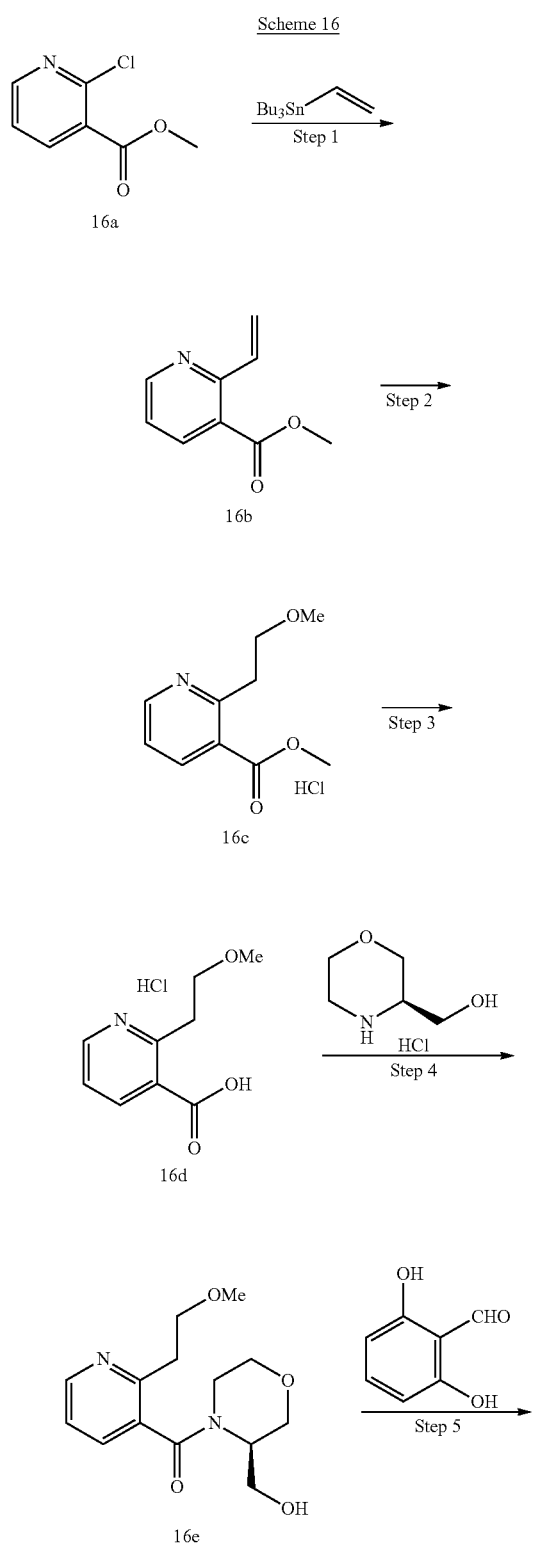

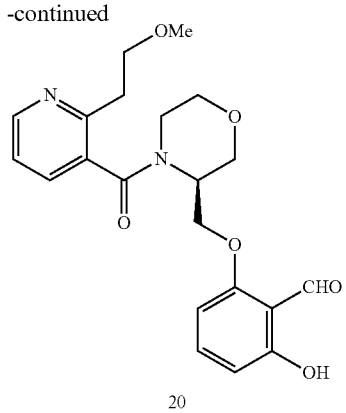

Step 1

Into a 250-mL round-bottom flask purged and maintained with an inert atmosphere of nitrogen, was placed methyl 2-chloropyridine-3-carboxylate (10.0 g, 58.28 mmol, 1.0 equiv), dioxane (100 mL), tributyl(ethenyl)stannane (37.0 g, 116.56 mmol, 2.0 equiv), and Pd(dppf)Cl2 (4.26 g, 5.83 mmol, 0.1 equiv). The mixture was stirred for 12 h at 80° C. in oil bath. After cooled to room temperature, the reaction mixture was concentrated under reduced pressure. The residue was purified by silica gel column with ethyl acetate/petroleum ether (1:3) as eluents. Methyl 2-ethenylpyridine-3-carboxylate was obtained. LCMS (ES) [M+1]+ m/z: 164.

Step 2

Into a 250-mL round-bottom flask, was placed methyl 2-ethenylpyridine-3-carboxylate (7.80 g, 47.90 mmol, 1.0 equiv) and MeOH (50 mL), HCl (c) (8.0 mL). The reaction solution was stirred for 12 h at 90° C. in oil bath. The reaction mixture was cooled to room temperature. Methyl 2-(2-methoxyethyl)pyridine-3-carboxylate hydrochloride was obtained and used in the next step directly without further purification. LCMS (ES) [M−HCl+1]+ m/z: 196.

Step 3

Into a 250-mL round-bottom flask, was placed methyl 2-(2-methoxyethyl)pyridine-3-carboxylate hydrochloride (7.0 g, 30.30 mmol, 1.0 equiv), MeOH/H2O (1:2) (150 mL), and NaOH (2.40 g, 60.60 mmol, 2.0 equiv). The mixture was stirred for 2 h at 50° C. in oil bath. After being cooled to room temperature, the solution was concentrated under reduced pressure. The pH value of the residue was adjusted to 6 with (6 M) HCl and purified by C18-120 g column with conditions: CH$_3$CN/H2O from 5% increased to 60% within 12 min. 2-(2-methoxyethyl)pyridine-3-carboxylic acid hydrochloride was obtained. LCMS (ES) [M−HCl+1]+ m/z: 182.

Step 4

Into a 50-mL 3-necked round-bottom flask purged and maintained with an inert atmosphere of nitrogen, was placed 2-(2-methoxyethyl)pyridine-3-carboxylic acid hydrochloride (1.0 g, 4.60 mmol, 1.0 equiv), DMF (20 mL), DIEA (2.38 g, 18.40 mmol, 4.0 equiv), and (3R)-morpholin-3-ylmethanol hydrochloride (0.85 g, 5.51 mmol, 1.2 equiv). This was followed by the addition of HATU (2.10 g, 5.51 mmol, 1.2 equiv) in several batches at 0° C. The reaction solution was stirred for 12 h at room temperature. The reaction solution was diluted with 30 mL of H₂O and extracted with 3×100 mL of ethyl acetate. The combined organic phase was washed with 3×50 mL of brine and dried over anhydrous sodium sulfate. The solution was filtered, and the filtrate was concentrated under reduced pressure. The residue was purified by silica gel column with ethyl acetate/petroleum ether (1:1). [(3R)-4-[2-(2-methoxyethyl)pyridine-3-carbonyl]morpholin-3-yl]methanol was obtained. LCMS (ES) [M+1]+ m/z: 281.

Step 5

Into a 10-mL round-bottom flask purged and maintained with an inert atmosphere of nitrogen, was placed [(2S)-1-[2-(2-methoxyethyl)pyridine-3-carbonyl]pyrrolidin-2-yl]methanol (280 mg, 1.06 mmol, 1.0 equiv), THF (10 mL), 2,6-dihydroxybenzaldehyde (176 mg, 1.27 mmol, 1.2 equiv), and PPh3 (333 mg, 1.27 mmol, 1.2 equiv). The mixture was cooled to 0° C. followed by the addition of a solution of DBAD (293 mg, 1.27 mmol, 1.2 equiv) in THF (2 mL) dropwise with stirring. After addition, the reaction solution was stirred for 12 h at room temperature. The resulting mixture was concentrated in vacuum to remove the solvent, and the crude product was purified by Prep-HPLC with the following conditions (IntelFlash-1): Column: Ascentis Express C18, 50*3.0 mm, 2.7 um, Mobile Phase A: Water/0.05% FA, Mobile Phase B: CH₃CN, Flow rate: 1.5 mL/min, Gradient: 5% B to 100% B within 1.2 min, hold 0.6 min. This resulted in isolation of 2-hydroxy-6-[[(2S)-1-[2-(2-methoxyethyl)pyridine-3-carbonyl]pyrrolidin-2-yl]methoxy]benzaldehyde. LCMS: (ES, m/z): [M+H]⁺: 401.2. ¹H-NMR: (300 MHz, DMSO-d6, ppm): δ 11.76 (s, 1H), 10.12 (s, 1H), 8.57 (dd, J=4.8, 1.8 Hz, 1H), 7.73-7.31 (m, 3H), 6.75 (d, J=8.4 Hz, 1H), 6.56 (d, J=8.1 Hz, 1H), 5.05-4.89 (m, 1H), 4.45-4.33 (m, 2H), 4.11-3.92 (m, 1H), 3.73-3.35 (m, 6H), 3.20-2.79 (m, 6H).

Example 17. 2-hydroxy-6-{[(3S)-4-[3-(2-hydroxyethyl)pyrazine-2-carbonyl]morpholin-3-yl]methoxy}benzaldehyde, Compound 21

Compound 21 was synthesized according to Scheme 17.

Scheme 17

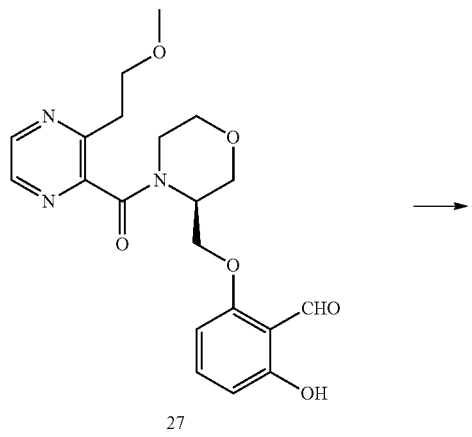

27

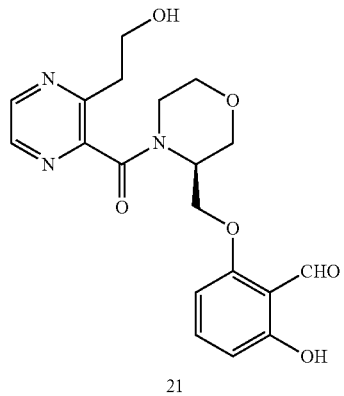

21

Into a 100-mL 3-necked round-bottom flask, was placed 2-hydroxy-6-[[(3S)-4-[3-(2-methoxyethyl)pyrazine-2-carbonyl]morpholin-3-yl]methoxy]benzaldehyde (500.00 mg, 1.25 mmol, 1.00 equiv), which was prepared as described in Scheme 23, and DCM (10.00 mL). This was followed by the addition of BBr₃/DCM (12.46 mL, 12.46 mmol, 10.00 equiv) dropwise with stirring at −78° C. The resulting solution was stirred for 2 h at 0° C. The resulting solution was extracted with 3×20 mL of dichloromethane, and the organic layers were combined, dried over anhydrous sodium sulfate, and concentrated. The crude product was purified by Prep-HPLC with the following conditions: Column, XBridge Prep C18 OBD Column, 19 cm, 150 mm, Sum; mobile phase, Water (0.1% HCOOH) and CAN (20% Phase B up to 50% in 11 min); Detector, 254. This resulted in 2-hydroxy-6-[[(3S)-4-[3-(2-hydroxyethyl)pyrazine-2-carbonyl]morpholin-3-yl]methoxy]benzaldehyde. LCMS: (ES, m/z): [M+H]⁺: 388. ¹H-NMR: (300 MHz, DMSO-d₆) δ 11.77 (d, J=11.9 Hz, 1H), 10.26 (d, J=13.1 Hz, 1H), 8.68-8.66 (m, 1H), 8.49-8.45 (m, 1H), 7.57 (d, J=8.4 Hz, 1H), 7.56-7.43 (m, 1H), 6.75-6.49 (m, 2H), 4.99-4.93 (m, 1H), 4.76-4.63 (m, 1H), 4.55-4.32 (m, 2H), 4.14-3.89 (m, 1H), 3.86-3.68 (m, 2H), 3.73-3.61 (m, 1H), 3.66-3.46 (m, 1H), 3.51-3.30 (m, 2H), 3.17-2.80 (m, 3H).

Example 18. 2-hydroxy-6-{[(3S)-4-[2-(2-hydroxyethyl)benzoyl]morpholin-3-yl]methoxy}benzaldehyde, Compound 22

Compound 22 was synthesized according to Scheme 18.

Scheme 18

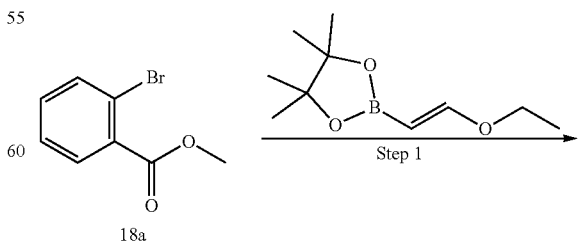

18a

Step 1

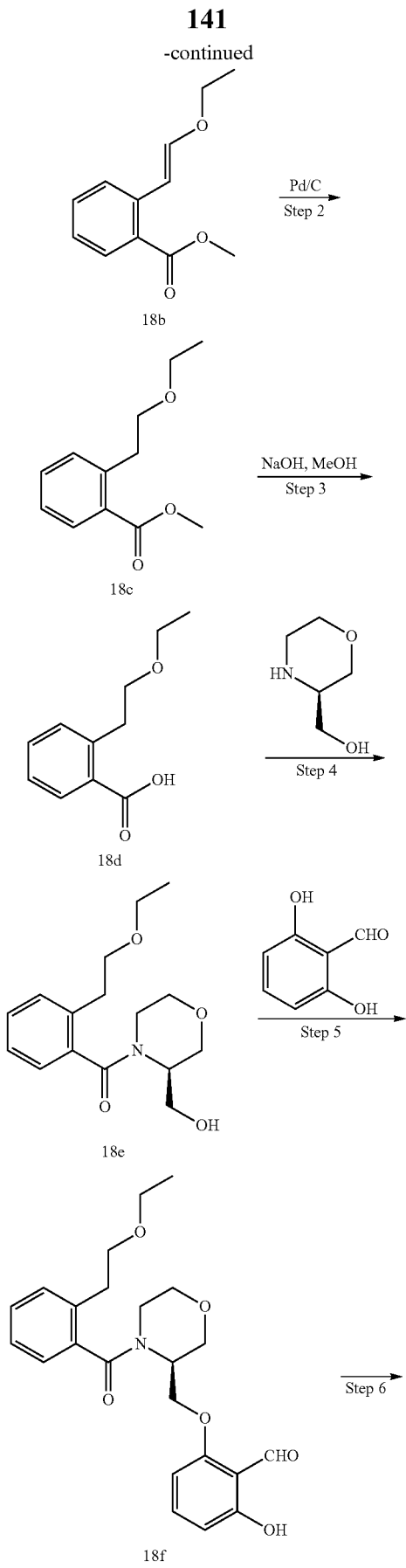

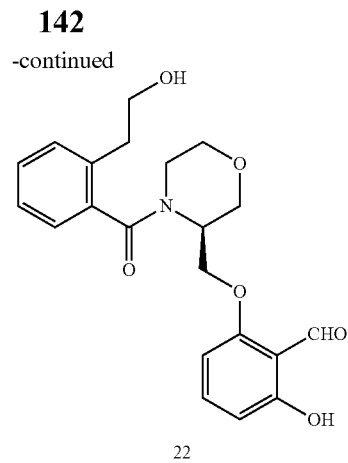

Step 1

Into a 250-mL round-bottom flask, was placed methyl 2-bromobenzoate (5.00 g, 23.251 mmol, 1.00 equiv), dioxane (60.00 mL), water (10 mL), 2-[(E)-2-ethoxyethenyl]-4,4,5,5-tetramethyl-1,3,2-dioxaborolane (6.91 g, 34.876 mmol, 1.50 equiv), sodium methaneperoxoate sodium (4.98 g, 46.502 mmol, 2.00 equiv), and tetrakis(triphenylphosphine)palladium(0) (2.69 g, 2.325 mmol, 0.10 equiv). The resulting solution was stirred for 16 hr at 80° C. The resulting mixture was concentrated. The residue was purified by silica gel column chromatography with ethyl acetate/petroleum ether (1:3) as eluents. The collected fractions were combined and concentrated. This resulted in methyl 2-[(E)-2-ethoxyethenyl]benzoate. LCMS (ES) $[M+1]^+$ m/z 207.1.

Step 2

Into a 100-mL round-bottom flask, was placed methyl 2-[(E)-2-ethoxyethenyl]benzoate (2.40 g, 11.637 mmol, 1.00 equiv), methanol (30.00 mL), and Pd/C (240.00 mg). The flask was evacuated and flushed three times with nitrogen, followed by flushing with hydrogen. The mixture was stirred 2 h at room temperature under an atmosphere of hydrogen. The solids were filtered out. The resulting filtrate was concentrated to give methyl 2-(2-ethoxyethyl)benzoate. LCMS (ES) $[M+1]^+$ m/z 209.1.

Step 3

Into a 50-mL round-bottom flask, was placed methyl 2-(2-ethoxyethyl)benzoate (2.00 g, 9.604 mmol, 1.00 equiv), methanol (10.00 mL), water (10.00 mL), caustic soda (0.77 g, 19.251 mmol, 2.00 equiv). The resulting solution was stirred for 4 hr at 25° C. The resulting solution was diluted with 50 mL of water. The pH value of the solution was adjusted to 5 with HCl (1 mol/L). The solids were collected by filtration to give 2-(2-ethoxyethyl)benzoic acid. LCMS (ES) $[M+1]^+$ m/z 195.1.

Step 4

Into a 100-mL round-bottom flask, was placed 2-(2-ethoxyethyl)benzoic acid (1.50 g, 7.723 mmol, 1.00 equiv), DCM (30.00 mL), (3R)-morpholin-3-ylmethanol (0.90 g, 7.723 mmol, 1.00 equiv), HATU (4.40 g, 11.584 mmol, 1.50 equiv), and DIEA (2.99 g, 23.168 mmol, 3.00 equiv). The resulting solution was stirred for 2 hr at 25° C. The resulting mixture was concentrated. The residue was purified by silica gel column with ethyl acetate/petroleum ether (1:1) as eluents. The collected fractions were combined and concentrated to give [(3R)-4-[2-(2-ethoxyethyl)benzoyl]morpholin-3-yl]methanol. LCMS (ES) [M+1]+ m/z 294.2.

Step 5

Into a 520-mL round-bottom flask, was placed [(3R)-4-[2-(2-ethoxyethyl)benzoyl]morpholin-3-yl]methanol (600.00 mg, 2.045 mmol, 1.00 equiv), tetrahydrofuran (20 mL), 2,6-dihydroxybenzaldehyde (282.49 mg, 2.045 mmol, 1.00 equiv), triphenylphosphine (643.74 mg, 2.454 mmol, 1.20 equiv), and DIAD (496.28 mg, 2.454 mmol, 1.20 equiv). The resulting solution was stirred for 16 hr at 25° C. The resulting mixture was concentrated. The residue was purified by silica gel column with ethyl acetate/petroleum ether (1:2) as eluents. The collected fractions were combined and concentrated. This resulted in 2-[[(3S)-4-[2-(2-ethoxyethyl)benzoyl]morpholin-3-yl]methoxy]-6-hydroxybenzaldehyde. LCMS (ES) [M+1]+ m/z 414.2.

Step 6

Into a 50-mL round-bottom flask, was placed 2-[[(3S)-4-[2-(2-ethoxyethyl)benzoyl]morpholin-3-yl]methoxy]-6-hydroxybenzaldehyde (200 mg, 0.48 mmol, 1.0 eq), DCM (20 mL). Then, boron tribromide (2.4 mL, 2.4 mmol, 5.0 eq, 1M) was added dropwise at −78° C. The resulting solution was stirred for 3 hr at 0° C. The reaction was then quenched by the addition of 10 mL of water. The resulting solution was extracted with 2×20 mL of dichloromethane and concentrated. The crude reaction mixture was filtered and subjected to reverse phase preparative HPLC (Prep-C18, 20-45M, 120 g, Tianjin Bonna-Agela Technologies; gradient elution of 25% MeCN in water to 35% MeCN in water over a 10 min period, where both solvents contain 0.1% FA) to provide 2-hydroxy-6-{1[(3S)-4-[2-(2-hydroxyethyl)benzoyl]morpholin-3-yl]methoxy}benzaldehyde. LCMS (ES) [M+1]+ m/z 386.1. $^1$H NMR (300 MHz, DMSO-d6) δ 11.76 (br, 1H), 10.29 (s, 1H), 7.62-7.50 (m, 1H), 7.48-6.95 (m, 4H), 6.88-6.48 (m, 2H), 5.00-4.20 (m, 4H), 4.17-3.41 (m, 7H), 3.23-29.5 (m, 1H), 2.94-2.57 (m, 2H).

Example 19. 2-hydroxy-6-{[(3S)-4-[2-(hydroxymethyl)benzoyl]morpholin-3-yl]methoxy}benzaldehyde, Compound 23

Compound 23 was synthesized according to Scheme 19.

Scheme 19

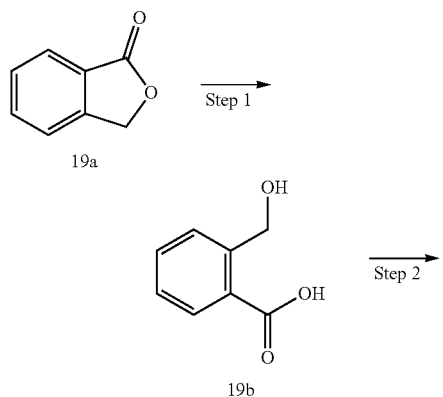

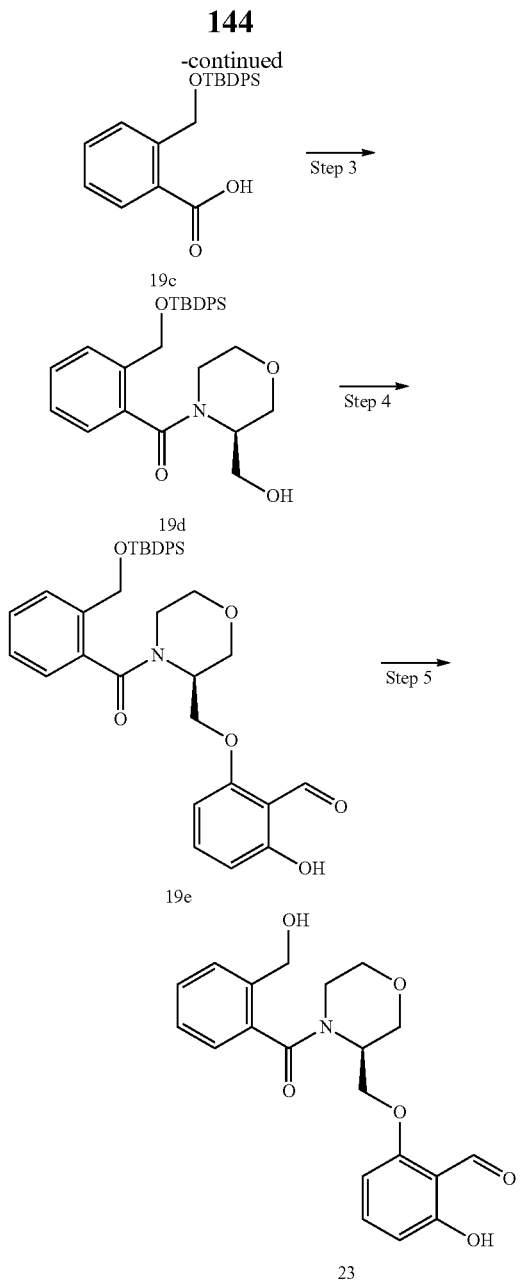

Step 1

Into a 500-mL round-bottom flask, was placed phthalide (11.00 g, 82.008 mmol, 1.00 equiv), H$_2$O (200.00 mL, 11101.675 mmol, 135.37 equiv), and NaOH (4.92 g, 123.009 mmol, 1.50 equiv). The resulting solution was stirred for overnight at 100° C. in an oil bath. The reaction mixture was cooled to 0° C. with a water/ice bath. The pH value of the solution was adjusted to 5 with HCl (6 mol/L). The solids were collected by filtration. The solid was dried in an oven. This resulted in 2-hydroxymethylbenzoic acid. LCMS (ES) [M−1]− m/z 151.1.

Step 2

Into a 250-mL round-bottom flask, was placed 2-hydroxymethylbenzoic acid (5.00 g, 32.863 mmol, 1.00 equiv), DCM (100.00 mL), and imidazole (4.47 g, 65.725 mmol, 2.00 equiv). This was followed by the addition of TBDPSCl (10.84 g, 39.435 mmol, 1.20 equiv) in several batches at 0° C. in 5 min. The resulting solution was stirred for 2 h at room temperature. The resulting solution was diluted with 60 mL of water. The resulting solution was extracted with 3×100 mL of dichloromethane, and the organic layer was washed with 1×60 mL of brine, dried over anhydrous sodium sulfate, and concentrated. The residue was purified by silica gel column chromatography with dichloromethane/ethyl acetate (10% EA-20% EA). This resulted in 2-[[(tert-butyldiphenylsilyl)oxy]methyl]benzoic acid. LCMS (ES) [M+1]+ m/z 391.2.

Step 3

Into a 250-mL round-bottom flask purged and maintained with an inert atmosphere of nitrogen, was placed 2-[[(tert-butyldiphenylsilyl)oxy]methyl]benzoic acid (2.00 g, 5.121 mmol, 1.00 equiv), DCM (120 mL), and oxalyl chloride (1.30 g, 10.242 mmol, 2.00 equiv). The resulting solution was stirred for 4 h at room temperature. The resulting mixture was concentrated under vacuum. Into another 250-mL 3-necked round-bottom flask purged and maintained with an inert atmosphere of nitrogen, was placed (3R)-morpholin-3-ylmethanol hydrochloride (0.94 g, 6.145 mmol, 1.20 equiv) and TEA (1.55 g, 15.318 mmol, 2.99 equiv). This was followed by the addition of a solution of 2-[[(tert-butyldiphenylsilyl)oxy]methyl]benzoyl chloride (2.00 g, 4.890 mmol, 1.00 equiv) in DCM (30 mL) dropwise with stirring at 0° C. in 30 min. The resulting solution was stirred for 2 h at room temperature. The resulting solution was diluted with 200 mL of DCM. The resulting mixture was washed with 1×100 mL of 1 M HCl. The mixture was dried over anhydrous sodium sulfate and concentrated. The residue was purified by silica gel column chromatography with ethyl acetate/petroleum ether (50% EA). This resulted in [(3R)-4-(2-[[(tert-butyldiphenylsilyl)oxy]methyl]benzoyl)morpholin-3-yl]methanol. LCMS (ES) [M+1]+ m/z 490.3.

Step 4

Into a 100-mL 3-necked round-bottom flask purged and maintained with an inert atmosphere of nitrogen, was placed [(3R)-4-(2-[[(tert-butyldiphenylsilyl)oxy]methyl]benzoyl)morpholin-3-yl]methanol (1.00 g, 2.042 mmol, 1.00 equiv), 2,6-dihydroxybenzaldehyde (0.56 g, 4.084 mmol, 2.00 equiv), PPh3 (1.07 g, 4.084 mmol, 2.00 equiv), and THF (60.00 mL). The resulting solution was stirred for 15 min at 0° C. This was followed by the addition of DIAD (825.87 mg, 4.084 mmol, 2.00 equiv) dropwise with stirring at 0° C. in 5 min. The resulting solution was stirred for 5 h at room temperature. The resulting solution was diluted with 30 mL of water. The resulting solution was extracted with 3×60 mL of dichloromethane; the organic layer was dried over anhydrous sodium sulfate and concentrated. The residue was purified by silica gel column chromatography with PE/THF (10% THF). This resulted in 2-[[(3S)-4-(2-[[(tert-butyldiphenylsilyl)oxy]methyl]benzoyl)morpholin-3-yl]methoxy]-6-hydroxybenzaldehyde. LCMS (ES) [M+1]+ m/z 610.3.

Step 5

Into a 100-mL round-bottom flask, was placed 2-[[(3S)-4-(2-[[(tert-butyldiphenylsilyl)oxy]methyl]benzoyl)morpholin-3-yl]methoxy]-6-hydroxybenzaldehyde (0.80 g, 1.312 mmol, 1.00 equiv), THF (30.00 mL), and TBAF (1.32 mL, 2.0 equiv, 2 M). The resulting solution was stirred for 2 hr at room temperature. The resulting solution was diluted with 10 mL of water. The resulting solution was extracted with 3×60 mL of dichloromethane, and the organic layer was dried over anhydrous sodium sulfate and concentrated. The residue was purified by silica gel column with PE/THF (55% THF) as eluents. The crude product was further purified by Flash-Prep-HPLC (Prep-C18, 20-45M, 120 g, Tianjin Bonna-Agela Technologies; gradient elution of 35% MeCN in water to 60% MeCN in water over a 10 min period, where both solvents contain 0.1% FA). This resulted in 2-hydroxy-6-[[(3S)-4-[2-(hydroxymethyl)benzoyl]morpholin-3-yl]methoxy]benzaldehyde. LCMS (ES) [M+1]+ m/z 372.1. 1H-NMR (300 MHz, DMSO-d6 ppm) δ 11.78 (s, 1H), 10.21 (s, 1H), 7.70-7.21 (m, 5H), 6.77 (d, J=8.2 Hz, 1H), 6.56 (d, J=8.4 Hz, 1H), 5.32-5.15 (m, 1H), 5.03-4.21 (m, 5H), 4.18-3.84 (m, 2H), 3.78-3.55 (m, 2H), 3.42-3.36 (m, 1H), 3.11-2.98 (m, 1H).

Example 20. 2-hydroxy-6-{[(2S)-1-[2-(2-methoxyethyl)pyridine-3-carbonyl]pyrrolidin-2-yl]methoxy}benzaldehyde, Compound 24

Compound 24 was synthesized according to Scheme 20.

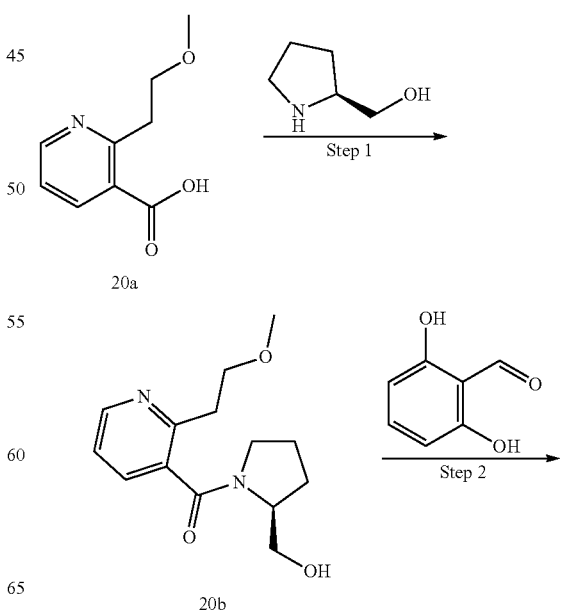

-continued

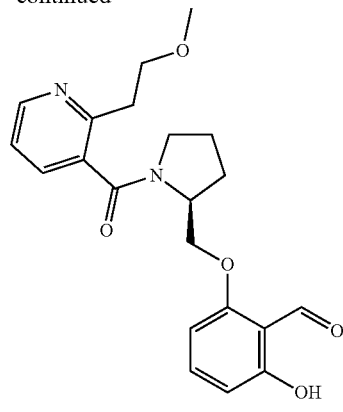

24

Step 1

Into a 50-mL 3-necked round-bottom flask purged and maintained with an inert atmosphere of nitrogen, was placed 2-(2-methoxyethyl)pyridine-3-carboxylic acid (1.0 g, 5.52 mmol, 1.0 equiv), DMF (20 mL), prolinol (670 mg, 6.62 mmol, 1.2 equiv), and DIEA (2.85 g, 22.08 mmol, 4.0 equiv). This was followed by the addition of HATU (2.52 g, 6.62 mmol, 1.2 equiv) in several batches at 0° C. After addition, the mixture was stirred for 12 h at room temperature. The reaction solution was diluted with 30 mL of H$_2$O and extracted with 3×100 mL of ethyl acetate. The combined organic phase was washed with 3*50 mL of brine and dried over anhydrous sodium sulfate. The solution was filtered, and the filtrate was concentrated under reduced pressure. The residue was purified by silica gel column with ethyl acetate. [(2S)-1-[2-(2-methoxyethyl)pyridine-3-carbonyl]pyrrolidin-2-yl]methanol was obtained. LCMS (ES) [M+1]$^+$ m/z: 265.

Step 2

Into a 50-mL round-bottom flask purged and maintained with an inert atmosphere of nitrogen, was placed [(2S)-1-[2-(2-methoxyethyl)pyridine-3-carbonyl]pyrrolidin-2-yl]methanol (380 mg, 1.44 mmol, 1.0 equiv), THF (20 mL), 2,6-dihydroxybenzaldehyde (199 mg, 1.44 mmol, 1.0 equiv), and PPh$_3$ (377 mg, 1.44 mmol, 1.0 equiv). The mixture was cooled to 0° C. and stirred for 15 min. This was followed by the addition of a solution of DBAD (331 mg, 1.44 mmol, 1.0 equiv) in THF (2 mL) dropwise with stirring. After addition, the reaction solution was stirred for 12 h at room temperature. The solution was then concentrated under reduced pressure to remove the solvent. The residue was purified by Flash-Prep-HPLC with the following conditions (IntelFlash-1): Column: Ascentis Express C18, 50*3.0 mm, 2.7 um, Mobile Phase A: Water/0.05% FA, Mobile Phase B: CH$_3$CN, Flow rate: 1.5 mL/min, Gradient: 5% B to 100% B within 1.2 min, hold 0.6 min. 2-hydroxy-6-{[(2S)-1-[2-(2-methoxyethyl)pyridine-3-carbonyl]pyrrolidin-2-yl]methoxy}benzaldehyde was obtained. LCMS: (ES, m/z): [M+H]$^+$: 385. $^1$H-NMR: (300 MHz, DMSO-d$_6$, ppm): δ 11.78 (s, 1H), 10.33 (s, 1H), 8.55 (dd, J=1.5, 4.8 Hz, 1H), 7.64 (dd, J=7.5, 1.8 Hz, 1H), 7.57-7.52 (m, 1H), 7.32-7.28 (m, 1H), 6.70 (d, J=8.4 Hz, 1H), 6.53 (d, J=8.4 Hz, 1H), 4.57-4.53 (m, 1H), 4.44-4.39 (m, 1H), 4.31-4.26 (m, 1H), 3.79-3.52 (m, 2H), 3.31-3.11 (m, 2H), 3.11 (s, 3H), 3.04-2.79 (m, 2H), 2.24-1.89 (m, 3H), 1.84-1.76 (m, 1H).

Example 21. 2-hydroxy-6-{[(2S)-1-[3-(2-methoxyethyl)pyrazine-2-carbonyl]pyrrolidin-2-yl]methoxy}benzaldehyde, Compound 25

Compound 25 was synthesized according to Scheme 21.

Scheme 21

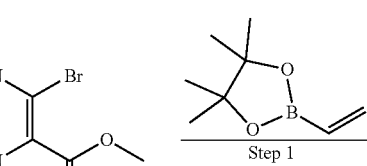

21a

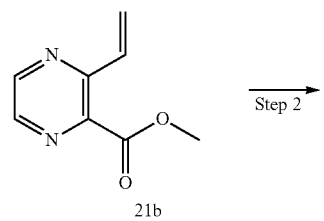

21b

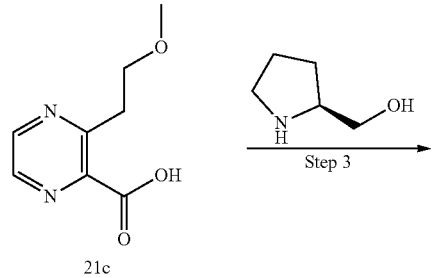

21c

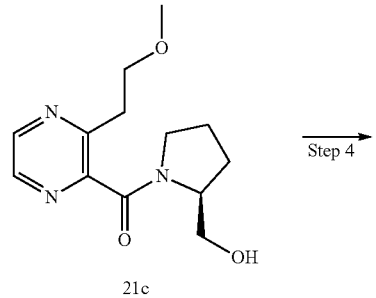

21c

-continued

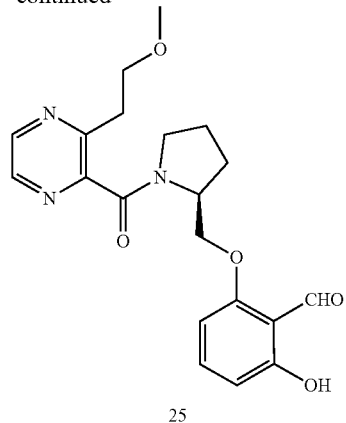

25

Step 1

Into a 250-mL round-bottom flask purged and maintained with an inert atmosphere of nitrogen, was placed methyl 3-bromopyrazine-2-carboxylate (5.00 g, 23.04 mmol, 1.00 equiv), 2-ethenyl-4,4,5,5-tetramethyl-1,3,2-dioxaborolane (4.26 g, 27.66 mmol, 1.20 equiv), dioxane (60.00 m), H$_2$O (10.00 mL), K$_2$CO$_3$ (6.37 g, 46.08 mmol, 2.00 equiv), and Pd(dppf)Cl$_2$ (1.69 g, 2.30 mmol, 0.10 equiv). The resulting solution was stirred for 5 h at 80° C. The reaction mixture was cooled to room temperature. The solids were filtered out. The resulting mixture was concentrated. The residue was purified by silica gel column chromatography with THF/PE (15%) as eluents. This resulted in methyl 3-ethenylpyrazine-2-carboxylate. LCMS (ES) [M+1]$^+$ m/z: 165.

Step 2

Into a 250-mL round-bottom flask, was placed methyl 3-ethenylpyrazine-2-carboxylate (3.50 g, 21.32 mmol, 1.00 equiv), MeOH (40.00 mL), and NaOMe (3.46 g, 64.05 mmol, 3.00 equiv). The resulting solution was stirred for overnight at 70° C. The resulting mixture was concentrated. The pH value of the solution was adjusted to 2-3 with HCl (1 mol/L). The resulting mixture was concentrated. The residue was purified by silica gel column with MeOH/DCM (10%) as eluents. This resulted in 3-(2-methoxyethyl)pyrazine-2-carboxylic acid. LCMS (ES) [M+1]$^+$ m/z: 183.

Step 3

Into a 250-mL 3-necked round-bottom flask, was placed 3-(2-methoxyethyl)pyrazine-2-carboxylic acid (1.50 g, 8.23 mmol, 1.00 equiv), prolinol (0.83 g, 8.21 mmol, 1.00 equiv), DIEA (3.19 g, 24.70 mmol, 3.00 equiv), and DMF (30.00 mL). This was followed by the addition of HATU (3.76 g, 9.88 mmol, 1.20 equiv) in portions at 0° C. The resulting solution was stirred for overnight at room temperature. The crude product was purified by Prep-HPLC with the following conditions: Column, XBridge Prep C18 OBD Column, 19 cm, 150 mm, 5um; mobile phase, Water (0.1% HCOOH) and MeCN (5% Phase B up to 20% in 10 min); Detector, 254. This resulted in [(2S)-1-[3-(2-methoxyethyl)pyrazine-2-carbonyl]pyrrolidin-2-yl]methanol. LCMS (ES) [M+1]$^+$ m/z: 266.

Step 4

Into a 100-mL 3-necked round-bottom flask purged and maintained with an inert atmosphere of nitrogen, was placed [(2S)-1-[3-(2-methoxyethyl)pyrazine-2-carbonyl]pyrrolidin-2-yl]methanol (1.00 g, 3.77 mmol, 1.00 equiv), 2,6-dihydroxybenzaldehyde (0.62 g, 4.49 mmol, 1.19 equiv), PPh$_3$ (1.19 g, 4.52 mmol, 1.20 equiv), and DCM (30.00 mL). This was followed by the addition of DIAD (0.91 g, 4.52 mmol, 1.20 equiv) dropwise with stirring at 0° C. The resulting solution was stirred for overnight at room temperature. The resulting mixture was concentrated. The residue was applied onto a silica gel column with EA/DCM (10%). This resulted in 2-hydroxy-6-[[(2S)-1-[3-(2-methoxyethyl)pyrazine-2-carbonyl]pyrrolidin-2-yl]methoxy]benzaldehyde. LCMS: (ES, m/z): [M+H]$^+$: 386.2. $^1$H-NMR: (300 MHz, DMSO-d$_6$) SS 11.77 (s, 1H), 10.34 (s, 1H), 8.67 (d, J=2.6 Hz, 1H), 8.51 (d, J=2.5 Hz, 1H), 7.57-7.40 (m, 1H), 6.72-6.33 (m, 2H), 4.58-4.24 (m, 3H), 3.83-3.43 (m, 2H), 3.39-3.19 (m, 2H), 3.13 (s, 3H), 3.10-2.86 (m, 2H), 2.23-1.73 (m, 4H).

Example 22. 2-hydroxy-6-{[(2S)-1-[2-(hydroxymethyl)benzoyl]pyrrolidin-2-yl]methoxy}benzaldehyde, Compound 26

Compound 26 was synthesized according to Scheme 22.

Scheme 22

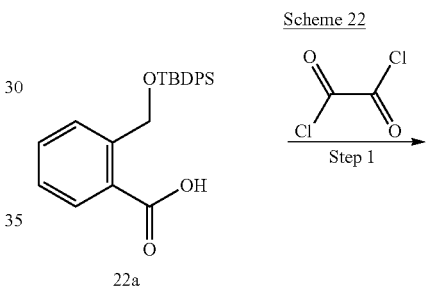

22a

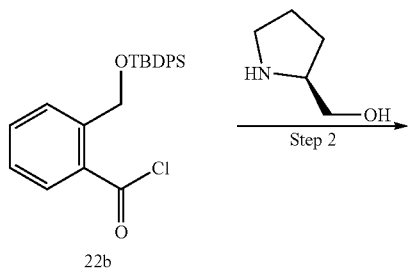

22b

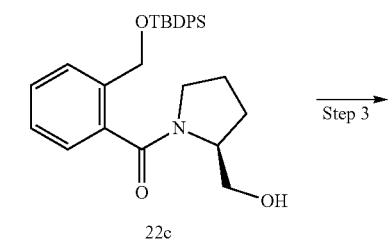

22c

-continued

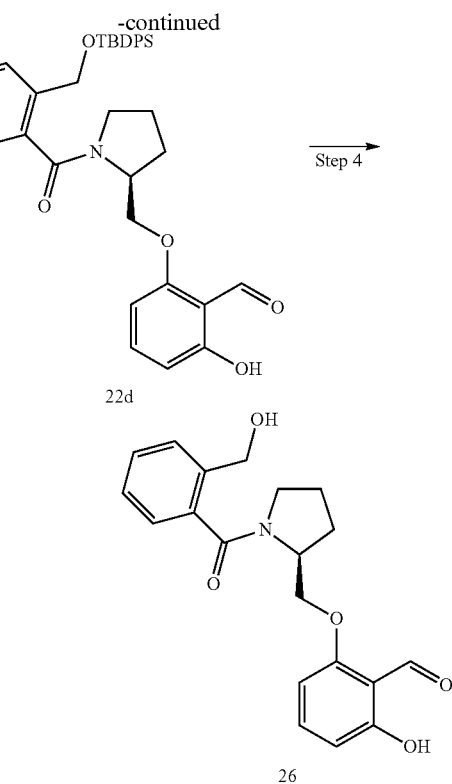

Step 1

Into a 100-mL round-bottom flask purged and maintained with an inert atmosphere of nitrogen, was placed 2-[[(tert-butyldiphenylsilyl)oxy]methyl]benzoic acid (2.00 g, 5.121 mmol, 1.00 equiv), DCM (60.00 mL), and DMF (0.05 mL, 0.646 mmol, 0.13 equiv). This was followed by the addition of oxalyl chloride (1.30 g, 10.243 mmol, 2.00 equiv). The resulting solution was stirred for 1 overnight at room temperature. The resulting mixture was concentrated. This resulted in 2-[[(tert-butyldiphenylsilyl)oxy]methyl]benzoyl chloride.

Step 2

Into a 250-mL 3-necked round-bottom flask purged and maintained with an inert atmosphere of nitrogen, was placed prolinol (0.59 g, 5.868 mmol, 1.2 equiv), TEA (1.48 g, 14.670 mmol, 3 equiv), and DCM (100.00 mL). This was followed by the addition of a solution of 2-[[(tert-butyldiphenylsilyl)oxy]methyl]benzoyl chloride (2.00 g, 4.890 mmol, 1.00 equiv) in DCM (30 mL) dropwise with stirring at 0° C. in 30 min. The resulting solution was stirred for 2 h at room temperature. The resulting solution was diluted with 100 mL of DCM. The resulting mixture was washed with 1×70 mL of 1 M HCl. The mixture was dried over anhydrous sodium sulfate and concentrated. The residue was purified by silica gel column chromatography with ethyl acetate/petroleum ether (55% EA) as eluents. This resulted in [(2S)-1-(2-[[(tert-butyldiphenylsilyl)oxy]methyl]benzoyl)pyrrolidin-2-yl]methanol. LCMS (ES) [M+1]+ m/z 474.2.

Step 3

Into a 100-mL 3-necked round-bottom flask purged and maintained with an inert atmosphere of nitrogen, was placed [(2S)-1-(2-[[(tert-butyldiphenylsilyl)oxy]methyl]benzoyl) pyrrolidin-2-yl]methanol (1.00 g, 2.111 mmol, 1.00 equiv), 2,6-dihydroxybenzaldehyde (0.58 g, 4.222 mmol, 2.00 equiv), PPh₃ (1.11 g, 4.222 mmol, 2.00 equiv), and THF (60 mL). The resulting solution was stirred for 15 min at 0° C. This was followed by the addition of DIAD (0.85 g, 4.222 mmol, 2.00 equiv) dropwise with stirring at 0° C. in 5 min. The resulting solution was stirred for 5 h at room temperature. The resulting solution was diluted with 30 mL of water. The resulting solution was extracted with 3×100 mL of dichloromethane; the organic layer was dried over anhydrous sodium sulfate and concentrated. The residue was purified by silica gel column chromatography with PE/THF (12% THF) as eluents. This resulted in 2-[[(2S)-1-(2-[[(tert-butyldiphenylsilyl)oxy]methyl]benzoyl)pyrrolidin-2-yl] methoxy]-6-hydroxybenzaldehyde. LCMS (ES) [M+1]+ m/z 594.3.

Step 4

Into a 100-mL round-bottom flask, was placed 2-[[(2S)-1-(2-[[(tert-butyldiphenylsilyl)oxy]methyl]benzoyl)pyrrolidin-2-yl]methoxy]-6-hydroxybenzaldehyde (1.10 g, 1.852 mmol, 1.00 equiv), THF (30.00 mL), and TBAF (1.9 mL, 2 M). The resulting solution was stirred for 2 h at room temperature. The resulting solution was diluted with 10 mL of water. The resulting solution was extracted with 3×60 mL of dichloromethane; the organic layer was dried over anhydrous sodium sulfate and concentrated. The residue was applied onto a silica gel column with PE/THF (52% THF). The crude product was purified by Flash-Prep-HPLC (Prep-C18, 20-45M, 120 g, Tianjin Bonna-Agela Technologies; gradient elution of 35% MeCN in water to 60% MeCN in water over a 10 min period, where both solvents contain 0.1% FA). This resulted in 2-hydroxy-6-[[(2S)-1-[2-(hydroxymethyl)benzoyl]pyrrolidin-2-yl]methoxy]benzaldehyde. LCMS (ES) [M+1]+ m/z 356.1. ¹H-NMR (300 MHz, DMSO-d₆ ppm) δ 11.72 (s, 1H), 10.22 (s, 1H), 7.80-7.13 (m, 5H), 6.78-6.41 (m, 2H), 5.22-5.10 (m, 1H), 4.58-4.28 (m, 4H), 4.07-3.46 (m, 1H), 3.38-3.09 (m, 6.8 Hz, 2H), 2.18-1.70 (m, 4H).

Example 23. 2-hydroxy-6-{[(3S)-4-[3-(2-methoxyethyl)pyrazine-2-carbonyl]morpholin-3-yl]methoxy}benzaldehyde, Compound 27

Compound 27 was synthesized according to Scheme 23.

Scheme 23

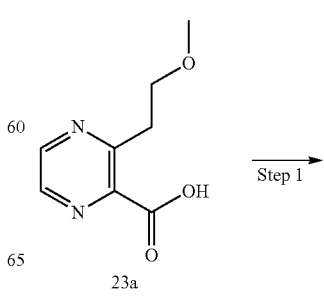

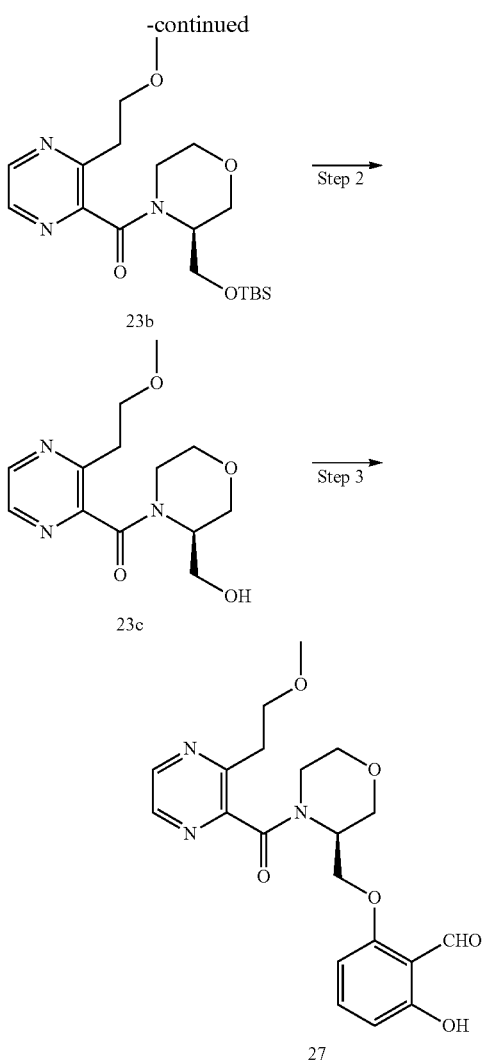

ethyl)pyrazine-2-carbonyl]morpholine (4 g, 10.11 mmol, 1.00 equiv) and EA (20.00 mL). To the above HCl$_{(g)}$ in EA (10.11 mL, 20.22 mmol, 2.00 equiv) was introduced in dropwise with stirring at 0° C. The resulting solution was stirred for 2 h at room temperature. The resulting mixture was concentrated. The pH value of the solution was adjusted to 7-8 with saturated NaHCO$_3$. The resulting solution was extracted with 5×30 mL of dichloromethane, and the organic layers were combined, dried over anhydrous sodium sulfate, and concentrated. The residue was purified by silica gel column with dichloromethane/methanol (100/3) as eluents. This resulted in [(3R)-4-[3-(2-methoxyethyl)pyrazine-2-carbonyl]morpholin-3-yl]methanol. LCMS (ES) [M+1]$^+$ m/z: 282.

Step 3

Into a 100-mL 3-necked round-bottom flask, was placed [(3R)-4-[3-(2-methoxyethyl)pyrazine-2-carbonyl]morpholin-3-yl]methanol (400.00 mg, 1.42 mmol, 1.00 equiv), 2,6-dihydroxybenzaldehyde (235.68 mg, 1.71 mmol, 1.20 equiv), DCM (10.00 mL), and PPh$_3$ (447.54 mg, 1.71 mmol, 1.20 equiv). This was followed by the addition of DIAD (345.03 mg, 1.71 mmol, 1.20 equiv) dropwise with stirring at 0° C. The resulting solution was stirred for overnight at room temperature. The resulting mixture was concentrated. The crude product was purified by Prep-HPLC with the following conditions: Column, XBridge Prep C18 OBD Column, 19 cm, 150 mm, 5 um; mobile phase, Water (0.1% HCOOH) and CAN (30% Phase B up to 50% in 11 min); Detector, 254. This resulted in 2-hydroxy-6-{[(3S)-4-[3-(2-methoxyethyl)pyrazine-2-carbonyl]morpholin-3-yl]methoxy}benzaldehyde. LCMS: (ES, m/z): [M+H]$^+$: 402. $^1$H-NMR: (300 MHz, DMSO-d$_6$) δ 11.79 (s, 1H), 10.31-10.20 (m, 1H), 8.69-8.66 (m, 1H), 8.52-8.47 (m, 1H), 7.58-7.45 (m, 1H), 6.79-6.70 (m, 1H), 6.64-6.48 (m, 1H), 5.00-4.94 (m, 1H), 4.52-4.31 (m, 2H), 4.14-3.92 (m, 1H), 3.81-3.23 (m, 6H), 3.14 (s, 3H), 3.09-2.88 (m, 3H).

Example 24.3-{3-[(3S)-3-[(2-formyl-3-hydroxyphenoxy)methyl]morpholine-4-carbonyl]pyridin-2-yl}propanenitrile, Compound 28

Compound 28 was synthesized according to Scheme 24.

Scheme 24

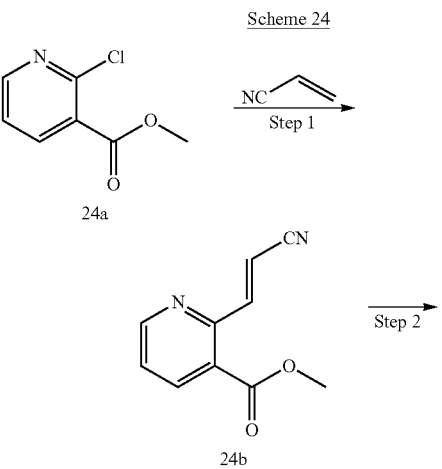

Step 1

Into a 100-mL 3-necked round-bottom flask, was placed 3-(2-methoxyethyl)pyrazine-2-carboxylic acid (2.00 g, 10.98 mmol, 1.00 equiv), (3S)-3-[[(tert-butyldimethylsilyl)oxy]methyl]morpholine (2.54 g, 10.98 mmol, 1.00 equiv), Et$_3$N (2.22 g, 21.94 mmol, 2.00 equiv), DCM (30 mL), and EDCI (2.53 g, 13.17 mmol, 1.20 equiv). This was followed by the addition of HOBt (1.78 g, 13.17 mmol, 1.20 equiv) in portions at 0° C. The resulting solution was stirred for overnight at room temperature. The reaction was then quenched by the addition of 30 mL of water. The resulting solution was extracted with 3×30 mL of dichloromethane, and the organic layers were combined, dried over anhydrous sodium sulfate, and concentrated. The residue was purified by silica gel column with THF/PE (40%) as eluents. This resulted in (3S)-3-[[(tert-butyldimethylsilyl)oxy]methyl]-4-[3-(2-methoxyethyl)pyrazine-2-carbonyl]morpholine. LCMS (ES) [M+1]$^+$ m/z: 396.

Step 2

Into a 100-mL round-bottom flask, was placed (3S)-3-[[(tert-butyldimethylsilyl)oxy]methyl]-4-[3-(2-methoxy-

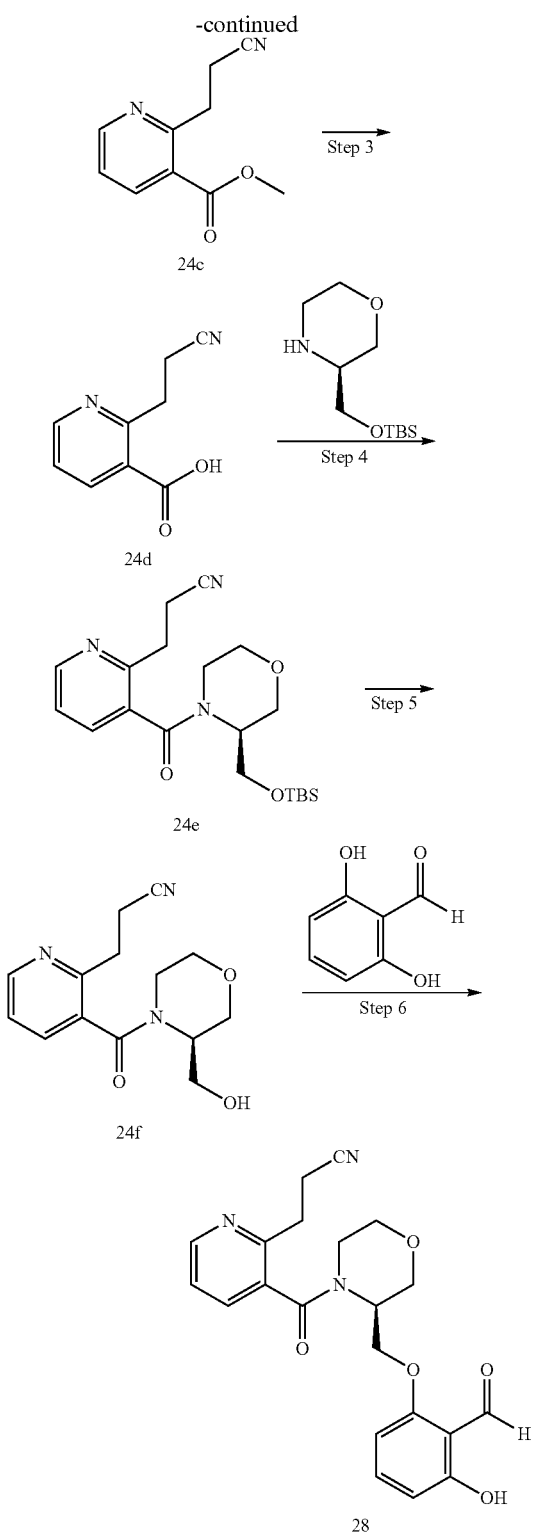

equiv). The resulting solution was stirred for overnight at 130° C. in an oil bath. The reaction was then quenched by water (20 mL) and extracted with EA (40 mL). The organic layer was washed by water (40 mL) two times, dried over anhydrous sodium sulfate and concentrated under vacuum. The residue was purified by silica gel column chromatography with ethyl acetate/petroleum ether (0-9.9%) as eluents. This resulted in methyl 2-[(1E)-2-cyanoeth-1-en-1-yl]pyridine-3-carboxylate. LCMS: (ES, m/z): [M+H]$^+$ 189.1.

Step 2

Into a 50-mL round-bottom flask, was placed methyl (E)-2-(2-cyanovinyl)nicotinate (1.40 g, 7.44 mmol, 1.00 equiv), CH$_3$OH (20 mL), and Pd/C (140.0 mg, 10%). To the above, H$_2$ was introduced. The resulting solution was stirred for 1 hr at room temperature. The solids were filtered out, and the mixture was concentrated and purified by silica gel column chromatography with ethyl acetate/petroleum ether (0-15%) as eluents. This resulted in methyl 2-(2-cyanoethyl)nicotinate. LCMS: (ES, m/z): [M+H]$^+$: 190.1.

Step 3

Into a 50-mL round-bottom flask, was placed methyl 2-(2-cyanoethyl)nicotinate (1.00 g, 5.26 mmol, 1.00 equiv) and THF (12 mL). Then, a solution of LiOH (0.44 g, 10.49 mmol, 1.99 equiv) in H$_2$O (6 mL) was added. The resulting solution was stirred for 1 hr at room temperature and concentrated. The pH value of the solution was adjusted to 5-6 with HCl (2 mol/L). The residue was purified with the following conditions: column, C18; mobile phase, water (0.05% FA) and CH$_3$CN (5% up to 80% in 8 min); Detector, 220 & 254 nm; Flow rate, 40 mL/min. This resulted in 2-(2-cyanoeth-yl)nicotinic acid. LCMS (ES, m/z): [M+H]$^+$: 177.1.

Step 4

Into a 50-mL round-bottom flask, was placed 2-(2-cyanoethyl)pyridine-3-carboxylic acid (300.0 mg, 1.70 mmol, 1.00 equiv), HATU (777.0 mg, 2.04 mmol, 1.20 equiv), DMF (10 mL), DIEA (550.2 mg, 4.26 mmol, 2.50 equiv), and (3S)-3-[[(tert-butyldimethylsilyl)oxy]methyl]morpholine cyclohexane (430.0 mg, 1.86 mmol, 1.09 equiv). The resulting solution was stirred for 2 hr at room temperature. The reaction was then quenched by the addition of water. The resulting solution was extracted with 3×20 mL of ethyl acetate, dried over anhydrous sodium sulfate, and concentrated. The residue was purified by silica gel column chromatography with ethyl acetate/petroleum ether (0-50%) as eluents. This resulted in (S)-3-(3-(3-(((tert-butyldimethylsilyl)oxy)methyl)morpholine-4-carbonyl)pyridin-2-yl)-propanenitrile. LCMS: (ES, m/z): [M+H]$^+$: 390.2.

Step 5

Into a 50-mL round-bottom flask, was placed (S)-3-(3-(3-(((tert-butyldimethylsilyl)oxy)methyl)-morpholine-4-carbonyl)pyridin-2-yl)-propanenitrile (0.63 g, 1.62 mmol, 1.00 equiv), THF (10 mL, 123.43 mmol, 76.3 equiv), and TBAF (1.0 M) (2.43 mL, 2.43 mmol, 1.50 equiv). The resulting solution was stirred for 2 hr at room temperature. The resulting mixture was concentrated and purified by silica gel column chromatography with dichloromethane/methanol (94.6:5.4) as eluents. This resulted in (R)-3-(3-(3-

Step 1

Into a 40-mL vial was placed methyl 2-chloropyridine-3-carboxylate (2.00 g, 11.66 mmol, 1.00 equiv), DMF (15.00 mL), NaOAc (1.91 g, 23.31 mmol, 2.00 equiv), PPh$_3$ (1.22 g, 4.66 mmol, 0.40 equiv), Pd(OAc)$_2$ (0.26 g, 1.17 mmol, 0.10 equiv), and acrylonitrile (3.09 g, 58.28 mmol, 5.00

(hydroxymethyl)morpholine-4-carbonyl)pyridin-2-yl)propanenitrile. LCMS (ES, m/z): [M+H]⁺: 276.1.

Step 6

Into a 40-mL vial purged and maintained with an inert atmosphere of nitrogen, was placed (R)-3-(3-(3-(hydroxymethyl)morpholine-4-carbonyl)pyridin-2-yl)propanenitrile (0.24 g, 0.87 mmol, 1.00 equiv), THF (10 mL), PPh₃ (274.4 mg, 1.05 mmol, 1.20 equiv), and 2,6-dihydroxybenzaldehyde (156.5 mg, 1.13 mmol, 1.30 equiv). Then, DBAD (240.9 mg, 1.05 mmol, 1.20 equiv) was dropwise at 0° C. After 20 min, the resulting solution was stirred at 40° C. for overnight. The resulting mixture was concentrated. The residue was purified by silica gel column chromatography with ethyl acetate/petroleum ether (0-80%) as eluents. The crude product was purified by Prep-HPLC with the following conditions: Column, Kinetex EVO C18, 21.2*150 mm, 5 um; Mobile phase; water (0.1% FA) and CH₃CN (35% up to 75% in 14 min). Detector; 220 nm. Flow rate, 20 mL/min. This resulted in 3-{3-[(3S)-3-[(2-formyl-3-hydroxyphenoxy)methyl]morpholine-4-carbonyl]pyridin-2-yl}propanenitrile. LCMS: (ES, m/z): [M+H]⁺: 396.2. ¹H-NM: (300 MHz, DMSO-d6, ppm): δ 11.72 (s, 1H), 10.17 (s, 1H), 8.62 (dd, J=4.9, 1.7 Hz, 1H), 7.78-7.36 (m, 3H), 6.76 (d, J=8.3 Hz, 1H), 6.55 (d, J=8.2 Hz, 1H), 4.94-4.89 (m, 1H), 4.49-4.27 (m, 2H), 4.10-3.45 (m, 5H), 3.16-2.93 (m, 5H).

Example 25. 2-hydroxy-6-{[(3S)-4-[2-(2-methoxyethyl)benzoyl]morpholin-3-yl]methoxy}benzaldehyde, Compound 29

Compound 29 was synthesized according to Scheme 25.

Scheme 25

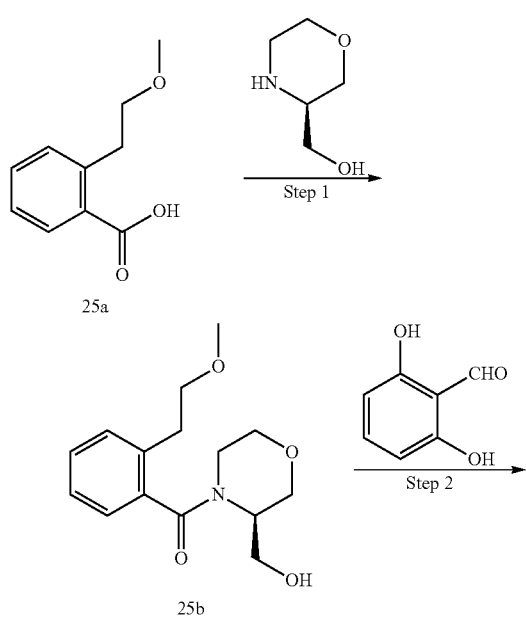

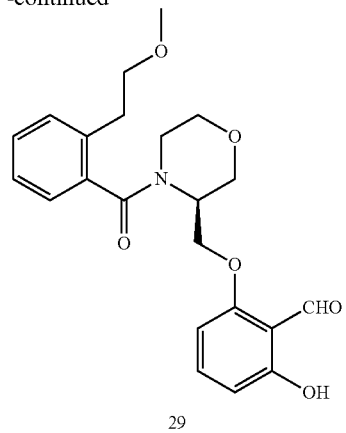

Step 1

Into a 100-mL round-bottom flask, was placed 2-(2-methoxyethyl)benzoic acid (500.00 mg, 2.775 mmol, 1.00 equiv), DCM (20.00 mL), (3R)-morpholin-3-ylmethanol (325.04 mg, 2.775 mmol, 1.00 equiv), HATU (1582.51 mg, 4.162 mmol, 1.50 equiv), and DIEA (1075.81 mg, 8.324 mmol, 3.00 equiv). The resulting solution was stirred for 3 hr at 25° C. The resulting mixture was concentrated. The residue was purified by silica gel column with ethyl acetate/petroleum ether (1:1) as eluents. The collected fractions were combined and concentrated. This resulted in [(3R)-4-[2-(2-methoxyethyl)benzoyl]morpholin-3-yl]methanol. LCMS (ES) [M+1]⁺ m/z 280.2.

Step 2

Into a 50-mL round-bottom flask, was placed [(3R)-4-[2-(2-methoxyethyl)benzoyl]morpholin-3-yl]methanol (200.00 mg, 0.716 mmol, 1.00 equiv), tetrahydrofuran (10 mL), 2,6-dihydroxybenzaldehyde (98.89 mg, 0.716 mmol, 1.00 equiv), triphenylphosphine (225.36 mg, 0.859 mmol, 1.20 equiv), and DIAD (173.73 mg, 0.859 mmol, 1.20 equiv). The resulting solution was stirred for 16 hr at 25° C. The resulting mixture was concentrated. The crude reaction mixture was filtered and subjected to reverse phase preparative HPLC (Prep-C18, 20-45M, 120 g, Tianjin Bonna-Agela Technologies; gradient elution of 25% MeCN in water to 35% MeCN in water over a 10 min period, where both solvents contain 0.1% FA) to provide 2-hydroxy-6-{[(3S)-4-[2-(2-methoxyethyl)benzoyl]morpholin-3-yl]methoxy}benzaldehyde. LCMS (ES) [M+1]⁺ m/z 400.2. ¹H NMR (300 MHz, DMSO-d6) δ 11.76 (br, 1H), 10.31 (s, 1H), 7.56 (t, J=8.4 Hz, 1H), 7.46-6.90 (m, 4H), 6.8-6.455 (m, 2H), 4.98-4.87 (m, 1H), 4.44-4.02 (m, 3H), 4.00-3.27 (m, 8H), 3.15-2.55 (m, 4H).

Example 26. 2-hydroxy-6-{[(3S)-4-[2-(2-methoxy-ethyl)benzoyl]morpholin-3-yl]methoxy}benzaldehyde, Compound 30

Compound 30 was synthesized according to Scheme 26.

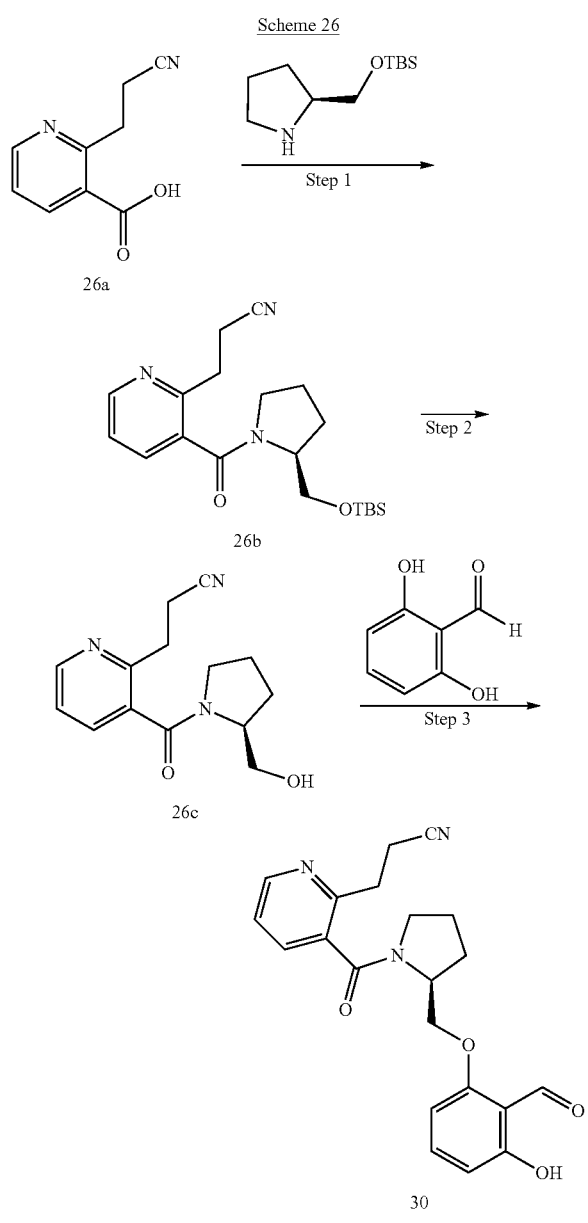

Step 1

Into a 50-mL round-bottom flask, was placed 2-(2-cyanoethyl)pyridine-3-carboxylic acid (0.30 g, 1.70 mmol, 1.00 equiv), HATU (777.0 mg, 2.04 mmol, 1.20 equiv), DMF (10.0 mL), DIEA (550.2 mg, 4.26 mmol, 2.50 equiv), and (2S)-2-[[(tert-butyldimethylsilyl)oxy]methyl]pyrrolidine (403.50 mg, 1.87 mmol, 1.10 equiv). The resulting solution was stirred for 2 hr at room temperature. The reaction was then quenched by the addition of water (20 mL), extracted with 3×20 mL of ethyl acetate, dried over anhydrous sodium sulfate and concentrated. The residue was purified by silica gel column chromatography with ethyl acetate/petroleum ether (0-60%) as eluents. This resulted (S)-3-(3-(2-(((tert-butyldimethylsilyl)oxy)methyl)pyrrolidine-1-carbonyl)pyridin-2-yl)propanenitrile. LCMS (ES, m/z): [M+H]$^+$: 374.2.

Step 2

Into a 50-mL round-bottom flask, was placed (S)-3-(3-(2-(((tert-butyldimethylsilyl)oxy)methyl)-pyrrolidine-1-carbonyl)pyridin-2-yl)propanenitrile (0.4 g, 1.07 mmol, 1.0 equiv), THF (10 mL), and TBAF (1.2 mL, 1.20 mmol, 1.1 equiv). The reaction solution was stirred for 2 hr at room temperature. The resulting mixture was concentrated and purified by silica gel column chromatography with ethyl MeOH/DCM (6:94) as eluents. This resulted in (S)-3-(3-(2-(hydroxymethyl)pyrrolidine-1-carbonyl)pyridin-2-yl)propanenitrile. LCMS (ES, m/z): [M+H]$^+$: 260.1.

Step 3

Into a 40-mL vial purged and maintained with an inert atmosphere of nitrogen, was placed (S)-3-(3-(2-(hydroxymethyl)pyrrolidine-1-carbonyl)pyridin-2-yl)propanenitrile (120.00 mg, 0.46 mmol, 1.00 equiv), PPh$_3$ (145.6 mg, 0.56 mmol, 1.20 equiv), THF (10 mL), and 1-(2,6-dihydroxyphenyl)ethanone (91.5 mg, 0.60 mmol, 1.30 equiv). Then, DBAD (127.9 mg, 0.56 mmol, 1.20 equiv) was dropwise at 0° C. After 20 min, the resulting solution was stirred at 40° C. for overnight. The resulting mixture was concentrated. The residue was purified by silica gel column chromatography with ethyl acetate/petroleum ether (0-90%) as eluents. The crude product was purified by Prep-HPLC with the following conditions: Column, Kinetex EVO C18, 21.2*150 mm, 5 um; Mobile phase water (0.1% FA) and CH$_3$CN (40% up to 70% in 14 min); Detector, 220 nm. Flow rate, 20 mL/min. This resulted in 2-hydroxy-6-{1[(3S)-4-[2-(2-methoxyethyl)benzoyl]morpholin-3-yl]methoxy}benzaldehyde. LCMS: (ES, m/z): [M+H]$^+$: 380.2. $^1$H-NMR (300 MHz, DMSO-d6, ppm): δ11.68 (s, 1H), 10.34 (s, 1H), 8.61 (dd, J=4.8, 1.7 Hz, 1H), 7.72 (dd, J=7.7, 1.8 Hz, 1H), 7.54 (t, J=8.4 Hz, 1H), 7.38 (dd, J=7.7, 4.8 Hz, 1H), 6.72 (d, J=8.4 Hz, 1H), 6.55 (d, J=8.4 Hz, 1H), 4.57-4.53 (m, 1H), 4.3-4.29 (m, 2H), 4.10-3.59 (m, 1H), 3.32-3.14 (m, 2H), 3.06-3.01 (m, 2H), 2.9-2.81 (m, 2H), 2.15-1.80 (m, 4H).

Example 27. 3-{2-[(3S)-3-[(2-formyl-3-hydroxyphenoxy)methyl]morpholine-4-carbonyl]phenyl}propanenitrile, Compound 31

Compound 31 was synthesized according to Scheme 27.

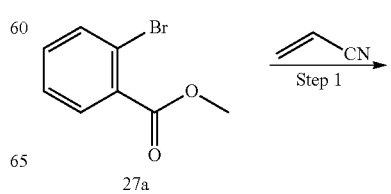

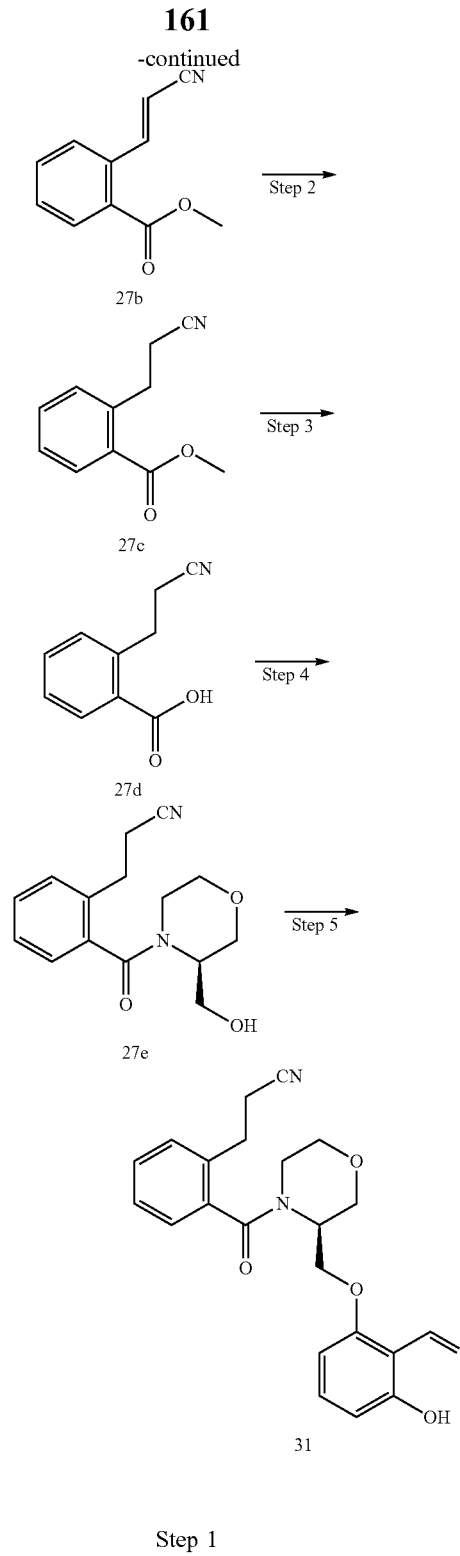

(10% EA) as eluents. This resulted in methyl 2-[(1E)-2-cyanoeth-1-en-1-yl]benzoate. LCMS (ES) [M+1]+ m/z 188.0.

Step 2

Into a 100-mL round-bottom flask, was placed methyl 2-[(1E)-2-cyanoeth-1-en-1-yl]benzoate (1.90 g, 10.150 mmol, 1.00 equiv), MeOH (40.00 mL, 987.956 mmol, 97.34 equiv), and Pd/C (0.80 g, 7.517 mmol, 0.74 equiv). The flask was evacuated and flushed three times with nitrogen, followed by flushing with hydrogen. The mixture was stirred 4 h at room temperature under an atmosphere of hydrogen (balloon). The solids were filtered out. The filtrate was concentrated. This resulted in methyl 2-(2-cyanoethyl)benzoate. LCMS (ES) [M+1]+ m/z 190.1.

Step 3

Into a 100-mL round-bottom flask, was placed methyl 2-(2-cyanoethyl)benzoate (1.90 g, 10.042 mmol, 1.00 equiv) and MeOH (50.00 mL). This was followed by the addition of a solution of LiOH (0.72 g, 30.065 mmol, 2.99 equiv) in H$_2$O (10 mL) at 0° C. in 5 min. The resulting solution was stirred for 16 h at room temperature. The pH value of the solution was adjusted to 5 with citric acid (3 mol/L). The resulting solution was extracted with 3×100 mL of DCM/MeOH=10:1. The mixture was dried over anhydrous sodium sulfate and concentrated under vacuum. This resulted in 2-(2-cyanoethyl)benzoic acid. LCMS (ES) [M−1]− m/z 174.3.

Step 4

Into a 20-mL sealed tube, was placed 2-(2-cyanoethyl) benzoic acid (0.50 g, 2.854 mmol, 1.00 equiv), (3R)-morpholin-3-ylmethanol hydrochloride (0.66 g, 4.281 mmol, 1.50 equiv), HATU (1.63 g, 4.281 mmol, 1.50 equiv), DIEA (1.11 g, 8.588 mmol, 3.01 equiv), and DMF (10.00 mL). The resulting solution was stirred for 2 h at room temperature. The resulting mixture was concentrated. The residue was purified by silica gel column chromatography with PE:THF (45% THF) as eluents. This resulted in 3-[2-[(3R)-3-(hydroxymethyl)morpholine-4-carbonyl]phenyl]propanenitrile. LCMS (ES) [M+1]+ m/z 275.1.

Step 5

Into a 100-mL round-bottom flask purged and maintained with an inert atmosphere of nitrogen, was placed 3-[2-[(3R)-3-(hydroxymethyl)morpholine-4-carbonyl]phenyl]propanenitrile (0.40 g, 1.458 mmol, 1.00 equiv), 2,6-dihydroxybenzaldehyde (0.40 g, 2.916 mmol, 2 equiv), PPh$_3$ (0.76 g, 2.916 mmol, 2 equiv), and THF (30.00 mL). The resulting solution was stirred for 15 min at 0° C. This was followed by the addition of DIAD (0.59 g, 2.918 mmol, 2.00 equiv) at 0° C. in 3 min. The resulting solution was stirred for 2 h at room temperature. The resulting mixture was concentrated. The residue was purified by silica gel column chromatography with PE/THF (22% THF) as eluents. The collected product was purified by Flash-Prep-HPLC (Prep-C18, 20-45M, 120 g, Tianjin Bonna-Agela Technologies; gradient elution of 45% MeCN in water to 65% MeCN in water over a 10 min period, where both solvents contain 0.1% FA). This resulted in 3-{2-[(3S)-3-[(2-formyl-3-hydroxyphenoxy) methyl]morpholine-4-carbonyl]phenyl}propanenitrile. LCMS (ES) [M+1]+ m/z 395.2. $^1$H NMR (300 MHz, Step 1

Into a 100-mL 3-necked round-bottom flask purged and maintained with an inert atmosphere of nitrogen, was placed methyl 2-bromobenzoate (3.00 g, 13.951 mmol, 1.00 equiv), acrylonitrile (1.48 g, 27.901 mmol, 2.00 equiv), DIEA (5.41 g, 41.859 mmol, 3.00 equiv), dioxane (50.00 mL), and Pd(P(t-Bu)$_3$)$_2$ (0.71 g, 1.389 mmol, 0.10 equiv). The resulting solution was stirred for 16 h at 100° C. in an oil bath. The resulting mixture was concentrated. The residue was purified by silica gel column with ethyl acetate/petroleum ether DMSO-d$_6$ ppm) δ 11.73 (s, 1H), 10.28 (s, 1H), 7.63-7.03 (m, 5H), 6.77 (d, J=8.3 Hz, 1H), 6.56 (d, J=8.5 Hz, 1H), 5.06-4.22 (m, 3H), 4.12-3.29 (m, 5H), 3.15-2.66 (m, 5H).

Example 28.3-{3-[(3S)-3-[(2-formyl-3-hydroxyphenoxy)methyl]morpholine-4-carbonyl]pyrazin-2-yl}propanenitrile, Compound 32

Compound 32 was synthesized according to Scheme 28.

Scheme 28

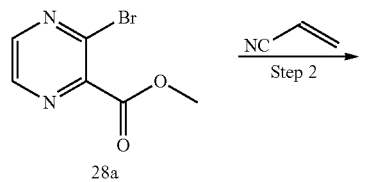

28a

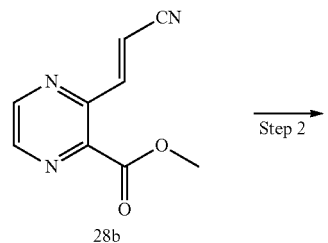

28b

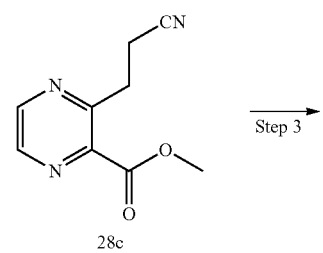

28c

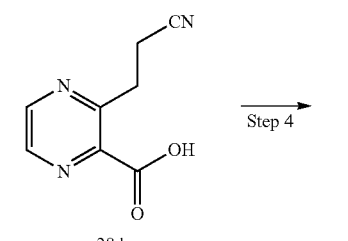

28d

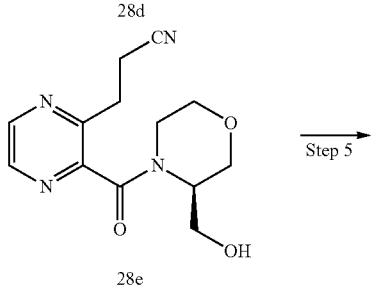

28e

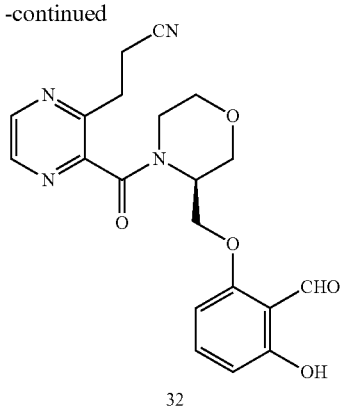

32

Step 1

Into a 100-mL 3-necked round-bottom flask purged and maintained with an inert atmosphere of nitrogen, was placed methyl 3-bromopyrazine-2-carboxylate (6.00 g, 27.647 mmol, 1.00 equiv), acrylonitrile (4.40 g, 82.941 mmol, 3 equiv), DIEA (10.72 g, 82.941 mmol, 3 equiv), dioxane (60.00 mL), and Pd(P(t-Bu)$_3$)$_2$ (1.41 g, 2.765 mmol, 0.1 equiv). The resulting solution was stirred for 16 h at 100° C. in an oil bath. The resulting mixture was concentrated. The residue was purified by silica gel column chromatography with (10%-20% EA) as eluents. This resulted in methyl 3-[(1E)-2-cyanoeth-1-en-1-yl]pyrazine-2-carboxylate. LCMS (ES) [M+1]$^+$ m/z 190.2.

Step 2

Into a 100-mL round-bottom flask, was placed methyl 3-[(1E)-2-cyanoeth-1-en-1-yl]pyrazine-2-carboxylate (1.60 g, 8.458 mmol, 1.00 equiv), MeOH (20.00 mL), and Pd/C (0.60 g, 5.638 mmol, 0.67 equiv). The flask was evacuated and flushed three times with nitrogen, followed by flushing with hydrogen. The resulting solution was stirred for 4 h at room temperature under an atmosphere of hydrogen (balloon). The solids were filtered out.

The filtrate was concentrated. This resulted in methyl 3-(2-cyanoethyl)pyrazine-2-carboxylate. LCMS (ES) [M+1]$^+$ m/z 192.2.

Step 3

Into a 100-mL round-bottom flask, was placed methyl 3-(2-cyanoethyl)pyrazine-2-carboxylate (0.70 g, 3.661 mmol, 1.00 equiv) and MeOH (50 mL). This was followed by the addition of a solution of LiOH.H$_2$O (0.31 g, 7.387 mmol, 2.02 equiv) in H$_2$O (10 mL) dropwise with stirring at 0° C. in 5 min. The resulting solution was stirred for 2 h at room temperature. The pH value of the solution was adjusted to 5 with citric acid (2 mol/L). The resulting solution was extracted with 20×100 mL of DCM/MeOH=10:1, and the organic layer was concentrated. This resulted in 3-(2-cyanoethyl)pyrazine-2-carboxylic acid. LCMS (ES) [M-1]$^-$ m/z 176.1.

Step 4

Into a 20-mL vial, was placed 3-(2-cyanoethyl)pyrazine-2-carboxylic acid (0.43 g, 2.427 mmol, 1.00 equiv), (3R)-morpholin-3-ylmethanol hydrochloride (0.34 g, 2.913 mmol, 1.2 equiv), HATU (1.11 g, 2.913 mmol, 1.20 equiv), DIEA (0.94 g, 7.281 mmol, 3.00 equiv), and DMF (10.00 mL). The resulting solution was stirred for 2 h at room temperature. The resulting mixture was concentrated. The residue was purified by silica gel column chromatography with PE/THF (50% THF) as eluents. This resulted in 3-[3-[(3R)-3-(hydroxymethyl)morpholine-4-carbonyl]pyrazin-2-yl]propanenitrile. LCMS (ES) [M+1]$^+$ m/z 277.1.

Step 5

Into a 100-mL 3-necked round-bottom flask purged and maintained with an inert atmosphere of nitrogen, was placed 3-[3-[(3R)-3-(hydroxymethyl)morpholine-4-carbonyl]pyrazin-2-yl]propanenitrile (200.00 mg, 0.724 mmol, 1.00 equiv), 2,6-dihydroxybenzaldehyde (199.96 mg, 1.448 mmol, 2.00 equiv), PPh$_3$ (379.72 mg, 1.448 mmol, 2.00 equiv), and THF (20.00 mL). The resulting solution was stirred for 15 min at 0° C. This was followed by the addition of DIAD (292.74 mg, 1.448 mmol, 2.00 equiv) dropwise with stirring at 0° C. in 5 min. The resulting solution was stirred for 2 h at room temperature. The resulting mixture was concentrated. The residue was purified by silica gel column chromatography with PE/THF (35% THF) as eluents. The collected product was further purified by Flash-Prep-HPLC (Prep-C18, 20-45M, 120 g, Tianjin Bonna-Agela Technologies; gradient elution of 35% MeCN in water to 60% MeCN in water over a 10 min period, where both solvents contain 0.1% FA). This resulted in 3-[(3S)-3-(2-formyl-3-hydroxyphenoxymethyl)morpholine-4-carbonyl]pyrazin-2-yl]propanenitrile. LCMS (ES) [M+1]$^+$ m/z 397.2. $^1$H NMR (300 MHz, DMSO-d$_6$ ppm) δ 11.75 (s, 1H), 10.32 (s, 1H), 8.72 (dd, J=8.2, 2.5 Hz, 1H), 8.55 (dd, J=13.7, 2.5 Hz, 1H), 7.62-7.51 (m, 1H), 6.80-6.48 (m, 2H), 5.03-4.94 (m, 1H), 4.53-4.31 (m, 2H), 4.12-3.38 (m, 5H), 3.21-3.04 (m, 3H), 2.99-2.90 (m, 2H).

Example 29. 2-hydroxy-6-{[(3S)-4-[3-(hydroxymethyl)pyrazine-2-carbonyl]morpholin-3-yl]methoxy}benzaldehyde, Compound 33

Compound 33 was synthesized according to Scheme 29.

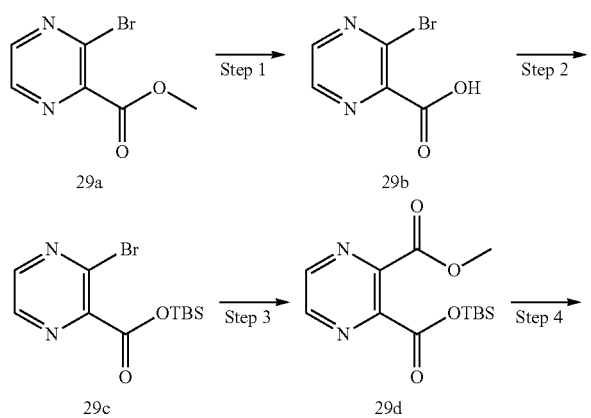

Step 1

Into a 250-mL round-bottom flask purged and maintained with an inert atmosphere of nitrogen, was placed methyl 3-bromopyrazine-2-carboxylate (5.00 g, 23.039 mmol, 1.00 equiv), H$_2$O (100.00 mL). This was followed by the addition of NaBH$_4$ (4.36 g, 115.243 mmol, 5.00 equiv) in several batches at 0° C. The resulting solution was stirred for overnight at room temperature. The reaction was quenched by the addition of 50 mL of EtOH and diluted with 150 mL of K$_2$CO$_{3(aq.)}$. The n the mixture was stirred for 0.5 h at room temperature. The resulting solution was extracted with 3×150 mL of ethyl acetate and extracted with 3×150 mL of dichloromethane; the organic layer was dried over anhydrous sodium sulfate and concentrated. This resulted in (3-bromopyrazin-2-yl)methanol. LCMS (ES) [M+1]$^+$ m/z 189.1.

Step 2

Into a 100-mL round-bottom flask, was placed (3-bromopyrazin-2-yl)methanol (3.00 g, 15.872 mmol, 1.00 equiv), DCM (60.00 mL), imidazole (2.16 g, 31.729 mmol, 2.00 equiv), and TBSCl (2.87 g, 19.042 mmol, 1.20 equiv). The resulting solution was stirred for 3 h at room temperature and diluted with 50 mL of H$_2$O. The resulting solution was extracted with 3×150 mL of dichloromethane; the organic layer was dried over anhydrous sodium sulfate and concentrated. The residue was purified by silica gel column chromatography with ethyl acetate/petroleum ether (20% EA) as eluents. This resulted in 2-bromo-3-[[(tert-butyldimethylsilyl)oxy]methyl]pyrazine. LCMS (ES) [M+1]$^+$ m/z 303.1.

Step 3

Into a 250-mL pressure tank reactor, was placed 2-bromo-3-[[(tert-butyldimethylsilyl)oxy]methyl]pyrazine (6.00 g, 19.784 mmol, 1.00 equiv), Pd(dppf)Cl$_2$ (1.45 g, 1.978 mmol, 0.10 equiv), TEA (6.01 g, 59.352 mmol, 3.00 equiv), MeOH (100.00 mL), and CO (gas). The resulting solution was stirred for overnight at 90° C. The resulting mixture was concentrated. The residue was purified by silica gel column chromatography with PE/THF (70% THF) as eluents. This resulted in methyl 3-[[(tert-butyldimethylsilyl)oxy]methyl]pyrazine-2-carboxylate. LCMS (ES) [M+1]$^+$ m/z 283.2.

Step 4

Into a 250-mL round-bottom flask, was placed methyl 3-[[(tert-butyldimethylsilyl)oxy]methyl]pyrazine-2-carboxylate (3.10 g, 10.977 mmol, 1.00 equiv), methanol (50.00 mL). This was followed by the addition of a solution of LiOH.H$_2$O (0.92 g, 21.924 mmol, 2.00 equiv) in H$_2$O (10 mL) dropwise with stirring at 0° C. in 5 min. The resulting solution was stirred for 5 h at room temperature. The pH value of the solution was adjusted to 5 with citric acid (2 mol/L). The resulting solution was extracted with 5×150 mL of dichloromethane; the organic layer was dried over anhydrous sodium sulfate and concentrated. This resulted in 3-[[(tert-butyldimethylsilyl)oxy]methyl]pyrazine-2-carboxylic acid. LCMS (ES) [M+1]$^+$ m/z 269.2.

Step 5

Into a 20-mL vial, was placed 3-[[(tert-butyldimethylsilyl)oxy]methyl]pyrazine-2-carboxylic acid (1.00 g, 3.726 mmol, 1.00 equiv), (3R)-morpholin-3-ylmethanol hydrochloride (0.68 g, 4.471 mmol, 1.20 equiv), dimethylformamide (10.00 mL), HATU (1.70 g, 4.471 mmol, 1.20 equiv), and DIEA (1.95 mL, 15.064 mmol, 3.00 equiv). The resulting solution was stirred for 3 h at room temperature. The resulting solution was diluted with 50 mL of H$_2$O. The resulting solution was extracted with 4×60 mL of dichloromethane, and the organic layer was washed with 2×100 mL of brine. The mixture was dried over anhydrous sodium sulfate and concentrated. The residue was purified by silica gel column chromatography with PE/THF (60% THF) as eluents. This resulted in [(3R)-4-(3-[[(tert-butyldimethylsilyl)oxy]methyl]pyrazine-2-carbonyl)morpholin-3-yl]methanol. LCMS (ES) [M+1]$^+$ m/z 368.2.

Step 6

Into a 100-mL 3-necked round-bottom flask purged and maintained with an inert atmosphere of nitrogen, was placed [(3R)-4-(3-[[(tert-butyldimethylsilyl)oxy]methyl]pyrazine-2-carbonyl)morpholin-3-yl]methanol (0.97 g, 2.639 mmol, 1.00 equiv), 2,6-dihydroxybenzaldehyde (0.73 g, 5.279 mmol, 2.00 equiv), PPh$_3$ (1.38 g, 5.261 mmol, 1.99 equiv), and THF (60 mL). The resulting solution was stirred for 15 min at 0° C. This was followed by the addition of DIAD (1.07 g, 5.279 mmol, 2.00 equiv) dropwise with stirring at 0° C. in 2 min. The resulting solution was stirred for 2 h at room temperature. The resulting mixture was concentrated. The residue was purified by silica gel column with PE/THF (50% THF) as eluents. This resulted in 2-[[(3S)-4-(3-[[(tert-butyldimethylsilyl)oxy]methyl]pyrazine-2-carbonyl)morpholin-3-yl]methoxy]-6-hydroxybenzaldehyde. LCMS (ES) [M+1]$^+$ m/z 488.2.

Step 7

Into a 100-mL round-bottom flask, was placed 2-[[(3S)-4-(3-[[(tert-butyldimethylsilyl)oxy]methyl]pyrazine-2-carbonyl)morpholin-3-yl]methoxy]-6-hydroxybenzaldehyde (0.8 g, 1.641 mmol, 1.00 equiv), THF (20.00 mL), and TBAF (2.5 mL, 1.5 equiv, 2M). The resulting solution was stirred for 2 h at room temperature. The resulting mixture was concentrated. The residue was purified by silica gel column chromatography with (60% THF) as eluents. The collected product was further purified by Flash-Prep-HPLC (Prep-C18, 20-45M, 120 g, Tianjin Bonna-Agela Technologies; gradient elution of 30% MeCN in water to 50% MeCN in water over a 10 min period, where both solvents contain 0.1% FA). This resulted in 2-hydroxy-6-{[(3S)-4-[3-(hydroxymethyl)pyrazine-2-carbonyl]morpholin-3-yl]methoxy}benzaldehyde. LCMS (ES) [M+1]$^+$ m/z 374.1. $^1$H-NMR (300 MHz, DMSO-d$_6$ ppm) δ 11.79 (s, 1H), 10.29 (d, J=3.6 Hz, 1H), 8.64 (t, J=2.4 Hz, 1H), 8.54 (dd, J=12.2, 2.6 Hz, 1H), 7.62-7.49 (m, 1H), 6.77-6.48 (m, 2H), 5.72-5.51 (m, 1H), 4.95-4.30 (m, 5H), 4.12-3.39 (m, 5H), 3.24-2.97 (m, 1H).

Example 30. 2-{[(2S)-1-[2-(1,2-dihydroxyethyl)benzoyl]piperidin-2-yl]methoxy}-6-hydroxybenzaldehyde, Compound 34

Compound 34 was synthesized according to Scheme 30.

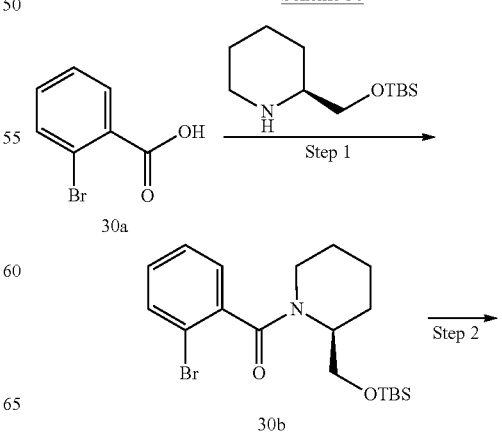

Scheme 30

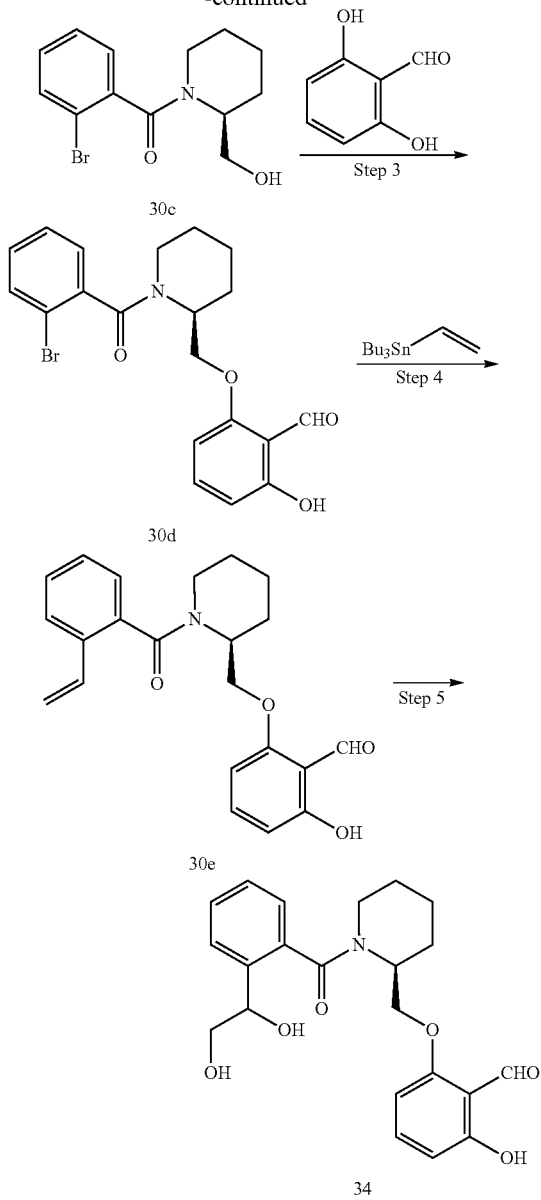

eridin-1-yl)methanone (5.0 g, 12.12 mmol, 1.0 equiv), THF (50 mL), and 1 M TBAF in THF (12.1 mL, 12.12 mmol, 1.0 equiv). The mixture was stirred for 2 h at room temperature. The mixture was concentrated to remove the solvent, and the residue was purified by silica gel column with ethyl acetate (100%) as eluents. This resulted in (S)-(2-bromophenyl)(2-(hydroxymethyl)piperidin-1-yl)methanone. LCMS (ES) [M+1]$^+$ m/z: 298.

Step 3

Into a 250-mL 3-necked round-bottom flask purged and maintained with an inert atmosphere of nitrogen, was placed (S)-(2-bromophenyl)(2-(hydroxymethyl)piperidin-1-yl)methanone (2.0 g, 6.71 mmol, 1.0 equiv), 2,6-dihydroxybenzaldehyde (1.12 g, 8.11 mmol, 1.2 equiv), THF (80 mL), and PPh$_3$ (2.10 g, 8.01 mmol, 1.2 equiv). This was followed by the addition of DIAD (1.63 g, 8.05 mmol, 1.2 equiv) at 0° C. The reaction solution was stirred overnight at room temperature. The solution was concentrated to remove the solvent, and the residue was purified by silica gel column with ethyl acetate/petroleum ether (80%) as eluents. This resulted in (S)-2-((1-(2-bromobenzoyl)piperidin-2-yl)methoxy)-6-hydroxybenzaldehyde. LCMS (ES) [M+1]$^+$ m/z: 418.

Step 4

Into a 50-mL round-bottom flask purged and maintained with an inert atmosphere of nitrogen, was placed (S)-2-((1-(2-bromobenzoyl)piperidin-2-yl)methoxy)-6-hydroxybenzaldehyde (1.57 g, 3.75 mmol, 1.0 equiv), dioxane (20 mL), tributyl(ethenyl)stannane (2.40 g, 7.54 mmol, 2.0 equiv), and Pd(dppf)Cl$_2$ (307 mg, 0.37 mmol, 0.10 equiv). The mixture was stirred overnight at 90° C. The mixture was concentrated to remove the solvent, and the residue was purified by silica gel column chromatography with ethyl acetate/petroleum ether (1/1) as eluents. This resulted in (S)-2-hydroxy-6-((1-(2-vinylbenzoyl)piperidin-2-yl)methoxy)benzaldehyde. LCMS (ES) [M+1]$^+$ m/z: 366.

Step 5

Into a 20-mL vial, was placed (S)-2-hydroxy-6-((1-(2-vinylbenzoyl)piperidin-2-yl)methoxy)benzaldehyde (604 mg, 1.65 mmol, 1.0 equiv), t-BuOH (4.0 mL), H$_2$O (4.0 mL), and ad-mix-alpha (2.60 g, 4.96 mmol, 3.0 equiv). The mixture was stirred for 3 h at room temperature. The crude product was purified by Prep-HPLC with the following conditions (SHIMADZU (HPLC-01)): Column, Kinetex EVO C18 Column, 21.2*150, 5 um, mobile phase, Water (0.1% FA) and CH$_3$CN (45% Phase B up to 65% in 9 min), Detector, UV 254 nm. 2-{[(2S)-1-[2-(1,2-dihydroxyethyl)benzoyl]piperidin-2-yl]methoxy}-6-hydroxybenzaldehyde was obtained. LCMS: (ES, m/z): [M+H]$^+$: 400.2. $^1$H-NMR: (300 MHz, DMSO-d$_6$, ppm): δ11.73 (s, 1H), 10.26 (s, 1H), 7.59-7.20 (m, 5H), 6.88-6.53 (m, 2H), 5.26-4.27 (m, 6H), 3.55-3.05 (m, 4H), 1.94-1.43 (m, 6H).

Example 31. 2-{[(3R)-4-{2-[(1S)-1,2-dihydroxyethyl]benzoyl}thiomorpholin-3-yl]methoxy}-6-hydroxybenzaldehyde and 2-{[(3R)-4-{2-[(1R)-1,2-dihydroxyethyl]benzoyl}thiomorpholin-3-yl]methoxy}-6-hydroxybenzaldehyde Compound 35, Diastereomer 1 and Compound 35, Diastereomer 2 were synthesized according to Scheme 31.

Step 1

Into a 100-mL 3-necked round-bottom flask, was placed o-bromobenzoic acid (5.0 g, 24.87 mmol, 1.0 equiv), (2S)-2-[[(tert-butyldimethylsilyl)oxy]methyl]piperidine (6.90 g, 30.07 mmol, 1.2 equiv), DCM (50.0 mL), and DIEA (6.50 g, 50.29 mmol, 2.0 equiv). This was followed by the addition of HATU (11.40 g, 29.98 mmol, 1.2 equiv) at 0° C. The reaction solution was stirred for 2 h at room temperature. The reaction was then quenched by the addition of water (30 mL), and extracted with 2×50 mL of dichloromethane. The residue was purified by silica gel column with ethyl acetate/petroleum ether (10%) as eluents. (S)-(2-bromophenyl)(2-(((tert-butyldimethylsilyl)oxy)methyl)piperidin-1-yl)methanone was obtained. LCMS (ES) [M+1]$^+$ m/z: 412.

Step 2

Into a 250-mL round-bottom flask, was placed (S)-(2-bromophenyl)(2-(((tert-butyldimethylsilyl)oxy)methyl)pip-

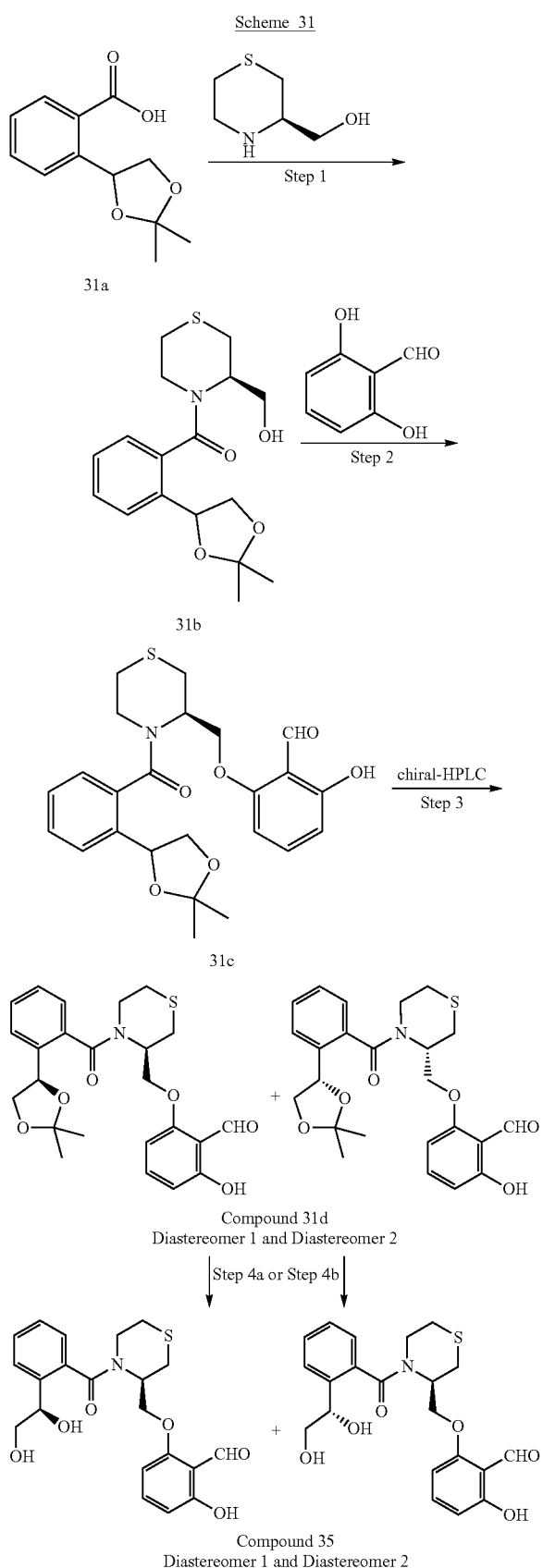

Scheme 31

31a

31b

31c

Compound 31d
Diastereomer 1 and Diastereomer 2

Step 4a or Step 4b

Compound 35
Diastereomer 1 and Diastereomer 2

Step 1

Into a 100-mL round-bottom flask, was placed 2-(2,2-dimethyl-1,3-dioxolan-4-yl)benzoic acid (900 mg, 4.05 mmol, 1.00 equiv), DMF (10.0 mL), (3R)-thiomorpholin-3-ylmethanol (593 mg, 4.45 mmol, 1.10 equiv), and DIEA (1.05 g, 8.09 mmol, 2.00 equiv). This was followed by the addition of HATU (2.31 g, 6.07 mmol, 1.50 equiv) at 0° C. The resulting solution was stirred for 2 hr at room temperature. The resulting solution was diluted with 50 mL of $H_2O$ and extracted with 3×30 mL of ethyl acetate, and the organic layers were combined, dried over anhydrous sodium sulfate, and concentrated. The residue was purified by silica gel column chromatography with ethyl acetate/petroleum ether (1/10) as eluents. This resulted in [(3R)-4-[2-(2,2-dimethyl-1,3-dioxolan-4-yl)benzoyl]thiomorpholin-3-yl]methanol. $[M+1]^+$ m/z: 338.1.

Step 2

Into a 50-mL round-bottom flask, was placed [(3R)-4-[2-(2,2-dimethyl-1,3-dioxolan-4-yl)benzoyl]thiomorpholin-3-yl]methanol (620 mg, 1.83 mmol, 1.00 equiv), DCE (8.0 mL), and DIEA (1.42 g, 11.02 mmol, 6.00 equiv). This was followed by the addition of MsCl (420 mg, 3.67 mmol, 2.00 equiv) dropwise with stirring at 0° C. The resulting solution was stirred for 1 hr at room temperature. To this solution was added 2,6-dihydroxybenzaldehyde (253 mg, 1.83 mmol, 1.00 equiv). The resulting solution was stirred for 6 hr at 80° C. The reaction mixture was cooled and concentrated. The resulting solution was diluted with 5 mL of ACN. The crude product was purified by Flash-Prep-HPLC with the following conditions (IntelFlash-1): Column, C18 silica gel; mobile phase, $H_2O$ (0.1% HCOOH)/ACN=1/1 increasing to $H_2O$ (0.1% HCOOH)/ACN=1/2 within 10 min; Detector, UV 254 nm. This resulted in 2-[[(3R)-4-[2-(2,2-dimethyl-1,3-dioxolan-4-yl)benzoyl]thiomorpholin-3-yl]methoxy]-6-hydroxybenzaldehyde. $[M+1]^+$ m/z: 458.2.

Step 3

2-hydroxy-6-[[(3R)-4-[2-(2-methyl-1,3-dioxolan-4-yl)benzoyl]thiomorpholin-3-yl]methoxy] benzaldehyde was purified by Chiral-Prep-HPLC with the following conditions: Mobile phase A: n-Hexane; Mobile phase B:EtOH; Flow rate: 20 mL/min; Column: DAICEL CHIRALPAK ID, 250*20 mm, 5um; Gradient:5% B in 20 min; Detector, UV 254 nm. The collected products were subjected to analytical chiral HPLC analysis (Instrument Name: Shimadzu LC-20AD; Mobile Phase A: n-Hexane; Mobile Phase B: Ethanol; Column: CHIRALPAK IC-3, 50*4.6 mm, 3 um IC30CC-SC002). This resulted in Compound 31d, Diastereomer 2 (Analytical HPLC Retention Time=2.188 min) and Compound 31d, Diastereomer 1 (Analytical HPLC Retention Time=2.988 min).

Step 4A: Compound 35, Diastereomer 1

Into a 50-mL round-bottom flask, was placed Compound 31, Diastereomer 1 (80 mg, 0.17 mmol, 1.00 equiv), ACN (2.0 mL), $Yb(OTf)_3 \cdot H_2O$ (54 mg, 0.08 mmol, 0.50 equiv). The resulting solution was stirred for 5 hr at room temperature. The resulting solution was diluted with 5 mL of ACN and filtered. The crude product was purified by Prep-HPLC with the following conditions (2 #SHIMADZU (HPLC-01)): Column, Welch Xtimate C18, 21.2*250 mm, 5 um; mobile phase, Water and ACN (15% Phase B up to 70% in 20 min); Detector, UV 254 nm. The product was analyzed by chiral SFC (Instrument Name: Shimadzu LC-30AD SF; Column: AS-3, 100*3 mm). This resulted in Compound 35, Diastereomer 1. SFC retention time=2.75 min. LCMS [M+1]+ m/z: 418.2. $^1$H NMR (300 MHz, DMSO-$d_6$) δ 11.76 (br, 1H), 10.43-10.06 (m, 1H), 7.64-6.88 (m, 5H), 6.87-6.45 (m, 2H), 5.57-5.15 (m, 2H), 4.93-4.37 (m, 4H), 3.68-3.37 (m, 3H), 3.24-2.83 (m, 2H), 2.83-2.59 (m, 2H), 2.48-2.22 (m, 1H).

Step 4B: Compound 35, Diastereomer 2

Into a 50-mL round-bottom flask was placed Compound 31d, Diastereomer 2 (90 mg, 0.19 mmol, 1.00 equiv), ACN (2.0 mL), and Yb(OTf)$_3$·H$_2$O (61 mg, 0.09 mmol, 0.50 equiv). The resulting solution was stirred for 5 hr at room temperature. The resulting solution was diluted with 5 mL of ACN and filtered. The crude product was purified by Prep-HPLC with the following conditions (2 #SHIMADZU (HPLC-01)): Column, Welch Xtimate C18, 21.2*250 mm, 5 um; mobile phase, Water and ACN (15% Phase B up to 70% in 18 min); Detector, UV 254 nm. The product was analyzed by chiral SFC (Instrument Name: Shimadzu LC-30AD SF; Column: AS-3, 100*3 mm). This resulted in Compound 35, Diastereomer 2. SFC retention time=2.44 min. LCMS [M+1]+ m/z: 418.2. $^1$H NMR (300 MHz, DMSO-$d_6$) δ 11.76 (br, 1H), 10.46-10.03 (m, 1H), 7.70-6.90 (m, 5H), 6.82-6.48 (m, 2H), 5.52-5.15 (m, 2H), 4.93-4.02 (m, 4H), 3.63-3.36 (m, 3H), 3.26-2.90 (m, 2H), 2.88-2.55 (m, 2H), 2.48-2.24 (m, 1H).

Example 32. 2-{[(2S)-1-[2-(1,2-dihydroxyethyl)pyridine-3-carbonyl]piperidin-2-yl]methoxy}-6-hydroxybenzaldehyde, Compound 36

Compound 36 was synthesized according to Scheme 32.

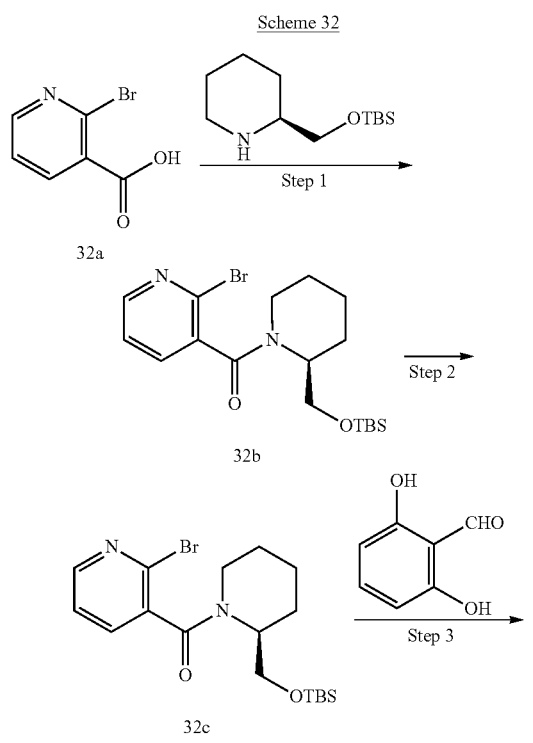

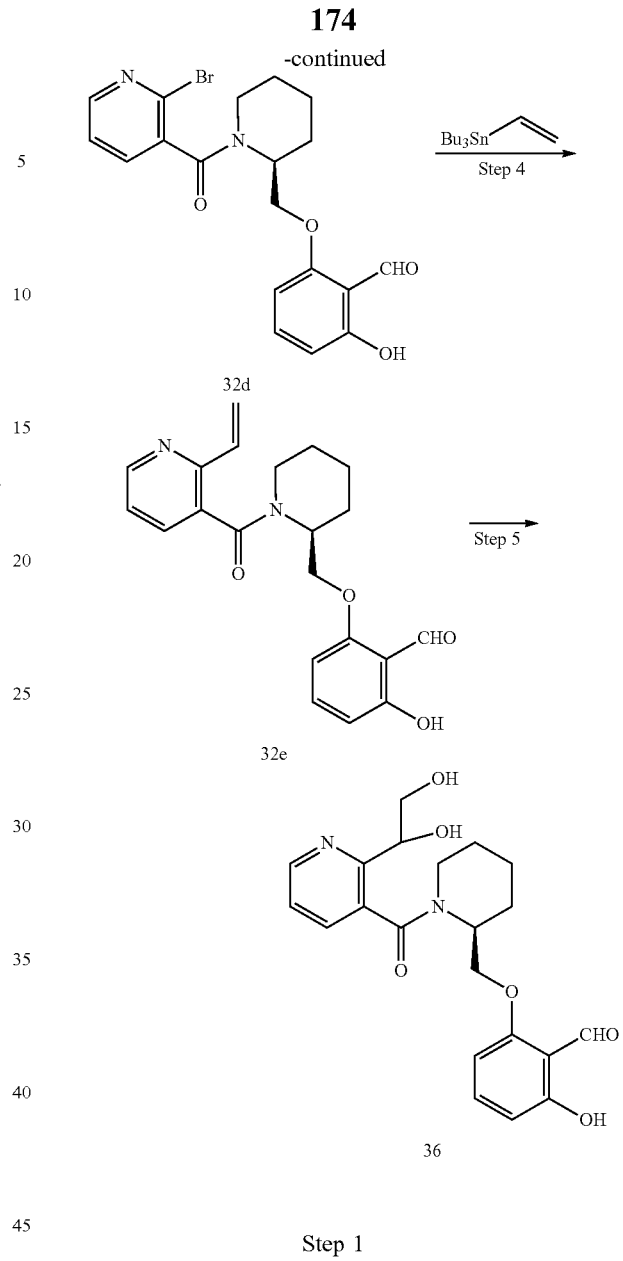

Step 1

Into a 100-mL 3-necked round-bottom flask, was placed 2-bromopyridine-3-carboxylic acid (4.0 g, 19.80 mmol, 1.0 equiv), (2S)-2-[[(tert-butyldimethylsilyl)oxy]methyl]piperidine (5.50 g, 23.97 mmol, 1.2 equiv), DCM (50 mL), and DIEA (5.13 g, 39.70 mmol, 2.0 equiv). This was followed by the addition of HATU (9.07 g, 23.85 mmol, 1.2 equiv) at 0° C. The reaction solution was stirred for 2 h at room temperature. The reaction was then quenched by the addition of water (50 mL), and extracted with 2×50 mL of dichloromethane. The combined organic phase was dried over anhydrous sodium sulfate and filtered, and the filtrate was concentrated under reduced pressure. The residue was purified by silica gel column with ethyl acetate/petroleum ether (1/4). (S)-(2-bromopyridin-3-yl)(2-(((tert-butyldimethylsilyl)oxy)methyl)piperidin-1-yl)methanone was obtained. LCMS (ES) [M+1]+ m/z: 413.

Step 2

Into a 250-mL round-bottom flask, was placed (S)-(2-bromopyridin-3-yl)(2-(((tert-butyldimethylsilyl)oxy)

methyl)piperidin-1-yl)methanone (8.0 g, 19.35 mmol, 1.0 equiv), THF (80 mL), and TBAF (1 M in THF) (20 mL, 20.0 mmol, 1.0 eq). The mixture was stirred for 2 h at room temperature and concentrated to remove the solvent. The residue was purified by silica gel column chromatography with ethyl acetate (100%) as eluents. This resulted in (S)-(2-bromopyridin-3-yl)(2-(hydroxymethyl)piperidin-1-yl)methanone. LCMS (ES) [M+1]+m/z: 299.

Step 3

Into a 250-mL 3-necked round-bottom flask purged and maintained with an inert atmosphere of nitrogen, was placed (S)-(2-bromopyridin-3-yl)(2-(hydroxymethyl)piperidin-1-yl)methanone (2.0 g, 6.69 mmol, 1.0 equiv), 2,6-dihydroxybenzaldehyde (1.10 g, 7.96 mmol, 1.2 equiv), PPh$_3$ (2.10 g, 8.01 mmol, 1.2 equiv), and THF (80 mL). This was followed by the addition of DIAD (1.63 g, 8.06 mmol, 1.2 equiv) at 0° C. After addition, the resulting solution was stirred overnight at room temperature. The mixture was concentrated to remove the solvent, and the residue was purified by silica gel column chromatography with ethyl acetate/petroleum ether (1/1) as eluents. This resulted in 2-(S)-2-((1-(2-bromonicotinoyl)piperidin-2-yl)methoxy)-6-hydroxybenzaldehyde. LCMS (ES) [M+1]$^+$ m/z: 419.

Step 4

Into a 100-mL round-bottom flask purged and maintained with an inert atmosphere of nitrogen, was placed 2-(S)-2-((1-(2-bromonicotinoyl)piperidin-2-yl)methoxy)-6-hydroxybenzaldehyde (3.20 g, 7.63 mmol, 1.0 equiv), dioxane (30 mL), tributyl(ethenyl)stannane (4.85 g, 15.30 mmol, 2.0 equiv), and Pd(dppf)Cl$_2$·CH$_2$Cl$_2$ (624 mg, 0.76 mmol, 0.10 equiv). The mixture was stirred overnight at 90° C. After cooling to room temperature, the reaction solution was concentrated to remove the solvent, and the residue was purified by silica gel column chromatography with ethyl acetate/petroleum ether (1/1) as eluents. This resulted in (S)-2-hydroxy-6-((1-(2-vinylnicotinoyl)piperidin-2-yl)methoxy)benzaldehyde. LCMS (ES) [M+1]$^+$ m/z: 367.

Step 5

Into a 100-mL round-bottom flask, was placed (S)-2-hydroxy-6-((1-(2-vinylnicotinoyl)piperidin-2-yl)methoxy)benzaldehyde (500 mg, 1.37 mmol, 1.0 equiv), t-BuOH (20.0 mL), H$_2$O (20.0 mL), and AD-mix-alpha (5.31 g, 6.82 mmol, 5.0 equiv). The mixture was stirred overnight at room temperature. The mixture was concentrated to remove the solvent, and the crude product was purified by Prep-HPLC with the following conditions (SHIMADZU (HPLC-01): Column, Kinetex EVO C18 Column, 21.2*150, 5 um, mobile phase, Water (0.1% FA) and CH$_3$CN (45% Phase B up to 65% in 9 min), Detector, UV 254 nm. This resulted in 2-{[(2S)-1-[2-(1,2-dihydroxyethyl)pyridine-3-carbonyl]piperidin-2-yl]methoxy}-6-hydroxybenzaldehyde. LCMS: (ES, m/z): [M+H]$^+$: 401.2. $^1$H-NMR (300 MHz, DMSO-d$_6$, ppm): δ 11.82-11.66 (m, 1H), 10.34-10.14 (m, 1H), 8.56 (d, 1H, J=1.8 Hz), 7.68-7.31 (m, 3H), 6.78-6.54 (m, 2H), 5.22-5.19 (m, 2H), 4.71-4.29 (m, 4H), 3.68-3.58 (m, 2H), 3.19-2.90 (m, 2H), 2.08-1.50 (m, 6H).

Example 33. 2-hydroxy-6-{[(3R)-4-[2-(2-hydroxyethyl)pyridine-3-carbonyl]morpholin-3-yl]methoxy}benzaldehyde, Compound 37

Compound 37 was synthesized according to Scheme 33.

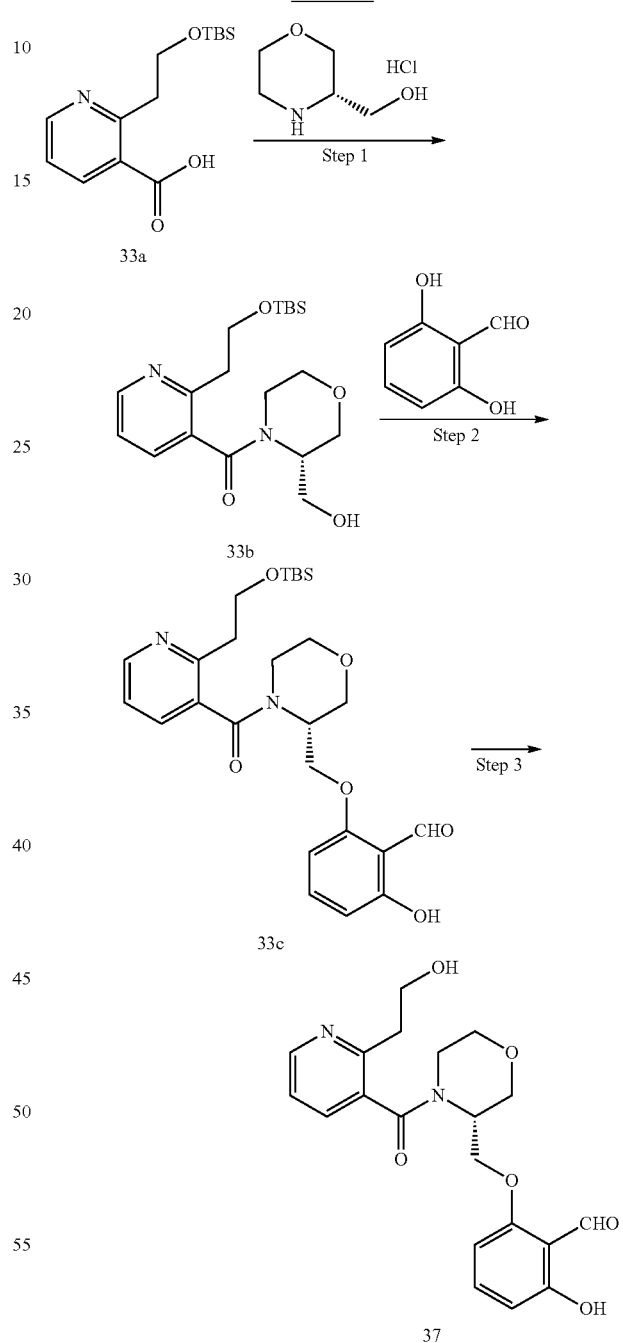

Step 1

Into a 50-mL 3-necked round-bottom flask, was placed 2-[2-[(tert-butyldimethylsilyl)oxy]ethyl]pyridine-3-carboxylic acid (1.50 g, 5.33 mmol, 1.0 equiv), (3S)-morpholin-3-ylmethanol hydrochloride (980 mg, 6.38 mmol, 1.2 equiv), DCM (15 mL), and DIEA (2.07 g, 16.02 mmol, 3.0 equiv). HATU (2.40 g, 6.31 mmol, 1.2 equiv) was added by 3 batches at 0° C. After addition, the mixture was stirred for 2 h at room temperature. The reaction was then quenched by the addition of water (20 mL), and extracted with 3×20 mL of dichloromethane. The combined organic phase was dried over anhydrous sodium sulfate and filtered, and the filtrate was concentrated under reduced pressure. The residue was purified by silica gel column chromatography with ethyl acetate/petroleum ether (80%) as eluents. This resulted in (S)-(2-(2-((tert-butyldimethylsilyl)oxy)ethyl)pyridin-3-yl)(3-(hydroxymethyl)morpholino)methanone. LCMS (ES) [M+1]$^+$ m/z: 381.

Step 2

Into a 250-mL 3-necked round-bottom flask purged and maintained with an inert atmosphere of nitrogen, was placed (S)-(2-(2-((tert-butyldimethylsilyl)oxy)ethyl)pyridin-3-yl)(3-(hydroxymethyl)morpholino)methanone (1.98 g, 5.20 mmol, 1.0 equiv), 2,6-dihydroxybenzaldehyde (863 mg, 6.25 mmol, 1.2 equiv), PPh$_3$ (1.64 g, 6.25 mmol, 1.2 equiv), and THF (80 mL). After cooling to 0° C., DBAD (1.44 g, 6.25 mmol, 1.2 equiv) was added in one portion. The mixture was stirred overnight at room temperature. The mixture was concentrated to remove the solvent, and the residue was purified by silica gel column chromatography with ethyl acetate/petroleum ether (80%) as eluents. This resulted in (R)-2-((4-(2-(2-((tert-butyldimethylsilyl)oxy)ethyl)nicotinoyl)morpholin-3-yl)methoxy)-6-hydroxybenzaldehyde. LCMS (ES) [M+1]$^+$ m/z: 501.

Step 3

Into a 20-mL vial, was placed (R)-2-((4-(2-(2-((tert-butyldimethylsilyl)oxy)ethyl)nicotinoyl)morpholin-3-yl)methoxy)-6-hydroxybenzaldehyde (300 mg, 0.60 mmol, 1.0 equiv), CH$_3$CN (5.0 mL), and HCOOH (1.0 mL). The reaction solution was stirred for 1 h at 50° C. and then concentrated to remove the solvent. The residue was purified by Prep-HPLC with the following conditions: Kinetex EVO C18 column, 21.2*150, 5 um, mobile phase, Water (0.1% FA) and CH$_3$CN (10% Phase B up to 50% within 15 min), detector, UV 254 nm. This resulted in 2-hydroxy-6-{[(3R)-4-[2-(2-hydroxyethyl)pyridine-3-carbonyl]morpholin-3-yl]methoxy}benzaldehyde. LCMS (ES, m/z): [M+H]$^+$: 387.1. $^1$H-NMR (300 MHz, DMSO-d$_6$, ppm): δ 11.74 (br, 1H), 10.33-10.12 (m, 1H), 8.56 (dd, J=4.8, 1.8 Hz, 1H), 7.71-7.29 (m, 3H), 6.78-6.52 (m, 2H), 5.03-4.89 (m, 1H), 4.65-4.34 (m, 3H), 4.11-3.34 (m, 7H), 3.11-2.84 (m, 3H).

Example 34. 2-hydroxy-6-{[(2R)-1-[2-(2-hydroxyethyl)pyridine-3-carbonyl]piperidin-2-yl]methoxy}benzaldehyde, Compound 38

Compound 38 was synthesized according to Scheme 34.

Scheme 34

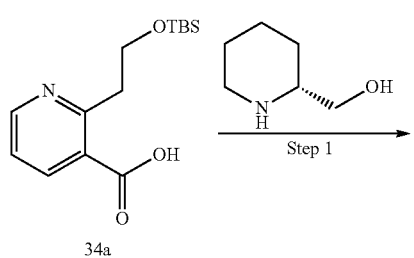

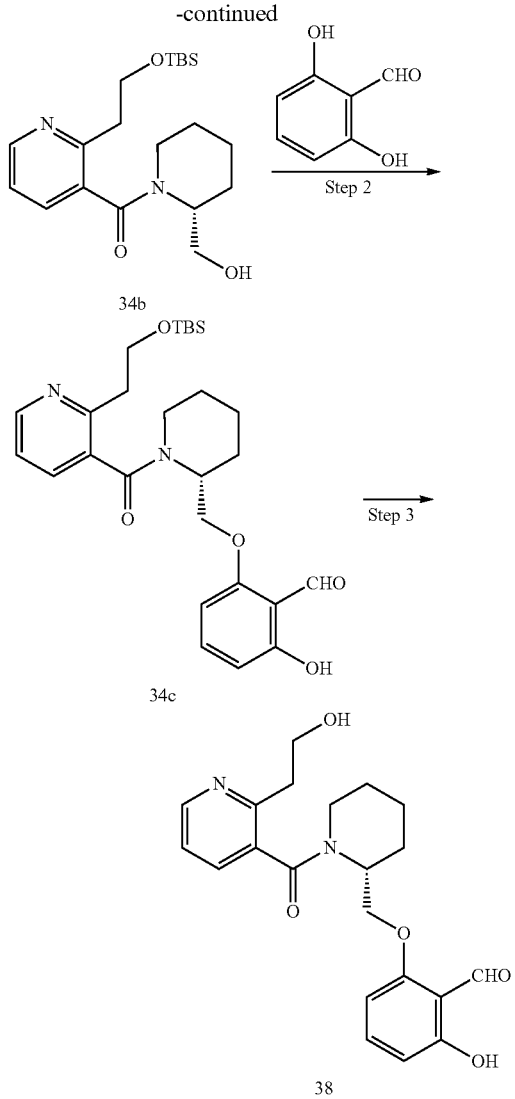

Step 1

Into a 50-mL 3-necked round-bottom flask purged and maintained with an inert atmosphere of nitrogen, was placed 2-[2-[(tert-butyldimethylsilyl)oxy]ethyl]pyridine-3-carboxylic acid (1.00 g, 3.55 mmol, 1.00 equiv), DMF (25.0 mL), (2R)-piperidin-2-ylmethanol (491 mg, 4.26 mmol, 1.20 equiv), and DIEA (551 mg, 4.26 mmol, 1.20 equiv). This was followed by the addition of HATU (1.62 g, 4.26 mmol, 1.2 equiv) in several batches at 0° C. The reaction solution was stirred overnight at room temperature. The reaction was diluted with 30 mL of H$_2$O and extracted with 3×100 mL of ethyl acetate. The combined organic phase was washed with 1×50 mL of brine and dried over anhydrous sodium sulfate. The mixture was filtered, and the filtrate was concentrated under reduced pressure. The residue was purified by silica gel column chromatography with ethyl acetate/petroleum ether (1:2) as eluents. This resulted in [(2R)-1-(2-[2-[(tert-butyldimethylsilyl)oxy]ethyl]pyridine-3-carbonyl)piperidin-2-yl]methanol. LCMS (ES) [M+1]$^+$ m/z: 379.

Step 2

Into a 100-mL 3-necked round-bottom flask purged and maintained with an inert atmosphere of nitrogen, was placed

[(2R)-1-(2-[2-[(tert-butyldimethylsilyl)oxy]ethyl]pyridine-3-carbonyl)piperidin-2-yl]methanol (1.20 g, 3.17 mmol, 1.00 equiv), THF (50.0 mL), 2,6-dihydroxybenzaldehyde (525 mg, 3.80 mmol, 1.20 equiv), and PPh₃ (998 mg, 3.80 mmol, 1.20 equiv). This was followed by the addition of a solution of DIAD (769 mg, 3.80 mmol, 1.20 equiv) in THF (2.00 mL) dropwise with stirring at 0° C. The reaction solution was stirred overnight at room temperature. After concentrating under reduced pressure, the residue was purified by silica gel column chromatography with ethyl acetate/petroleum ether (1:1) as eluents. This resulted in 2-[[(2R)-1-(2-[2-[(tert-butyldimethylsilyl)oxy]ethyl]pyridine-3-carbonyl)piperidin-2-yl]methoxy]-6-hydroxybenzaldehyde. LCMS (ES) [M+1]⁺ m/z: 499.

Step 3

Into a 50-mL round-bottom flask, was placed 2-[[(2R)-1-(2-[2-[(tert-butyldimethylsilyl)oxy]ethyl]pyridine-3-carbonyl)piperidin-2-yl]methoxy]-6-hydroxybenzaldehyde (300 mg, 0.60 mmol, 1.00 equiv), CH₃CN (5.00 mL), and HCOOH (1.00 mL). The mixture was stirred for 3 h at 50° C. in oil bath. The reaction mixture was cooled to room temperature and concentrated under reduced pressure. The crude product was purified by Flash-Prep-HPLC with the following conditions (IntelFlash-1): Column: Ascentis Express C18, 50*3.0 mm, 2.7 um, Mobile Phase A: Water/0.05% FA, Mobile Phase B: CH₃CN; Flow rate: 1.5 mL/min, Gradient: 5% B to 100% B in 1.2 min, hold 0.6 min. This resulted in 2-hydroxy-6-{[(2R)-1-[2-(2-hydroxyethyl)pyridine-3-carbonyl]piperidin-2-yl]methoxy}benzaldehyde. LCMS (ES, m/z): [M+H]⁺: 385. ¹H-NMR (300 MHz, DMSO-d₆, ppm): δ 11.73 (br, 1H), 10.22 (s, 1H), 8.54 (s, 1H), 7.69-7.23 (m, 3H), 6.75 (d, J=8.4 Hz, 2H), 5.21-5.20 (m, 1H), 4.65-4.27 (m, 3H), 3.78-3.65 (m, 2H), 3.20-2.68 (m, 4H), 1.95-1.39 (m, 6H).

Example 35. 2-hydroxy-6-{[(3S)-4-[2-(2-hydroxy-2-methylpropyl)pyridine-3-carbonyl]morpholin-3-yl]methoxy}benzaldehyde, Compound 39

Compound 39 was synthesized according to Scheme 35.

Scheme 35

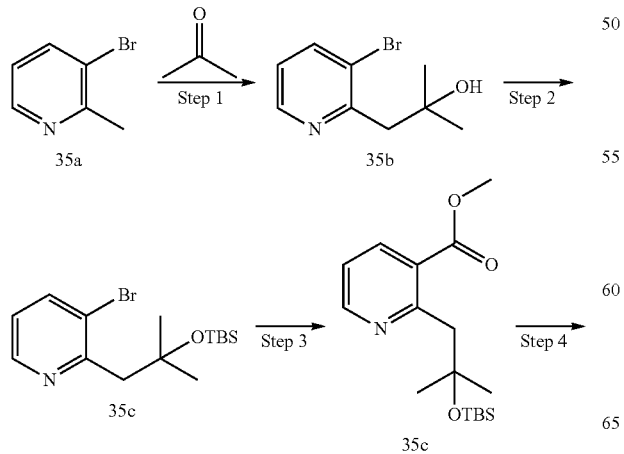

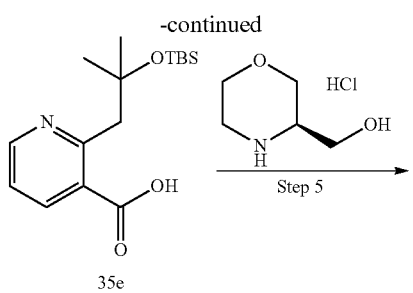

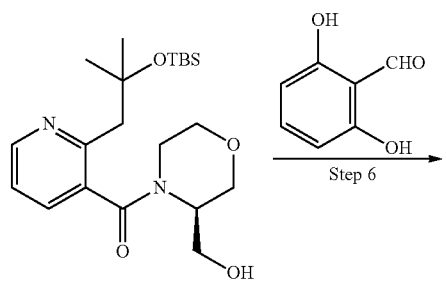

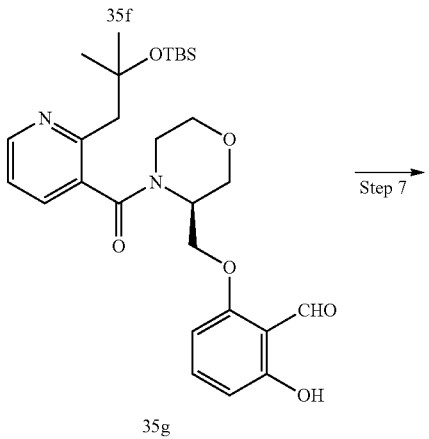

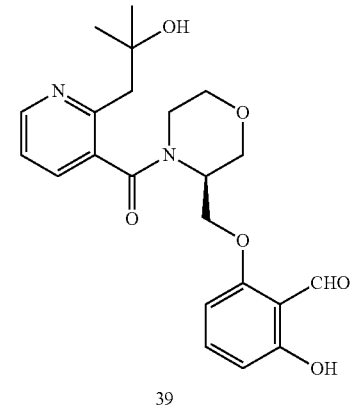

Step 1

Into a 1-L 3-necked round-bottom flask purged and maintained with an inert atmosphere of nitrogen, was placed 3-bromo-2-methylpyridine (20.0 g, 116.26 mmol, 1.0 equiv) and THF (400 mL). This was followed by the addition of LDA (2M in THF) (69.8 mL, 139.51 mmol, 1.2 equiv) at −78° C. and stirred for 0.5 h. To this was added acetone (7.46 g, 128.45 mmol, 1.1 equiv) at the same temperature. The mixture was stirred for 1 hr at −78° C. The reaction was then quenched by the addition of NH₄Cl₍aq₎ (300 mL) and extracted with 3×500 mL of ethyl acetate. The combined organic phase was dried over anhydrous sodium sulfate and filtered, and the filtrate was concentrated under reduced pressure. The residue was purified by silica gel column chromatography with ethyl acetate/petroleum ether (15%) as eluents. This resulted in 1-(3-bromopyridin-2-yl)-2-methylpropan-2-ol. LCMS (ES) [M+1]+m/z: 230.

Step 2

Into a 250-mL round-bottom flask, was placed 1-(3-bromopyridin-2-yl)-2-methylpropan-2-ol (4.0 g, 17.38 mmol, 1.0 equiv), TBSCl (3.10 g, 20.86 mmol, 1.2 eq), DMF (40 mL), imidazole (2.38 g, 34.76 mmol, 2.0 eq), and DMAP (212 mg, 1.74 mmol, 0.10 equiv). The reaction solution was stirred 24 h at 60° C. After cooling to room temperature, the reaction was then quenched by the addition of water (50 mL) and extracted with 3×50 mL of ethyl acetate. The combined organic phase was washed with 2×50 mL of brine and dried over anhydrous sodium sulfate. The mixture was filtered, and the filtrate was concentrated under reduced pressure; the residue was purified by silica gel column chromatography with ethyl acetate/petroleum ether (1/20) as eluents. This resulted in 3-bromo-2-(2-((tert-butyldimethylsilyl)oxy)-2-methylpropyl)pyridine. LCMS (ES) [M+1]$^+$ m/z: 344.

Step 3

Into a 250-mL pressure tank reactor, was placed 3-bromo-2-(2-((tert-butyldimethylsilyl)oxy)-2-methylpropyl)pyridine (4.18 g, 12.14 mmol, 1.0 equiv), MeOH (80 mL), TEA (2.45 g, 24.28 mmol, 2.0 equiv), and Pd(dppf)Cl$_2$CH$_2$Cl$_2$ (495 mg, 0.61 mmol, 0.05 eq). The mixture was stirred for 12 h at 130° C. under CO$_{(g)}$ atmosphere at 30 atm. The mixture was concentrated to remove the solvent; the residue was purified by silica gel column chromatography with ethyl acetate/petroleum (1/3) as eluents. This resulted in methyl 2-(2-((tert-butyldimethylsilyl)oxy)-2-methylpropyl)nicotinate. LCMS (ES) [M+1]$^+$ m/z: 324.

Step 4

Into a 50-mL round-bottom flask, was placed methyl 2-(2-((tert-butyldimethylsilyl)oxy)-2-methylpropyl)nicotinate (2.0 g, 6.18 mmol, 1.0 equiv), MeOH (16 mL), and H$_2$O (8 mL). This was followed by the addition of LiOH (520 mg, 12.26 mmol, 2.0 equiv) at 0° C. The mixture was stirred for 2 h at 50° C. After cooling to room temperature, the pH value of the solution was adjusted to 7 with citric acid. The solids were collected by filtration and dried under infrared lamp. This resulted in 2-(2-((tert-butyldimethylsilyl)oxy)-2-methylpropyl)nicotinic acid. LCMS (ES) [M+1]$^+$ m/z: 310.

Step 5

Into a 50-mL 3-necked round-bottom flask, was placed 2-(2-((tert-butyldimethylsilyl)oxy)-2-methylpropyl)nicotinic acid (1.60 g, 5.17 mmol, 1.0 equiv), (3R)-morpholin-3-ylmethanol hydrochloride (951 mg, 6.19 mmol, 1.2 equiv), DMF (16 mL), and DIEA (2.0 g, 15.48 mmol, 3.0 equiv). This was followed by the addition of HATU (2.36 g, 6.21 mmol, 1.20 equiv) at 0° C. The reaction solution was stirred for 2 h at room temperature. The reaction was then quenched by the addition of water (30 mL) and extracted with 3×30 mL of ethyl acetate. The combined organic phase was washed with brine (30 mL×3) and dried over anhydrous sodium sulfate. The mixture was filtered, and the filtrate was concentrated under reduced pressure. The residue was purified by silica gel column chromatography with ethyl acetate/petroleum ether (1/1) as eluents. This resulted in (R)-(2-(2-((tert-butyldimethylsilyl)oxy)-2-methylpropyl)pyridin-3-yl)(3-(hydroxymethyl)morpholino)methanone. LCMS (ES) [M+1]$^+$ m/z: 409.

Step 6

Into a 100-mL 3-necked round-bottom flask purged and maintained with an inert atmosphere of nitrogen, was placed (R)-(2-(2-((tert-butyldimethylsilyl)oxy)-2-methylpropyl)pyridin-3-yl)(3-(hydroxymethyl)morpholino)methanone (1.0 g, 2.45 mmol, 1.0 equiv), 2,6-dihydroxybenzaldehyde (406 mg, 2.94 mmol, 1.2 equiv), PPh$_3$ (770 mg, 2.94 mmol, 1.2 equiv), and THF (50 mL). This was followed by the addition of DIAD (594 mg, 2.94 mmol, 1.2 equiv) at 0° C. The mixture was stirred overnight at room temperature. The mixture was concentrated to remove the solvent, and the residue was purified by silica gel column chromatography with ethyl acetate/petroleum ether (1/1). This resulted in (S)-2-((4-(2-(2-((tert-butyldimethylsilyl)oxy)-2-methylpropyl)nicotinoyl)morpholin-3-yl)methoxy)-6-hydroxybenzaldehyde. LCMS (ES) [M+1]$^+$ m/z: 529.

Step 7

Into a 20-mL vial, was placed (S)-2-((4-(2-(2-((tert-butyldimethylsilyl)oxy)-2-methylpropyl)nicotinoyl)morpholin-3-yl)methoxy)-6-hydroxybenzaldehyde (600 mg, 1.14 mmol, 1.0 equiv), CH$_3$CN (5.0 mL), and HCOOH (1.0 mL). The mixture was stirred for 1 h at 50° C. After cooling to room temperature, the reaction solution was directly purified by Prep-HPLC with conditions: Column, Ascentis Express C18, 50*3.0 mm, 2.7 um, Mobile Phase A: Water/0.05% FA, Mobile Phase B: CH$_3$CN, Flow rate: 1.5 mL/min, Gradient: 5% B to 100% B in 1.2 min, hold 0.6 min. This resulted in (S)-2-hydroxy-6-((4-(2-(2-hydroxy-2-methylpropyl)nicotinoyl)morpholin-3-yl)methoxy)benzaldehyde. LCMS (ES, m/z): [M+H]$^+$: 415.2. $^1$H-NMR (300 MHz, DMSO-d$_6$, ppm): δ 11.75 (br, 1H), 10.20 (s, 1H), 8.57 (s, 1H), 7.78-7.28 (m, 3H), 6.81-6.53 (m, 2H), 5.19-4.35 (m, 4H), 4.11-3.88 (m, 1H), 3.71-3.35 (m, 4H), 3.15-2.59 (m, 3H), 1.31-0.92 (m, 6H).

Example 36. 2-hydroxy-6-({4-[2-(hydroxymethyl)benzoyl]thiomorpholin-3-yl}methoxy)benzaldehyde, Compound 40

Compound 40 was synthesized according to Scheme 36.

Scheme 36

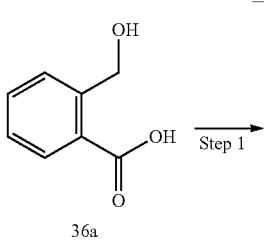

36a

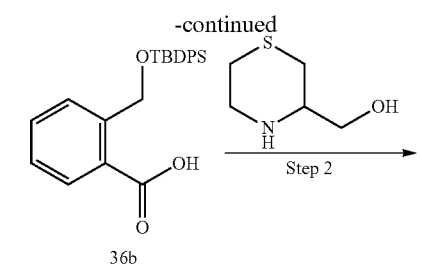

Step 1

Into a 500-mL 3-necked round-bottom flask, was placed 2-hydroxymethylbenzoic acid (10.0 g, 65.7 mmol, 1.00 equiv), imidazole (8.95 g, 131 mmol, 2.00 equiv), and DCM (200 mL). To this solution was added TBDPS-Cl (21.6 g, 78.8 mmol, 1.20 equiv) dropwise at 0° C. The resulting solution was stirred for 16 hr at 0-25° C. The reaction was then quenched by the addition of 50 mL of water. The resulting solution was extracted with 3×100 mL of DCM. The organic layer was dried and concentrated. The residue was purified by silica gel column chromatography with ethyl acetate/petroleum ether (1:50 to 1:1) as eluents. This resulted in 2-[[(tert-butyldiphenylsilyl)oxy]methyl]benzoic acid. LCMS (ES) [M+1]$^+$ m/z: 391.2.

Step 2

To a solution of 2-[[(tert-butyldiphenylsilyl)oxy]methyl]benzoic acid (2.00 g, 5.12 mmol, 1.00 equiv) in DCM (20.0 mL) was added (COCl)$_2$ (1.30 g, 10.2 mmol, 2.00 equiv) dropwise at 0° C. The resulting solution was heated to 40° C. for 5 h. The reaction was then concentrated to give a residue. The residue was dissolved in THF (20.0 mL), and TEA (1.55 g, 15.3 mmol, 3.00 equiv) was added. To this solution was added thiomorpholin-3-ylmethanol (0.68 g, 5.12 mmol, 1.00 equiv) in portions at 0° C. The resulting solution was stirred for 16 hr at 0-25° C. The reaction was then quenched by the addition of 10 mL of water. The resulting solution was extracted with 3×20 mL of ethyl acetate, dried over anhydrous sodium sulfate, and concentrated. The residue was purified by silica gel column with ethyl acetate/petroleum ether (1:50 to 1:5) as eluents. This resulted in [4-(2-[[(tert-butyldiphenylsilyl)oxy]methyl]benzoyl)thiomorpholin-3-yl]methanol. LCMS (ES) [M+1]+m/z: 506.7.

Step 3

Into a 100-mL 3-necked round-bottom flask under N$_2$ atmosphere, was placed [4-(2-[[(tert-butyldiphenylsilyl)oxy]methyl]benzoyl)thiomorpholin-3-yl]methanol (1.80 g, 3.55 mmol, 1.00 equiv), 2,6-dihydroxybenzaldehyde (0.74 g, 5.33 mmol, 1.50 equiv), PPh$_3$ (1.40 g, 5.33 mmol, 1.50 equiv), and DCM (30.0 mL). To this solution was added a solution of DBAD (1.23 g, 5.33 mmol, 1.5.0 equiv) in DCM (3.0 mL) drop wise at 0° C. The resulting solution was stirred for 15 hr at 0-25° C. The resulting mixture was concentrated. The residue was applied onto a silica gel column with ethyl acetate/petroleum ether (1:100 to 1:1). This resulted in 2-[[4-(2-[[(tert-butyldiphenylsilyl)oxy]methyl]benzoyl)thiomorpholin-3-yl]methoxy]-6-hydroxybenzaldehyde. LCMS (ES) [M+1]$^+$ m/z: 626.2

Step 4

Into a 100-mL 3-necked round-bottom flask, was placed 2-[[4-(2-[[(tert-butyldiphenylsilyl) oxy]methyl]benzoyl)thiomorpholin-3-yl]methoxy]-6-hydroxybenzaldehyde (1.05 g, 1.67 mmol, 1.00 equiv), THF (5.00 mL) and TBAF (0.33 mL, 0.330 mmol, 0.20 equiv). The resulting solution was stirred for 2 hr at 0-25° C. The resulting mixture was concentrated. The residue was purified by silica gel column with ethyl acetate/petroleum ether (50:1-1:1) as eluents. This resulted in 2-hydroxy-6-({4-[2-(hydroxymethyl)benzoyl]thiomorpholin-3-yl}methoxy)benzaldehyde. LCMS (ES) [M+Na]$^+$ m/z:410.1; $^1$H NMR (300 MHz, DMSO-d$_6$) δ 12.00 (s, 1H), 10.38 (s, 1H), 7.51-7.13 (m, 5H), 6.68-6.41 (m, 2H), 5.79-5.48 (m, 1H), 5.01-4.30 (m, 6H), 3.84-2.31 (m, 5H).

Example 37. 2-hydroxy-6-{[(3S)-4-[2-(hydroxymethyl)benzoyl]thiomorpholin-3-yl]methoxy}benzaldehyde and 2-hydroxy-6-{[(3R)-4-[2-(hydroxymethyl)benzoyl]thiomorpholin-3-yl]methoxy}benzaldehyde

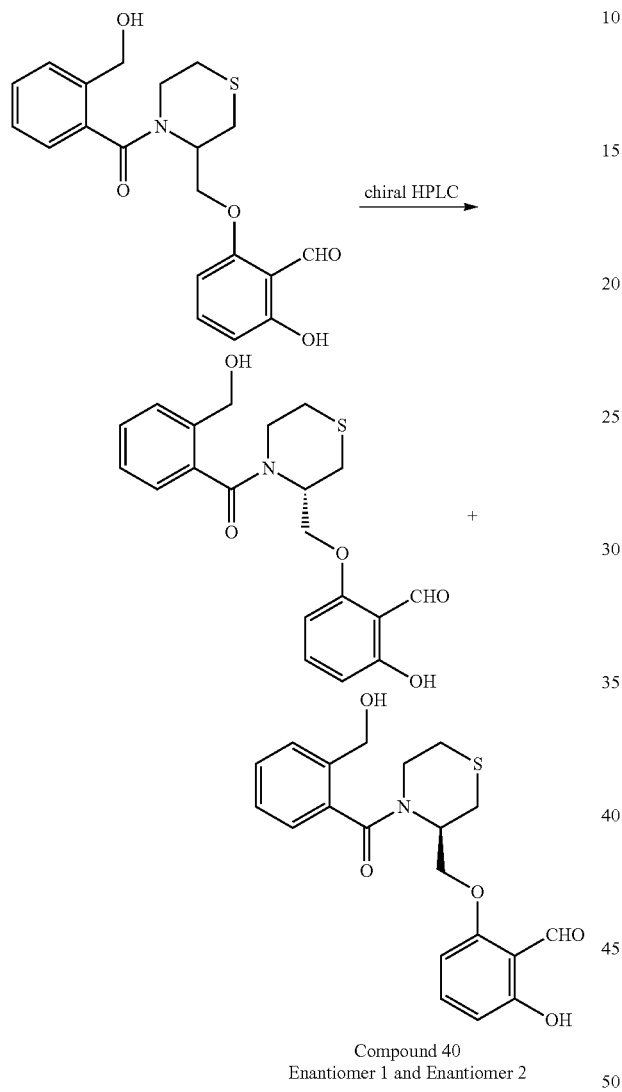

Compound 40 was purified by Chiral-Prep-HPLC (Conditions: Column: Lux Cellulose-4, 4.6*100 mm, 3 μm; mobile phase, A: n-Hexane B: Ethanol (35% B in 18 min); Flow rate: 30 mL/min; Detector, 220 nm) and was analyzed by analytical chiral HPLC (Conditions: instrument name: Shimadzu LC-20AD; Mobile Phase A: n-Hexane/DCM=5/1; Mobile Phase B: Ethanol; Column: CHIRALPAK IA-3, 50*4.6 mm, 3 um IA30CC-UL005). This resulted in Enantiomer 1 and Enantiomer 2 of Compound 40.

Compound 40, Enantiomer 1: Analytical chiral HPLC retention time=2.42 min; LCMS (ES) [M+Na]$^+$ m/z:410.1; $^1$H NMR (300 MHz, DMSO-d6) δ 11.81-11.70 (m, 1H), 10.32-10.16 (m, 1H), 7.59-7.22 (m, 5H), 6.76 (d, J=8.3 Hz, 1H), 6.56 (d, J=8.4 Hz, 1H), 5.42-4.41 (m, 6H), 3.47-3.32 (m, 1H), 3.32-2.90 (m, 2H), 2.63-2.51 (m, 2H), 2.50-2.40 (m, 1H).

Compound 40, Enantiomer 2: Analytical chiral HPLC retention time=4.50 min. LCMS (ES) [M+Na]$^+$ m/z:410.1; $^1$H NMR (300 MHz, CDCl$_3$) δ 11.98-11.87 (m, 1H), 10.36 (br, 1H), 7.54-7.34 (m, 4H), 7.26-7.15 (m, 1H), 6.59-6.52 (m, 2H), 5.71-4.35 (m, 5H), 3.91-3.03 (m, 3H), 3.02-2.33 (m, 4H).

Example 38. 2-hydroxy-6-{[(3R)-4-[2-(hydroxymethyl)benzoyl]thiomorpholin-3-yl]methoxy}benzaldehyde

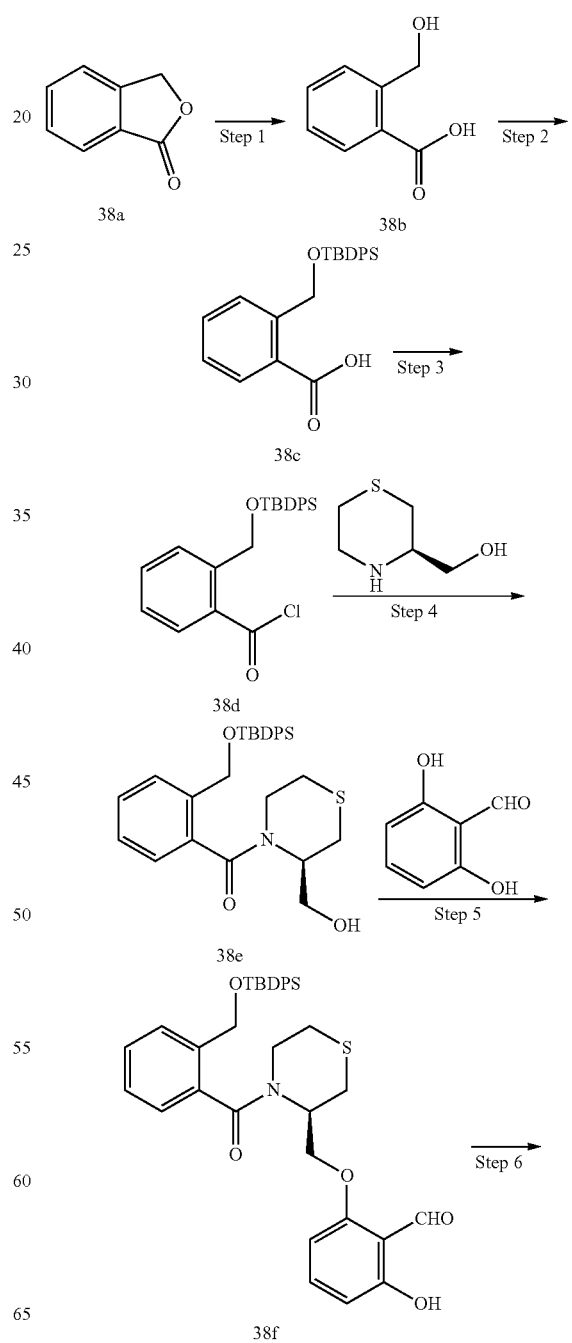

-continued

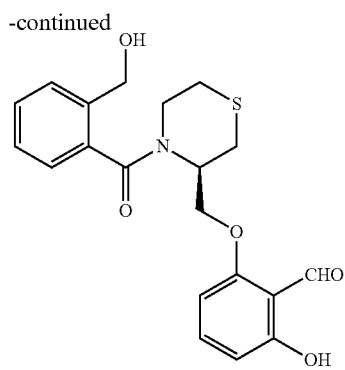

Step 1

Into a 1-L round-bottom flask, was placed phthalide (25.0 g, 186.3 mmol, 1.0 equiv), H$_2$O (250 mL) and NaOH (14.91 g, 372.762 mmol, 2 equiv). The resulting solution was stirred for 3 h at 100° C. in an oil bath. The reaction mixture was cooled to 0° C. Solids were precipitated out after the pH value of the solution was adjusted to 1 with HCl (12 mol/L). The solids product was collected by filtrate. This resulted in 2-hydroxymethylbenzoic acid. LCMS (ES) [M+1]$^+$ m/z: 153.1. $^1$H NMR (300 MHz, DMSO-d$_6$) δ 12.88 (br, 1H), 7.85 (dd, J=1.5, 7.8 Hz, 1H), 7.72 (dd, J=1.8, 7.8 Hz, 1H), 7.57 (td, J=1.5, 7.5 Hz, 1H), 7.34 (td, J=1.5, 7.8 Hz, 1H), 4.84 (s, 2H).

Step 2

Into a 500-mL 3-necked round-bottom flask, was placed 2-hydroxymethylbenzoic acid (15.0 g, 98.6 mmol, 1.0 equiv), DCM (200 mL), and imidazole (10.0 g, 147.8 mmol, 1.5 equiv). After the reaction was cooled to 0° C., TBDPSCl (32.5 g, 118.3 mmol, 1.2 equiv) was added dropwise with stirring at 0° C. The resulting solution was stirred for 16 h at 25° C. The reaction was then quenched by the addition of 300 mL of water. The resulting solution was extracted with 3×250 mL of ethyl acetate, dried over anhydrous sodium sulfate, and concentrated. The residue was purified by silica gel column chromatography with ethyl acetate/petroleum ether (1:50 to 1:1) as eluents. This resulted in 2-[[(tert-butyldiphenylsilyl)oxy]methyl]benzoic acid. LCMS (ES) [M+1]$^+$ m/z: 391.1. $^1$H NMR (300 MHz, DMSO-d$_6$) δ 12.88 (s, 1H), 7.93 (td, J=1.8, 7.8, Hz, 2H), 7.70-7.64 (m, 5H), 7.50-7.37 (m, 7H), 5.15 (s, 2H), 1.06 (s, 9H).

Step 3

Into a 500-mL 3-necked round-bottom flask, was placed 2-[[(tert-butyldiphenylsilyl)oxy]methyl]benzoic acid (15.0 g, 38.4 mmol, 1.0 equiv), DCM (250 mL) and two drops of DMF. After the reaction was cooled to 0° C., (COCl)$_2$ (5.8 g, 46.1 mmol, 1.2 equiv) was added dropwise with stirring at 0° C. The resulting solution was stirred for 5 h at 40° C. The mixture was concentrated under vacuum. This resulted in 2-[[(tert-butyldiphenylsilyl)oxy]methyl]benzoyl chloride, which was used for next step without further purification.

Step 4

To a solution of (3R)-thiomorpholin-3-ylmethanol (5.3 g, 40.3 mmol, 1.05 equiv) and TEA (7.8 g, 76.7 mmol, 2.0 equiv) in THF (250 mL) was added 2-[[(tert-butyldiphenylsilyl)oxy]methyl]benzoyl chloride (15.7 g, 38.3 mmol, 1.0 equiv) in THF (50 mL) dropwise at 0° C. After the addition, the resulting solution was stirred for 5 h at 0-25° C. The reaction was then quenched by the addition of 50 mL of water. The resulting solution was extracted with 3×150 mL of ethyl acetate, dried over anhydrous sodium sulfate, and concentrated. The residue was purified by silica gel column chromatography with ethyl acetate/petroleum ether (1:50 to 1:5) as eluents. This resulted in [(3R)-4-(2-[[(tert-butyldiphenylsilyl)oxy]methyl]benzoyl) thiomorpholin-3-yl]methanol. LCMS (ES) [M+1]+m/z: 506; $^1$H NMR (300 MHz, DMSO-d$_6$) δ 7.65-7.63 (m, 5H), 7.62-7.27 (m, 9H), 4.84-4.53 (m, 4H), 3.80-3.52 (m, 3H), 3.30-2.67 (m, 3H), 2.43-1.99 (m, 2H), 1.06 (s, 9H).

Step 5

Into a 2.5-L 3-necked round-bottom flask purged and maintained with an inert atmosphere of argon, was placed [(3R)-4-(2-[[(tert-butyldiphenylsilyl)oxy]methyl]benzoyl) thiomorpholin-3-yl]methanol (18.0 g, 35.5 mmol, 1.00 equiv), 2,6-dihydroxybenzaldehyde (5.4 g, 39.1 mmol, 1.1 equiv), DCM (900.00 mL) and PPh$_3$ (14.0 g, 53.3 mmol, 1.5 equiv). This was followed by the addition of DBAD (9.8 g, 42.7 mmol, 1.2 equiv) in DCM (100 mL) dropwise with stirring at 0° C. The resulting solution was stirred for 15 hr at 0-25° C. The resulting mixture was concentrated. The residue was purified by silica gel column chromatography with ethyl acetate/petroleum ether (1:100 to 1:1) as eluents. This resulted in 2-[[(3R)-4-(2-[[(tert-butyldiphenylsilyl)oxy]methyl]benzoyl)thiomorpholin-3-yl]methoxy]-6-hydroxybenzaldehyde. LCMS (ES) [M+1]$^+$ m/z: 626.2; $^1$H NMR (300 MHz, DMSO-d$_6$) δ 11.71 (s, 1H), 10.19 (s, 1H), 7.61-7.41 (m, 16H), 6.55 (d, J=8.4 Hz, 1H), 5.23-5.19 (m, 1H), 4.69-4.21 (m, 5H), 3.41-3.37 (m, 2H), 3.07-2.85 (m, 2H), 2.16-1.99 (m, 1H), 1.06 (s, 9H).

Step 6

Into a 500-mL 3-necked round-bottom flask, was placed 2-[[(3R)-4-(2-[[(tert-butyldiphenylsilyl)oxy]methyl]benzoyl)thiomorpholin-3-yl]methoxy]-6-hydroxybenzaldehyde (14.0 g, 22.3 mmol, 1.0 equiv) and THF (140 mL). To this solution was added a solution of TBAF (4.5 mL, 4.50 mmol, 0.20 equiv, 1 M in THF) dropwise with stirring at 0° C. The resulting solution was stirred for 3 hr at 0-25° C. The resulting mixture was concentrated. The residue was applied onto a silica gel column with ethyl acetate/petroleum ether (1:50 to 1:1) to give crude product. The crude product was purified by Flash-Prep-HPLC with the following conditions (IntelFlash-1): Column, C18 silica gel; mobile phase, MeCN/H$_2$O=1:9 increasing to MeCN/H$_2$O=1:1 within 15; Detector, 220. This resulted in 2-hydroxy-6-{[(3R)-4-[2-(hydroxymethyl)benzoyl]thiomorpholin-3-yl] methoxy}benzaldehyde, which was subjected to chiral analytical HPLC analysis with the following conditions: Instrument Name: Shimadzu LC-20AD; Mobile Phase A: n-Hexane/DCM=5/1; Mobile Phase B: Ethanol; Column: CHIRALPAK IA-3, 50*4.6 mm, 3 um IA30CC-UL005. Analytical Chiral HPLC retention time: 4.540 min. LCMS (ES, m/z): [M+Na]$^+$: 410.1; $^1$H NMR (300 MHz, DMSO-d$_6$) δ 11.81-11.70 (m, 1H), 10.32-10.10 (m, 1H), 7.59-7.22 (m, 5H), 6.77-6.55 (m, 2H), 5.42-4.08 (m, 6H), 3.42-3.37 (m, 1H), 3.21-2.90 (m, 2H), 2.71-2.95 (m, 2H), 2.44-2.40 (m, 1H).

Based on the product of Scheme 38, it was determined that Compound 40, Enantiomer 2 corresponds to 2-hydroxy-6-{[(3R)-4-[2-(hydroxymethyl)benzoyl]thiomorpholin-3-yl]methoxy}benzaldehyde.

Example 39. 2-{[(2S)-1-{2-[(1R)-1,2-dihydroxyethyl]benzoyl}piperidin-2-yl]methoxy}-6-hydroxybenzaldehyde and 2-{[(2S)-1-{2-[(1S)-1,2-dihydroxyethyl]benzoyl}piperidin-2-yl]methoxy}-6-hydroxybenzaldehyde

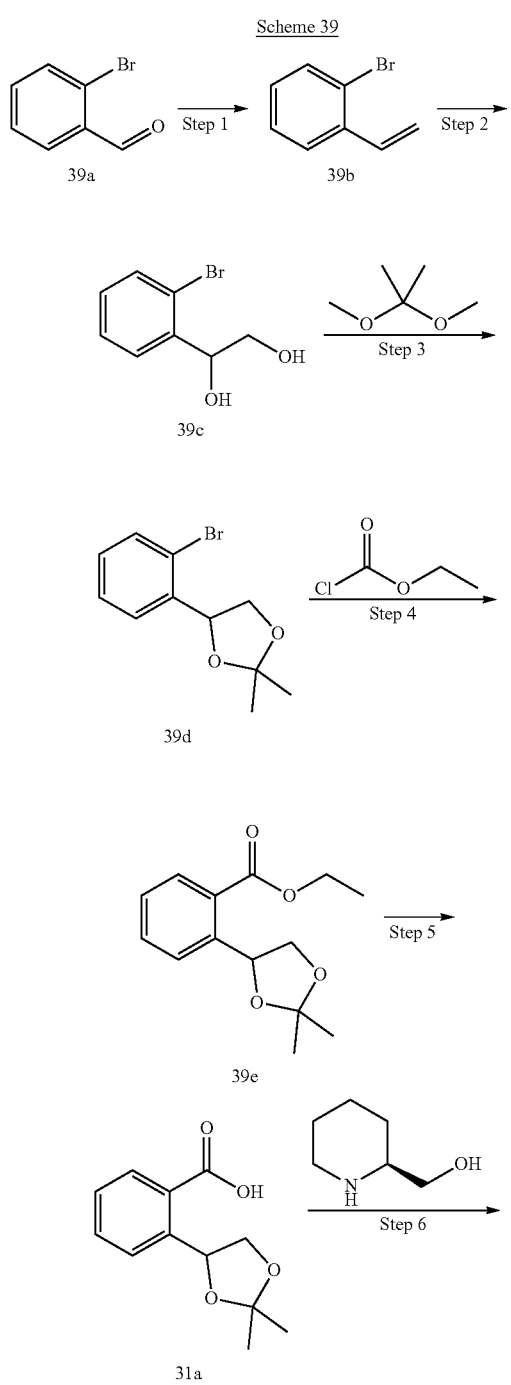

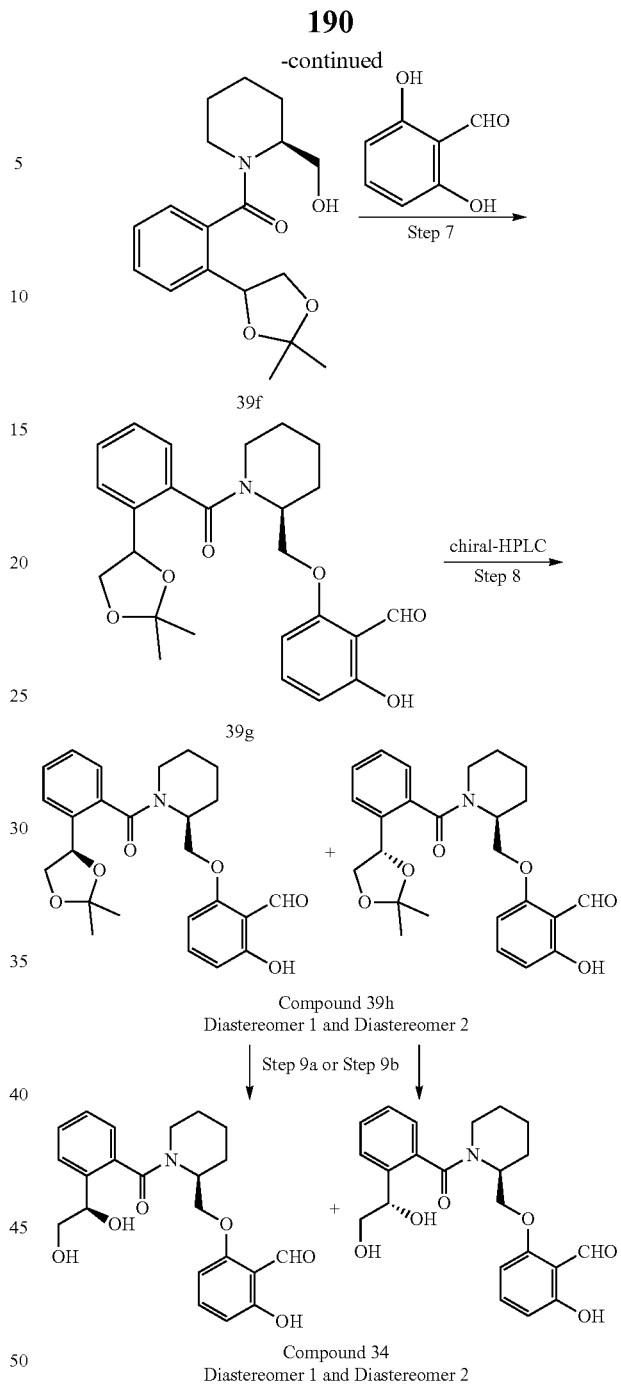

Step 1

Into a 500-mL 3-necked round-bottom flask, was placed 2-bromobenzaldehyde (10.0 g, 54.05 mmol, 1.0 equiv), methyltriphenyl-lambda5-phosphane hydrobromide (23.20 g, 64.58 mmol, 1.2 equiv), and DMF (100 mL). This was followed by the addition of NaH (60% in mineral oil) (9.67 g, 241.69 mmol, 4.5 equiv) carefully at 0° C. by four batches. The mixture was stirred overnight at room temperature. The reaction was then quenched by the addition of water/ice (100 mL), extracted with 3×100 mL of ethyl acetate. The combined organic phase was washed with brine (80 mL×3) and dried over anhydrous sodium sulfate. The mixture was filtered, and the filtrate was concentrated under reduced pressure. The residue was purified by silica gel column chromatography with PE (100%) as eluents. This resulted in 1-bromo-2-vinylbenzene. GCMS:182.

Step 2

Into a 250-mL round-bottom flask, was placed 1-bromo-2-vinylbenzene (8.50 g, 46.43 mmol, 1.0 equiv), acetone (130 mL), $H_2O$ (13 mL), NMO (5.43 g, 46.35 mmol, 1.0 equiv), and $K_2OsO_4 \cdot 2H_2O$ (730 mg, 2.32 mmol, 0.05 equiv). The mixture was stirred overnight at room temperature. The mixture was concentrated to remove the solvent, and the residue was purified by silica gel column chromatography with THF/PE (15%) as eluents. This resulted in -(2-bromophenyl)ethane-1,2-diol. LCMS (ES) $[M+1]^+$ m/z: 217.

Step 3

Into a 250-mL round-bottom flask, was placed 1-(2-bromophenyl)ethane-1,2-diol (5.10 g, 23.50 mmol, 1.0 equiv), 2,2-dimethoxypropane (4.17 g, 40.04 mmol, 1.7 equiv), TsOH (812 mg, 4.72 mmol, 0.20 equiv), and DMF (75 mL). The reaction solution was stirred for 5 h at room temperature. The reaction was then quenched by the addition of water (100 mL) and extracted with 3×100 mL of ethyl acetate. The combined organic phase was washed with brine (100 mL*3) and dried over anhydrous sodium sulfate. The mixture was filtered, and the filtrate was concentrated under reduced pressure. The residue was purified by silica gel column chromatography with PE (100%) as eluents. This resulted in 4-(2-bromophenyl)-2,2-dimethyl-1,3-dioxolane. GCMS: 256.

Step 4

Into a 100-mL 3-necked round-bottom flask purged and maintained with an inert atmosphere of nitrogen, was placed 4-(2-bromophenyl)-2,2-dimethyl-1,3-dioxolane (2.50 g, 9.72 mmol, 1.0 equiv), THF (50 mL). This was followed by the addition of n-BuLi (2.5 M in THF) (4.68 mL, 11.68 mmol, 1.2 equiv) at −78° C. The reaction solution was stirred for 30 min at −78° C. To this ethyl chloroformate (2.11 g, 19.44 mmol, 2.0 equiv) was added at −78° C. The resulting solution was stirred for additional 1 h at room temperature. The reaction was then quenched by the addition of $NH_4Cl$(aq) (60 mL) and extracted with 3×50 mL of ethyl acetate. The combined organic phase was dried over anhydrous sodium sulfate and filtered, and the filtrate was concentrated under reduced pressure. The residue was purified by silica gel column chromatography with ethyl acetate/petroleum ether (1:10) as eluents. This resulted in ethyl 2-(2,2-dimethyl-1,3-dioxolan-4-yl)benzoate. GCMS: 250.

Step 5

Into a 100-mL round-bottom flask, was placed ethyl 2-(2,2-dimethyl-1,3-dioxolan-4-yl)benzoate (1.60 g, 6.39 mmol, 1.0 equiv), EtOH (10.0 mL), $H_2O$ (50.0 mL), and $LiOH \cdot H_2O$ (538 mg, 12.82 mmol, 2.0 equiv). The reaction solution was stirred overnight at room temperature. The mixture was concentrated to remove the solvent, and the pH value of the residue was adjusted to 4 with 2N HCl. The solid was collected by filtration and dried under infrared lamp. This resulted in 2-(2,2-dimethyl-1,3-dioxolan-4-yl) benzoic acid. LCMS (ES) $[M-1]^+$ m/z: 221.

Step 6

Into a 50-mL 3-necked round-bottom flask, was placed 2-(2,2-dimethyl-1,3-dioxolan-4-yl)benzoic acid (865 mg, 3.89 mmol, 1.0 equiv), (2S)-piperidin-2-ylmethanol (537 mg, 4.66 mmol, 1.2 equiv), DMF (20 mL), and DIEA (1.0 g, 7.74 mmol, 2.0 equiv). This was followed by the addition of HATU (1.78 g, 4.68 mmol, 1.2 equiv) at 0° C. The mixture was stirred for 2 h at room temperature. The reaction was then quenched by the addition of water (30 mL) and extracted with 3×20 mL of ethyl acetate. The combined organic phase was dried over anhydrous sodium sulfate and filtered, and the filtrate was concentrated in vacuum. The residue was purified by silica gel column chromatography with ethyl acetate/petroleum ether (1/3) as eluents. This resulted in (2-(2,2-dimethyl-1,3-dioxolan-4-yl)phenyl)((S)-2-(hydroxymethyl)piperidin-1-yl)methanone. LCMS (ES) $[M+1]^+$ m/z:320.

Step 7 and Step 8

Into a 250-mL 3-necked round-bottom flask purged and maintained with an inert atmosphere of nitrogen, was placed (2-(2,2-dimethyl-1,3-dioxolan-4-yl)phenyl)((S)-2-(hydroxymethyl)piperidin-1-yl)methanone (900 mg, 2.82 mmol, 1.0 equiv), 2,6-dihydroxybenzaldehyde (467 mg, 3.38 mmol, 1.2 equiv), $PPh_3$ (887 mg, 3.38 mmol, 1.20 equiv), and THF (60 mL). This was followed by the addition of DIAD (684 mg, 3.38 mmol, 1.2 equiv) at 0° C. After addition, the reaction solution was stirred overnight at room temperature. The mixture was concentrated to remove the solvent, and the residue was purified by silica gel column chromatography with ethyl acetate/petroleum ether (1/1) as eluents.

The collected racemate product was separated by Chiral-Prep-HPLC with the following conditions: Mobile phase: A: n-Hexane, B: Ethanol, Flow rate: 20 mL/min, Column: CHIRALPAK IC-3, 4.6*50 mm, 3 μm, Gradient: 30% B in 18 min, 220 nm.

The separated enantiomers were subjected to analytical chiral HPLC analysis (Instrument Name: Shimadzu LC-20AD; Mobile Phase A: n-Hexane; Mobile Phase B: Ethanol; Column: CHIRALPAK IC-3, 50*4.6 mm, 3 um IC30CC-SC002). This resulted in Compound 39h, Diastereomer 1 (chiral-HPLC analysis conditions: Rt=2.03 min) and Compound 39h, Diastereomer 2 (chiral-HPLC analysis conditions: Rt=2.89 min). LCMS (ES) $[M+1]^+$ m/z: 440

Step 9a

Into a 25-mL vial, was placed Compound 39h, Diastereomer 1 (288 mg, 0.66 mmol, 1.0 equiv), $CH_3CN$ (8.0 mL), and $Yb(OTf)_3$ (203 mg, 0.33 mmol, 0.50 equiv). The mixture was stirred for 2 h at room temperature. The reaction solution was directly purified by Prep-HPLC with the following conditions (SHIMADZU (HPLC-01): Column, XBridge C18 OBD Prep Column, 10 μm, 19 mm×250 mm, mobile phase, Water (0.1% FA) and $CH_3CN$ (5% Phase B up to 50% in 12 min), Detector, UV 254 nm. This resulted in Compound 34, Diastereomer 1. LCMS (ES, m/z): $[M+H]^+$: 400. $^1H$-NMR (300 MHz, DMSO-$d_6$, ppm): δ 11.83-11.73 (m, 1H), 10.30-10.19 (m, 1H), 7.57-7.21 (m, 5H), 6.79-6.53 (m, 2H), 5.25-4.56 (m, 6H), 3.47-2.88 (m, 4H), 1.93-1.37 (m, 6H).

Step 9b

Into a 25-mL round-bottom flask, was placed Compound 39h, Diastereomer 2 (307 mg, 0.70 mmol, 1.0 equiv), CH₃CN (8.0 mL), Yb(OTf)₃ (203 mg, 0.35 mmol, 0.50 equiv). The reaction solution was stirred for 2 h at room temperature. The reaction solution was directly purified by Prep-HPLC with the following conditions (SHIMADZU (HPLC-01): Column, XBridge C18 OBD Prep Column, 10 µm, 19 mm×250 mm, mobile phase, Water (0.1% FA) and CH₃CN (5% Phase B up to 50% in 12 min), Detector, UV 254 nm. Compound 34, Diastereomer 2 was obtained. LCMS (ES, m/z): [M+H]⁺: 400. ¹H-NMR (300 MHz, DMSO-d₆, ppm): δ 11.83-11.73 (m, 1H), 10.33-10.10 (m, 1H), 7.59-7.20 (m, 5H), 6.79-6.53 (m, 2H), 5.25-4.56 (m, 6H), 3.47-2.88 (m, 4H), 1.94-1.37 (m, 6H).

Example 40. 2-hydroxy-6-{[(3S)-4-{2-[(1S)-1-hydroxyethyl]pyridine-3-carbonyl}morpholin-3-yl]methoxy}benzaldehyde and 2-hydroxy-6-{[(3S)-4-{2-[(1R)-1-hydroxyethyl]pyridine-3-carbonyl}morpholin-3-yl]methoxy}benzaldehyde Compound 41, Diastereomer 1 and Compound 41, Diastereomer 2 were synthesized according to Scheme 40.

Scheme 40

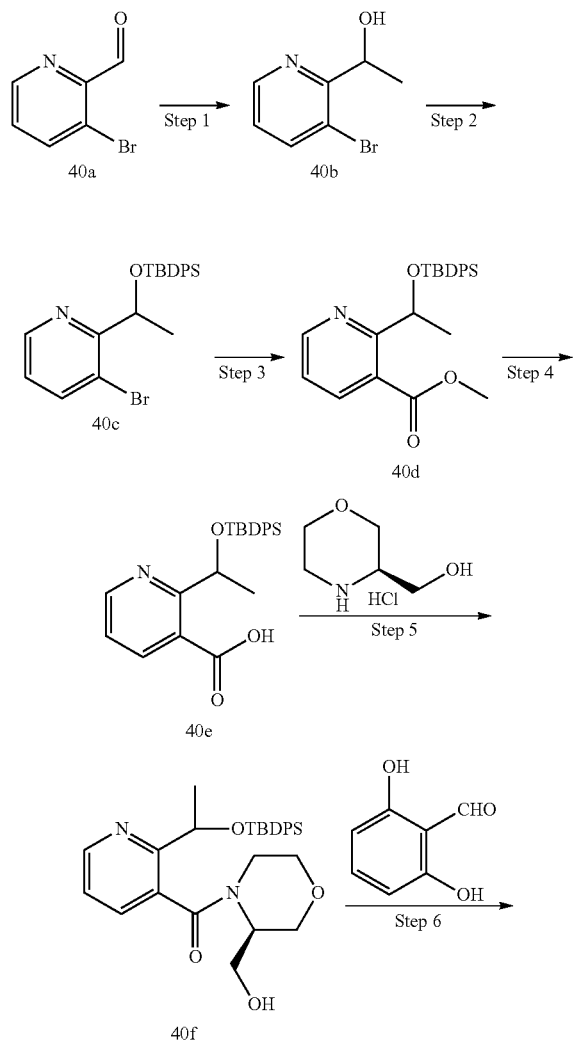

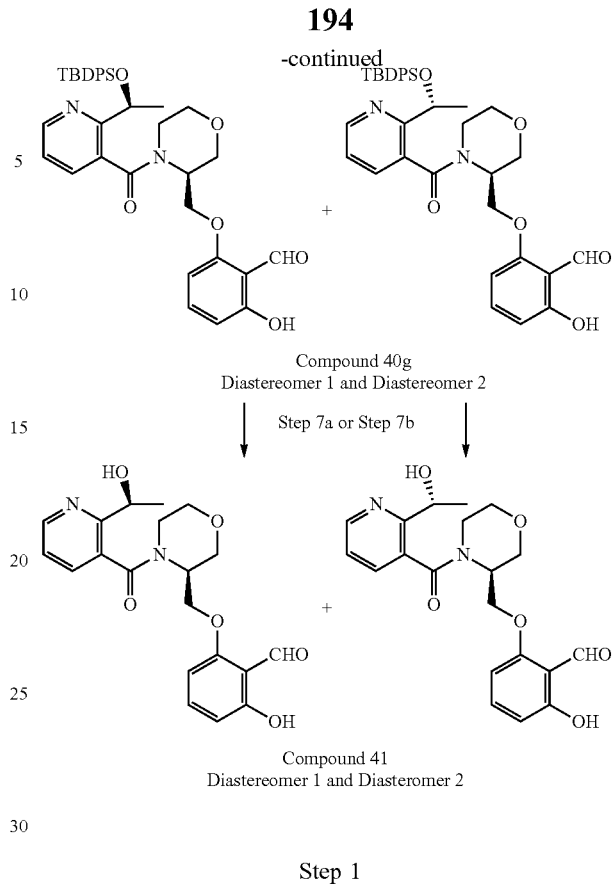

Compound 40g
Diastereomer 1 and Diastereomer 2

Step 7a or Step 7b

Compound 41
Diastereomer 1 and Diasteromer 2

Step 1

Into a 250-mL 3-necked round-bottom flask purged and maintained with an inert atmosphere of nitrogen, was placed a mixture of 3-bromopyridine-2-carbaldehyde (10.0 g, 53.7 mmol, 1.00 equiv), tetrahydrofuran (150 mL), and bromo (methyl)magnesium (35.8 mL, 2.0 equiv) was dropwised at −78° C. The solution was stirred for 30 minutes at −78° C. and then allowed to room temperature over 30 minutes. The reaction was then quenched by the addition of 100 mL. The resulting solution was extracted with 3×100 mL of ethyl acetate. The resulting mixture was washed with 1×100 mL of brine. The mixture was dried over anhydrous sodium sulfate and concentrated. This resulted in 1-(3-bromopyridin-2-yl)ethanol. LCMS (ES) [M+1]⁺ m/z: 202.

Step 2

Into a 250-mL round-bottom flask, was placed a mixture of 1-(3-bromopyridin-2-yl)ethanol (8.00 g, 39.5 mmol, 1.00 equiv), DMF (80.0 mL), tert-butyl(chloro)diphenylsilane (16.3 g, 59.3 mmol, 1.50 equiv), and imidazole (5.39 g, 79.1 mmol, 2.00 equiv). The resulting solution was stirred for 16 hours at room temperature. The reaction was then quenched by the addition of 500 mL of water. The resulting solution was extracted with 3×150 mL of ethyl acetate. The resulting mixture was washed with 1×150 mL of brine. The mixture was dried over anhydrous sodium sulfate and concentrated. The residue was applied onto a silica gel column with ethyl acetate/petroleum ether (1/9). This resulted in 3-bromo-2-[1-[(tert-butyldiphenylsilyl)oxy]ethyl]pyridine. LCMS (ES) [M+1]⁺ m/z: 440.1.

Step 3

Into a 1000 mL pressure tank reactor, was placed a mixture of 3-bromo-2-[1-[(tert-butyldiphenylsilyl)oxy]

ethyl]pyridine (14.0 g, 31.7 mmol, 1.00 equiv), methanol (200 mL), Et₃N (6.43 g, 63.5 mmol, 2.00 equiv), and Pd(dppf)Cl₂ (2.33 g, 3.18 mmol, 0.10 equiv). The reactor was evacuated and flushed three times with nitrogen, followed by flushing with 30 atm CO. The resulting solution was stirred for 16 hours at 110° C. The resulting mixture was concentrated. The residue was purified by silica gel column chromatography with ethyl acetate/petroleum ether (2/23) as eluent. This resulted in methyl 2-[1-[(tert-butyldiphenylsilyl)oxy]ethyl]pyridine-3-carboxylate. LCMS (ES) [M+1]⁺ m/z: 420.2.

Step 4

Into a 250-mL round-bottom flask, was placed a mixture of methyl 2-[1-[(tert-butyldiphenylsilyl)oxy]ethyl]pyridine-3-carboxylate (10.0 g, 23.8 mmol, 1.00 equiv), MeOH (100 mL), and LiOH (1.71 g, 71.4 mmol, 3.00 equiv). The resulting solution was stirred for 3 hours at 50 degrees C. The resulting mixture was concentrated. The resulting solution was diluted with 100 mL of H₂O. The pH value of the solution was adjusted to 3 with HCl (2 mol/L). The solids were collected by filtration. This resulted in 2-[1-[(tert-butyldiphenylsilyl)oxy]ethyl]pyridine-3-carboxylic acid. LCMS (ES) [M+1]⁺ m/z: 406.2.

Step 5

Into a 250-mL round-bottom flask, was placed a mixture of 2-[1-[(tert-butyldiphenylsilyl)oxy]ethyl]pyridine-3-carboxylic acid (7.00 g, 17.6 mmol, 1.00 equiv), DCM (100 mL), (3R)-morpholin-3-ylmethanol hydrochloride (3.45 g, 22.4 mmol, 1.30 equiv), DIEA (6.69 g, 51.7 mmol, 3.0 equiv), and HATU (7.88 g, 20.7 mmol, 1.2 equiv). The resulting solution was stirred for 3 hours at room temperature. The resulting mixture was concentrated. The residue was purified by silica gel column chromatography with ethyl acetate/petroleum ether (3/2) as eluent. This resulted in [(3R)-4-(2-[1-[(tert-butyldiphenylsilyl)oxy]ethyl]pyridine-3-carbonyl)morpholin-3-yl]methanol. LCMS (ES) [M+1]⁺ m/z: 505.3.

Step 6

Into a 250-mL 3-necked round-bottom flask purged and maintained with an inert atmosphere of nitrogen, was placed a mixture of [(3R)-4-[2-[(1S)-1-[(tert-butyldiphenylsilyl)oxy]ethyl]pyridine-3-carbonyl]morpholin-3-yl]methanol (2.0 g, 3.96 mmol, 1.00 equiv), DCM (100 mL), 2,6-dihydroxybenzaldehyde (0.71 g, 5.15 mmol, 1.30 equiv), and PPh₃ (1.56 g, 5.94 mmol, 1.50 equiv). DBAD (1.00 g, 4.35 mmol, 1.10 equiv) was added dropwise at 0° C. The resulting solution was stirred for 16 hours at room temperature. The resulting mixture was concentrated. The residue was purified by silica gel column chromatography with ethyl acetate/petroleum ether (1/1) as eluents.

This resulted in Compound 40g, Diastereomer 1 (LCMS, Retention time: 1.896 min). and Compound 40g, Diastereomer 2 (LCMS retention time: 1.872 min, (ES) [M+1]⁺ m/z: 625.2). LCMS analysis conditions: Instrument: Shimadzu LC2020; Column: Kinetex XB-C18, 50*3.0 mm, Particle size 2.6 um; Mobile phase A: Water/0.05% TFA; Mobile phase B: Acetonitrile/0.05% TFA; Gradient: 5-100% B in 3 min.

Step 7A

Into a 20-mL vial, was placed a solution of Compound 40g, Diastereomer 1 (400 mg, 0.640 mmol, 1.00 equiv), THF (4.00 mL), and TBAF/THF (3.21 mL, 3.20 mmol, 5.00 equiv). The resulting solution was stirred for 3 hours at 45 degrees C. The residue was applied onto a silica gel column with ethyl acetate/petroleum ether (99/1-1/9). The crude reaction mixture was filtered and subjected to reverse phase preparative HPLC (XB-C18, 50-250 mm, 10 mM; gradient elution of 10% MeCN in water to 45% MeCN in water over a 20 min period, where both solvents contain 0.1% formic acid), and the product was analyzed by analytical chiral HPLC (Instrument: Shimadzu LC-20AD; Mobile Phase A: n-Hexane (0.1% TFA); Mobile Phase B:EtOH/MeOH=1/1; Conc. of Phase B: 20.0%; Column: CHIRALPAK IC-3, 50*4.6 mm, 3 um IC30CC-SC002; Column ID: AY30CC-SK001; Flow Rate: 1.000 mL/min). This resulted in Compound 41, Diastereomer 1. Analytical chiral HPLC Retention time=5.801 min. LCMS (ES) [M+1]⁺ m/z: 387.1. ¹H NMR (300 MHz, DMSO-d₆) δ 11.84-11.69 (m, 1H), 10.35-10.14 (m, 1H), 8.58-8.54 (m, 1H), 7.69-7.32 (m, 3H), 6.75-6.54 (m, 2H), 5.33-4.21 (m, 5H), 4.20-3.63 (m, 4H), 3.60-3.35 (m, 1H), 3.23-2.91 (m, 1H), 1.51-1.25 (m, 3H).

Step 7B

Into a 20-mL vial, was placed a solution of Compound 40g, Diastereomer 2 (500 mg, 0.800 mmol, 1.00 equiv), THF (5.00 mL), and TBAF (4.01 mL, 4.00 mmol, 5.00 equiv). The resulting solution was stirred for 3 hours at 45 degrees C. The residue was applied onto a silica gel column with ethyl acetate/petroleum ether (99/1-1/9). The crude reaction mixture was filtered and subjected to reverse phase preparative HPLC (XB-C18, 50-250 mm, 10 mM; gradient elution of 10% MeCN in water to 45% MeCN in water over a 20 min period, where both solvents contain 0.1% formic acid), and the product was analyzed by analytical chiral HPLC (Instrument: Shimadzu LC-20AD; Mobile Phase A: n-Hexane (0.1% TFA); Mobile Phase B:EtOH/MeOH=1/1; Conc. of Phase B: 20.0%; Column: CHIRALPAK IC-3, 50*4.6 mm, 3 um IC30CC-SC002; Column ID: AY30CC-SK001; Flow Rate: 1.000 mL/min). This resulted in Compound 41, Diastereomer 2. Analytical chiral HPLC Retention time=4.128 min. LCMS (ES) [M+1]⁺ m/z: 387.1. ¹H NMR (300 MHz, DMSO-d₆) δ 11.84-11.20 (br, 1H), 10.38-10.15 (m, 1H), 8.58-8.53 (m, 1H), 7.70-7.30 (m, 3H), 6.77-6.51 (m, 2H), 5.33-4.75 (m, 3H), 4.55-3.63 (m, 7H), 3.21-3.02 (m, 1H), 1.51-1.10 (m, 3H).

Example 41. 2-hydroxy-6-{[(3S)-4-{2-[(2S)-2-hydroxypropyl]pyridine-3-carbonyl}morpholin-3-yl]methoxy}benzaldehyde and 2-hydroxy-6-{[(3S)-4-{2-[(2R)-2-hydroxypropyl]pyridine-3-carbonyl}morpholin-3-yl]methoxy}benzaldehyde Compound 42, Diastereomer 1 and Compound 42, Diastereomer 2 were synthesized according to Scheme 41.

Scheme 41

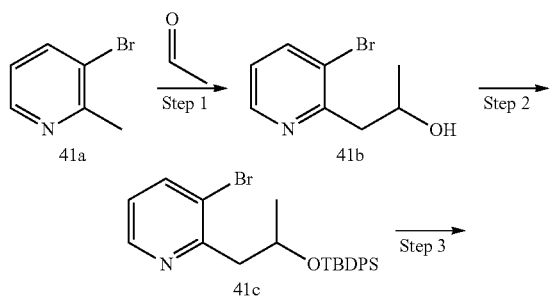

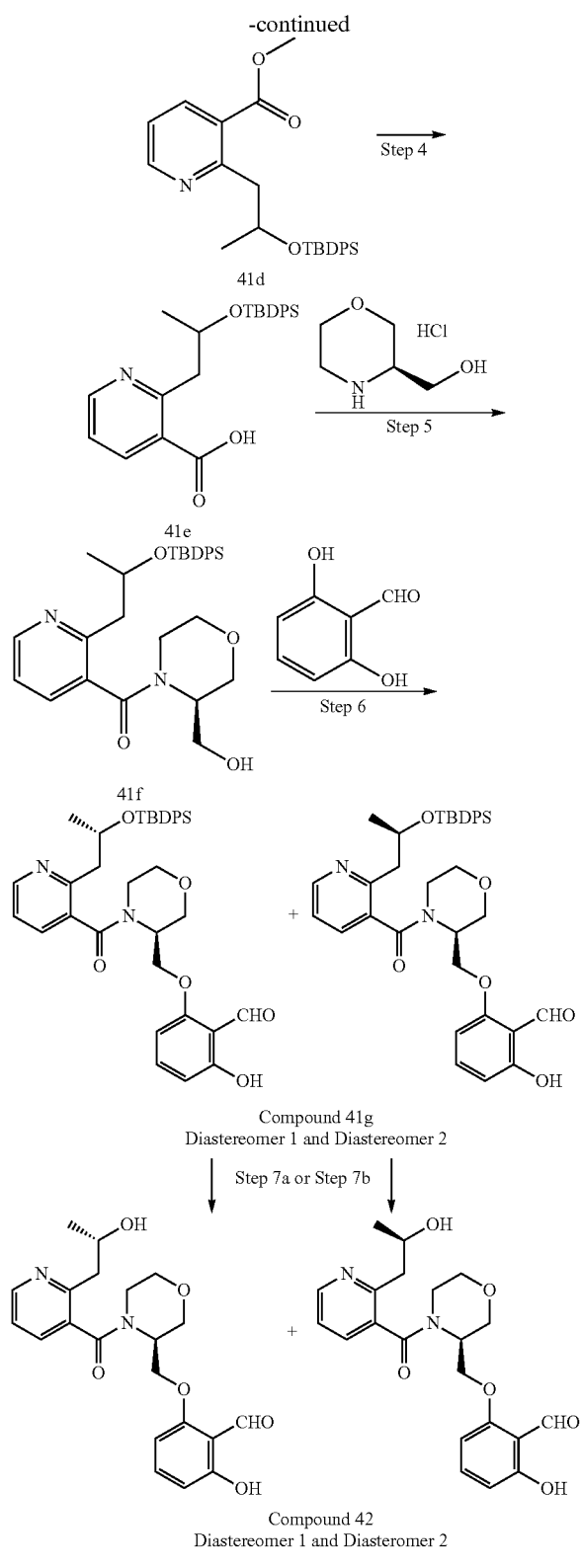

and THF (500.00 mL). This was followed by the addition of LDA (87.20 mL, 174.40 mmol, 1.20 equiv) dropwise with stirring at −78° C. The resulting solution was stirred for 1 h at −78° C. To this mixture was added acetaldehyde (7.04 g, 159.81 mmol, 1.10 equiv) dropwise with stirring at −78° C. The resulting solution was stirred for 1 h at −78° C. The reaction was then quenched by the addition of 300 mL of saturated $NH_4Cl$ solution. The resulting mixture was extracted with 3×300 mL of ethyl acetate, and the organic layers were combined, dried over anhydrous sodium sulfate, and concentrated. The residue was purified by silica gel column chromatography using THF/PE (20%) as eluent to yield 1-(3-bromopyridin-2-yl)propan-2-ol. LCMS (ES) $[M+1]^+$ m/z: 216.

Step 2

Into a 1000-mL round-bottom flask, was placed 1-(3-bromopyridin-2-yl)propan-2-ol (15.00 g, 69.42 mmol, 1.00 equiv), imidazole (9.45 g, 138.81 mmol, 2.00 equiv), DMF (300.00 mL), DMAP (0.85 g, 6.94 mmol, 0.1 equiv) and TBDPSCl (22.90 g, 83.30 mmol, 1.20 equiv). The resulting solution was stirred for overnight at 60° C. The reaction mixture was cooled to room temperature. The reaction was then quenched by the addition of 300 mL of water. The resulting solution was extracted with 3×300 mL of ethyl acetate, and the organic layers were combined, dried over anhydrous sodium sulfate, and concentrated. The residue was purified by silica gel column chromatography using THF/PE (5%) to yield 3-bromo-2-[2-[(tert-butyldiphenylsilyl)oxy]propyl]pyridine. LCMS (ES) $[M+1]^+$ m/z: 454.

Step 3

Into a 2000-mL pressure tank reactor was placed 3-bromo-2-[2-[(tert-butyldiphenylsilyl)oxy]propyl]pyridine (25.00 g, 55.00 mmol, 1.00 equiv), MeOH (800.00 mL), TEA (11.13 g, 110.01 mmol, 2.00 equiv), and $Pd(dppf)Cl_2$ (4.02 g, 5.49 mmol, 0.10 equiv). The reactor was evacuated and flushed three times with nitrogen, followed by flushing with 30 atm CO. The resulting solution was stirred for overnight at 110° C. The reaction mixture was cooled to room temperature. The resulting mixture was concentrated. The residue was purified with silica gel column chromatography using THF/PE (7%) to yield methyl 2-[2-[(tert-butyldiphenylsilyl)oxy]propyl]pyridine-3-carboxylate. LCMS (ES) $[M+1]^+$ m/z: 434.

Step 4

Into a 1000-mL round-bottom flask, was placed methyl 2-[2-[(tert-butyldiphenylsilyl)oxy]propyl]pyridine-3-carboxylate (20.00 g, 46.12 mmol, 1.00 equiv), MeOH (400 mL), $H_2O$ (200 mL), and LiOH $H_2O$ (3.87 g, 92.22 mmol, 2.00 equiv). The resulting solution was stirred for 4 h at 50° C. The reaction mixture was cooled to room temperature. The resulting mixture was concentrated. The resulting solution was extracted with 200 mL of ethyl acetate, and the aqueous layers combined. The pH value of the solution was adjusted to 4-5 with HCl (1 mol/L). The resulting precipitates were collected by filtration and dried under infrared light. This resulted in 2-[2-[(tert-butyldiphenylsilyl)oxy]propyl]pyridine-3-carboxylic acid. LCMS (ES) $[M+1]^+$ m/z: 420.

Step 5

Into a 250-mL 3-necked round-bottom flask, was placed 2-[2-[(tert-butyldiphenylsilyl)oxy]propyl]pyridine-3-car- Step 1

Into a 1000-mL 3-necked round-bottom flask purged and maintained with an inert atmosphere of nitrogen was placed 3-bromo-2-methylpyridine (25 g, 145.33 mmol, 1.00 equiv)

boxylic acid (4.00 g, 9.53 mmol, 1.00 equiv), (3R)-morpholin-3-ylmethanol hydrochloride (1.76 g, 11.46 mmol, 1.20 equiv), DCM (100.00 mL), and DIEA (3.70 g, 28.59 mmol, 3.00 equiv). This was followed by the addition of HATU (4.35 g, 11.44 mmol, 1.20 equiv) in portions at 0° C. The resulting solution was stirred for 3 h at room temperature. The reaction was then quenched by the addition of 100 mL of water. The resulting solution was extracted with 3×100 mL of dichloromethane, and the organic layers were combined, dried over anhydrous sodium sulfate, and concentrated. The residue was purified with silica gel column chromatography using THF/PE (25%) as eluent to yield [(3R)-4-(2-[2-[(tert-butyldiphenylsilyl)oxy]propyl]pyridine-3-carbonyl)morpholin-3-yl]methanol. LCMS (ES) [M+1]$^+$ m/z: 519.

Step 6

Into a 250-mL 3-necked round-bottom flask, was placed 2,6-dihydroxybenzaldehyde (0.96 g, 6.94 mmol, 1.20 equiv), [(3R)-4-(2-[2-[(tert-butyldiphenylsilyl)oxy]propyl]pyridine-3-carbonyl)morpholin-3-yl]methanol (3.00 g, 5.78 mmol, 1.00 equiv), PPh$_3$ (1.82 g, 6.94 mmol, 1.20 equiv), and DCM (100.00 mL). This was followed by the addition of DIAD (1.40 g, 6.92 mmol, 1.20 equiv) dropwise with stirring at 0° C. The resulting solution was stirred for overnight at room temperature. The resulting mixture was concentrated. The residue was purified with silica gel column using THF/PE (30%) as eluent to give crude product. The crude product was purified by Prep-HPLC with the following conditions: Column: Welch XB-C18 50*250 mm, 10 um, mobile phase, Water (0.1% TFA) and ACN (50% in 100 min); Detector, 254. This resulted in Compound 41g, Diastereomer 1 (Retention time=70 min) and Compound 41g, Diastereomer 2 (Retention time=90 min). LCMS (ES) [M+1]$^+$ m/z: 639.

Step 7A

Into a 40-mL vial, was placed Compound 41g, Diastereomer 1 (1.2 g, 1.88 mmol, 1.00 equiv), THF (9.00 mL), and TBAF/THF (9.39 mL, 9.39 mmol, 5.00 equiv). The resulting solution was stirred for 5 h at 45° C. The reaction mixture was cooled to room temperature. The crude product was purified by Prep-HPLC with the following conditions: Column, XBridge Prep C18 OBD Column, 19 cm, 150 mm, 5 um; mobile phase, Water (0.1% HCOOH) and ACN (5% to 55% in 15 min); Detector, 254. This resulted in Compound 42, Diastereomer 1. The final compound was analyzed with Chiral HPLC with these conditions: Instrument: SHIMADZU LC-20AT; Mobile Phase A: n-Hexane; Mobile Phase B: Mobile Phase B; Conc. of Phase B: 50.0%, Flow Rate Column: 1.000 mL/min: CHIRALPAK AY-3, 4.6*50 mm, 3 μm; Column ID: AY30CC-SK001; Retention time=3.35 min. LCMS: (ES, m/z): [M+H]$^+$: 401. $^1$H-NMR (300 MHz, DMSO-d$_6$, ppm): δ 11.80-11.67 (m, 1H), 10.34-10.23 (m, 1H), 8.58 (dd, J=4.9, 1.7 Hz, 1H), 7.75 (d, J=7.9 Hz, 1H), 7.57 (t, J=8.4 Hz, 1H), 7.33 (d, J=5.7 Hz, 1H), 6.75 (d, J=8.1 Hz, 1H), 6.55 (dd, J=8.5, 4.9 Hz, 1H), 5.04-4.89 (m, 1H), 4.49-4.29 (m, 4H), 4.09 (d, J=12.1 Hz, 1H), 3.99-3.63 (m, 3H), 3.57-3.07 (m, 3H), 2.94-2.60 (m, 1H), 1.19-0.81 (m, 3H).

Step 7B

Into a 40-mL vial, was placed Compound 41g, Diastereomer 2 (1.20 g, 1.88 mmol, 1.00 equiv), THF (9.00 mL), and TBAF (9.39 mL, 9.39 mmol, 5.00 equiv). The resulting solution was stirred for 5 h at 45° C. The reaction mixture was cooled to room temperature. The crude product was purified by Prep-HPLC with the following conditions: Column, XBridge Prep C18 OBD Column, 19 cm, 150 mm, Sum; mobile phase, Water (0.1% HCOOH) and ACN (5% to 55% in 15 min); Detector, 254. This resulted in Compound 42, Diastereomer 2. The final compound was analyzed with Chiral HPLC with these conditions: Instrument: SHIMADZU LC-20AT; Mobile Phase A: n-Hexane; Mobile Phase B: Mobile Phase B; Conc. of Phase B: 50.0%; Flow Rate Column: 1.000 mL/min: CHIRALPAK AY-3, 4.6*50 mm, 3 μm; Column ID: AY30CC-SK001; Retention time=1.91 min. LCMS: (ES, m/z): [M+H]$^+$: 401. $^1$H-NMR: (300 MHz, DMSO-d$_6$, ppm): δ 11.82-11.69 (m, 1H), 10.33-10.23 (m, 1H), 8.58 (dd, J=4.9, 1.8 Hz, 1H), 7.84-7.26 (m, 3H), 6.76 (d, J=8.3 Hz, 1H), 6.56 (d, J=8.4 Hz, 1H), 4.95 (s, 1H), 4.45-4.15 (m, 4H), 4.09-3.61 (m, 4H), 3.46-3.12 (m, 3H), 2.95-2.66 (m, 1H), 1.20-0.83 (m, 3H).

Example 42. 2-hydroxy-6-{[(3R)-4-{2-[(1S)-1-hydroxyethyl]pyridine-3-carbonyl}thiomorpholin-3-yl]methoxy}benzaldehyde and 2-hydroxy-6-{[(3R)-4-{2-[(1R)-1-hydroxyethyl]pyridine-3-carbonyl}thiomorpholin-3-yl]methoxy}benzaldehyde Compound 43, Diastereomer 1 and Compound 43, Diastereomer 2 were synthesized according to Scheme 42.

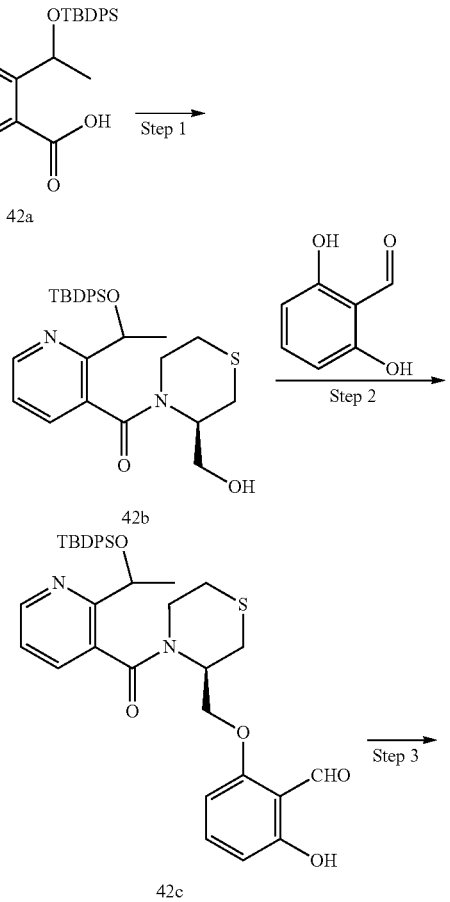

Scheme 42

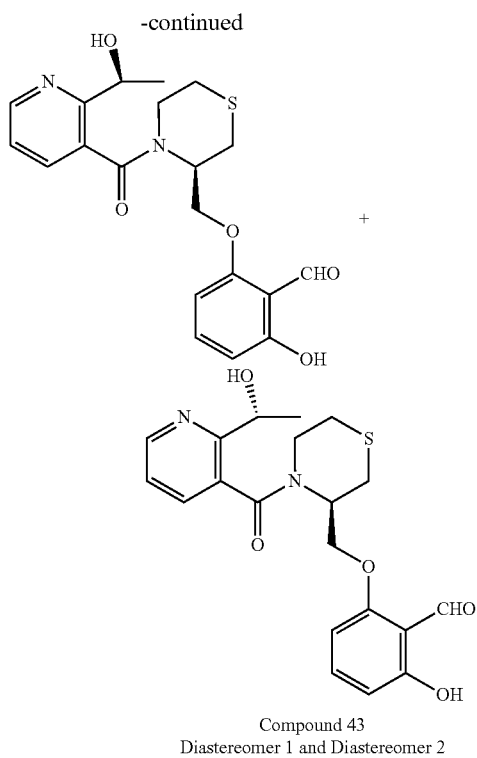

Compound 43
Diastereomer 1 and Diastereomer 2

Step 1

To a solution of 2-[1-[(tert-butyldiphenylsilyl)oxy]ethyl]pyridine-3-carboxylic acid (2.0 g, 4.93 mmol, 1.0 equiv)) in DMF (20.0 mL) was added DIPEA (1.27 g, 9.8 mmol, 2.0 equiv) and HATU (2.25 g, 5.9 mmol, 1.2 equiv) at 0° C. After the reaction mixture was stirred at 0° C. for 20 min, (3R)-thiomorpholin-3-ylmethanol (720 mg, 5.42 mmol, 1.10 equiv) was added in portions. The resulting solution was stirred for 2 h at 25° C. The reaction was then quenched by the addition of 50 mL of water. The resulting solution was extracted with 3×80 mL of ethyl acetate. The combined organic layer was dried over anhydrous sodium sulfate and concentrated under vacuum. The residue was purified by silica gel column chromatography using ethyl acetate/petroleum ether (1:100 to 1:1) as eluent. This resulted in [(3R)-4-(2-[1-[(tert-butyldiphenylsilyl)oxy]ethyl]pyridine-3-carbonyl)thiomorpholin-3-yl]methanol. LCMS (ES) [M+1]$^+$ m/z: 521.2; $^1$H-NMR: (300 MHz, DMSO-d6, ppm): δ 8.75 (d, J=5.4 Hz, 1H), 7.96 (s, 1H), 7.71-7.26 (m, 11H), 4.98-4.44 (m, 3H), 4.07-3.54 (m, 2H), 3.12-2.97 (m, 1H), 2.91-2.84 (m, 1H), 2.74-2.70 (m, 1H), 2.38-2.33 (m, 1H), 1.79-1.69 (m, 1H), 1.59-1.10 (m, 3H), 0.92 (s, 9H).

Step 2

A solution of [(3R)-4-(2-[1-[(tert-butyldiphenylsilyl)oxy]ethyl]pyridine-3-carbonyl)thiomorpholin-3-yl]methanol (1.3 g, 2.5 mmol, 1.0 equiv), 2,6-dihydroxybenzaldehyde (380 mg, 2.72 mmol, 1.1 equiv) and PPh$_3$ (980 mg, 3.75 mmol, 1.5 equiv) in DCM (200 mL) was cooled to 0° C. under Argon atmosphere. A solution of DBAD (690 mg, 3.0 mmol, 1.2 equiv) in DCM (30 mL) was added dropwise. After the addition, the resulting solution was stirred for 16 h at 0-25° C. The reaction was concentrated under vacuum. The residue was purified by silica gel column using ethyl acetate/petroleum ether (1:100 to 1:5) as eluent. This resulted in 2-[[(3R)-4-(2-[1-[(tert-butyldiphenylsilyl)oxy]ethyl]pyridine-3-carbonyl)thiomorpholin-3-yl]methoxy]-6-hydroxybenzaldehyde. LCMS (ES) [M+1]$^+$ m/z: 641.2; $^1$H-NMR (300 MHz, CDCl$_3$, ppm): δ 11.96 (s, 1H), 10.25 (br, 1H), 8.89-8.78 (m, 1H), 7.81-7.19 (m, 13H), 6.63-6.28 (m, 2H), 5.21-4.89 (m, 2H), 4.45-4.13 (m, 2H), 3.71-3.66 (m, 1H), 3.18-2.92 (m, 2H), 2.75-2.35 (m, 3H), 1.74-1.50 (m, 3H), 0.92 (s, 9H).

Step 3

Into a 100-mL 3-necked round-bottom flask, was placed 2-[[(3R)-4-(2-[1-[(tert-butyldiphenylsilyl)oxy]ethyl]pyridine-3-carbonyl)thiomorpholin-3-yl]methoxy]-6-hydroxybenzaldehyde (2.0 g, 3.12 mmol, 1.0 equiv) and THF (10 mL). After the reaction was cooled to 0° C., TBAF (163 g, 6.24 mmol, 2.0 equiv) was added in portions. The resulting solution was stirred for 5 h at 45° C. The resulting solution was quenched with NH$_4$Cl (20 mL, 2N) and extracted with ethyl acetate (50 mL×3); the organic layers were combined and concentrated. The residue was purified by silica gel column eluted with PE/EA=100:1 to 1:1 to give the racemate product, which was purified by Preparative Chiral-HPLC with the following conditions: Column:Lux Amylose-1, 50*250 mm, 10 um; Mobile phase: A:n-Hexane B:Ethanol; Flow rate: 90 mL/min; Gradient:50% B in 50 min; 220 nm. The isolated diastereomers were analyzed by analytical HPLC using the following conditions: Instrument: SHIMADZU LC-20AT; Mobile Phase A: n-Hexane; Mobile Phase B: Ethanol; Conc. of Phase B: 50.0%; Flow Rate: 1.000 mL/min; Column: Lux Amylose-1, 4.6*100 mm, 3 μm; Column ID: H18-344853. This resulted in Compound 43, Diastereomer 1 and Compound 43, Diastereomer 2.

Data for Compound 43, Diastereomer 1: Chiral HPLC retention time 8.31 min; LCMS (ES, m/z): [M+H]$^+$: 403.1; $^1$H-NMR: (300 MHz, DMSO-d6, ppm): δ 11.85 (br, 1H), 10.35-10.16 (m, 1H), 8.57-8.53 (m, 1H), 7.75-7.32 (m, 3H), 6.77-6.55 (m, 2H), 5.42-5.27 (m, 2H), 4.88-4.03 (m, 3H), 3.47-3.44 (m, 2H), 3.21-2.73 (m, 3H), 2.50-2.44 (m, 1H), 1.43-1.34 (m, 3H).

Data for Compound 43, Diastereomer 2: Chiral HPLC retention time 5.30 min; LCMS (ES, m/z): [M+H]$^+$: 403.1; $^1$H-NMR: (300 MHz, DMSO-d6, ppm): δ 11.79 (br, 1H), 10.32-10.16 (m, 1H), 8.60-8.53 (m, 1H), 7.77-7.28 (m, 3H), 6.77-6.55 (m, 2H), 5.43-5.5.33 (m, 2H), 4.88-4.06 (m, 3H), 3.50-3.34 (m, 2H), 3.15-2.36 (m, 4H), 1.46-1.34 (m, 3H).

Example 43. 2-hydroxy-6-{[(3R)-4-{2-[(2S)-2-hydroxypropyl]pyridine-3-carbonyl}thiomorpholin-3-yl]methoxy}benzaldehyde and 2-hydroxy-6-{[(3R)-4-{2-[(2R)-2-hydroxypropyl]pyridine-3-carbonyl}thiomorpholin-3-yl]methoxy}benzaldehyde Compound 44, Diastereomer 1 and Compound 44, Diastereomer 2 were synthesized according to Scheme 43.

Scheme 43

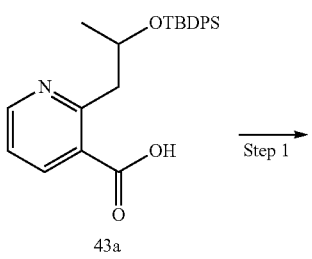

43a

-continued

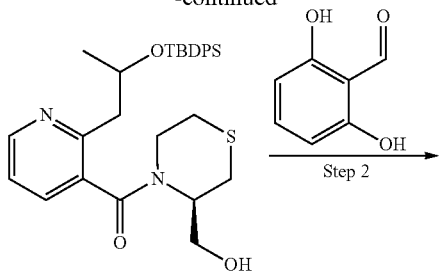

43b

43c

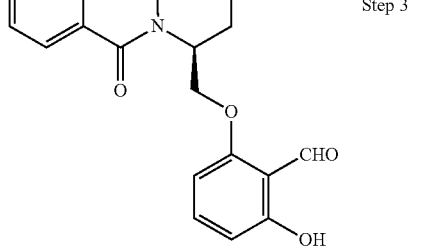

+

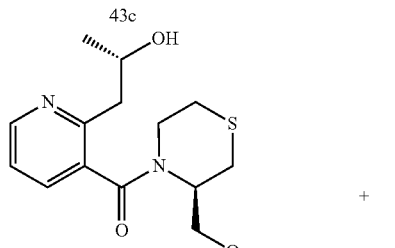

Compound 44
Diastereomer 1 and 2

Step 1

To a solution of 2-[2-[(tert-butyldiphenylsilyl)oxy]propyl]pyridine-3-carboxylic acid (2.0 g, 4.76 mmol, 1.0 equiv) in DMF (20.0 mL) was added DIPEA (1.23 g, 9.5 mmol, 2 equiv) and HATU (2.17 g, 5.720 mmol, 1.20 equiv) at 0° C. After the reaction mixture was stirred at 0° C. for 20 min, (3R)-thiomorpholin-3-ylmethanol (0.70 g, 5.243 mmol, 1.1 equiv) was added in portions. The resulting solution was stirred for 2 h at 25° C. The reaction was then quenched by the addition of 50 mL of water. The resulting solution was extracted with 3×80 mL of ethyl acetate, dried over anhydrous sodium sulfate, and concentrated under vacuum. The residue was purified by silica gel column chromatography using ethyl acetate/petroleum ether (1:100 to 1:1) as eluent. This resulted in [(3R)-4-(2-[2-[(tert-butyldiphenylsilyl)oxy]propyl]pyridine-3-carbonyl)thiomorpholin-3-yl]methanol. LCMS (ES) [M+1]$^+$ m/z: 535.2.

Step 2

Into a 250-mL 3-necked round-bottom flask purged and maintained with an inert atmosphere of argon, was placed [(3R)-4-(2-[2-[(tert-butyldiphenylsilyl)oxy]propyl]pyridine-3-carbonyl)thiomorpholin-3-yl]methanol (1.5 g, 2.8 mmol, 1.0 equiv), 2,6-dihydroxybenzaldehyde (0.43 g, 3.1 mmol, 1.1 equiv), DCM (150.00 mL) and PPh$_3$ (1.1 g, 4.2 mmol, 1.5 equiv). After the reaction was cooled to 0° C., a solution of DBAD (0.78 g, 3.36 mmol, 1.2 equiv) in DCM (10 mL) was added dropwise. The resulting solution was stirred for 16 h at 0 to 25° C. The resulting mixture was concentrated under vacuum. The residue was purified by silica gel column chromatography with ethyl acetate/petroleum ether (1:100 to 1:5) as eluent. This resulted in 1-[[(3R)-4-(2-[2-[(tert-butyldiphenylsilyl)oxy]propyl]pyridine-3-carbonyl)thiomorpholin-3-yl]methoxy]-6-hydroxybenzaldehyde. LCMS (ES) [M+1]$^+$ m/z: 655.2; $^1$H-NMR: (300 MHz, DMSO-d6, ppm): δ 11.76 (br, 1H), 10.39 (br, 1H), 8.54-8.48 (m, 1H), 7.86-7.27 (m, 13H), 6.78-6.55 (m, 2H), 5.41 (br, 1H), 4.83-4.44 (m, 3H), 3.39-3.14 (m, 4H), 3.10-2.70 (m, 3H), 2.41-2.11 (m, 1H), 1.02-0.81 (m, 12H).

Step 3

Into a 100-mL 3-necked round-bottom flask, was placed 2-[[(3R)-4-(2-[2-[(tert-butyldiphenylsilyl)oxy]propyl]pyridine-3-carbonyl)thiomorpholin-3-yl]methoxy]-6-hydroxybenzaldehyde (1.0 g, 1.52 mmol, 1.0 eq.) and THF (10 mL). After the reaction was cooled to 0° C., a solution of TEA-3HF (1.0 g, 80.9 mmol, 3.0 equiv) was added dropwise. The resulting solution was stirred for 5 h at 45° C. The pH value of the solution was adjusted to 8 with NaHCO$_3$(2 mol/L). The reaction was extracted with ethyl acetate (50 mL×3), and the organic layers combined and concentrated. The crude product was purified by silica gel column chromatography eluted with PE/EA=100:1 to 1:1 to give the racemate product.

The racemate product was purified by Chiral-HPLC (Conditions: Column:Lux Amylose-1, 50*250 mm, 10 um; Mobile phase: A:n-Hexane B:Ethanol; Flow rate: 90 mL/min; Gradient:50% B in 36 min; 220 nm) and was analyzed by analytical HPLC (Conditions: Instrument: SHIMADZU LC-20AT; Mobile Phase A: n-Hexane; Mobile Phase B: Ethanol; Conc. of Phase B: 50.0%; Flow Rate: 1.000 mL/min; Column: Lux Amylose-1, 4.6*100 mm, 3 µm; Column ID: H18-344853). This resulted in Compound 44, Diastereomer 1 and Compound 44, Diastereomer 2.

Data for Compound 44, Diastereomer 1: Chiral HPLC retention time=4.85 min; LCMS (ES, m/z): [M+H]$^+$: 417.2; $^1$H-NMR: (300 MHz, DMSO-d6, ppm): δ 11.77 (br, 1H), 10.33 (s, 1H), 8.56 (dd, J=1.8, 4.8 Hz, 1H), 7.76-7.29 (m, 3H), 6.75-6.55 (m, 2H), 5.43-5.41 (m, 1H), 4.81-4.13 (m, 4H), 3.49-3.41 (m, 2H), 3.11-2.41 (m, 6H), 1.08-0.92 (m, 3H).

Data for Compound 44, Diastereomer 2: Chiral HPLC retention time 6.94 min; LCMS (ES, m/z): [M+H]$^+$: 417.2; 1H-NMR: (300 MHz, DMSO-d6, ppm): δ 10.33 (s, 1H), 8.57-8.48 (m, 1H), 7.80-7.27 (m, 3H), 6.75-6.54 (m, 2H), 5.53-41 (m, 1H), 4.56-4.06 (n, 4H), 3.58-3.40 (m, 2H), 3.15-2.67 (m, 5H), 2.43-2.38 (m, 1H), 1.14-0.89 (m, 3H).

Compounds 6-9, and 18 in Table 3 were synthesized according to the methods described herein and appropriate modifications thereof.

TABLE 3

| Compound Number | Structure | Mass Spectrometry Data |
|---|---|---|
| 6 | 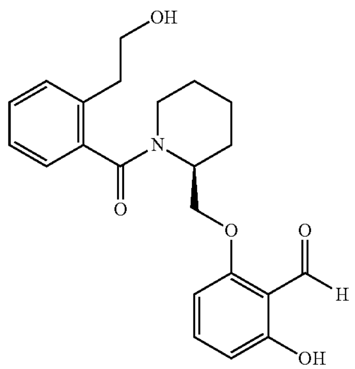 [SMILES: O=Cc1c(O)cccc1OC[C@@H]1CCCCN1C(=O)c1ccccc1CCO] | 384.1 (MH+) |
| 7 | 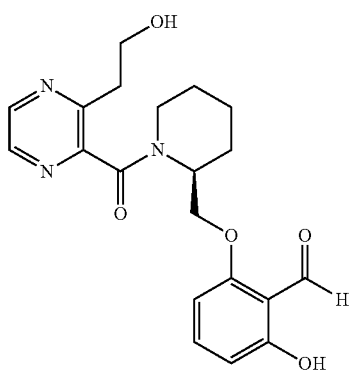 [SMILES: O=Cc1c(O)cccc1OC[C@@H]1CCCCN1C(=O)c1nccnc1CCO] | 386.2 (MH+) |
| 8 | 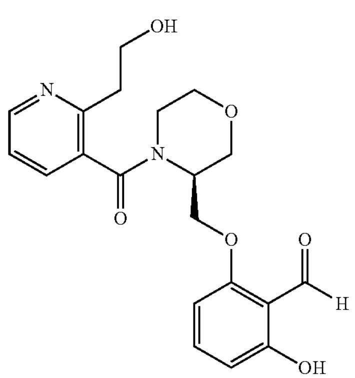 [SMILES: O=Cc1c(O)cccc1OC[C@@H]1COCCN1C(=O)c1cccnc1CCO] | 387.1 (MH+) |
| 9 | | 371.1 (MH+) |
| 18 | | LCMS (ES) [M + 1]$^+$ m/z 399.2 |

Biological Assays

Whole blood assay: Oxygen equilibrium curves (OECs) were collected using a TCS Hemox Analyzer (TCS Scientific Company, New Hope, Pa., USA) to measure changes in the binding affinity of $O_2$ to Hb. Whole blood was incubated for 1 h at 37° C. with the indicated compounds in an equimolar ratio of hemoglobin to compound and diluted into TES (2-[[1,3-dihydroxy-2-(hydroxymethyl)propan-2-yl]amino]ethanesulfonic acid)/saline buffer prior to measurements. For example, for whole blood at 20% hematocrit [Hct], which corresponds to 1 mM Hb, a compound concentration of 1 mM was used (for example, for compounds 1-5), and the incubated sample diluted 50- to 100-fold. The concentration for compounds 6-44 (Diastereomers 1 and 2) varied but remained in equimolar ratio to hemoglobin. The diluted samples were then oxygenated with compressed air within the Hemox Analyzer and the OECs were collected during deoxygenation as previously described (Guarnone et al., Haematologica, 1995, 80, 426-430). p 50 (partial pressure of $O_2$ at which Hb is 50% saturated with $O_2$) values were obtained using a non-linear regression analysis. Percentage change in p50 [Δp50(%)] was calculated as follows: Δp50(%)=[(p50 of control)−p50 with compound)/p50 control]×100. Resulting data is shown in Table 4. Enantiomer 1 and Enantiomer 2 of Compound 13 also exhibit a Δp50 of about 61.0% to about 80.6%.

TABLE 4

| Compound Number | Delta-p50 (%) |
|---|---|
| 1 | 77.3 |
| 2 | 84.4 |
| 3 | 85.8 |
| 4 | 75.5 |
| 5 | 81.0 |
| 6 | 74.5 |
| 7 | 62.7 |
| 8 | 79.8 |
| 9 | 62.2 |
| 10 (Enantiomer 1) | 65.6 |
| 10 (Enantiomer 2) | 87.3 |
| 11 | 79.3 |
| 12 | 76.7 |
| 13 (Enantiomer 1) | 80.6 |
| 13 (Enantiomer 2) | 61.0 |
| 14 | 74.56 |
| 15 | 80.5 |
| 16 | 49.55 |
| 17 | 27.09 |
| 18 | 79.67 |
| 19 | 54.67 |
| 20 | 78.32 |
| 21 | 60.21 |
| 22 | 70.32 |
| 23 | 70.92 |
| 24 | 65.51 |
| 25 | 53.36 |
| 26 | 51.72 |
| 27 | 66.58 |
| 28 | 83.35 |
| 29 | 78.79 |
| 30 | 74.19 |
| 31 | 74.03 |
| 32 | 60.55 |
| 33 | 49.03 |
| 34 | 79.46 |
| 34 (Diastereomer 1) | 80.43 |
| 34 (Diastereomer 2) | 81.59 |
| 35 (Diastereomer 1) | 81.35 |
| 35 (Diastereomer 2) | 83.1 |
| 36 | 77.04 |
| 37 | 60.58 |
| 38 | 60.85 |
| 39 | 77.98 |
| 40 | 72.82 |
| 40 (Enantiomer 1) | 64.31 |
| 40 (Enantiomer 2) | 83.36 |
| 41 (Diastereomer 1) | 66.71 |
| 41 (Diastereomer 2) | 53.94 |
| 42 (Diastereomer 1) | 76.39 |
| 42 (Diastereomer 2) | 75.05 |
| 43 (Diastereomer 1) | 64.50 |
| 43 (Diastereomer 2) | 64.56 |
| 44 (Diastereomer 1) | 66.57 |
| 44 (Diastereomer 2) | 54.34 |

CYP (PXR) Assay: PXR nuclear receptor activation utilizing stably-transfected human hepatoma cell lines (DPX2) were seeded in a 96-well plate. Twenty-four hours after seeding, the cells were treated with selected concentrations of compounds in duplicate wells, and cells then returned to the incubator for an additional 24 h. At the end of this incubation period, the number of viable cells/well were determined using Promega's Cell Titer Fluor cytotoxicity assay. Subsequently, Promega's ONE-Glo were added to the same wells and reporter gene activity were assessed. The average luminescent units for each compound dose of two replicates were divided by the average for the DMSO solvent control to determine the fold-induction. In accordance with industry standard, a threshold of ≥2.5-fold was used to flag compounds that have in vivo CYP induction risk.

Structures of reference compounds (Compound A, Compound B, and Compound C) are shown below in Table 5.

TABLE 5

| | Reference Compound A | Reference Compound B | Reference Compound C |
|---|---|---|---|
| Structure | [chemical structure] | [chemical structure] | [chemical structure] |

Results for various compounds disclosed herein and select reference compounds are summarized in Table 6.

TABLE 6

| Compound | CYP (PXR) Flag |
|---|---|
| Reference Compound A | Y |
| Reference Compound B | Y |
| Reference Compound C | Y[1] |
| 1 | N[1] |
| 8 | N |
| 12 | N |
| Compound 13 (Enantiomer 1) | N |

CYP (PXR) Flag based on fold PXR activation (human, at 30 μM):
Y, PXR activation ≥ 2.5-fold;
N, PXR activation < 2.5-fold.
[1]at 25 μM.

Rat PK: A group of fasted male Sprague-Dawley rats were dosed via oral gavage at 10 mg/kg with test articles formulated in 0.5% methylcellulose suspension. Blood samples were collected through jugular vein at pre-selected time points. Blood samples were prepared by protein precipitation with ACN, vortexed and then centrifuged before supernatants were transferred for bioanalysis. Test article concentrations were measured by HPLC-MS-MS. Pharmacokinetic parameters were calculated using non-compartment analysis. The blood/plasma ratio was calculated by dividing the $AUC_{last}$ (i.e., the area under the curve calculated from t=0 to the last detectable time-point) in blood by the $AUC_{last}$ in plasma. The $T_{1/2}$ was calculated via a linear regression of the terminal phase of the blood-time concentration profile.

Results for various compounds disclosed herein and select reference compounds (Compound A and Compound B) are summarized in Table 7.

TABLE 7

| Compound | $T_{1/2}$ (h) | Blood/Plasma ratio |
|---|---|---|
| Reference Compound A | 29 | 75 |
| Reference Compound B | 29.8 | 98 |
| 1 | 58 | 162 |
| 8 | 69 | 105 |
| 10 (Enantiomer 2) | 112 | 212 |
| 11 | 55 | 126 |
| 12 | 58 | 131 |
| 20 | 65 | 45 |
| 23 | 62 | 59 |
| 36 | 56 | 115 |
| 39 | 52 | 52 |
| 40 (Enantiomer 2) | 117 | 424 |
| 13 (Enantiomer 1) | 88 | 230 |
| 35 (Diastereomer 1) | 102 | 493 |
| 35 (Diastereomer 2) | 89 | 636 |

* * *

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula I:

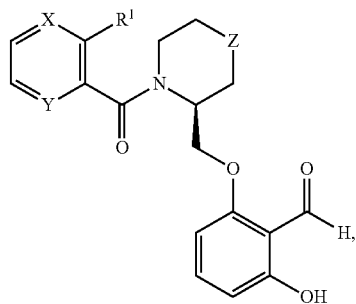

or an isotopically enriched analog, stereoisomer, or mixture of stereoisomers thereof, or a pharmaceutically acceptable salt of each thereof, wherein:

X is CH or N;

Y is CH or N;

Z is absent, $CH_2$, O, or S; and $R^1$ is mono-hydroxy-($C_{1-4}$ alkyl), di-hydroxy-($C_{1-4}$ alkyl), —$CH_2CH_2OCH_3$, —$CH_2CH_2CN$, or

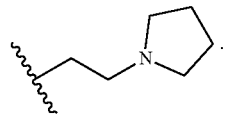

2. The compound of claim 1, wherein X is CH.

3. The compound of claim 1, wherein X is N.

4. The compound of claim 1, wherein Y is CH.

5. The compound of claim 1, wherein Y is N.

6. The compound of claim 1, wherein Z is absent, $CH_2$, or O.

7. The compound of claim 1, wherein Z is absent.

8. The compound of claim 1, wherein Z is $CH_2$.

9. The compound of claim 1, wherein Z is O.

10. The compound of claim 1, wherein Z is S.

11. The compound of claim 1, wherein $R^1$ is —$CH_2OH$, —$CH_2CH_2OH$, —$CH_2CH_2CN$, or

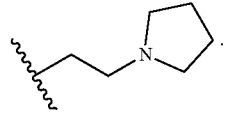 [SMILES: *CCN1CCCC1]

12. The compound of claim 1, wherein $R^1$ is —$CH_2OH$ or —$CH_2CH_2OH$.

13. The compound of claim 1, wherein $R^1$ is mono-hydroxy-($C_{1-4}$ alkyl) or di-hydroxy-($C_{1-4}$ alkyl).

14. The compound of claim 1, wherein $R^1$ is hydroxymethyl, 1-hydroxyethyl, 2-hydroxyethyl, 1,2-dihydroxyethyl, 2-hydroxypropyl, 3-hydroxypropyl, or 2-hydroxy-2-methylpropyl.

15. A compound of formula:
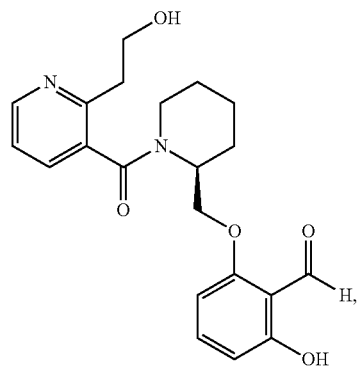
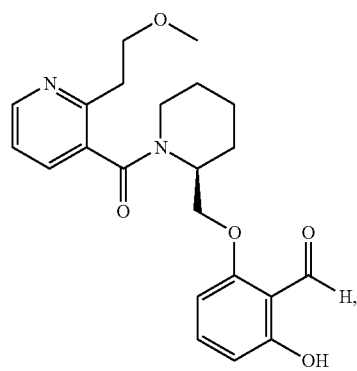
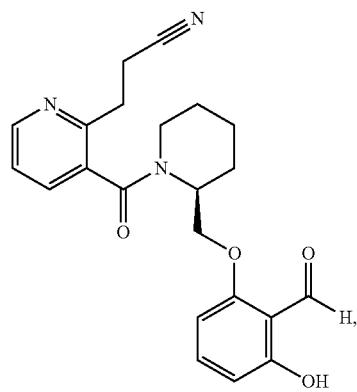
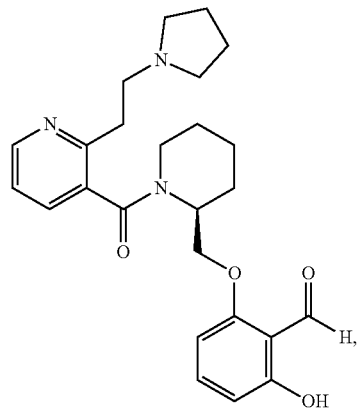
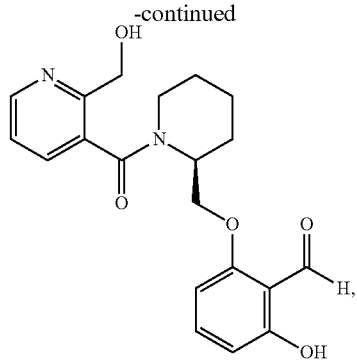
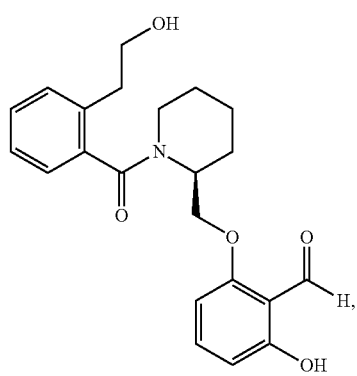
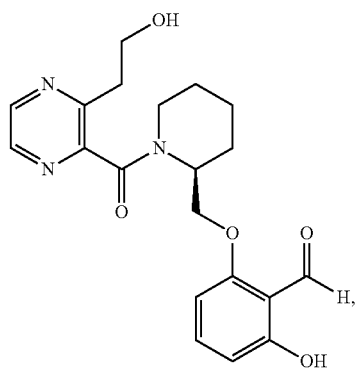
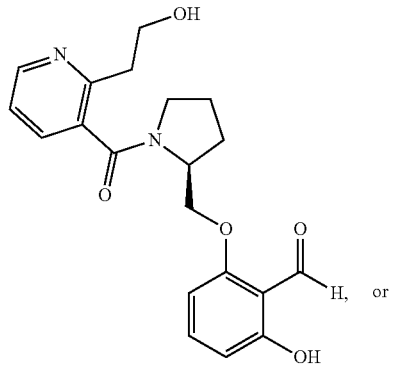

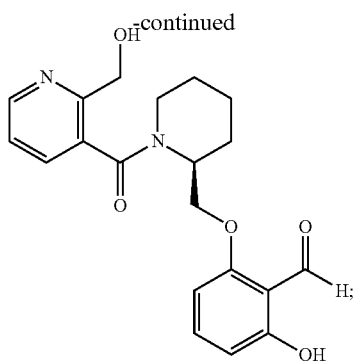

or an isotopically enriched analog, stereoisomer, or mixture of stereoisomers thereof, or a pharmaceutically acceptable salt of each thereof.

16. A pharmaceutical composition comprising a compound according to claim 1, and a pharmaceutically acceptable excipient.

17. A method for increasing oxygen affinity of hemoglobin S in a subject in need thereof, comprising administering to the subject a therapeutically effective amount of a compound according to claim 1.

18. A method for treating a disorder mediated by hemoglobin in a subject in need thereof, comprising administering to the subject a therapeutically effective amount of a compound according to claim 1.

19. The method of claim 18, wherein the hemoglobin is sickle hemoglobin.

20. A method for treating sickle cell disease in a subject in need thereof, comprising administering to the subject a therapeutically effective amount of a compound according to claim 1.

* * * * *